(12) United States Patent
Burger et al.

(10) Patent No.: US 8,217,035 B2
(45) Date of Patent: Jul. 10, 2012

(54) PYRIMIDINE DERIVATIVES USED AS PI-3-KINASE INHIBITORS

(75) Inventors: Matthew Burger, Emeryville, CA (US);
Zhi-Jie Ni, Emeryville, CA (US);
Sabina Pecchi, Emeryville, CA (US);
Gordana Atallah, Emeryville, CA (US);
Sarah Bartulis, Emeryville, CA (US);
Kelly Frazier, Emeryville, CA (US);
Aaron Smith, Emeryville, CA (US);
Joelle Verhagen, Emeryville, CA (US);
Yanchen Zhang, Emeryville, CA (US);
Allan Wagman, Emeryville, CA (US);
Simon Ng, Emeryville, CA (US); Keith Pfister, Emeryville, CA (US); Daniel Poon, Emeryville, CA (US); Alicia Louie, Emeryville, CA (US); Teresa Pick, Emeryville, CA (US); Paul Barsanti, Emeryville, CA (US); Edwin Iwanowicz, Emeryville, CA (US);
Wendy Fantl, Emeryville, CA (US);
Thomas Hendrickson, Emeryville, CA (US); Mark Knapp, Emeryville, CA (US); Hanne Merritt, Emeryville, CA (US); Charles Voliva, Emeryville, CA (US); Marion Wiesmann, Emeryville, CA (US); Xiaohua Xin, Emeryville, CA (US)

(73) Assignee: Novartis AG, Basel (CH)

( * ) Notice: Subject to any disclaimer, the term of this patent is extended or adjusted under 35 U.S.C. 154(b) by 317 days.

(21) Appl. No.: 12/161,537

(22) PCT Filed: Jan. 22, 2007

(86) PCT No.: PCT/US2007/001708
§ 371 (c)(1),
(2), (4) Date: Jul. 31, 2009

(87) PCT Pub. No.: WO2007/084786
PCT Pub. Date: Jul. 26, 2007

(65) Prior Publication Data
US 2010/0249126 A1    Sep. 30, 2010

Related U.S. Application Data

(60) Provisional application No. 60/760,789, filed on Jan. 20, 2006.

(51) Int. Cl.
*A61K 31/535* (2006.01)
*C07D 413/14* (2006.01)
(52) U.S. Cl. .................... 514/232.2; 544/122
(58) Field of Classification Search .......... 544/122; 514/232.2
See application file for complete search history.

(56) References Cited

U.S. PATENT DOCUMENTS

| | | | |
|---|---|---|---|
| 3,975,384 | A | 8/1976 | Narr |
| 4,929,726 | A | 5/1990 | Strekowski |
| 5,786,355 | A | 7/1998 | Konno |
| 5,976,758 | A | 11/1999 | Fukui |
| 5,990,105 | A | 11/1999 | Bös |
| 6,251,900 | B1 | 6/2001 | Kawashima |
| 6,288,228 | B1 | 9/2001 | Henkin |
| 6,495,558 | B1 | 12/2002 | Armistead |
| 6,599,926 | B2 | 7/2003 | Pinto |
| 6,603,000 | B2 | 8/2003 | Yee |
| 6,743,788 | B2 | 6/2004 | Cirillo |
| 6,846,928 | B2 | 1/2005 | Bebbington |
| 7,423,148 | B2 | 9/2008 | Nuss |
| 7,893,063 | B2 | 2/2011 | Pass |
| 2004/0002496 | A1 | 1/2004 | Bebbington |
| 2004/0009974 | A1 | 1/2004 | Bebbington |
| 2004/0009981 | A1 | 1/2004 | Bebbington |
| 2005/0014753 | A1 | 1/2005 | Ding |
| 2010/0048547 | A1 | 2/2010 | Atallah et al. |

FOREIGN PATENT DOCUMENTS

| | | |
|---|---|---|
| DE | 2341925 A1 | 3/1975 |
| EP | 0459 830 A1 | 12/1991 |
| EP | 1 277 738 A1 | 1/2003 |
| EP | 1 277 741 A1 | 1/2003 |
| WO | 00/43373 A2 | 7/2000 |
| WO | 01/72745 A1 | 10/2001 |

(Continued)

OTHER PUBLICATIONS

Science (1999), vol. 2866, 531-537.*

(Continued)

*Primary Examiner* — Rebecca Anderson
(74) *Attorney, Agent, or Firm* — Scott W. Reid

(57) ABSTRACT

Phosphatidylinositol (PI) 3-kinase inhibitor compounds (I), their pharmaceutically acceptable salts, and prodrugs thereof; compositions of the new compounds, either alone or in combination with at least one additional therapeutic agent, with a pharmaceutically acceptable carrier; and uses of the new compounds, either alone or in combination with at least one additional therapeutic agent, in the prophylaxis or treatment of proliferative diseases characterized by the abnormal activity of growth factors, protein serine/threonine kinases, and phospholipid kinases.

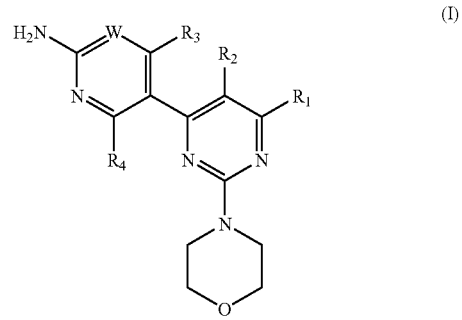

7 Claims, 5 Drawing Sheets

FOREIGN PATENT DOCUMENTS

| | | |
|---|---|---|
| WO | 01/83456 A1 | 11/2001 |
| WO | 02/22606 A1 | 3/2002 |
| WO | 02/22608 A1 | 3/2002 |
| WO | 02/36586 A1 | 5/2002 |
| WO | 02/062789 A1 | 8/2002 |
| WO | 02/102313 A2 | 12/2002 |
| WO | 03/030909 A1 | 4/2003 |
| WO | 2004/048365 A1 | 6/2004 |
| WO | 2004/084824 A2 | 10/2004 |
| WO | 2005/007648 A2 | 1/2005 |
| WO | 2005/009977 A1 | 2/2005 |
| WO | 2005/028444 A1 | 3/2005 |
| WO | 2006/005914 A1 | 1/2006 |
| WO | WO 2007/080382 A1 | 7/2007 |

OTHER PUBLICATIONS

Cancer and Metastasis Reviews (1998), 17(1), 91-106.*
Buonamici et al., Sci Transl Med 2, (2010), vol. 2, Issue 51, pp. 1-8.*
Voskoglou-Nomikos et al., Clinical Cancer Research, vol. 9, 4227-4239.*
ptcl.chem.ox.ac.uk/MSDS structure activity relationship; Jaworska, 1-8, 2004.*
Sanjay Babu Katiyar, "Syntheses of 2,4,6-Trisubstituted Pyrimidine Derivatives as a New Class of Antifilarial Topoisomerase II Inhibitors", Bioorganic & Medicinal Chemistry Letters 15 (2005) 47-50, Science Direct.
Andrisano, R., "Pyrimidine. IV," *Bollettino Scientifico della Facolta di Chimica Industriale di Bologna* 5:48-51, 1947. Volume Date 1944-1947. CA 44:19897, 1950 (1 page).
Balant, L.P., and E. Doelker, "Metabolic Considerations in Prodrug Design," in M.W. Wolff (ed.), *Burger's Medicinal Chemistry and Drug Discovery*, vol. 1, *Principles and Practice*, 5th ed., Wiley, New York, 1995, pp. 975-977.
Banker, G.S. and C.T. Rhodes (eds.), *Modern Pharmaceutics*, 3rd ed., Marcel Dekker, New York, 1996, pp. 451 and 596.
Bennet, J.C., and F. Plum (eds.), *Cecil Textbook of Medicine*, 20th ed., W.B. Saunders, Philadelphia, 1996, Part XIV, *Oncology*, pp. 1004-1101.
Brown, D.M., and G.A.R. Kon, "Some Heterocyclic Analogues of Stilbenes," *Journal of the Chemical Society*, 1948, pp. 2147-2153.
Bundy, G.L., et al., "Synthesis of 2,4-Diaminopyrrolo[2,3-d]pyrimidines *Via* Thermal Fischer Indolization. Pyrazole Formation With Ytterbium Triflate Catalysis," *Journal of Heterocyclic Chemistry* 37:1471-1477, Nov.-Dec. 2000.
Bundy, G.L., et al., "Synthesis of Novel 2,4-Diaminopyrrolo[2,3-*d*] pyrimidines With Antioxidant, Neuroprotective, and Antiasthma Activity," *Journal of Medicinal Chemistry* 38(21:4161-4163, Oct. 1995.
Cabaj, J.E., et al., "Bromine-Mediated Addition of Nucleophiles to the Electron-Rich Pyrimidine Subunit of Tirilazad," *Journal of Organic Chemistry* 59(17):5090-5092, Aug. 1994.
Caine, G.J., et al., "Coagulopathic Complications in Breast Cancer," *Cancer* 98(8):1578-1586, Oct. 2003.
Crowder, R.J., and M.J. Ellis, "Treating Breast Cancer Through Novel Inhibitors of the Phosphatidylinositol 3'-Kinase Pathway," *Breast Cancer Research* 7(5):212-214, Oct. 2005.
Falco, E.A., et al., "2,4-Diaminopyrimidines. A New Series of Antimalarials," *British Journal of Pharmacology and Chemotherapy* 6(2):185-200, Jun. 1951. CA 46:27482, 1952 (1 page).
Font, D., et al., "Development of an Efficient and Straightforward Methodology Toward the Synthesis of Molecularly Diverse 2,6-Disubstituted 3,4-Dihydropyrimidin-4(3*H*)-ones," *Synthesis* 13:1833-1842, Sep. 2002.
Kothari, S., et al., "A Facile One Pot Conversion of 3',5'-dibromo-4'-hydroxy Substituted Chalcones to Pyrimidine Derivatives and Their Antibacterial and Herbicidal Activity," *Indian Journal of Heterocyclic Chemistry* 8(4):285-288, 1999. CA 131:257250, 1999 (1 page).
Kowalewski, A., et al., "Unfused Heterobicycles as Amplifiers of Phleomycin. IV. 4,5'-Bipyrimidines With Dimethylamino and/or Dimethylaminoethylamino Substituents," *Australian Journal of Chemistry* 34(12):2929-2933, 1981.
Li, S.Y., et al., "*PIK3CA* Mutations in Breast Cancer Are Associated With Poor Outcome," *Breast Cancer Research and Treatment* 96(1);91-95, Mar. 2006.
Mamaev, V.P., et al., "Reaction Kinetics of Substituted 2-Chloropyrimidines With Piperidine," *Reaktsionnaya Sposobnost Organicheskikh Soedinenii* 5(3):824-837, 1968. CA 70:76976, 1969 (1 page).
Mikhaleva, M.A., et al, Pyrimidines. 70. Relative Reactivity of the Chlorine Atoms of 2,2'4-Trichloro-4',5-bipyrimidine in the Reaction With Piperidine, *Khimiya Geterotsiklicheskikh Soedinenii* 6:821-826, 1979. CA 91:107951, 1979 (1 page).
Mokrosz, M.J., et al., "Structure-Activity Relationship Studies of CNS Agents. Part 25: 4,6-Di(hyteroaryl)-2-(N-methylpiperazino)pyrimidines as New, Potent 5HT2A Receptor Ligands: A Verification of the Topographic Model," *Archiv der Pharmazie* 328(9):659-666, 1995. CA 124:223, 1995 (1 page).
Nahta, R., et al., "Signal Transduction Inhibitors in the Treatment of Breast Cancer," *Current Medicinal Chemistry—Anti-Cancer Agents* 3(3):201-216, May 2003.
Ouf, A.A.A., et al., "Preparation of Some Methyl Pyrimidines Expected to Be Antimetabolites," *Egyptian Journal of Pharmaceutical Science* 14(2):180-195, 1973.
Sharma, P., et al., "A Convenient One-Pot Synthesis of 2-Substituted-4,6-diaryl Pyrimidines," *Indian Journal of Chemisty* 38B:966-968, Aug. 1999. CA 132:207818, 2000 (1 page).
Sukhwal, S., et al., "A New Route to 2-Piperidino-4,6-diarylpyrimidines," *Indian Journal of Heterocyclic Chemistry* 4(1):67-68, 1994. CA 122 105796, 1995 (2 pages).
Tani, H., et al., "2,4,6-Trisubstituted Pyrimidines," JP 49021148, May 30, 1974, CA 82:140173, 1975 (1 page).
Patani, George A. et al., "Bioisosterism: A Rational Approach in Drug Design", Chem. Rev. 1996, vol. 96, No. 8, pp. 3147-3176.
Silverman, Richard B., "The Organic Chemistry of Drug Design and Drug Action", Elsevier Academic Press, 2004, 2nd ed., pp. 29-34.

* cited by examiner

PYRIMIDINE DERIVATIVES USED AS PI-3-KINASE INHIBITORS

FIELD OF THE INVENTION

The present invention relates to new phosphatidylinositol (PI) 3-kinase inhibitor compounds, their pharmaceutically acceptable salts, and prodrugs thereof; compositions of the new compounds, either alone or in combination with at least one additional therapeutic agent, with a pharmaceutically acceptable carrier; and uses of the new compounds, either alone or in combination with at least one additional therapeutic agent, in the prophylaxis or treatment of a number of diseases, in particular, those characterized by the abnormal activity of growth factors, receptor tyrosine kinases, protein serine/threonine kinases, G protein coupled receptors and phospholipid kinases and phosphatases.

BACKGROUND OF THE INVENTION

Phosphatidylinositol 3-kinases (PI3Ks) comprise a family of lipid and serine/threonine kinases that catalyze the transfer of phosphate to the D-3' position of inositol lipids to produce phosphoinositol-3-phosphate (PIP), phosphoinositol-3,4-diphosphate ($PIP_2$) and phosphoinositol-3,4,5-triphosphate ($PIP_3$) that, in turn, act as second messengers in signaling cascades by docking proteins containing pleckstrin-homology, FYVE, Phox and other phospholipid-binding domains into a variety of signaling complexes often at the plasma membrane ((Vanhaesebroeck et al., *Annu. Rev. Biochem* 70:535 (2001); Katso et al., *Annu. Rev. Cell Dev. Biol.* 17:615 (2001)). Of the two Class 1 PI3Ks, Class 1A PI3Ks are heterodimers composed of a catalytic p110 subunit (α, β, δ isoforms) constitutively associated with a regulatory subunit that can be p85α, p55α, p50α, p85β or p55γ. The Class 1B sub-class has one family member, a heterodimer composed of a catalytic p110γ subunit associated with one of two regulatory subunits, p101 or p84 (Fruman et al., *Annu Rev. Biochem.* 67:481 (1998); Suire et al., *Curr. Biol.* 15:566 (2005)). The modular domains of the p85/55/50 subunits include Src Homology (SH2) domains that bind phosphotyrosine residues in a specific sequence context on activated receptor and cytoplasmic tyrosine kinases, resulting in activation and localization of Class 1A PI3Ks. Class 1B PI3K is activated directly by G protein-coupled receptors that bind a diverse repertoire of peptide and non-peptide ligands (Stephens et al., *Cell* 89:105 (1997)); Katso et al., *Annu. Rev. Cell Dev. Biol.* 17:615-675 (2001)). Consequently, the resultant phospholipid products of class I PI3K link upstream receptors with downstream cellular activities including proliferation, survival, chemotaxis, cellular trafficking, motility, metabolism, inflammatory and allergic responses, transcription and translation (Cantley et al., *Cell* 64:281 (1991); Escobedo and Williams, *Nature* 335:85 (1988); Fantl et al., *Cell* 69:413 (1992)).

In many cases, PIP2 and PIP3 recruit Akt, the product of the human homologue of the viral oncogene v-Akt, to the plasma membrane where it acts as a nodal point for many intracellular signaling pathways important for growth and survival (Fantl et al., *Cell* 69:413-423 (1992); Bader et al., *Nat Rev. Cancer* 5:921 (2005); Vivanco and Sawyer, *Nat. Rev. Cancer* 2:489 (2002)). Aberrant regulation of PI3K, which often increases survival through Akt activation, is one of the most prevalent events in human cancer and has been shown to occur at multiple levels. The tumor suppressor gene PTEN, which dephosphorylates phosphoinositides at the 3' position of the inositol ring and in so doing antagonizes PI3K activity, is functionally deleted in a variety of tumors. In other tumors, the genes for the p110α isoform, PIK3CA, and for Akt are amplified and increased protein expression of their gene products has been demonstrated in several human cancers. Furthermore, mutations and translocation of p85α that serve to up-regulate the p85-p110 complex have been described in a few human cancers. Finally, somatic missense mutations in PIK3CA that activate downstream signaling pathways have been described at significant frequencies in a wide diversity of human cancers (Kang et al., *Proc. Natl. Acad. Sci. USA* 102:802 (2005); Samuels et al., *Science* 304:554 (2004); Samuels et al., *Cancer Cell* 7:561-573 (2005)). These observations show that deregulation of phosphoinositol-3 kinase and the upstream and downstream components of this signaling pathway is one of the most common deregulations associated with human cancers and proliferative diseases (Parsons et al., *Nature* 436:792 (2005); Hennessey et al., *Nature Rev. Drug Dis.* 4:988-1004 (2005)).

SUMMARY OF THE INVENTION

The present invention provides new phosphatidylinositol 3-kinase (PI3K) inhibitor compounds, pharmaceutical formulations that include the compounds, methods of inhibiting phosphatidylinositol 3-kinase (PI3K), and methods of treating proliferative diseases.

In one aspect of the present invention, new phosphatidylinositol 3-kinase (PI3K) inhibitor compounds that are pyrimidine-based compounds, their pharmaceutically acceptable salts, and prodrugs thereof are provided. The pyrimidine compounds, pharmaceutically acceptable salts, and prodrugs are PI3K inhibitors and are useful in the treatment of cellular proliferative diseases.

One embodiment of the invention provides a compound having Formula I:

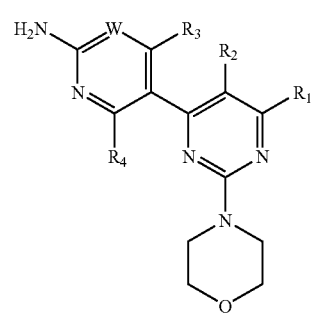

or a stereoisomer, tautomer, or pharmaceutically acceptable salt thereof, wherein, W is $CR_w$ or N, wherein $R_w$ is selected from the group consisting of
(1) hydrogen,
(2) cyano,
(3) halogen,
(4) methyl,
(5) trifluoromethyl,
(6) sulfonamido;

$R_1$ is selected from the group consisting of
(1) hydrogen,
(2) cyano,
(3) nitro,
(4) halogen,
(5) substituted and unsubstituted alkyl,
(6) substituted and unsubstituted alkenyl, (7) substituted and unsubstituted alkynyl,
(8) substituted and unsubstituted aryl,
(9) substituted and unsubstituted heteroaryl,
(10) substituted and unsubstituted heterocyclyl,
(11) substituted and unsubstituted cycloalkyl,
(12) —$COR_{1a}$,
(13) —$CO_2R_{1a}$,
(14) —$CONR_{1a}R_{1b}$,
(15) —$NR_{1a}R_{1b}$,
(16) —$NR_{1a}COR_{1b}$,
(17) —$NR_{1a}SO_2R_{1b}$,
(18) —$OCOR_{1a}$,
(19) —$OR_{1a}$,
(20) —$SR_{1a}$,
(21) —$SOR_{1a}$,
(22) —$SO_2R_{1a}$, and
(23) —$SO_2NR_{1a}R_{1b}$,
wherein $R_{1a}$, and $R_{1b}$ are independently selected from the group consisting of
(a) hydrogen,
(b) substituted or unsubstituted alkyl,
(c) substituted and unsubstituted aryl,
(d) substituted and unsubstituted heteroaryl,
(e) substituted and unsubstituted heterocyclyl, and
(f) substituted and unsubstituted cycloalkyl;
$R_2$ is selected from the group consisting of
(1) hydrogen,
(2) cyano,
(3) nitro,
(4) halogen,
(5) hydroxy,
(6) amino,
(7) substituted and unsubstituted alkyl,
(8) —$COR_{2a}$, and
(9) —$NR_{2a}COR_{2b}$,
wherein $R_{2a}$, and $R_{2b}$ are independently selected from the group consisting of
(a) hydrogen, and
(b) substituted or unsubstituted alkyl;
$R_3$ is selected from the group consisting of
(1) hydrogen,
(2) cyano,
(3) nitro,
(4) halogen,
(5) substituted and unsubstituted alkyl,
(6) substituted and unsubstituted alkenyl,
(7) substituted and unsubstituted alkynyl,
(8) substituted and unsubstituted aryl,
(9) substituted and unsubstituted heteroaryl,
(10) substituted and unsubstituted heterocyclyl,
(11) substituted and unsubstituted cycloalkyl,
(12) —$COR_{3a}$,
(13) —$NR_{3a}R_{3b}$,
(14) —$NR_{3a}COR_{3b}$,
(15) —$NR_{3a}SO_2R_{3b}$,
(16) —$OR_{3a}$,
(17) —$SR_{3a}$,
(18) —$SOR_{3a}$,
(19) —$SO_2R_{3a}$, and
(20) —$SO_2NR_{3a}R_{3b}$,
wherein $R_{3a}$, and $R_{3b}$ are independently selected from the group consisting of
(a) hydrogen,
(b) substituted or unsubstituted alkyl,
(c) substituted and unsubstituted aryl,
(d) substituted and unsubstituted heteroaryl,
(e) substituted and unsubstituted heterocyclyl, and
(f) substituted and unsubstituted cycloalkyl; and
$R_4$ is selected from the group consisting of
(1) hydrogen, and
(2) halogen.

In another embodiment thereof, $R_1$ comprises substituted or unsubstituted arylalkyl, substituted or unsubstituted heteroarylalkyl, substituted or unsubstituted cycloalkylalkyl, or substituted or unsubstituted heterocyclylalkyl.

In a more particular embodiment, W is CH.

In another embodiment, W is N. In a more particular embodiment thereof, $R_3$ is =O.

In another embodiment, $R_1$ is selected from the group consisting of
(1) substituted and unsubstituted alkyl,
(2) substituted and unsubstituted aryl,
(3) substituted and unsubstituted heteroaryl,
(4) substituted and unsubstituted heterocyclyl,
(5) substituted and unsubstituted cycloalkyl,
(6) —$OR_{1a}$, and
(7) —$NR_{1a}R_{1b}$,
wherein $R_{1a}$ and $R_{1b}$ are independently selected from the group consisting of
(a) substituted and unsubstituted heteroaryl, and
(b) substituted and unsubstituted heterocyclyl.

In another embodiment $R_1$ is substituted or unsubstituted heterocyclyl, or substituted or unsubstituted —O-heterocyclyl. In another embodiment, $R_1$ is substituted or unsubstituted morpholinyl; more particular still, $R_1$ is unsubstituted N-linked morpholinyl.

In another embodiment thereof, $R_1$ comprises substituted or unsubstituted heterocyclylalkyl, or substituted or unsubstituted heteroarylalkyl. In another embodiment, $R_1$ comprises substituted or unsubstituted morpholinyl; more particular still, morpholinyl comprises N-linked morpholinyl.

In another embodiment, $R_1$ is substituted or unsubstituted tetrahydropyran or substituted or unsubstituted tetrahydropyranyloxy. More particular still, $R_1$ is unsubstituted 4-tetrahydropyranyloxy.

In another embodiment thereof, $R_1$ comprises substituted or unsubstituted tetrahydropyran. In a more particular embodiment, tetrahydropyran comprises 4-tetrahydropyranyloxy.

In another embodiment, $R_1$ is substituted or unsubstituted tetrahydrofuran or substituted or unsubstituted tetrahydrofuranyloxy. More particular still, $R_1$ is unsubstituted 3-tetrahydrofuranyloxy.

In another embodiment, $R_1$ comprises substituted or unsubstituted tetrahydrofuran. In another embodiment thereof, tetrahydrofuran comprises 3-tetrahydrofuranyloxy.

In another embodiment, $R_2$ is selected from the group consisting
(1) hydrogen,
(2) cyano,
(3) hydroxy,
(4) halogen,
(5) amino,
(6) methyl, and
(7) trifluoromethyl.

In another embodiment, $R_2$ is hydrogen or halogen. In a more particular embodiment, $R_2$ is hydrogen.

In another embodiment, $R_3$ is selected from the group consisting of
(1) cyano,
(2) nitro,
(3) halogen,
(4) hydroxy, (5) amino, and
(6) trifluoromethyl.

In another embodiment, $R_3$ is trifluoromethyl. In another embodiment, $R_3$ is cyano.

Another embodiment of the invention provides a compound having Formula II:

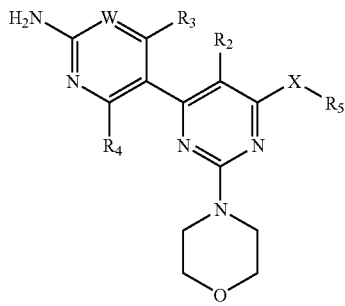

or a stereoisomer, tautomer, or pharmaceutically acceptable salt thereof, wherein, W is $CR_w$ or N, wherein $R_w$ is selected from the group consisting of
(1) hydrogen,
(2) cyano,
(3) halogen,
(4) methyl,
(5) trifluoromethyl, and
(6) sulfonamido;

X is O, S, NH, or a direct bond;

$R_2$ is selected from the group consisting
(1) hydrogen,
(2) cyano,
(3) nitro,
(4) halogen,
(5) hydroxy,
(6) amino,
(7) substituted and unsubstituted alkyl,
(8) —$COR_{2a}$, and
(9) —$NR_{2a}COR_{2b}$, wherein $R_{2a}$, and $R_{2b}$ are independently selected from the group consisting of
(a) hydrogen, and
(b) substituted or unsubstituted alkyl;

$R_3$ is selected from the group consisting of
(1) hydrogen,
(2) cyano,
(3) nitro,
(4) halogen,
(5) substituted and unsubstituted alkyl,
(6) substituted and unsubstituted alkenyl,
(7) substituted and unsubstituted alkynyl,
(8) substituted and unsubstituted aryl,
(9) substituted and unsubstituted heteroaryl,
(10) substituted and unsubstituted heterocyclyl,
(11) substituted and unsubstituted cycloalkyl,
(12) —$COR_{3a}$,
(13) —$NR_{3a}R_{3b}$,
(14) —$NR_{3a}COR_{3b}$,
(15) —$NR_{3a}SO_2R_{3b}$,
(16) —$OR_{3a}$,
(17) —$SR_{3a}$,
(18) —$SOR_{3a}$,
(19) —$SO_2R_{3a}$, and
(20) —$SO_2NR_{3a}R_{3b}$, wherein $R_{3a}$, and $R_{3b}$ are independently selected from the group consisting of
(a) hydrogen,
(b) substituted or unsubstituted alkyl,
(c) substituted and unsubstituted aryl,
(d) substituted and unsubstituted heteroaryl,
(e) substituted and unsubstituted heterocyclyl, and
(f) substituted and unsubstituted cycloalkyl;

$R_4$ is selected from the group consisting of
(1) hydrogen, and
(2) halogen; and $R_5$ is selected from the group consisting of
(1) substituted and unsubstituted cycloalkyl,
(2) substituted and unsubstituted heterocyclyl,
(3) substituted and unsubstituted aryl, and
(4) substituted and unsubstituted heteroaryl.

In another embodiment of Formula II, $R_2$ is selected from the group consisting of
(1) hydrogen,
(2) cyano,
(3) hydroxy,
(4) amino,
(5) halogen, and
(6) substituted and unsubstituted $C_{1-3}$ alkyl.

In another embodiment of Formula II, $R_3$ is selected from the group consisting of
(1) hydrogen,
(2) cyano,
(3) thio,
(4) halogen,
(5) nitro,
(6) substituted and unsubstituted alkyl,
(7) substituted and unsubstituted alkenyl,
(8) substituted and unsubstituted alkynyl,
(9) —$OR_{3a}$,
(10) —$NR_{3a}R_{3b}$,
(11) —$COR_{3a}$, and
(12) —$NR_{3a}COR_{3b}$, wherein $R_{3a}$, and $R_{3b}$ are independently selected from the group consisting of
(a) hydrogen, and
(b) substituted or unsubstituted alkyl.

In another embodiment of Formula II, $R_3$ is trifluoromethyl. In another embodiment, W is CH. In another embodiment, $R_2$ is H.

In another embodiment of Formula II, $R_5$ is selected from the group consisting of
(1) substituted or unsubstituted morpholinyl,
(2) substituted or unsubstituted tetrahydropyranyl, and
(3) substituted or unsubstituted tetrahydropyranyl.

In a more particular embodiment thereof, $R_5$ is N-linked morpholinyl; more particular still, X is a direct link. In another more particular embodiment, $R_5$ is 4-tetrahydropyranyl; more particular still, X is O. In another embodiment, $R_5$ is 3-tetrahydrofuranyl; more particular still, X is O.

In another embodiment, W is N. In a more particular embodiment thereof, $R_3$ is =O.

Another embodiment of the invention provides a compound having Formula III:

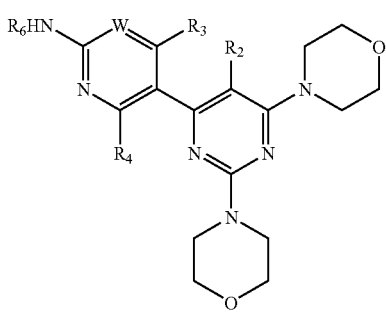

or a stereoisomer, tautomer, or pharmaceutically acceptable salt thereof, wherein, W is $CR_w$ or N, wherein $R_w$ is selected from the group consisting of
(1) hydrogen,
(2) cyano,
(3) halogen,
(4) methyl,
(5) trifluoromethyl, and
(6) sulfonamido;

$R_2$ is selected from the group consisting
(1) hydrogen,
(2) cyano,
(3) nitro,
(4) halogen,
(5) hydroxy,
(6) amino,
(7) substituted and unsubstituted alkyl,
(8) —$COR_{2a}$, and
(9) —$NR_{2a}COR_{2b}$, wherein $R_{2a}$, and $R_{2b}$ are independently selected from the group consisting of
(a) hydrogen, and
(b) substituted or unsubstituted alkyl;

$R_3$ is selected from the group consisting of
(1) hydrogen,
(2) cyano,
(3) nitro,
(4) halogen,
(5) substituted and unsubstituted alkyl,
(6) substituted and unsubstituted alkenyl,
(7) substituted and unsubstituted alkynyl,
(8) substituted and unsubstituted aryl,
(9) substituted and unsubstituted heteroaryl,
(10) substituted and unsubstituted heterocyclyl,
(11) substituted and unsubstituted cycloalkyl,
(12) —$COR_{3a}$,
(13) —$NR_{3a}R_{3b}$,
(14) —$NR_{3a}COR_{3b}$,
(15) —$NR_{3a}SO_2R_{3b}$,
(16) —$OR_{3a}$,
(17) —$SR_{3a}$,
(18) —$SOR_{3a}$,
(19) —$SO_2R_{3a}$, and
(20) —$SO_2NR_{3a}R_{3b}$, wherein $R_{3a}$, and $R_{3b}$ are independently selected from the group consisting of
(a) hydrogen,
(b) substituted or unsubstituted alkyl,
(c) substituted and unsubstituted aryl,
(d) substituted and unsubstituted heteroaryl,
(e) substituted and unsubstituted heterocyclyl, and
(f) substituted and unsubstituted cycloalkyl;

$R_4$ is selected from the group consisting of
(1) hydrogen, and
(2) halogen; and $R_6$ is selected from the group consisting of
(1) hydrogen,
(2) substituted and unsubstituted alkyl, and
(3) substituted and unsubstituted cycloalkyl.

In another embodiment of Formula III, $R_2$ is selected from the group consisting
(1) hydrogen,
(2) cyano,
(3) hydroxy,
(4) halogen,
(5) amino,
(6) methyl, and
(7) trifluoromethyl.

In another embodiment of Formula III, $R_3$ is selected from the group consisting of
(1) cyano,
(2) nitro,
(3) halogen,
(4) hydroxy,
(5) amino, and
(6) trifluoromethyl.

In another embodiment of Formula III, $R_6$ is selected from the group consisting
(1) hydrogen,
(2) methyl, and
(3) ethyl.

Another embodiment provides a method for inhibiting phosphorylation of Akt in a human or animal subject, comprising administering to a human or animal subject an effective amount of a compound of any one of the embodiments provided herein.

Another embodiment provides a composition, comprising a pharmaceutically acceptable carrier and an amount of a compound of any one of the embodiments provided herein effective to inhibit PI3-K activity in a human or animal subject when administered thereto. In a more particular embodiment thereof, the composition is effective to inhibit PI3-K alpha activity in a human or animal subject when administered thereto.

Another embodiment provides a composition, comprising a pharmaceutically acceptable carrier, an amount of a compound of any one of the embodiments provided herein effective to inhibit PI3-K activity in a human or animal subject when administered thereto, and at least one additional agent for the treatment of cancer. In a more particular embodiment thereof, at least one additional agent for the treatment of cancer is vatalanib (PTK-787), imatinib or gefitinib. Alternatively, the at least one additional agent for the treatment of cancer is selected from the kinase inhibitors, anti-estrogens, anti-androgens, other inhibitors, cancer chemotherapeutic drugs, alkylating agents, chelating agents, biological response modifiers, cancer vaccines, or antisense therapies (groups A-J) listed below. Further, the at least one additional agent for the treatment of cancer is selected from radiation, nucleoside analogues, or antimitotic agents.

Another embodiment provides a method for treating a condition by modulation of PI3-K activity comprising administering to a human or animal subject in need of such treatment an effective amount of a compound of any one of the embodiments provided herein. In a more particular embodiment, the compound has an $IC_{50}$ value of less than about 1 μM with respect to inhibition of PI3K. In another more particular embodiment, the condition is cancer.

Another embodiment provides a method for inhibiting PI3-K activity in a human or animal subject, comprising administering to the human or animal subject a composition comprising an amount of a compound of any one of the embodiments provided herein effective to inhibit PI3-K activity the human or animal subject.

Another embodiment provides a method for treating a cancer disorder in a human or animal subject, comprising administering to the human or animal subject a composition comprising an amount of a compound of any one of the embodiments provided herein effective to inhibit PI3-K activity the human or animal subject. A more particular embodiment further comprises administering to the human or animal subject at least one additional agent for the treatment of cancer. In another embodiment, the at least one additional agent for the treatment of cancer is vatalanib, imatinib or gefitinib. Alternatively, the at least one additional agent for the treatment of cancer is selected from the kinase inhibitors, anti-estrogens, anti-androgens, other inhibitors, cancer chemotherapeutic drugs, alkylating agents, chelating agents, biological response modifiers, cancer vaccines, or antisense therapies (groups A-J) listed below.

In another embodiment of any of the aforementioned, the cancer is breast cancer, bladder cancer, colon cancer, glioma, glioblastoma, lung cancer, hepatocellular cancer, gastric cancer, melanoma, thyroid cancer, endometrial cancer, renal cancer, cervical cancer, pancreatic cancer, esophageal cancer, prostate cancer, brain cancer, or ovarian cancer.

Another embodiment provides a method for modulating phosphorylation of Akt comprising contacting a compound of any one of the embodiments described herein with a cell. Another embodiment provides a method for modulating phosphorylation of Akt comprising contacting a cell with a compound of any one of the embodiments described herein. In a more particular embodiment thereof, said modulation is inhibiting. In a more particular embodiment, the compound has an $EC_{50}$ value of less than about 1 µM with respect to inhibition of pAKT. In a more particular embodiment still, the compound has an $EC_{50}$ value of less than about 0.5 µM with respect to inhibition of pAKT. In an even more particular embodiment, the compound has an $EC_{50}$ value of less than about 0.1 µM with respect to inhibition of pAKT.

Another embodiment provides a compound of any one of the embodiments described herein for use in the treatment of cancer.

Another embodiment provides for the use of a compound of any one of the embodiments described herein in the manufacture of a medicament for the treatment for cancer.

Another embodiment provides a method of modulating phosphorylation of Akt comprising contacting a compound of the present invention with a cell. In a more particular embodiment thereof, the compound has an $EC_{50}$ value of less than about 1 µM with respect to inhibition of pAKT.

Another embodiment provides a compound of any one of the embodiments described herein, and a package insert or other labeling including directions for treating a cellular proliferative disease by administering a PI3-K inhibitory amount of the compound.

The invention further provides compositions, kits, methods of use, and methods of manufacture as described in the detailed description of the invention.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Figure 1:
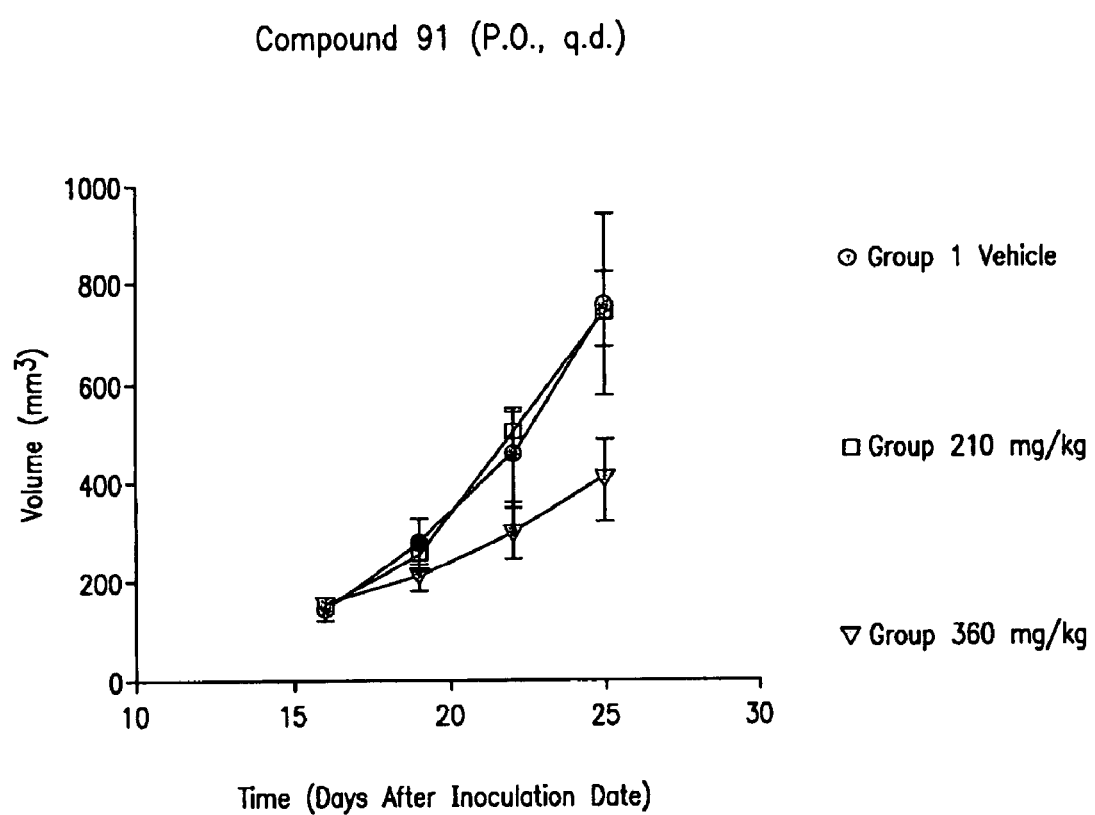
FIG. 1 is a graph illustrating tumor growth inhibition for a representative compound of the invention at two dosages compared to a control vehicle.

Phosphotidylinositol-3-kinase (PI3K) mediates the signal from various growth factors to regulate cell proliferation and survival. A Serine/Threonine (Ser/Thr, or S/T) protein kinase, termed Akt, is identified as a downstream target of PI 3-kinase. This protein kinase is recruited to the cell membrane by interaction of its pleckstrin homology domain with PI3K products, phosphatidylinositol-3,4,5-triphosphate ($PIP_3$), and phosphatidylinositol-3,4-biphosphate ($PIP_2$), where it is activated by phosphorylation of its catalytic domain by 3-Phosphoinositide-dependent Kinase-1 (PDK-1). Akt is further activated by phosphorylation of a serine in its C-terminal hydrophobic motif by another candidate kinase (PDK-2). The activation of Akt acts downstream to regulate additional kinases many of which are implicated in cellular processes that control survival, proliferation, metabolism and growth translation. PI3K can also drive cellular processes that impact transformation, cellular proliferation, cytoskeletal rearrangement and survival through a parallel pathway that does not involve Akt (Hennessy et al., *Nat. Rev. Drug Disc.* 4:988-1004 (2005)). Two of these pathways are activation of the small GTP-binding proteins Cdc42 and Rac1 and activation of the serum and glucocorticoid-inducible kinase (SGK). Cdc42 and Rac1, which regulate cytoskeletal movement and cell motility and can function as oncogenes when over-expressed, are also linked to the RAS pathway. Thus, PI3K activity generates 3'-phosphatidylinositol lipids that act as a nodal point to stimulate a diversity of downstream signaling pathways.

That these pathways impact cellular properties proliferation, survival, motility and morphology that are often disrupted in cancer, proliferative diseases, thrombotic diseases and inflammation, among others, suggests that compounds inhibiting PI3K (and isoforms thereof) have utility, either as a single agent or in combination, in the treatment of these diseases. In cancer, deregulation of the PI3K/Akt pathway is extensively documented, including overexpression of the PIK3CA gene, activating mutations of the PIK3CA gene, overexpression of Akt, mutations of PDK-1, and deletions/inactivation of PTEN (Parsons et al., *Nature* 436:792 (2005); Hennessy et al., *Nat. Rev. Drug Disc.* 4:988 (2005); Stephens et al., *Curr. Opin. Pharmacol.* 5:1 (2005); Bonneau and Longy, *Human Mutation* 16:109 (2000) and Ali et al., *J. Natl. Can. Inst.* 91:1922 (1999)). Recent findings indicate that PIK3CA is frequently mutated (>30%) in various solid tumors in humans (Samuels and Ericson, *Curr. Opin. Oncology* 18:77 (2005)) and the most frequent of these mutations promote cell growth and invasion (Samuels et al., *Cancer Cell* 7:561 (2005), and are transforming (Kang et al., *Proc. Natl. Acad. Sci. USA* 102:802 (2005), Zhao et al., *Proc. Natl. Acad. Sci. USA* 102:18443 (2005)). Thus, inhibitors of PI3K, particularly of the p110α isoform encoded by PIK3CA and its mutations, will be useful in the treatment of cancers driven by these mutations and deregulations.

The present invention provides novel compounds that act as inhibitors of serine threonine kinases, lipid kinases, and, more particularly, as inhibitors of phosphatidylinositol 3-kinase (PI3K) function. The compounds provided herein can be formulated into pharmaceutical formulations that are useful in treating patients with a need for an inhibitor of PI3K, especially, in particular embodiments, to provide compositions and methods for reducing cellular proliferation and increasing cell death in the treatment of cancer.

In one aspect of the present invention, new phosphatidylinositol 3-kinase (PI3K) inhibitor compounds, their pharmaceutically acceptable salts, and prodrugs thereof are provided. The PI3K inhibitor compounds are pyrimidine-based compounds. The pyrimidine compounds, pharmaceutically acceptable salts, and prodrugs are PI3K inhibitors and are useful in the treating cellular proliferative diseases.

In one embodiment, the phosphatidylinositol 3-kinase (PI3K) inhibitor compounds of the invention have the formula (I):

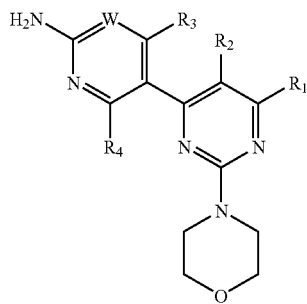

or a stereoisomer, tautomer, or pharmaceutically acceptable salt thereof, wherein, W is $CR_w$ or N, wherein $R_w$ is selected from the group consisting of
(1) hydrogen,
(2) cyano,
(3) halogen,
(4) methyl,
(5) trifluoromethyl, and
(6) sulfonamido;

$R_1$ is selected from the group consisting of
(1) hydrogen,
(2) cyano,
(3) nitro,
(4) halogen,
(5) substituted and unsubstituted alkyl,
(6) substituted and unsubstituted alkenyl,
(7) substituted and unsubstituted alkynyl,
(8) substituted and unsubstituted aryl,
(9) substituted and unsubstituted heteroaryl,
(10) substituted and unsubstituted heterocyclyl,
(11) substituted and unsubstituted cycloalkyl,
(12) —$COR_{1a}$,
(13) —$CO_2R_{1a}$,
(14) —$CONR_{1a}R_{1b}$,
(15) —$NR_{1a}R_{1b}$,
(16) —$NR_{1a}COR_{1b}$,
(17) —$NR_{1a}SO_2R_{1b}$,
(18) —$OCOR_{1a}$,
(19) —$OR_{1a}$,
(20) —$SR_{1a}$,
(21) —$SOR_{1a}$,
(22) —$SO_2R_{1a}$, and
(23) —$SO_2NR_{1a}R_{1b}$,
wherein $R_{1a}$ and $R_{1b}$ are independently selected from the group consisting of
(a) hydrogen,
(b) substituted or unsubstituted alkyl,
(c) substituted and unsubstituted aryl,
(d) substituted and unsubstituted heteroaryl,
(e) substituted and unsubstituted heterocyclyl, and
(f) substituted and unsubstituted cycloalkyl;

$R_2$ is selected from the group consisting
(1) hydrogen,
(2) cyano,
(3) nitro,
(4) halogen,
(5) hydroxy,
(6) amino,
(7) substituted and unsubstituted alkyl,
(8) —$COR_{2a}$, and
(9) —$NR_{2a}COR_{2b}$,
wherein $R_{2a}$ and $R_{2b}$ are independently selected from the group consisting of
(a) hydrogen, and
(b) substituted or unsubstituted alkyl;

$R_3$ is selected from the group consisting of
(1) hydrogen,
(2) cyano,
(3) nitro,
(4) halogen,
(5) substituted and unsubstituted alkyl,
(6) substituted and unsubstituted alkenyl,
(7) substituted and unsubstituted alkynyl,
(8) substituted and unsubstituted aryl,
(9) substituted and unsubstituted heteroaryl,
(10) substituted and unsubstituted heterocyclyl,
(11) substituted and unsubstituted cycloalkyl,
(12) —$COR_{3a}$,
(13) —$NR_{3a}R_{3b}$,
(14) —$NR_{3a}COR_{3b}$,
(15) —$NR_{3a}SO_2R_{3b}$,
(16) —$OR_{3a}$,
(17) —$SR_{3a}$,
(18) —$SOR_{3a}$,
(19) —$SO_2R_{3a}$, and
(20) —$SO_2NR_{3a}R_{3b}$,
wherein $R_{3a}$ and $R_{3b}$ are independently selected from the group consisting of
(a) hydrogen,
(b) substituted or unsubstituted alkyl,
(c) substituted and unsubstituted aryl,
(d) substituted and unsubstituted heteroaryl,
(e) substituted and unsubstituted heterocyclyl, and
(f) substituted and unsubstituted cycloalkyl; and $R_4$ is selected from the group consisting of
(1) hydrogen, and
(2) halogen.

Substituted $R_1$ comprises substituted or unsubstituted arylalkyl, substituted or unsubstituted heteroarylalkyl, substituted or unsubstituted cycloalkylalkyl, or substituted or unsubstituted heterocyclylalkyl.

In one embodiment, W is CH.

In another embodiment, W is N. In a more particular embodiment thereof, $R_3$ is =O.

In one embodiment, $R_1$ is selected from the group consisting of
(1) substituted and unsubstituted alkyl,
(2) substituted and unsubstituted aryl,
(3) substituted and unsubstituted heteroaryl,
(4) substituted and unsubstituted heterocyclyl,
(5) substituted and unsubstituted cycloalkyl,
(6) —$OR_{1a}$, and
(7) —$NR_{1a}R_{1b}$,
wherein $R_{1a}$ and $R_{1b}$ are independently selected from the group consisting of
(a) substituted and unsubstituted heteroaryl, and
(b) substituted and unsubstituted heterocyclyl.

In another embodiment $R_1$ is substituted or unsubstituted heterocyclyl, or substituted or unsubstituted —O-heterocyclyl. In another embodiment, $R_1$ is substituted or unsubstituted morpholinyl; more particular still, $R_1$ is unsubstituted N-linked morpholinyl.

In another embodiment, $R_1$ is substituted or unsubstituted tetrahydropyran or substituted or unsubstituted tetrahydropyranyloxy. More particular still, $R_1$ is unsubstituted 4-tetrahydropyranyloxy.

In another embodiment, $R_1$ is substituted or unsubstituted tetrahydrofuran or substituted or unsubstituted tetrahydrofuranyloxy. More particular still, $R_1$ is unsubstituted 3-tetrahydrofuranyloxy.

In one embodiment, $R_1$ comprises substituted or unsubstituted heterocyclylalkyl, or substituted or unsubstituted heteroarylalkyl. In one embodiment, $R_1$ comprises substituted or unsubstituted morpholinyl. In one embodiment, morpholinyl comprises N-linked morpholinyl. In one embodiment, $R_1$ comprises substituted or unsubstituted tetrahydropyran. In one embodiment, tetrahydropyran comprises 4-tetrahydropyranyloxy. In one embodiment, tetrahydropyran comprises 3-tetrahydropyranyloxy. In one embodiment, $R_1$ comprises substituted or unsubstituted tetrahydrofuran. In one embodiment, tetrahydrofuran comprises 3-tetrahydrofuranyloxy. In one embodiment, $R_1$ comprises substituted or unsubstituted piperidine. In one embodiment, piperidine comprises 4-piperidinyloxy. In another embodiment, piperidine comprises 3-piperidinyloxy. In one embodiment, $R_1$ comprises substituted or unsubstituted pyrrolidine. In one embodiment, pyrrolidine comprises 3-pyrrolidinyloxy.

In one embodiment, $R_2$ is selected from the group consisting
(1) hydrogen,
(2) cyano,
(3) hydroxy,
(4) halogen,
(5) amino,
(6) methyl, and
(7) trifluoromethyl.

In one embodiment, $R_3$ is selected from the group consisting of
(1) cyano,
(2) nitro,
(3) halogen,
(4) hydroxy,
(5) amino, and
(6) trifluoromethyl.

In one embodiment, $R_3$ is trifluoromethyl. In one embodiment, $R_3$ is cyano.

In one embodiment, the phosphatidylinositol 3-kinase (PI3K) inhibitor compounds of the invention have the formula (II):

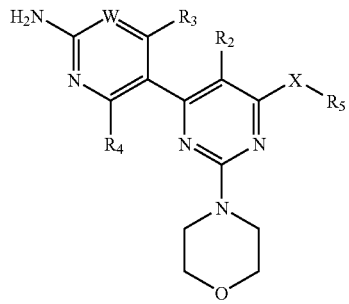

or a stereoisomer, tautomer, or pharmaceutically acceptable salt thereof, wherein, W is $CR_w$ or N, wherein $R_w$ is selected from the group consisting of
(1) hydrogen,
(2) cyano,
(3) halogen,
(4) methyl,
(5) trifluoromethyl, and
(6) sulfonamido;

X is O, S, NH, or a direct bond;

$R_2$ is selected from the group consisting
(1) hydrogen,
(2) cyano,
(3) nitro,
(4) halogen,
(5) hydroxy,
(6) amino,
(7) substituted and unsubstituted alkyl,
(8) —$COR_{2a}$, and
(9) —$NR_{2a}COR_{2b}$,
wherein $R_{2a}$, and $R_{2b}$ are independently selected from the group consisting of
(a) hydrogen, and
(b) substituted or unsubstituted alkyl;

$R_3$ is selected from the group consisting of
(1) hydrogen,
(2) cyano,
(3) nitro,
(4) halogen,
(5) substituted and unsubstituted alkyl,
(6) substituted and unsubstituted alkenyl,
(7) substituted and unsubstituted alkynyl,
(8) substituted and unsubstituted aryl,
(9) substituted and unsubstituted heteroaryl,
(10) substituted and unsubstituted heterocyclyl,
(11) substituted and unsubstituted cycloalkyl,
(12) —$COR_{3a}$,
(13) —$NR_{3a}R_{3b}$,
(14) —$NR_{3a}COR_{3b}$,
(15) —$NR_{3a}SO_2R_{3b}$,
(16) —$OR_{3a}$,
(17) —$SR_{3a}$,
(18) —$SOR_{3a}$,
(19) —$SO_2R_{3a}$, and
(20) —$SO_2NR_{3a}R_{3b}$,
wherein $R_{3a}$, and $R_{3b}$ are independently selected from the group consisting of (a) hydrogen,
(b) substituted or unsubstituted alkyl,
(c) substituted and unsubstituted aryl,
(d) substituted and unsubstituted heteroaryl,
(e) substituted and unsubstituted heterocyclyl, and
(f) substituted and unsubstituted cycloalkyl;

$R_4$ is selected from the group consisting of
(1) hydrogen, and
(2) halogen; and $R_5$ is selected from the group consisting of
(1) substituted and unsubstituted cycloalkyl,
(2) substituted and unsubstituted heterocyclyl,
(3) substituted and unsubstituted aryl, and
(4) substituted and unsubstituted heteroaryl.

In one embodiment, W is CH.

In one embodiment, W is N. In a more particular embodiment thereof, $R_3$ is =O.

In one embodiment, $R_2$ is selected from the group consisting of
(1) hydrogen,
(2) cyano,
(3) hydroxy,
(4) amino,
(5) halogen, and
(6) substituted and unsubstituted $C_{1-3}$ alkyl.

In one embodiment, $R_3$ is selected from the group consisting of
(1) hydrogen,
(2) cyano,
(3) —$SR_{3a}$,
(4) halogen,
(5) nitro,
(6) substituted and unsubstituted alkyl,
(7) substituted and unsubstituted alkenyl,
(8) substituted and unsubstituted alkynyl,
(9) —$OR_{3a}$,
(10) —$NR_{3a}R_{3b}$,
(11) —$COR_{3a}$, and
(12) —$NR_{3a}COR_{3b}$, wherein $R_{3a}$, and $R_{3b}$ are independently selected from the group consisting of
(a) hydrogen, and
(b) substituted or unsubstituted alkyl.

In one embodiment, $R_3$ is trifluoromethyl.

In one embodiment, $R_5$ is selected from the group consisting of
(1) substituted or unsubstituted morpholinyl,
(2) substituted or unsubstituted tetrahydropyranyl, and
(3) substituted or unsubstituted tetrahydrofuranyl.

In a more particular embodiment thereof, $R_5$ is N-linked morpholinyl; more particular still, X is a direct link. In another more particular embodiment, $R_5$ is 4-tetrahydropyranyl; more particular still, X is O. In another embodiment, $R_5$ is 3-tetrahydrofuranyl; more particular still, X is O.

In one embodiment, the phosphatidylinositol 3-kinase (PI3K) inhibitor compounds of the invention have the formula (III):

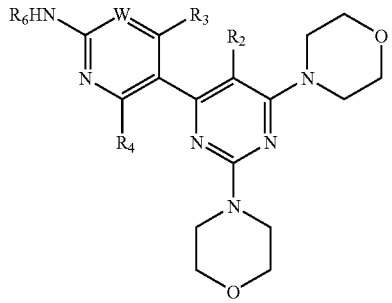

or a stereoisomer, tautomer, or pharmaceutically acceptable salt thereof, wherein, W is $CR_w$ or N, wherein $R_w$ is selected from the group consisting of
(1) hydrogen,
(2) cyano,
(3) halogen,
(4) methyl,
(5) trifluoromethyl, and
(6) sulfonamido;

$R_2$ is selected from the group consisting
(1) hydrogen,
(2) cyano,
(3) nitro,
(4) halogen,
(5) hydroxy,
(6) amino,
(7) substituted and unsubstituted alkyl,
(8) —$COR_{2a}$, and
(9) —$NR_{2a}COR_{2b}$, wherein $R_{2a}$, and $R_{2b}$ are independently selected from the group consisting of
(a) hydrogen, and
(b) substituted or unsubstituted alkyl;

$R_3$ is selected from the group consisting of
(1) hydrogen,
(2) cyano,
(3) nitro,
(4) halogen,
(5) substituted and unsubstituted alkyl,
(6) substituted and unsubstituted alkenyl,
(7) substituted and unsubstituted alkynyl,
(8) substituted and unsubstituted aryl,
(9) substituted and unsubstituted heteroaryl,
(10) substituted and unsubstituted heterocyclyl,
(11) substituted and unsubstituted cycloalkyl,
(12) —$COR_{3a}$,
(13) —$NR_{3a}R_{3b}$,
(14) —$NR_{3a}COR_{3b}$,
(15) —$NR_{3a}SO_2R_{3b}$,
(16) —$OR_{3a}$,
(17) —$SR_{3a}$,
(18) —$SOR_{3a}$,
(19) —$SO_2R_{3a}$, and
(20) —$SO_2NR_{3a}R_{3b}$, wherein $R_{3a}$, and $R_{3b}$ are independently selected from the group consisting of
(a) hydrogen,
(b) substituted or unsubstituted alkyl,
(c) substituted and unsubstituted aryl,
(d) substituted and unsubstituted heteroaryl, (e) substituted and unsubstituted heterocyclyl, and
(f) substituted and unsubstituted cycloalkyl;
$R_4$ is selected from the group consisting of
(1) hydrogen, and
(2) halogen; and
$R_6$ is selected from the group consisting of
(1) hydrogen,
(2) substituted and unsubstituted alkyl, and
(3) substituted and unsubstituted cycloalkyl.

In one embodiment, $R_2$ is selected from the group consisting
(1) hydrogen,
(2) cyano,
(3) hydroxy,
(4) halogen,
(5) amino,
(6) methyl, and
(7) trifluoromethyl.

In one embodiment, $R_3$ is selected from the group consisting of
(1) cyano,
(2) nitro,
(3) halogen,
(4) hydroxy,
(5) amino, and
(6) trifluoromethyl.

In one embodiment, $R_5$ is selected from the group consisting
(1) hydrogen,
(2) methyl, and
(3) ethyl.

It should be understood that the inhibitor compounds according to the invention may exhibit the phenomenon of tautomerism. As the chemical structures within this specification can only represent one of the possible tautomeric forms, it should be understood that the invention encompasses any tautomeric form of the drawn structure.

For the compounds of formulas (I)-(III), representative substituted alkyl groups include arylalkyl, heteroarylalkyl, heterocyclyalkyl, aminoalkyl, alkylaminoalkyl, dialkylaminoalkyl, and sulfonamidoalkyl groups. Representative substituted aryl groups include sulfonamidoaryl groups. Representative substituted heteroaryl groups include alkylheteroaryl groups.

The syntheses of representative PI3K inhibitor compounds of the invention are described in the methods presented in the Examples Section below and the preparation of representative compounds are described in Examples 1-31.

Representative PI3K inhibitor compounds of the invention are shown in Table 1.

In other aspects, the present invention provides methods for manufacture of PI3K inhibitor compounds. It is further contemplated that, in addition to the compounds of formulas (I)-(III), intermediates, and their corresponding methods of syntheses are included within the scope of the invention.

Another embodiment provides a method of inhibiting phosphorylation of Akt comprising administering a compound of Formula I, II, or III to a human in need thereof. Another embodiment provides a method of treating cancer responsive to inhibition of phosphorylation of Akt, comprising administering a compound of Formula I, II, or III. Another embodiment provides a method of inhibiting phosphorylation of Akt comprising contacting a cell with a compound of Formula I, II, or III.

Another embodiment provides a method of inhibiting phosphorylation of Aid comprising orally administering a compound of Formula I, II, or III to a human in need thereof.

In a more particular embodiment the human is suffering from cancer. In a more particular embodiment the cancer is responsive to treatment with a compound that inhibits phosphorylation of Akt. In another embodiment the compound is orally bioavailable.

Another embodiment provides a method of treating cancer comprising orally administering a compound of Formula I, II, or III, wherein said compound is capable of inhibiting activity of pAkt.

In some embodiments of the method of inhibiting PI3K using a PI3K inhibitor compound of the invention, the $IC_{50}$ value of the compound is less than or equal to 1 mM with respect to PI3K. In other such embodiments, the $IC_{50}$ value is less than or equal to 100 μM, is less than or equal to 25 μM, is less than or equal to 10 μM, is less than or equal to 1 μM, is less than or equal to 0.1 μM, is less than or equal to 0.050 μM, or is less than or equal to 0.010 μM.

The compounds of the present invention are also useful in assays evaluating relative activity of PI3 kinase inhibition. In such assays a compound of the present invention can be used to determine relative inhibitory activity of a compound in comparison to a second compound. When so employed, the compound of the present invention is employed in an amount sufficient to allow the skilled artisan to detect inhibition of PI3 kinase. Such an amount is sometimes referred to herein as an "effective inhibitory amount." In a preferred embodiment the inhibitory amount is an amount that will reduce PI3 kinase activity by approximately 50% as compared to the activity in the absence of a compound. Other compounds can then be evaluated as providing greater or lesser inhibition at the same concentration so as to provide a ranking of relative activity. Such information is useful in determining structural changes and other modifications to the test compound to improve its activity. Accordingly the present invention provides a method for inhibiting the activity of PI3 kinase which method comprises contacting said PI3 kinase with an effective inhibitory amount of a compound of the present invention as disclosed herein. Also provided is a method for inhibiting the activity of PI3 kinase activity in a cell, which method comprises contacting said cell with an effective inhibitory amount of a compound as claimed herein.

Some embodiments provide methods of inhibiting phosphorylation of Akt using a compound of the invention having an $EC_{50}$ value of less than about 10 μM with respect to inhibition of pAKT. In another more particular embodiment, the compound has an $EC_{50}$ value of less than about 1 μM with respect to inhibition of pAKT. In a more particular embodiment still, the compound has an $EC_{50}$ value of less than about 0.5 μM with respect to inhibition of pAKT. In an even more particular embodiment, the compound has an $EC_{50}$ value of less than about 0.1 μM with respect to inhibition of pAKT.

In certain embodiments, components of the present invention are capable of inhibition of phosphorylation of Akt. In certain embodiments, components of the invention are capable of inhibition of phosphorylation of Akt in a human or animal subject (i.e., in vivo).

In one embodiment, a method of reducing pAkt activity in a human or animal subject is provided. In the method, a compound of the invention is administered in an amount effective to reduce pAkt activity.

In some embodiments of the method of inhibiting PI3K using a PI3K inhibitor compound of the invention, the $EC_{50}$ value of the compound is between 1 nM to 10 nM. In other such embodiments, the $EC_{50}$ value is between 10 nM to 50 nM, between 50 nM to 100 nM, between 100 nM to 1 μM, between 1 μM to 25 μM, or is between 25 μM to 100 μM.

The compounds of the present invention are also useful in assays evaluating relative activity of inhibition of phosphorylation of AKT. In such assays a compound of the present invention can be used to determine relative inhibitory activity of a compound in comparison to a second compound. When so employed, the compound of the present invention is employed in an amount sufficient to allow the skilled artisan to detect inhibition AKT phosphorylation. Such an amount is sometimes referred to herein as an "effective inhibitory amount." In a preferred embodiment the inhibitory amount is an amount that will reduce phosphorylation of AKT activity by approximately 50% as compared to the activity in the absence of a compound. Other compounds can then be evaluated as providing greater or lesser inhibition at the same concentration so as to provide a ranking of relative activity. Such information is useful in determining structural changes and other modifications to the test compound to improve its activity. Accordingly the present invention provides a method for inhibiting the AKT phosphorylation which method comprises contacting a cell with an effective inhibitory amount of a compound of the present invention, as described herein. Also provided is a method for inhibiting the activity of PI3 kinase activity in a cell, which method comprises contacting said cell with an effective inhibitory amount of a compound as claimed herein.

In another embodiment, the invention provides methods of treating a PI3K-mediated disorder. In one method, an effective amount of a PI3K inhibitor compound is administered to a patient (e.g., a human or animal subject) in need thereof to mediate (or modulate) PI3K activity.

The compounds of the present invention are useful in pharmaceutical compositions for human or veterinary, use where inhibition of PI3K is indicated, for example, in the treatment of cellular proliferative diseases such as tumor and/or cancerous cell growth mediated by PI3K. In particular, the compounds are useful in the treatment of human or animal (e.g., murine) cancers, including, for example, lung and bronchus; prostate; breast; pancreas; colon and rectum; thyroid; liver and intrahepatic bile duct; hepatocellular; gastric; glioma/glioblastoma; endometrial; melanoma; kidney and renal pelvis; urinary bladder; uterine corpus; uterine cervix; ovary; multiple myeloma; esophagus; acute myelogenous leukemia; chronic myelogenous leukemia; lymphocytic leukemia; myeloid leukemia; brain; oral cavity and pharynx; larynx; small intestine; non-Hodgkin lymphoma; melanoma; and villous colon adenoma.

Agents of the invention, in particular, those which have selectivity for PI3 kinase gamma inhibition, are particularly useful in the treatment of inflammatory or obstructive airways diseases, resulting, for example, in reduction of tissue damage, airways inflammation, bronchial hyperreactivity, remodeling or disease progression. Inflammatory or obstructive airways diseases to which the present invention is applicable include asthma of whatever type of genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection. Treatment of asthma is also to be understood as embracing treatment of subjects, e.g. of less than 4 or 5 years of age, exhibiting wheezing symptoms and diagnosed or diagnosable as "wheezy infants", an established patient category of major medical concern and now often identified as incipient or early-phase asthmatics ("wheezy infant syndrome").

Compounds of the invention that are selective for one PI3 Kinase isoform ($\alpha$, $\beta$, $\gamma$, $\delta$) over a different isoform are compounds that preferentially inhibit one isoform. For example, a compound may preferentially inhibit the alpha isoform over the gamma isoform. Alternatively, a compound may preferentially inhibit the gamma isoform over the alpha isoform. To determine a compound's selectivity, the compound's activity is determined according to the Biological Methods described herein. For example, the $IC_{50}$ value, or the $EC_{50}$ value, of a compound is determined for two or more PI3 Kinase isoforms, e.g, alpha and gamma, according to Biological Methods 1 and 2, respectively. The obtained values are then compared to determine the selectivity of the tested compound. Preferably, the compounds of the invention are selective for one isoform over a second isoform by at least two-fold, five-fold or ten-fold. Even more preferably, the compounds of the invention are selective for one isoform over a second isoform by at least fifty-fold or 100-fold. Even more preferably, the compounds of the invention are selective for one isoform over a second isoform by at least 1000-fold.

Other inflammatory or obstructive airways diseases and conditions to which the present invention is applicable include acute lung injury (ALI), adult respiratory distress syndrome (ARDS), chronic obstructive pulmonary, airways or lung disease (COPD, COAD or COLD), including pulmonary fibrosis, chronic bronchitis or dyspnea associated therewith, emphysema, as well as exacerbation of airways hyperreactivity consequent to other drug therapy, in particular other inhaled drug therapy. The invention is also applicable to the treatment of bronchitis of whatever type or genesis including, e.g., acute, arachidic, catarrhal, croupus, chronic or phthinoid bronchitis. Further inflammatory or obstructive airways diseases to which the present invention is applicable include pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, abestosis, chalicosis, ptilosis, siderosis, silicosis, tabacosis and byssinosis.

Having regard to their anti-inflammatory activity, in particular in relation to inhibition of eosinophil activation, agents of the invention are also useful in the treatment of eosinophil related disorders, e.g. eosinophilia, in particular eosinophil related disorders of the airways (e.g. involving morbid eosinophilic infiltration of pulmonary tissues) including hypereosinophilia as it effects the airways and/or lungs as well as, for example, eosinophil-related disorders of the airways consequential or concomitant to Loffler's syndrome, eosinophilic pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction.

Agents of the invention are also useful in the treatment of inflammatory or allergic conditions of the skin, for example psoriasis, contact dermatitis, atopic dermatitis, alopecia areata, erythema multiforme, dermatitis herpetiformis, scleroderma, vitiligo, hypersensitivity angiitis, urticaria, bullous pemphigoid, lupus erythematosus, pemphisus, epidermolysis bullosa acquisita, and other inflammatory or allergic conditions of the skin.

Agents of the invention may also be used for the treatment of other diseases or conditions, in particular diseases or conditions having an inflammatory component, for example, treatment of diseases and conditions of the eye such as conjunctivitis, keratoconjunctivitis sicca, and vernal conjunctivitis, diseases affecting the nose including allergic rhinitis, and inflammatory disease in which autoimmune reactions are implicated or having an autoimmune component or aetiology, including autoimmune haematogical disorders (e.g. haemolytic anaemia, aplastic anaemia, pure red cell anaemia and idiopathic thrombocytopenia), systemic lupus erythematosus, polychondritis, scleroderma, Wegener granulomatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), endocrine ophthalmopathy, Grave's disease, sarcoidosis, alveolitis, chronic hypersensitivity pneumonitis, multiple sclerosis, primary biliary cirrhosis, uveitis (anterior and posterior), interstitial lung fibrosis, psoriatic arthritis and glomerulonephritis (with and without nephritic syndrome, e.g. including idiopathic nephritic syndrome or minal change nephropathy).

In another embodiment, the invention is a method for inhibiting leucocytes, in particular neutrophils and B and T lymphocytes. Exemplary medical conditions that can be treated include those conditions characterized by an undesirable neutrophil function selected from the group consisting of stimulated superoxide release, stimulated exocytosis, and chemotactic migration, preferably without inhibiting phagocytic activity or bacterial killing by the neutrophils.

In another embodiment the invention is a method for disrupting the function of osteoclasts and ameliorating a bone resorption disorder, such as osteoporosis.

In another embodiment, diseases or conditions which may be treated with agents of the invention include septic shock, allograft rejection following transplantation, bone disorders such as but not limited to rheumatoid arthritis, ankylosing spondylitis osteoarthritis, obesity, restenosis, diabetes, e.g. diabetes mellitus type I (juvenile diabetes) and diabetes mellitus type II, diarrheal diseases.

In other embodiments, the PI3K-mediated condition or disorder is selected from the group consisting of cardiovascular diseases, atherosclerosis, hypertension, deep venous thrombosis, stroke, myocardial infarction, unstable angina, thromboembolism, pulmonary embolism, thrombolytic diseases, acute arterial ischemia, peripheral thrombotic occlusions, and coronary artery disease, reperfusion injuries, retinopathy, such as diabetic retinopathy or hyperbaric oxygen-induced retinopathy, and conditions characterized by elevated intraocular pressure or secretion of ocular aqueous humor, such as glaucoma.

As described above, since PI3K serves as a second messenger node that integrates parallel signaling pathways, evidence is emerging that the combination of a PI3K inhibitor with inhibitors of other pathways will be useful in treating cancer and proliferative diseases in humans:

Approximately 20-30% of human breast cancers overexpress Her-2/neu-ErbB2, the target for the drug trastuzumab. Although trastuzumab has demonstrated durable responses in some patients expressing Her2/neu-ErbB2, only a subset of these patients respond. Recent work has indicated that this limited response rate can be substantially improved by the combination of trastuzumab with inhibitors of PI3K or the PI3K/AKT pathway (Chan et al., *Breast Can. Res. Treat.* 91:187 (2005), Woods Ignatoski et al., *Brit. J. Cancer* 82:666 (2000), Nagata et al., *Cancer Cell* 6:117 (2004)).

A variety of human malignancies express activating mutations or increased levels of Her1/EGFR and a number of antibody and small molecule inhibitors have been developed against this receptor tyrosine kinase including tarceva, gefitinib and erbitux. However, while EGFR inhibitors demonstrate anti-tumor activity in certain human tumors (e.g., NSCLC), they fail to increase overall patient survival in all patients with EGFR-expressing tumors. This may be rationalized by the fact that many downstream targets of Her1/EGFR are mutated or deregulated at high frequencies in a variety of malignancies, including the PI3K/Akt pathway. For example, gefitinib inhibits the growth of an adenocarcinoma cell line in in vitro assays. Nonetheless, sub-clones of these cell lines can be selected that are resistant to gefitinib that demonstrate increased activation of the PI3/Akt pathway. Down-regulation or inhibition of this pathway renders the resistant sub-clones sensitive to gefitinib (Kokubo et al., *Brit. J. Cancer* 92:1711 (2005)). Furthermore, in an in vitro model of breast cancer with a cell line that harbors a PTEN mutation and over-expresses EGFR inhibition of both the PI3K/Akt pathway and EGFR produced a synergistic effect (She et al., *Cancer Cell* 8:287-297 (2005)). These results indicate that the combination of gefitinib and PI3K/Akt pathway inhibitors would be an attractive therapeutic strategy in cancer.

The combination of AEE778 (an inhibitor of Her-2/neu/ErbB2, VEGFR and EGFR) and RAD001 (an inhibitor of mTOR, a downstream target of Akt) produced greater combined efficacy that either agent alone in a glioblastoma xenograft model (Goudar et al., *Mol. Cancer. Ther.* 4:101-112 (2005)).

Anti-estrogens, such as tamoxifen, inhibit breast cancer growth through induction of cell cycle arrest that requires the action of the cell cycle inhibitor p27Kip. Recently, it has been shown that activation of the Ras-Raf-MAP Kinase pathway alters the phosphorylation status of p27Kip such that its inhibitory activity in arresting the cell cycle is attenuated, thereby contributing to anti-estrogen resistance (Donovan, et al, *J. Biol. Chem.* 276:40888, 2001). As reported by Donovan et al., inhibition of MAPK signaling through treatment with MEK inhibitor reversed the aberrant phosphorylation status of p27 in hormone refractory breast cancer cell lines and in so doing restored hormone sensitivity. Similarly, phosphorylation of p27Kip by Akt also abrogates its role to arrest the cell cycle (Viglietto et al., *Nat Med.* 8:1145 (2002)). Accordingly, in one aspect, the compounds of formula (I) may be used in the treatment of hormone dependent cancers, such as breast and prostate cancers, to reverse hormone resistance commonly seen in these cancers with conventional anticancer agents.

In hematological cancers, such as chronic myelogenous leukemia (CML), chromosomal translocation is responsible for the constitutively activated BCR-Abl tyrosine kinase. The afflicted patients are responsive to imatinib, a small molecule tyrosine kinase inhibitor, as a result of inhibition of Abl kinase activity. However, many patients with advanced stage disease respond to imatinib initially, but then relapse later due to resistance-conferring mutations in the Abl kinase domain. In vitro studies have demonstrated that BCR-Abl employs the Ras-Raf kinase pathway to elicit its effects. In addition, inhibiting more than one kinase in the same pathway provides additional protection against resistance-conferring mutations. Accordingly, in another aspect of the invention, the compounds of formula (I) are used in combination with at least one additional agent, such as Gleevec®, in the treatment of hematological cancers, such as chronic myelogenous leukemia (CML), to reverse or prevent resistance to at least one additional agent.

Because activation of the PI3K/Akt pathway drives cell survival, inhibition of the pathway in combination with therapies that drive apoptosis in cancer cells, including radiotherapy and chemotherapy, will result in improved responses (Ghobrial et al., *CA Cancer J. Clin* 55:178-194 (2005)). As an example, combination of PI3 kinase inhibitor with carboplatin demonstrated synergistic effects in both in vitro proliferation and apoptosis assays as well as in in vivo tumor efficacy in a xenograft model of ovarian cancer (Westfall and Skinner, Mol. Cancer Ther 4:1764-1771 (2005)).

In addition to cancer and proliferative diseases, there is accumulating evidence that inhibitors of Class 1A and 1B PI3 kinases would be therapeutically useful in others disease areas. The inhibition of p110γ, the PI3K isoform product of the PIK3CB gene, has been shown to be involved in shear-induced platelet activation (Jackson et al., *Nature Medicine* 11:507-514 (2005)). Thus, a PI3K inhibitor that inhibits p110γ would be useful as a single agent or in combination in anti-thrombotic therapy. The isoform p110γ the product of the PIK3CD gene, is important in B cell function and differentiation (Clayton et al., *J. Exp. Med.* 196:753-763 (2002)), T-cell dependent and independent antigen responses (Jou et al., *Mol. Cell. Biol* 22:8580-8590 (2002)) and mast cell differentiation (Ali et al., *Nature* 431:1007-1011 (2004)). Thus, it is expected that p110γ-inhibitors would be useful in the treatment of B-cell driven autoimmune diseases and asthma. Finally, the inhibition of p110γ, the isoform product of the PI3KCG gene, results in reduced T, but not B cell, response (Reif et al., J. Immunol. 173:2236-2240 (2004)) and its inhibition demonstrates efficacy in animal models of autoimmune diseases (Camps et al., Nature Medicine 11:936-943 (2005), Barber et al., Nature Medicine 11:933-935 (2005)).

The present invention provides pharmaceutical compositions comprising at least one PI3K inhibitor compound (e.g., a compound of formulas (I)-(III)) together with a pharmaceutically acceptable carrier suitable for administration to a human or animal subject, either alone or together with other anticancer agents.

In one embodiment, the present invention provides methods of treating human or animal subjects suffering from a cellular proliferative disease, such as cancer. The present invention provides methods of treating a human or animal subject in need of such treatment, comprising administering to the subject a therapeutically effective amount of a PI3K inhibitor compound (e.g., a compound of formulas (I)-(III)), either alone or in combination with other anticancer agents.

In particular, compositions will either be formulated together as a combination therapeutic or administered separately. Anticancer agents for use with the invention include, but are not limited to, one or more of the following set forth below:

A. Kinase Inhibitors

Kinase inhibitors for use as anticancer agents in conjunction with the compositions of the present invention include inhibitors of Epidermal Growth Factor Receptor (EGFR) kinases such as small molecule quinazolines, for example gefitinib (U.S. Pat. No. 5,457,105, U.S. Pat. No. 5,616,582, and U.S. Pat. No. 5,770,599), ZD-6474 (WO 01/32651), erlotinib (Tarceva®, U.S. Pat. No. 5,747,498 and WO 96/30347), and lapatinib (U.S. Pat. No. 6,727,256 and WO 02/02552); Vascular Endothelial Growth Factor Receptor (VEGFR) kinase inhibitors, including SU-11248 (WO 01/60814), SU 5416 (U.S. Pat. No. 5,883,113 and WO 99/61422), SU 6668 (U.S. Pat. No. 5,883,113 and WO 99/61422), CHIR-258 (U.S. Pat. No. 6,605,617 and U.S. Pat. No. 6,774,237), vatalanib or PTK-787 (U.S. Pat. No. 6,258,812), VEGF-Trap (WO 02/57423), B43-Genistein (WO-09606116), fenretinide (retinoic acid p-hydroxyphenylamine) (U.S. Pat. No. 4,323,581), IM-862 (WO 02/62826), bevacizumab or Avastin® (WO 94/10202), KRN-951, 3-[5-(methylsulfonylpiperadine methyl)-indolyl]-quinolone, AG-13736 and AG-13925, pyrrolo[2,1-f][1,2,4]triazines, ZK-304709, Veglin®, VMDA-3601, EG-004, CEP-701 (U.S. Pat. No. 5,621,100), Cand5 (WO 04/09769); Erb2 tyrosine kinase inhibitors such as pertuzumab (WO 01/00245), trastuzumab, and rituximab; Akt protein kinase inhibitors, such as RX-0201; Protein Kinase C (PKC) inhibitors, such as LY-317615 (WO 95/17182), and perifosine (US 2003171303); Raf/Map/MEK/Ras kinase inhibitors including sorafenib (BAY 43-9006), ARQ-350RP, LErafAON, BMS-354825 AMG-548, and others disclosed in WO 03/82272; Fibroblast Growth Factor Receptor (FGFR) kinase inhibitors; Cell Dependent Kinase (CDK) inhibitors, including CYC-202 or roscovitine (WO 97/20842 and WO 99/02162); Platelet-Derived Growth Factor Receptor (PGFR) kinase inhibitors such as CHIR-258, 3G3 mAb, AG-13736, SU-11248 and SU6668; and Bcr-Abl kinase inhibitors and fusion proteins such as STI-571 or Gleevec® (imatinib).

B. Anti-Estrogens

Estrogen-targeting agents for use in anticancer therapy in conjunction with the compositions of the present invention include Selective Estrogen Receptor Modulators (SERMs) including tamoxifen, toremifene, raloxifene; aromatase inhibitors including Arimidex® or anastrozole; Estrogen Receptor Downregulators (ERDs) including Faslodex® or fulvestrant.

C. Anti-Androgens

Androgen-targeting agents for use in anticancer therapy in conjunction with the compositions of the present invention include flutamide, bicalutamide, finasteride, aminoglutethamide, ketoconazole, and corticosteroids.

D. Other Inhibitors

Other inhibitors for use as anticancer agents in conjunction with the compositions of the present invention include protein farnesyl transferase inhibitors including tipifarnib or R-115777 (US 2003134846 and WO 97/21701), BMS-214662, AZD-3409, and FTI-277; topoisomerase inhibitors including merbarone and diflomotecan (BN-80915); mitotic kinesin spindle protein (KSP) inhibitors including SB-743921 and MKI-833; protease modulators such as bortezomib or Velcade® (U.S. Pat. No. 5,780,454), XL-784; and cyclooxygenase 2 (COX-2) inhibitors including non-steroidal antiinflammatory drugs I (NSAIDs).

E. Cancer Chemotherapeutic Drugs

Particular cancer chemotherapeutic agents for use as anticancer agents in conjunction with the compositions of the present invention include anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®, US 2004073044), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®).

F. Alkylating Agents

Alkylating agents for use in conjunction with the compositions of the present invention for anticancer therapeutics include VNP-40101M or cloretizine, oxaliplatin (U.S. Pat. No. 4,169,846, WO 03/24978 and WO 03/04505), glufosfamide, mafosfamide, etopophos (U.S. Pat. No. 5,041,424), prednimustine; treosulfan; busulfan; irofluven (acylfulvene); penclomedine; pyrazoloacridine (PD-115934); O6-benzylguanine; decitabine (5-aza-2-deoxycytidine); brostallicin; mitomycin C (MitoExtra); TLK-286 (Telcyta®); temozolomide; trabectedin (U.S. Pat. No. 5,478,932); AP-5280 (Platinate formulation of Cisplatin); porfiromycin; and clearazide (meclorethamine).

G. Chelating Agents

Chelating agents for use in conjunction with the compositions of the present invention for anticancer therapeutics include tetrathiomolybdate (WO 01/60814); RP-697; Chimeric T84.66 (cT84.66); gadofosveset (Vasovist®); deferoxamine; and bleomycin optionally in combination with electroporation (EPT).

H. Biological Response Modifiers

Biological response modifiers, such as immune modulators, for use in conjunction with the compositions of the present invention for anticancer therapeutics include staurosprine and macrocyclic analogs thereof; including UCN-01, CEP-701 and midostaurin (see WO 02/30941, WO 97/07081, WO 89/07105, U.S. Pat. No. 5,621,100, WO 93/07153, WO 01/04125, WO 02/30941, WO 93/08809, WO 94/06799, WO 00/27422, WO 96/13506 and WO 88/07045); squalamine (WO 01/79255); DA-9601 (WO 98/04541 and U.S. Pat. No. 6,025,387); alemtuzumab; interferons (e.g. IFN-a, IFN-b etc.); interleukins, specifically IL-2 or aldesleukin as well as IL-1, IL-3, IL-4, IL-5, IL-6, IL-7, IL-8, IL-9, IL-10, IL-11, IL-12, and active biological variants thereof having amino acid sequences greater than 70% of the native human sequence; altretamine (Hexalen®); SU 101 or leflunomide (WO 04/06834 and U.S. Pat. No. 6,331,555); imidazoquinolines such as resiquimod and imiquimod (U.S. Pat. Nos. 4,689,338, 5,389,640, 5,268,376, 4,929,624, 5,266,575, 5,352,784, 5,494,916, 5,482,936, 5,346,905, 5,395,937, 5,238,944, and 5,525,612); and SMIPs, including benzazoles, anthraquinones, thiosemicarbazones, and tryptanthrins (WO 04/87153, WO 04/64759, and WO 04/60308).

I. Cancer Vaccines:

Anticancer vaccines for use in conjunction with the compositions of the present invention include Avicine® (Tetrahedron Letters 26, 1974 2269-70); oregovomab (OvaRex®); Theratope® (STn-KLH); Melanoma Vaccines; GI-4000 series (GI-4014, GI-4015, and GI-4016), which are directed to five mutations in the Ras protein; GlioVax-1; MelaVax; Advexin® or INGN-201 (WO 95/12660); Sig/E7/LAMP-1, encoding HPV-16 E7; MAGE-3 Vaccine or M3TK (WO 94/05304); HER-2VAX; ACTIVE, which stimulates T-cells specific for tumors; GM-CSF cancer vaccine; and Listeria monocytogenes-based vaccines.

J. Antisense Therapy:

Anticancer agents for use in conjunction with the compositions of the present invention also include antisense compositions, such as AEG-35156 (GEM-640); AP-12009 and AP-11014 (TGF-beta2-specific antisense oligonucleotides); AVI-4126; AVI-4557; AVI-4472; oblimersen (Genasense®); JFS2; aprinocarsen (WO 97/29780); GTI-2040 (R2 ribonucleotide reductase mRNA antisense oligo) (WO 98/05769); GTI-2501 (WO 98/05769); liposome-encapsulated c-Raf antisense oligodeoxynucleotides (LErafAON) (WO 98/43095); and Sirna-027 (RNAi-based therapeutic targeting VEGFR-1 mRNA).

The compounds of the invention can also be combined in a pharmaceutical composition with bronchiodilatory or antihistamine drugs substances. Such bronchiodilatory drugs include anticholinergic or antimuscarinic agents, in particular ipratropium bromide, oxitropium bromide, and tiotropium bromide, and β-2-adrenoreceptor agonists such as salbutamol, terbutaline, salmeterol and, especially, formoterol. Co-therapeutic antihistamine drug substances include cetirizine hydrochloride, clemastine fumarate, promethazine, loratadine, desloratadine, diphenhydramine and fexofenadine hydrochloride.

The effectiveness of an agent of the invention in inhibiting inflammatory conditions, for example in inflammatory airways diseases, may be demonstrated in an animal model, e.g. a mouse or rat model, of airways inflammation or other inflammatory conditions, for example as described by Szarka et al, J. Immunol. Methods (1997) 202:49-57; Renzi et al, Am. Rev. Respir. Dis. (1993) 148:932-939; Tsuyuki et al., J. Clin. Invest. (1995) 96:2924-2931; and Cernadas et al (1999) Am. J. Respir. Cell Mol. Biol. 20:1-8.

The agents of the invention are also useful as co-therapeutic agents for use in combination with other drug substances such as anti-inflammatory, bronchodilatory or antihistamine drug substances, particularly in the treatment of obstructive or inflammatory airways diseases such as those mentioned hereinbefore, for example as potentiators of therapeutic activity of such drugs or as a means of reducing required dosaging or potential side effects of such drugs. An agent of the invention may be mixed with the other drug substance in a fixed pharmaceutical composition or it may be administered separately, before, simultaneously with or after the other drug substance. Accordingly the invention includes a combination of an agent of the invention as hereinbefore described with an anti-inflammatory, bronchodilatory or antihistamine drug substance, said agent of the invention and said drug substance being in the same or different pharmaceutical composition. Such anti-inflammatory drugs include steroids, in particular glucocorticosteroids such as budesonide, beclamethasone, fluticasone, ciclesonide or mometasone, LTB4 antagonists such as those described in U.S. Pat. No. 5,451,700, LTD4 antagonists such as montelukast and zafirlukast, dopamine receptor agonists such as cabergoline, bromocriptine, ropinirole and 4-hydroxy-7-[2-[[2-[[3-(2-phenylethoxy)propyl]-sulfonyl]ethyl]-amino]ethyl]-2(3H)-benzothiazolone and pharmaceutically acceptable salts thereof (the hydrochloride being Viozan®—AstraZeneca), and PDE4 inhibitors such as Ariflo® (GlaxoSmith Kline), Roflumilast (Byk Gulden), V-11294A (Napp), BAY19-8004 (Bayer), SCH-351591 (Schering-Plough), Arofylline (Almirall Prodesfarma) and PD189659 (Parke-Davis). Such bronchodilatory drugs include anticholinergic or antimuscarinic agents, in particular ipratropium bromide, oxitropium bromide and tiotropium bromide, and beta-2 adrenoceptor agonists such as salbutamol, terbutaline, salmeterol and, especially, formoterol and pharmaceutically acceptable salts thereof, and compounds (in free or salt or solvate form) of formula I of PCT International patent publication No. WO 00/75114, which document is incorporated herein by reference, preferably compounds of the Examples thereof, especially a compound of formula

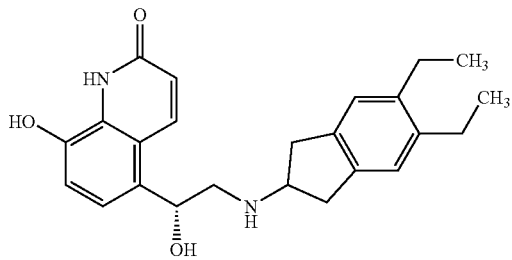

and pharmaceutically acceptable salts thereof. Co-therapeutic antihistamine drug substances include cetirizine hydrochloride, acetaminophen, clemastine fumarate, promethazine, loratidine, desloratidine, diphenhydramine and fexofenadine hydrochloride. Combinations of agents of the invention and steroids, beta-2 agonists, PDE4 inhibitors or LTD4 antagonists may be used, for example, in the treatment of COPD or, particularly, asthma. Combinations of agents of the invention and anticholinergic or antimuscarinic agents, PDE4 inhibitors, dopamine receptor agonists or LTB4 antagonists may be used, for example, in the treatment of asthma or, particularly, COPD.

Other useful combinations of agents of the invention with anti-inflammatory drugs are those with antagonists of chemokine receptors, e.g. CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists such as Schering-Plough antagonists SC-351125, SCH-55700 and SCH-D, Takeda antagonists such as N-[[4-[[[6,7-dihydro-2-(4-methylphenyl)-5H-benzocyclohepten-8-yl]carbonyl]amino]phenyl]-methyl]tetrahydro-N,N-dimethyl-2H-pyran-4-aminium chloride (TAK-770), and CCR-5 antagonists described in U.S. Pat. No. 6,166,037 (particularly claims 18 and 19), WO 00/66558 (particularly claim 8), and WO 00/66559 (particularly claim 9).

The compounds of the invention can also be combined in a pharmaceutical composition with compounds that are useful for the treatment of a thrombolytic disease, heart disease, stroke, etc., (e.g., aspirin, streptokinase, tissue plasminogen activator, urokinase, anticoagulants, antiplatelet drugs (e.g, PLAVIX; clopidogrel bisulfate), a statin (e.g., LIPITOR or Atorvastatin calcium), ZOCOR (Simvastatin), CRESTOR (Rosuvastatin), etc.), a Beta blocker (e.g., Atenolol), NORVASC (amlodipine besylate), and an ACE inhibitor (e.g., lisinopril).

The compounds of the invention can also be combined in a pharmaceutical composition with compounds that are useful for the treatment of antihypertension agents such as, ACE inhibitors, lipid lowering agents such as statins, LIPITOR (Atorvastatin calcium), calcium channel blockers dush as NORVASC (amlodipine besylate). The compounds of the present invention may also be used in combination with fibrates, beta-blockers, NEPI inhibitors, Angiotensin-2 receptor antagonists and platelet aggregation inhibitors.

For the treatment of inflammatory diseases, including rheumatoid arthritis, the compounds of the invention may be combined with agents such as TNF-α inhibitors such as anti-TNF-α monoclonal antibodies (such as REMICADE, CDP-870) and D2E7 (HUMIRA) and TNF receptor immunoglobulin fusion molecules (such as ENBREL), IL-1 inhibitors, receptor antagonists or soluble IL-1Rα (e.g. KINERET or ICE inhibitors), nonsterodial anti-inflammatory agents (NSAIDS), piroxicam, diclofenac, naproxen, flurbiprofen, fenoprofen, ketoprofen ibuprofen, fenamates, mefenamic acid, indomethacin, sulindac, apazone, pyrazolones, phenylbutazone, aspirin, COX-2 inhibitors (such as CELEBREX (celecoxib), PREXIGE (lumiracoxib)), metalloprotease inhibitors (preferably MMP-13 selective inhibitors), p2X7 inhibitors, α2δ inhibitors, NEUROTIN, pregabalin, low dose methotrexate, leflunomide, hydroxychloroquine, d-penicillamine, auranofin or parenteral or oral gold.

The compounds of the invention can also be used in combination with the existing therapeutic agents for the treatment of osteoarthritis. Suitable agents to be used in combination include standard non-steroidal anti-inflammatory agents (hereinafter NSAID's) such as piroxicam, diclofenac, propionic acids such as naproxen, flurbiprofen, fenoprofen, ketoprofen and ibuprofen, fenamates such as mefenamic acid, indomethacin, sulindac, apazone, pyrazolones such as phenylbutazone, salicylates such as aspirin, COX-2 inhibitors such as celecoxib, valdecoxib, lumiracoxib and etoricoxib, analgesics and intraarticular therapies such as corticosteroids and hyaluronic acids such as hyalgan and synvisc.

The compounds of the invention may also be used in combination with antiviral agents such as Viracept, AZT, acyclovir and famciclovir, and antisepsis compounds such as Valant.

The compounds of the present invention may also be used in combination with CNS agents such as antidepressants (sertraline), anti-Parkinsonian drugs (such as deprenyl, L-dopa, Requip, Mirapex, MAOB inhibitors such as selegine and rasagiline, comP inhibitors, such as Tasmar, A-2inhibitors, dopamine reuptake inhibitors, NMDA antagonists, Nicotine agonists, Dopamine agonists, and inhibitors of neuronal nitric oxide synthase), and anti-Alzheimer's drugs such as donepezil, tacrine, α2δ inhibitors, NEUROTIN, pregabalin, COX-2 inhibitors, propentofylline or metryfonate.

The compounds of the present invention may also be used in combination with osteoporosis agents such as EVISTA (raloxifene hydrochloride), droloxifene, lasofoxifene or fosomax and immunosuppressant agents such as FK-506 and rapamycin.

In another aspect of the invention, kits that include one or more compounds of the invention are provided. Representative kits include a PI3K inhibitor compound of the invention (e.g., a compound of formulas (I)-(III)) and a package insert or other labeling including directions for treating a cellular proliferative disease by administering an PI3K inhibitory amount of the compound.

The following definitions are provided to better understand the invention.

"Alkyl" refers to alkyl groups that do not contain heteroatoms. Thus the phrase includes straight chain alkyl groups such as methyl, ethyl, propyl, butyl, pentyl, hexyl, heptyl, octyl, nonyl, decyl, undecyl, dodecyl and the like. The phrase also includes branched chain isomers of straight chain alkyl groups, including but not limited to, the following which are provided by way of example: —CH(CH$_3$)$_2$, —CH(CH$_3$)(CH$_2$CH$_3$), —CH(CH$_2$CH$_3$)$_2$, —C(CH$_3$)$_3$, —C(CH$_2$CH$_3$)$_3$, —CH$_2$CH(CH$_3$)$_2$, —CH$_2$CH(CH$_3$)(CH$_2$CH$_3$), —CH$_2$CH(CH$_2$CH$_3$)$_2$, —CH$_2$C(CH$_3$)$_3$, —CH$_2$C(CH$_2$CH$_3$)$_3$, —CH(CH$_3$)—CH(CH$_3$)(CH$_2$CH$_3$), —CH$_2$CH$_2$CH(CH$_3$)$_2$, —CH$_2$CH$_2$CH(CH$_3$)(CH$_2$CH$_3$), —CH$_2$CH$_2$CH(CH$_2$CH$_3$)$_2$, —CH$_2$CH$_2$C(CH$_3$)$_3$, —CH$_2$CH$_2$C(CH$_2$CH$_3$)$_3$, —CH(CH$_3$)CH$_2$CH(CH$_3$)$_2$, —CH(CH$_3$)CH(CH$_3$)CH(CH$_3$)$_2$, —CH(CH$_2$CH$_3$)CH(CH$_3$)CH(CH$_3$)(CH$_2$CH$_3$), and others. Thus the phrase "alkyl groups" includes primary alkyl groups, secondary alkyl groups, and tertiary alkyl groups. Preferred alkyl groups include straight and branched chain alkyl groups having 1 to 12 carbon atoms or 1 to 6 carbon atoms.

"Alkylene" refers to the same residues as noted above for "alkyl," but having two points of attachment. Exemplary alkylene groups include ethylene (—$CH_2CH_2$—), propylene (—$CH_2CH_2CH_2$—), dimethylpropylene (—$CH_2C(CH_3)_2CH_2$—), and cyclohexylpropylene (—$CH_2CH_2CH(C_6H_{13})$—).

"Alkenyl" refers to straight chain, branched, or cyclic groups from 2 to about 20 carbon atoms such as those described with respect to alkyl groups as defined above, except having one or more carbon-carbon double bonds. Examples include, but are not limited to vinyl, —CH=C(H)($CH_3$), —CH=C($CH_3$)$_2$, —C($CH_3$)=C(H)$_2$, —C($CH_3$)=C(H)($CH_3$), —C($CH_2CH_3$)=$CH_2$, cyclohexenyl, cyclopentenyl, cyclohexadienyl, butadienyl, pentadienyl, and hexadienyl among others. Preferred alkenyl groups include straight chain and branched alkenyl groups and cyclic alkenyl groups having 2 to 12 carbon atoms or 2 to 6 carbon atoms.

"Alkynyl" refers to straight chain, branched, or cyclic groups from 2 to about 20 carbon atoms such as those described with respect to alkyl groups as defined above, except having one or more carbon-carbon triple bonds. Examples include, but are not limited to —C≡C(H), —C≡C($CH_3$), —C≡C($CH_2CH_3$), —C($H_2$)C≡C(H), —C(H)$_2$C≡C($CH_3$), and —C(H)$_2$C≡C($CH_2CH_3$) among others. Preferred alkynyl groups include straight chain and branched alkynyl groups having 2 to 12 carbon atoms or 2 to 6 carbon atoms.

Alkyl, alkenyl, and alkynyl groups may be substituted. "Substituted alkyl" refers to an alkyl group as defined above in which one or more bonds to a carbon(s) or hydrogen(s) are replaced by a bond to non-hydrogen and non-carbon atoms such as, but not limited to, a halogen atom such as F, Cl, Br, and I; an oxygen atom in groups such as hydroxyl groups, alkoxy groups, aryloxy groups, and ester groups; a sulfur atom in groups such as thiol groups, alkyl and aryl sulfide groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as in trialkylsilyl groups, dialkylarylsilyl groups, alkyldiarylsilyl groups, and triarylsilyl groups; and other heteroatoms in various other groups. Substituted alkyl groups also include groups in which one or more bonds to a carbon(s) or hydrogen(s) atom is replaced by a higher-order bond (e.g., a double- or triple-bond) to a heteroatom such as oxygen in oxo, carbonyl, carboxyl, and ester groups; nitrogen in groups such as imines, oximes, hydrazones, and nitriles. Substituted alkyl groups further include alkyl groups in which one or more bonds to a carbon(s) or hydrogen(s) atoms is replaced by a bond to an aryl, heteroaryl, heterocyclyl, or cycloalkyl group. Preferred substituted alkyl groups include, among others, alkyl groups in which one or more bonds to a carbon or hydrogen atom is/are replaced by one or more bonds to fluoro, chloro, or bromo group. Another preferred substituted alkyl group is the trifluoromethyl group and other alkyl groups that contain the trifluoromethyl group. Other preferred substituted alkyl groups include those in which one or more bonds to a carbon or hydrogen atom is replaced by a bond to an oxygen atom such that the substituted alkyl group contains a hydroxyl, alkoxy, or aryloxy group. Other preferred substituted alkyl groups include alkyl groups that have an amine, or a substituted or unsubstituted alkylamine, dialkylamine, arylamine, (alkyl)(aryl)amine, diarylamine, heterocyclylamine, diheterocyclylamine, (alkyl)(heterocyclyl)amine, or (aryl)(heterocyclyl)amine group. Still other preferred substituted alkyl groups include those in which one or more bonds to a carbon(s) or hydrogen(s) atoms is replaced by a bond to an aryl, heteroaryl, heterocyclyl, or cycloalkyl group. Examples of substituted alkyl are: —($CH_2$)$_3$$NH_2$, —($CH_2$)$_3$NH($CH_3$), —($CH_2$)$_3$NH($CH_3$)$_2$, —$CH_2$C(=$CH_2$)$CH_2NH_2$, —$CH_2$C(=O)$CH_2NH_2$, —$CH_2$S(=O)$_2$$CH_3$, —$CH_2OCH_2NH_2$, —$CO_2H$. Examples of substituents of substituted alkyl are: —$CH_3$, —$C_2H_5$, —$CH_2OH$, —OH, —$OCH_3$, —$OC_2H_5$, —$OCF_3$, —OC(=O)$CH_3$, —OC(=O)$NH_2$, —OC(=O)N($CH_3$)$_2$, —CN, —$NO_2$, —C(=O)$CH_3$, —$CO_2H$, —$CO_2CH_3$, —$CONH_2$, —$NH_2$, —N($CH_3$)$_2$, —$NHSO_2CH_3$, —$NHCOCH_3$, —$NHCOCH_3$, —NHC(=O)$OCH_3$, —NHSO—$_2$$CH_3$, —$SO_2CH_3$, —$SO_2NH_2$, Halo.

"Substituted alkenyl" has the same meaning with respect to alkenyl groups that substituted alkyl groups had with respect to unsubstituted alkyl groups. A substituted alkenyl group includes alkenyl groups in which a non-carbon or non-hydrogen atom is bonded to a carbon double bonded to another carbon and those in which one of the non-carbon or non-hydrogen atoms is bonded to a carbon not involved in a double bond to another carbon.

"Substituted alkynyl" has the same meaning with respect to alkynyl groups that substituted alkyl groups had with respect to unsubstituted alkyl groups. A substituted alkynyl group includes alkynyl groups in which a non-carbon or non-hydrogen atom is bonded to a carbon triple bonded to another carbon and those in which a non-carbon or non-hydrogen atom is bonded to a carbon not involved in a triple bond to another carbon.

"Alkoxy" refers to RO— wherein R is alkyl. Representative examples of alkoxy groups include methoxy, ethoxy, t-butoxy, trifluoromethoxy, and the like.

"Halogen" or "halo" refers to chloro, bromo, fluoro, and iodo groups. The term "haloalkyl" refers to an alkyl radical substituted with one or more halogen atoms. The term "haloalkoxy" refers to an alkoxy radical substituted with one or more halogen atoms.

"Amino" refers herein to the group —$NH_2$. The term "alkylamino" refers herein to the group —NRR' where R is alkyl and R' is hydrogen or alkyl. The term "arylamino" refers herein to the group —NRR' where R is aryl and R' is hydrogen, alkyl, or aryl. The term "aralkylamino" refers herein to the group —NRR' where R is aralkyl and R' is hydrogen, alkyl, aryl, or aralkyl.

"Alkoxyalkyl" refers to the group -alk$_1$-O-alk$_2$ where alk$_1$ is alkyl or alkenyl, and alk$_2$ is alkyl or alkenyl. The term "aryloxyalkyl" refers to the group -alkyl O-aryl. The term "aralkoxyalkyl" refers to the group -alkylenyl-O-aralkyl.

"Alkoxyalkylamino" refers herein to the group —NR-(alkoxyalkyl), where R is typically hydrogen, aralkyl, or alkyl.

"Aminocarbonyl" refers herein to the group —C(O)—$NH_2$. "Substituted aminocarbonyl" refers herein to the group —C(O)—NRR' where R is alkyl and R' is hydrogen or alkyl. The term "arylaminocarbonyl" refers herein to the group —C(O)—NRR' where R is aryl and R' is hydrogen, alkyl or aryl. "Aralkylaminocarbonyl" refers herein to the group —C(O)—NRR' where R is aralkyl and R' is hydrogen, alkyl, aryl, or aralkyl.

"Aminosulfonyl" refers herein to the group —S(O)$_2$—$NH_2$. "Substituted aminosulfonyl" refers herein to the group —S(O)$_2$—NRR' where R is alkyl and R' is hydrogen or alkyl. The term "aralkylaminosulfonlyaryl" refers herein to the group -aryl-S(O)$_2$—NH-aralkyl.

"Carbonyl" refers to the divalent group —C(O)—.

"Carbonyloxy" refers generally to the group —C(O)—O. Such groups include esters, —C(O)—O—R, where R is alkyl, cycloalkyl, aryl, or aralkyl. The term "carbonyloxycycloalkyl" refers generally herein to both a "carbonyloxycarbocycloalkyl" and a "carbonyloxyheterocycloalkyl," i.e., where R is a carbocycloalkyl or heterocycloalkyl, respectively. The term "arylcarbonyloxy" refers herein to the group —C(O)—O-aryl, where aryl is a mono- or polycyclic, carbocycloaryl or heterocycloaryl. The term "aralkylcarbonyloxy" refers herein to the group —C(O)—O-aralkyl.

"Sulfonyl" refers herein to the group —SO$_2$—. "Alkylsulfonyl" refers to a substituted sulfonyl of the structure —SO$_2$R— in which R is alkyl. Alkylsulfonyl groups employed in compounds of the present invention are typically alkylsulfonyl groups having from 1 to 6 carbon atoms in its backbone structure. Thus, typical alkylsulfonyl groups employed in compounds of the present invention include, for example, methylsulfonyl (i.e., where R is methyl), ethylsulfonyl (i.e., where R is ethyl), propylsulfonyl (i.e., where R is propyl), and the like. The term "arylsulfonyl" refers herein to the group —SO$_2$-aryl. The term "aralkylsulfonyl" refers herein to the group —SO$_2$-aralkyl. The term "sulfonamido" refers herein to —SO$_2$NH$_2$.

"Carbonylamino" refers to the divalent group —NH—C(O)— in which the hydrogen atom of the amide nitrogen of the carbonylamino group can be replaced alkyl, aryl, or aralkyl group. Such groups include moieties such as carbamate esters (—NH—C(O)—O—R) and amides —NH—C(O)—R, where R is a straight or branched chain alkyl, cycloalkyl, or aryl or aralkyl. The term "alkylcarbonylamino" refers to alkylcarbonylamino where R is alkyl having from 1 to about 6 carbon atoms in its backbone structure. The term "arylcarbonylamino" refers to group —NH—C(O)—R where R is an aryl. Similarly, the term "aralkylcarbonylamino" refers to carbonylamino where R is aralkyl.

"Guanidino" or "guanidyl" refers to moieties derived from guanidine, H$_2$N—C(=NH)—NH$_2$. Such moieties include those bonded at the nitrogen atom carrying the formal double bond (the "2"-position of the guanidine, e.g., diaminomethyleneamino, (H$_2$N)$_2$C=NH—)) and those bonded at either of the nitrogen atoms carrying a formal single bond (the "1-" and/or "3"-positions of the guanidine, e.g., H$_2$N—C(=NH)—NH—)). The hydrogen atoms at any of the nitrogens can be replaced with a suitable substituent, such as alkyl, aryl, or aralkyl.

"Amidino" refers to the moieties R—C(=N)—NR'— (the radical being at the "N$^1$" nitrogen) and R(NR')C=N— (the radical being at the "N$^2$" nitrogen), where R and R' can be hydrogen, alkyl, aryl, or aralkyl.

"Cycloalkyl" refers to a mono- or polycyclic, heterocyclic or carbocyclic alkyl substituent. Representative cycloalkyl groups include cyclopropyl, cyclobutyl, cyclopentyl, cyclohexyl, cycloheptyl, and cyclooctyl and such rings substituted with straight and branched chain alkyl groups as defined above. Typical cycloalkyl substituents have from 3 to 8 backbone (i.e., ring) atoms in which each backbone atom is either carbon or a heteroatom. The term "heterocycloalkyl" refers herein to cycloalkyl substituents that have from 1 to 5, and more typically from 1 to 4 heteroatoms in the ring structure. Suitable heteroatoms employed in compounds of the present invention are nitrogen, oxygen, and sulfur. Representative heterocycloalkyl moieties include, for example, morpholino, piperazinyl, piperadinyl, and the like. Carbocycloalkyl groups are cycloalkyl groups in which all ring atoms are carbon. When used in connection with cycloalkyl substituents, the term "polycyclic" refers herein to fused and non-fused alkyl cyclic structures.

"Substituted heterocycle," "heterocyclic group," "heterocycle," or "heterocyclyl," as used herein refers to any 3- or 4-membered ring containing a heteroatom selected from nitrogen, oxygen, and sulfur or a 5- or 6-membered ring containing from one to three heteroatoms selected from the group consisting of nitrogen, oxygen, or sulfur; wherein the 5-membered ring has 0-2 double bonds and the 6-membered ring has 0-3 double bonds; wherein the nitrogen and sulfur atom maybe optionally oxidized; wherein the nitrogen and sulfur heteroatoms maybe optionally quarternized; and including any bicyclic group in which any of the above heterocyclic rings is fused to a benzene ring or another 5- or 6-membered heterocyclic ring independently defined above. Examples of heterocyclyl groups include, but are not limited to: unsaturated 3- to 8-membered rings containing 1 to 4 nitrogen atoms such as, but not limited to pyrrolyl, dihydropyridyl, pyrimidyl, pyrazinyl, tetrazolyl, (e.g., 1H-tetrazolyl, 2H-tetrazolyl); condensed unsaturated heterocyclic groups containing 1 to 4 nitrogen atoms such as, but not limited to, isoindolyl, indolinyl, indolizinyl, quinolyl, indazolyl; unsaturated 3- to 8-membered rings containing 1 to 2 oxygen atoms and 1 to 3 nitrogen atoms such as, but not limited to, oxadiazolyl (e.g., 1,2,4-oxadiazolyl, 1,3,4-oxadiazolyl, 1,2,5-oxadiazolyl); saturated 3- to 8-membered rings containing 1 to 2 oxygen atoms and 1 to 3 nitrogen atoms such as, but not limited to, morpholinyl; unsaturated condensed heterocyclic groups containing 1 to 2 oxygen atoms and 1 to 3 nitrogen atoms, for example, benzoxadiazolyl, benzoxazinyl (e.g., 2H-1,4-benzoxazinyl); unsaturated 3- to 8-membered rings containing 1 to 3 sulfur atoms and 1 to 3 nitrogen atoms such as, but not limited to, thiadiazolyl (e.g., 1,2,3-thiadiazolyl, 1,2,4-thiadiazolyl, 1,3,4-thiadiazolyl, 1,2,-thiadiazolyl); saturated 3- to 8-membered rings containing 1 to 2 sulfur atoms and 1 to 3 nitrogen atoms such as, but not limited to, thiazolodinyl; saturated and unsaturated 3- to 8-membered rings containing 1 to 2 sulfur atoms such as, but not limited to, dihydrodithienyl, dihydrodithionyl, tetrahydrothiophene, tetra-hydrothiopyran; unsaturated condensed heterocyclic rings containing 1 to 2 sulfur atoms and 1 to 3 nitrogen atoms such as, but not limited to, benzothiadiazolyl, benzothiazinyl (e.g., 2H-1,4-benzothiazinyl), dihydrobenzothiazinyl (e.g., 2H-3,4-dihydrobenzothiazinyl), unsaturated 3- to 8-membered rings containing oxygen atoms such as, but not limited to furyl; unsaturated condensed heterocyclic rings containing 1 to 2 oxygen atoms such as benzodioxoyl (e.g., 1,3-benzodioxoyl); unsaturated 3- to 8-membered rings containing an oxygen atom and 1 to 2 sulfur atoms such as, but not limited to, dihydrooxathienyl; saturated 3- to 8-membered rings containing 1 to 2 oxygen atoms and 1 to 2 sulfur atoms such as 1,4-oxathiane; unsaturated condensed rings containing 1 to 2 sulfur atoms such as benzodithienyl; and unsaturated condensed heterocyclic rings containing an oxygen atom and 1 to 2 oxygen atoms such as benzoxathienyl. Preferred heterocycles include, for example: diazapinyl, pyrryl, pyrrolinyl, pyrrolidinyl, pyrazolyl, pyrazolinyl, pyrazolidinyl, imidazoyl, imidazolinyl, imidazolidinyl, pyridyl, piperidinyl, pyrazinyl, piperazinyl, N-methyl piperazinyl, azetidinyl, N-methylazetidinyl, pyrimidinyl, pyridazinyl, oxazolyl, oxazolidinyl, isoxazolyl, isoxazolidinyl, morpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl, triazolyl, and benzothienyl. Heterocyclyl groups also include those described above in which one or more S atoms in the ring is double-bonded to one or two oxygen atoms (sulfoxides and sulfones). For example, heterocyclyl groups include tetrahydrothiophene, tetrahydrothiophene oxide, and tetrahydrothiophene 1,1-dioxide. Preferred heterocyclyl groups contain 5 or 6 ring members. More preferred heterocyclyl groups include piperazine, 1,2, 3-triazole, 1,2,4-triazole, tetrazole, thiomorpholine, homopiperazine, oxazolidin-2-one, pyrrolidin-2-one, quinuclidine, and tetrahydrofuran.

Heterocyclic moieties can be unsubstituted or monosubstituted or disubstituted with various substituents independently selected from hydroxy, halo, oxo (C=O), alkylimino (RN=, wherein R is alkyl or alkoxy group), amino, alkylamino, dialkylamino, acylaminoalkyl, alkoxy, thioalkoxy, polyalkoxy, alkyl, cycloalkyl or haloalkyl. "Unsubstituted heterocyclyl" includes condensed heterocyclic rings such as benzimidazolyl, it does not include heterocyclyl groups that have other groups such as alkyl or halo groups bonded to one of the ring members as compounds such as 2-methylbenzimidazolyl are substituted heterocyclyl groups.

The heterocyclic groups may be attached at various positions as will be apparent to those having skill in the organic and medicinal chemistry arts in conjunction with the disclosure herein.

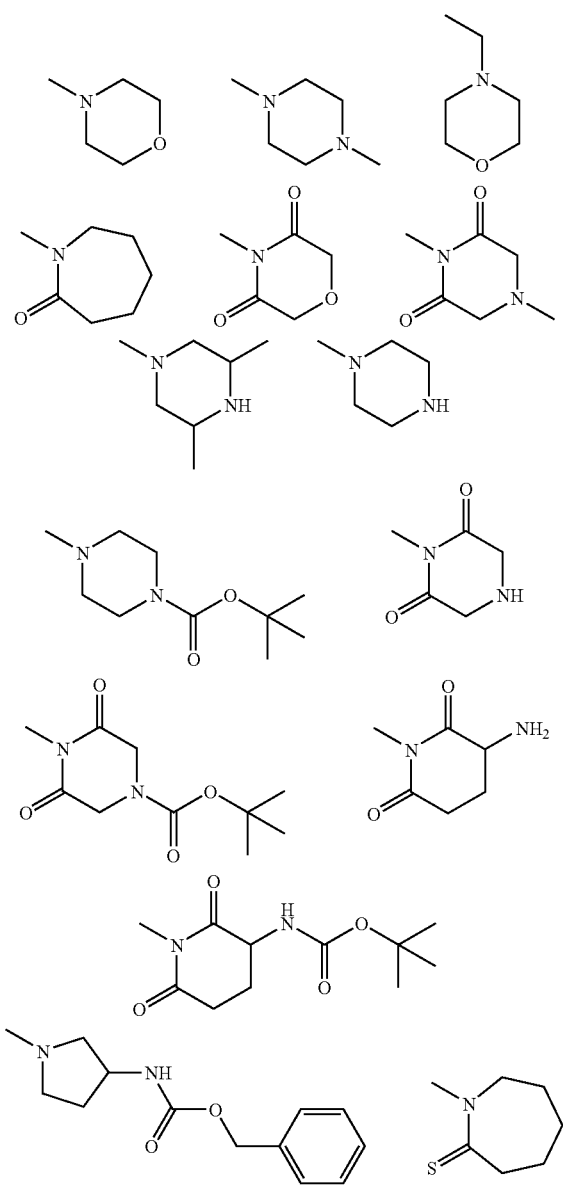
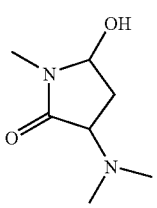
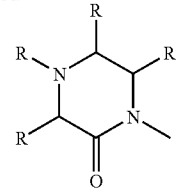

where R is H or a heterocyclic substituent, as described herein.

Representative heterocyclics include, for example, imidazolyl, pyridyl, piperazinyl, azetidinyl, thiazolyl, furanyl, triazolyl benzimidazolyl, benzothiazolyl, benzoxazolyl, quinolinyl, isoquinolinyl, quinazolinyl, quinoxalinyl, phthalazinyl, indolyl, naphthpyridinyl, indazolyl, and quinolizinyl.

"Aryl" refers to optionally substituted monocyclic and polycyclic aromatic groups having from 3 to 14 backbone carbon or hetero atoms, and includes both carbocyclic aryl groups and heterocyclic aryl groups. The term refers to, but is not limited to, groups such as phenyl, biphenyl, anthracenyl, naphthenyl by way of example. Carbocyclic aryl groups are aryl groups in which all ring atoms in the aromatic ring are carbon. The term "heteroaryl" refers herein to aryl groups having from 1 to 4 heteroatoms as ring atoms in an aromatic ring with the remainder of the ring atoms being carbon atoms.

"Unsubstituted aryl" includes groups containing condensed rings such as naphthalene. It does not include aryl groups that have other groups such as alkyl or halo groups bonded to one of the ring members, as aryl groups such as tolyl are considered herein to be substituted aryl groups as described below. A preferred unsubstituted aryl group is phenyl. Unsubstituted aryl groups may be bonded to one or more carbon atom(s), oxygen atom(s), nitrogen atom(s), and/or sulfur atom(s) in the parent compound, however.

"Substituted aryl group" has the same meaning with respect to unsubstituted aryl groups that substituted alkyl groups had with respect to unsubstituted alkyl groups. However, a substituted aryl group also includes aryl groups in which one of the aromatic carbons is bonded to one of the non-carbon or non-hydrogen atoms described above and also includes aryl groups in which one or more aromatic carbons of the aryl group is bonded to a substituted and/or unsubstituted alkyl, alkenyl, or alkynyl group as defined herein. This includes bonding arrangements in which two carbon atoms of an aryl group are bonded to two atoms of an alkyl, alkenyl, or alkynyl group to define a fused ring system (e.g., dihydronaphthyl or tetrahydronaphthyl). Thus, the phrase "substituted aryl" includes, but is not limited to tolyl, and hydroxyphenyl among others.

"Substituted heteroaryl" as used herein refers to a heteroaryl group as defined herein substituted by independent replacement of one, two or three of the hydrogen atoms thereon with Cl, Br, F, I, —OH, —CN, $C_1$-$C_3$-alkyl, $C_1$-$C_6$-alkoxy, $C_1$-$C_6$-alkoxy substituted with aryl, haloalkyl, thioalkoxy, amino, alkylamino, dialkylamino, mercapto, nitro, carboxaldehyde, carboxy, alkoxycarbonyl and carboxamide. In addition, any one substituent may be an aryl, heteroaryl, or heterocycloalkyl group.

When used in connection with aryl substituents, the term "polycyclic aryl" refers herein to fused and non-fused cyclic structures in which at least one cyclic structure is aromatic, such as, for example, benzodioxole (which has a heterocyclic structure fused to a phenyl group, i.e.,

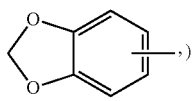

naphthyl, and the like. Exemplary aryl or heteroaryl moieties employed as substituents in compounds of the present invention include phenyl, pyridyl, pyrimidinyl, thiazolyl, indolyl, imidazolyl, oxadiazolyl, tetrazolyl, pyrazinyl, triazolyl, thiophenyl, furanyl, quinolinyl, purinyl, naphthyl, benzothiazolyl, benzopyridyl, and benzimidazolyl, and the like.

"Aralkyl" or "arylalkyl" refers to an alkyl group substituted with an aryl group. Typically, aralkyl groups employed in compounds of the present invention have from 1 to 6 carbon atoms incorporated within the alkyl portion of the aralkyl group. Suitable aralkyl groups employed in compounds of the present invention include, for example, benzyl, picolyl, and the like.

Representative heteroaryl groups include, for example, those shown below. These heteroaryl groups can be further substituted and may be attached at various positions as will be apparent to those having skill in the organic and medicinal chemistry arts in conjunction with the disclosure herein.

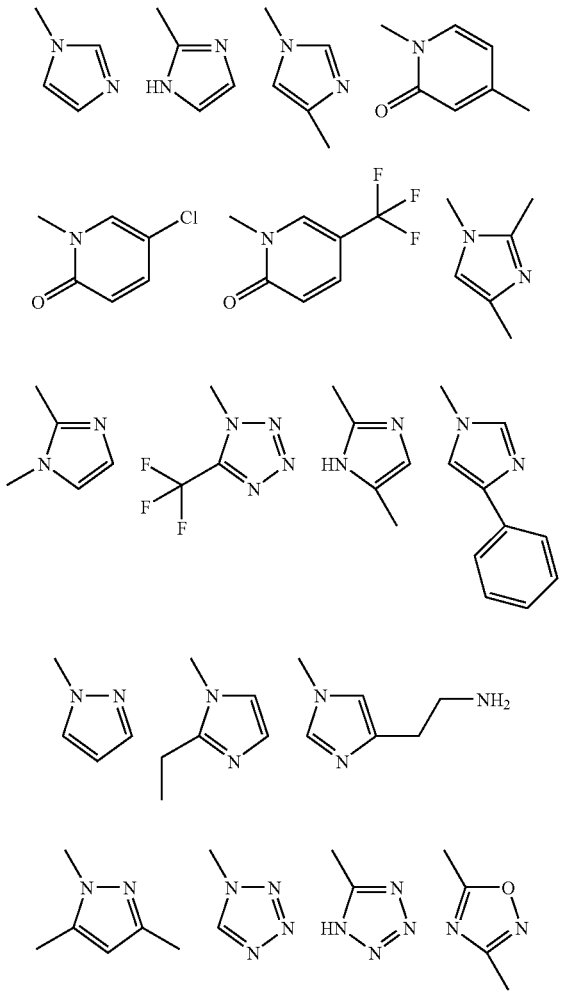

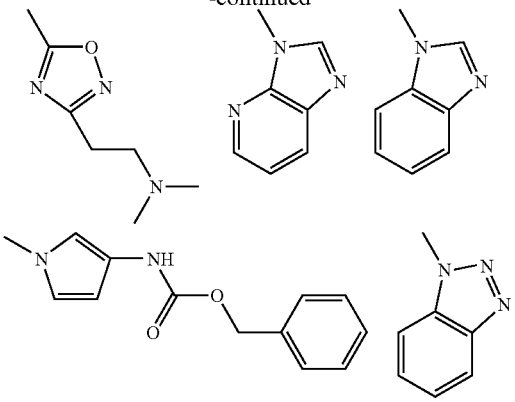

Representative heteroaryls include, for example, imidazolyl, pyridyl, thiazolyl, triazolyl benzimidazolyl, benzothiazolyl, and benzoxazolyl.

"Biaryl" refers to a group or substituent to which two aryl groups, which are not condensed to each other, are bound. Exemplary biaryl compounds include, for example, phenylbenzene, diphenyldiazene, 4-methylthio-1-phenylbenzene, phenoxybenzene, (2-phenylethynyl)benzene, diphenyl ketone, (4-phenylbuta-1,3-diynyl)benzene, phenylbenzylamine, (phenylmethoxy)benzene, and the like. Preferred optionally substituted biaryl groups include: 2-(phenylamino)-N-[4-(2-phenylethynyl)-phenyl]acetamide, 1,4-diphenylbenzene, N-[4-(2-phenylethynyl)phenyl]-2-[benzyl-amino]-acetamide, 2-amino-N-[4-(2-phenylethynyl) phenyl]propanamide, 2-amino-N-[4-(2-phenyl-ethynyl) phenyl]acetamide, 2-(cyclopropylamino)-N-[4-(2-phenylethynyl)-phenyl]-acetamide, 2-(ethylamino)-N-[4-(2-phenylethynyl)phenyl]acetamide, 2-[(2-methyl-propyl) amino]-N-[4-(2-phenylethynyl)phenyl]acetamide, 5-phenyl-2H-benzo-[d]1,3-dioxolene, 2-chloro-1-methoxy-4-phenylbenzene, 2-[(imidazolylmethyl)-amino]-N-[4-(2-phenylethynyl)phenyl]acetamide, 4-phenyl-1-phenoxybenzene, N-(2-amino-ethyl)-[4-(2-phenylethynyl) phenyl]carboxamide, 2-{[(4-fluorophenyl)methyl]-amino}-N-[4-(2-phenylethynyl)phenyl]acetamide, 2-{[(4-methylphenyl)methyl]amino}-N-[4-(2-phenyl-ethynyl) phenyl]acetamide, 4-phenyl-1-(trifluoromethyl)benzene, 1-butyl-4-phenylbenzene, 2-(cyclohexylamino)-N-[4-(2-phenylethynyl)phenyl]acetamide, 2-(ethyl-methyl-amino)-N-[4-(2-phenylethynyl)phenyl]acetamide, 2-(butylamino)-N-[4-(2-phenyl-ethynyl)-phenyl]acetamide, N-[4-(2-phenylethynyl)phenyl]-2-(4-pyridylamino)-acetamide, N-[4-(2-phenylethynyl)phenyl]-2-(quinuclidin-3-ylamino) acetamide, N-[4-(2-phenyl-ethynyl)phenyl]pyrrolidin-2-yl-carboxamide, 2-amino-3-methyl-N-[4-(2-phenyl-ethynyl)-phenyl]butanamide, 4-(4-phenylbuta-1,3-diynyl) phenylamine, 2-(dimethyl-amino)-N-[4-(4-phenylbuta-1,3-diynyl)phenyl]acetamide, 2-(ethylamino)-N-[4-(4-phenylbuta-1,3-diynyl)-phenyl]acetamide, 4-ethyl-1-phenylbenzene, 1-[4-(2-phenyl-ethynyl)-phenyl]ethan-1-one, N-(1-carbamoyl-2-hydroxypropyl)[4-(4-phenylbuta-1, 3-diynyl)-phenyl]-carbox-amide, N-[4-(2-phenylethynyl) phenyl]propanamide, 4-methoxy-phenyl phenyl ketone, phenyl-N-benzamide, (tert-butoxy)-N-[(4-phenylphenyl)-methyl]-carboxamide, 2-(3-phenyl-phenoxy)ethanehydroxamic acid, 3-phenylphenyl propanoate, 1-(4-ethoxyphenyl)-4-methoxybenzene, and [4-(2-phenylethynyl)phenyl] pyrrole.

"Heteroarylaryl" refers to a biaryl group where one of the aryl groups is a heteroaryl group. Exemplary heteroarylaryl groups include, for example, 2-phenylpyridine, phenylpyrrole, 3-(2-phenylethynyl)pyridine, phenylpyrazole, 5-(2-phenyl-ethynyl)-1,3-dihydropyrimidine-2,4-dione, 4-phenyl-1,2,3-thiadiazole, 2-(2-phenylethynyl)pyrazine, 2-phenylthiophene, phenylimidazole, 3-(2-piperazinyl-phenyl)-furan, 3-(2,4-dichlorophenyl)-4-methylpyrrole, and the like. Preferred optionally substituted heteroarylaryl groups include: 5-(2-phenylethynyl)pyrimidine-2-ylamine, 1-methoxy-4-(2-thienyl)benzene, 1-methoxy-3-(2-thienyl)benzene, 5-methyl-2-phenyl-pyridine, 5-methyl-3-phenylisoxazole, 2-[3-(trifluoromethyl)phenyl]furan, 3-fluoro-5-(2-furyl)-2-methoxy-1-prop-2-enylbenzene, (hydroxyimino)(5-phenyl(2-thienyl))-methane, 5-[(4-methylpiperazinyl)methyl]-2-phenylthiophene, 2-(4-ethylphenyl)-thiophene, 4-methylthio-1-(2-thienyl)benzene, 2-(3-nitrophenyl)thiophene, (tert-butoxy)-N-[(5-phenyl-(3-pyridyl))methyl]carboxamide, hydroxy-N-[(5-phenyl(3-pyridyl))methyl]-amide, 2-(phenyl-methylthio)pyridine, and benzylimidazole.

"Heteroarylheteroaryl" refers to a biaryl group where both of the aryl groups is a heteroaryl group. Exemplary heteroarylheteroaryl groups include, for example, 3-pyridylimidazole, 2-imidazolylpyrazine, and the like. Preferred optionally substituted heteroarylheteroaryl groups include: 2-(4-piperazinyl-3-pyridyl)furan, diethyl-(3-pyrazin-2-yl(4-pyridyl))amine, and dimethyl{2-[2-(5-methylpyrazin-2-yl)ethynyl](4-pyridyl)}amine.

"Optionally substituted" or "substituted" refers to the replacement of hydrogen with one or more monovalent or divalent radical. Suitable substitution groups include, for example, hydroxyl, nitro, amino, imino, cyano, halo, thio, sulfonyl, thioamido, amidino, imidino, oxo, oxamidino, methoxamidino, imidino, guanidino, sulfonamido, carboxyl, formyl, alkyl, substituted alkyl, haloalkyl, alkyamino, haloalkylamino, alkoxy, haloalkoxy, alkoxy-alkyl, alkylcarbonyl, aminocarbonyl, arylcarbonyl, aralkylcarbonyl, heteroarylcarbonyl, heteroaralkyl-carbonyl, alkylthio, aminoalkyl, cyanoalkyl, aryl, benzyl, pyridyl, pyrazolyl, pyrrole, thiophene, imidazolyl, and the like.

The substitution group can itself be substituted. The group substituted onto the substitution group can be carboxyl, halo, nitro, amino, cyano, hydroxyl, alkyl, alkoxy, aminocarbonyl, —SR, thioamido, —SO₃H, —SO₂R, or cycloalkyl, where R is typically hydrogen, hydroxyl or alkyl.

When the substituted substituent includes a straight chain group, the substitution can occur either within the chain (e.g., 2-hydroxypropyl, 2-aminobutyl, and the like) or at the chain terminus (e.g., 2-hydroxyethyl, 3-cyanopropyl, and the like). Substituted substituents can be straight chain, branched or cyclic arrangements of covalently bonded carbon or heteroatoms.

Representative substituted aminocarbonyl groups include, for example, those shown below. These can be further substituted by heterocyclyl groups and heteroaryl groups as will be apparent to those having skill in the organic and medicinal chemistry arts in conjunction with the disclosure herein. Preferred aminocarbonyl groups include: N-(2-cyanoethyl)carboxamide, N-(3-methoxypropyl)carboxamide, N-cyclopropylcarboxamide, N-(2-hydroxy-isopropyl)carboxamide, methyl 2-carbonylamino-3-hydroxypropanoate, N-(2-hydroxypropyl)carboxamide, N-(2-hydroxy-isopropyl)carboxamide, N-[2-hydroxy-1-(hydroxymethyl)ethyl]carboxamide, N-(2-carbonylaminoethyl)acetamide, N-(2-(2-pyridyl)ethyl)carboxamide, N-(2-pyridylmethyl)carboxamide, N-(oxolan-2-ylmethyl)-carboxamide, N-(4-hydroxypyrrolidin-2-yl)carboxamide, N-[2-(2-hydroxyethoxy)ethyl]-carboxamide, N-(4-hydroxycyclohexyl)carboxamide, N-[2-(2-oxo-4-imidazolinyl)ethyl]-carboxamide, N-(carbonylaminomethyl)acetamide, N-(3-pyrrolidinylpropyl)carboxamide, N-[1-(carbonylaminomethyl)pyrrolidin-3-yl]acetamide, N-(2-morpholin-4-ylethyl)carboxamide, N-[3-(2-oxopyrrolidinyl)propyl]carboxamide, 4-methyl-2-oxopiperazinecarbaldehyde, N-(2-hydroxy-3-pyrrolidinylpropyl)carboxamide, N-(2-hydroxy-3-morpholin-4-ylpropyl)carboxamide, N-{2-[(5-cyano-2-pyridyl)amino]ethyl}carboxamide, 3-(dimethylamino)pyrrolidinecarbaldehyde, N-[(5-methylpyrazin-2-yl)methyl]carboxamide, 2,2,2-trifluoro-N-(1-formylpyrrolidin-3-yl)acetamide,

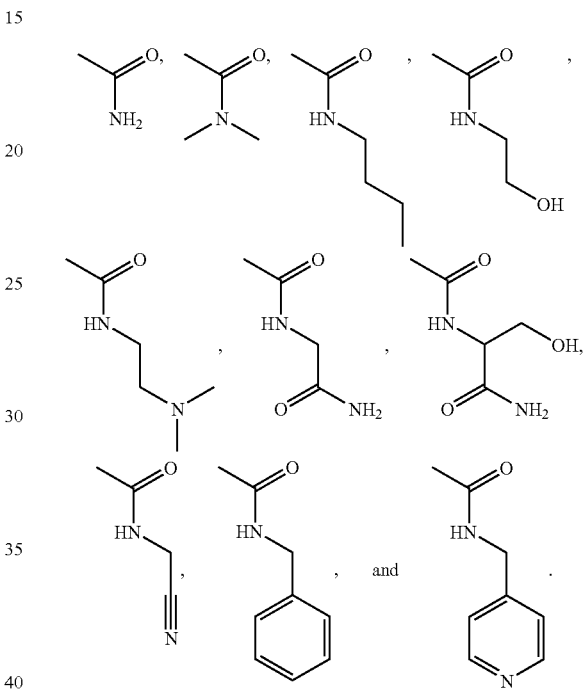

Representative substituted alkoxycarbonyl groups include, for example, those shown below. These alkoxycarbonyl groups can be further substituted as will be apparent to those having skill in the organic and medicinal chemistry arts in conjunction with the disclosure herein.

Representative substituted alkoxycarbonyl groups include, for example, those shown below. These alkoxycarbonyl groups can be further substituted as will be apparent to those having skill in the organic and medicinal chemistry arts in conjunction with the disclosure herein.

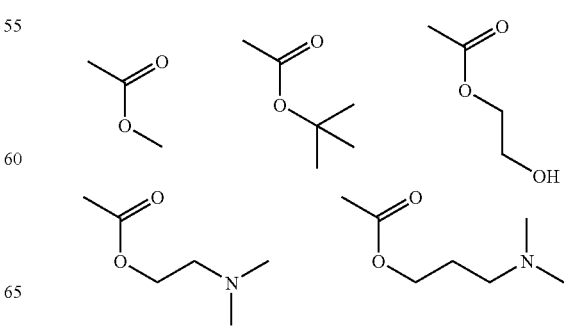

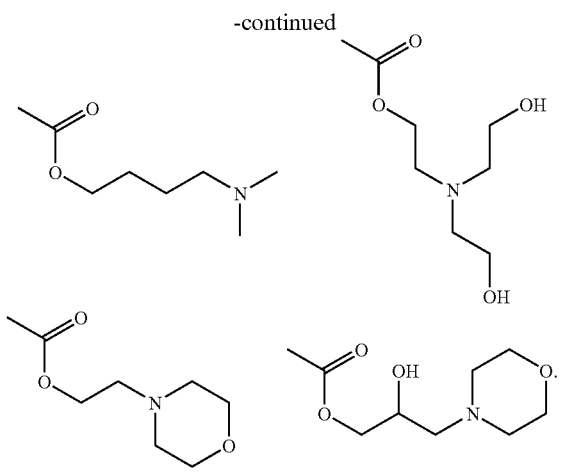

The term "protected" with respect to hydroxyl groups, amine groups, and sulfhydryl groups refers to forms of these functionalities which are protected from undesirable reaction with a protecting group known to those skilled in the art such as those set forth in *Protective Groups in Organic Synthesis*, Greene, T. W.; Wuts, P. G. M., John Wiley & Sons, New York, N.Y., (3rd Edition, 1999) which can be added or removed using the procedures set forth therein. Examples of protected hydroxyl groups include, but are not limited to, silyl ethers such as those obtained by reaction of a hydroxyl group with a reagent such as, but not limited to, t-butyldimethyl-chlorosilane, trimethylchlorosilane, triisopropylchlorosilane, triethylchlorosilane; substituted methyl and ethyl ethers such as, but not limited to methoxymethyl ether, methylthiomethyl ether, benzyloxymethyl ether, t-butoxymethyl ether, 2-methoxyethoxymethyl ether, tetrahydropyranyl ethers, 1-ethoxyethyl ether, allyl ether, benzyl ether; esters such as, but not limited to, benzoylformate, formate, acetate, trichloroacetate, and trifluoroacetate. Examples of protected amine groups include, but are not limited to, amides such as, formamide, acetamide, trifluoroacetamide, and benzamide; imides, such as phthalimide, and dithiosuccinimide; and others. Examples of protected sulfhydryl groups include, but are not limited to, thioethers such as S-benzyl thioether, and S-4-picolyl thioether; substituted S-methyl derivatives such as hemithio, dithio and aminothio acetals; and others.

"Carboxy-protecting group" refers to a carbonyl group which has been esterified with one of the commonly used carboxylic acid protecting ester groups employed to block or protect the carboxylic acid function while reactions involving other functional sites of the compound are carried out. In addition, a carboxy protecting group can be attached to a solid support whereby the compound remains connected to the solid support as the carboxylate until cleaved by hydrolytic methods to release the corresponding free acid. Representative carboxy-protecting groups include, for example, alkyl esters, secondary amides and the like.

Certain compounds of the invention comprise asymmetrically substituted carbon atoms. Such asymmetrically substituted carbon atoms can result in the compounds of the invention comprising mixtures of stereoisomers at a particular asymmetrically substituted carbon atom or a single stereoisomer. As a result, racemic mixtures, mixtures of diastereomers, as well as single diastereomers of the compounds of the invention are included in the present invention. The terms "S" and "R" configuration, as used herein, are as defined by the IUPAC 1974 "RECOMMENDATIONS FOR SECTION E, FUNDAMENTAL STEREOCHEMISTRY," *Pure Appl. Chem.* 45:13-30, 1976. The terms α and β are employed for ring positions of cyclic compounds. The α-side of the reference plane is that side on which the preferred substituent lies at the lower numbered position. Those substituents lying on the opposite side of the reference plane are assigned β descriptor. It should be noted that this usage differs from that for cyclic stereoparents, in which "α" means "below the plane" and denotes absolute configuration. The terms α and β configuration, as used herein, are as defined by the "Chemical Abstracts Index Guide," Appendix IV, paragraph 203, 1987.

As used herein, the term "pharmaceutically acceptable salts" refers to the nontoxic acid or alkaline earth metal salts of the pyrimidine compounds of the invention. These salts can be prepared in situ during the final isolation and purification of the pyrimidine compounds, or by separately reacting the base or acid functions with a suitable organic or inorganic acid or base, respectively. Representative salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemi-sulfate, heptanoate, hexanoate, fumarate, hydrochloride, hydrobromide, hydroiodide, 2-hydroxyethanesulfonate, lactate, maleate, methanesulfonate, nicotinate, 2-naphth-alenesulfonate, oxalate, pamoate, pectinate, persulfate, 3-phenylproionate, picrate, pivalate, propionate, succinate, sulfate, tartrate, thiocyanate, p-toluenesulfonate, and undecanoate. Also, the basic nitrogen-containing groups can be quaternized with such agents as alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl, and stearyl chlorides, bromides and iodides, aralkyl halides like benzyl and phenethyl bromides, and others. Water or oil-soluble or dispersible products are thereby obtained.

Examples of acids that may be employed to form pharmaceutically acceptable acid addition salts include such inorganic acids as hydrochloric acid, hydroboric acid, nitric acid, sulfuric acid and phosphoric acid and such organic acids as formic acid, acetic acid, trifluoroacetic acid, fumaric acid, tartaric acid, oxalic acid, maleic acid, methanesulfonic acid, succinic acid, malic acid, methanesulfonic acid, benzenesulfonic acid, and p-toluenesulfonic acid, citric acid, and acidic amino acids such as aspartic acid and glutamic acid.

Basic addition salts can be prepared in situ during the final isolation and purification of the pyrimidine compounds, or separately by reacting carboxylic acid moieties with a suitable base such as the hydroxide, carbonate or bicarbonate of a pharmaceutically acceptable metal cation or with ammonia, or an organic primary, secondary or tertiary amine. Pharmaceutically acceptable salts include, but are not limited to, cations based on the alkali and alkaline earth metals, such as sodium, lithium, potassium, calcium, magnesium, aluminum salts and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, piperazine, pyridine, picoline, triethanolamine and the like, and basic amino acids such as arginine, lysine and ornithine.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Representative examples of particular esters include, but are not limited to, formates, acetates, propionates, butyrates, acrylates and ethylsuccinates.

The term "pharmaceutically acceptable prodrugs" as used herein refers to those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in Higuchi, T., and V. Stella, "Pro-drugs as Novel Delivery Systems," *A.C.S. Symposium Series* 14, and in "Bioreversible Carriers in Drug Design," in Edward B. Roche (ed.), *American Pharmaceutical Association*, Pergamon Press, 1987, both of which are incorporated herein by reference.

"Treating" within the context of the instant invention, means an alleviation of symptoms associated with a disorder or disease, or halt of further progression or worsening of those symptoms, or prevention or prophylaxis of the disease or disorder. For example, within the context of treating patients in need of an inhibitor of PI3K, successful treatment may include a reduction in the proliferation of capillaries feeding a tumor or diseased tissue, an alleviation of symptoms related to a cancerous growth or tumor, proliferation of capillaries, or diseased tissue, a halting in capillary proliferation, or a halting in the progression of a disease such as cancer or in the growth of cancerous cells. Treatment may also include administering the pharmaceutical formulations of the present invention in combination with other therapies. For example, the compounds and pharmaceutical formulations of the present invention may be administered before, during, or after surgical procedure and/or radiation therapy. The compounds of the invention can also be administered in conjunction with other anti-cancer drugs including those used in antisense and gene therapy.

As used herein, "limit", "treat" and "treatment" are interchangeable terms as are "limiting" and "treating" and, as used herein, include preventative (e.g., prophylactic) and palliative treatment or the act of providing preventative or palliative treatment.

The term "PI3K-mediated disorder" refers to a disorder that can be beneficially treated by the inhibition of PI3K.

The term "cellular proliferative diseases" refers to diseases including, for example, cancer, tumor, hyperplasia, restenosis, cardiac hypertrophy, immune disorder and inflammation.

The term "cancer" refers to cancer diseases that can be beneficially treated by the inhibition of PI3K, including, for example, lung and bronchus; prostate; breast; pancreas; colon and rectum; thyroid; liver and intrahepatic bile duct; hepatocellular; gastric; glioma/glioblastoma; endometrial; melanoma; kidney and renal pelvis; urinary bladder; uterine corpus; uterine cervix; ovary; multiple myeloma; esophagus; acute myelogenous leukemia; chronic myelogenous leukemia; lymphocytic leukemia; myeloid leukemia; brain; oral cavity and pharynx; larynx; small intestine; non-Hodgkin lymphoma; melanoma; and villous colon adenoma.

The PI3K inhibitors of this invention, as described herein, can be administered in the form of acid addition salts. The salts are conveniently formed by reacting a compound, if basic, with a suitable acid, such as have been described above. The salts are quickly formed in high yields at moderate temperatures, and often are prepared by merely isolating the compound from a suitable acidic wash as the final step of the synthesis. The salt-forming acid is dissolved in an appropriate organic solvent, or aqueous organic solvent, such as an alkanol, ketone or ester. On the other hand, if the compound of this invention is desired in the free base form, it is isolated from a basic final wash step, according to the usual practice. A preferred technique for preparing hydrochlorides is to dissolve the free base in a suitable solvent and dry the solution thoroughly, as over molecular sieves, before bubbling hydrogen chloride gas through it. It will also be recognized that it is possible to administer amorphous forms of the PI3K inhibitors.

The invention also provides isotopically-labeled PI3K inhibitors, which are structurally identical to those disclosed above, but for the fact that one or more atoms are replaced by an atom having an atomic mass or mass number different from the atomic mass or mass number usually found in nature. Examples of isotopes that can be incorporated into compounds, of the invention include isotopes of hydrogen, carbon, nitrogen, oxygen, phosphorous, sulfur, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$ and $^{36}Cl$, respectively. Compounds of the present invention, prodrugs thereof, and pharmaceutically acceptable salts of said compounds and of said prodrugs which contain the aforementioned isotopes and/or other isotopes of other atoms are within the scope of this invention. Certain isotopically labeled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, may afford certain therapeutic advantages resulting from greater metabolic stability, for example increased in vivo half-life or reduced dosage requirements and, hence, may be preferred in some circumstances. Isotopically labeled compounds of this invention and prodrugs thereof can generally be prepared by carrying out known or referenced procedures and by substituting a readily available isotopically labeled reagent for a non-isotopically labeled reagent.

The compounds of the invention are useful in vitro or in vivo in inhibiting the growth of cancer cells. The compounds may be used alone or in compositions together with a pharmaceutically acceptable carrier or excipient. Pharmaceutical compositions of the present invention comprise a therapeutically effective amount of a phosphatidylinositol 3-kinase inhibitor compound described herein formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol;

esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. Other suitable pharmaceutically acceptable excipients are described in "Remington's Pharmaceutical Sciences," Mack Pub. Co., New Jersey, 1991, incorporated herein by reference.

The compounds of the present invention may be administered to humans and other animals orally, parenterally, sublingually, by aerosolization or inhalation spray, rectally, intracisternally, intravaginally, intraperitoneally, bucally, or topically in dosage unit formulations containing conventional nontoxic pharmaceutically acceptable carriers, adjuvants, and vehicles as desired. Topical administration may also involve the use of transdermal administration such as transdermal patches or ionophoresis devices. The term parenteral as used herein includes subcutaneous injections, intravenous, intramuscular, intrasternal injection, or infusion techniques.

Methods of formulation are well known in the art and are disclosed, for example, in Remington: *The Science and Practice of Pharmacy*, Mack Publishing Company, Easton, Pa., 19th Edition (1995). Pharmaceutical compositions for use in the present invention can be in the form of sterile, non-pyrogenic liquid solutions or suspensions, coated capsules, suppositories, lyophilized powders, transdermal patches or other forms known in the art.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-propanediol or 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid find use in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form may be accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations may also be prepared by entrapping the drug in liposomes or microemulsions, which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, acetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, EtOAc, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulations, ear drops, and the like are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Compositions of the invention may also be formulated for delivery as a liquid aerosol or inhalable dry powder. Liquid aerosol formulations may be nebulized predominantly into particle sizes that can be delivered to the terminal and respiratory bronchioles.

Aerosolized formulations of the invention may be delivered using an aerosol forming device, such as a jet, vibrating porous plate or ultrasonic nebulizer, preferably selected to allow the formation of an aerosol particles having with a mass medium average diameter predominantly between 1 to 5 µm. Further, the formulation preferably has balanced osmolarity ionic strength and chloride concentration, and the smallest aerosolizable volume able to deliver effective dose of the compounds of the invention to the site of the infection. Additionally, the aerosolized formulation preferably does not impair negatively the functionality of the airways and does not cause undesirable side effects.

Aerosolization devices suitable for administration of aerosol formulations of the invention include, for example, jet, vibrating porous plate, ultrasonic nebulizers and energized dry powder inhalers, that are able to nebulize the formulation of the invention into aerosol particle size predominantly in the size range from 1-5 μm. Predominantly in this application means that at least 70% but preferably more than 90% of all generated aerosol particles are within 1-5 μm range. A jet nebulizer works by air pressure to break a liquid solution into aerosol droplets. Vibrating porous plate nebulizers work by using a sonic vacuum produced by a rapidly vibrating porous plate to extrude a solvent droplet through a porous plate. An ultrasonic nebulizer works by a piezoelectric crystal that shears a liquid into small aerosol droplets. A variety of suitable devices are available, including, for example, AERONEB and AERODOSE vibrating porous plate nebulizers (AeroGen, Inc., Sunnyvale, Calif.), SIDESTREAM nebulizers (Medic-Aid Ltd., West Sussex, England), PARI LC and PART LC STAR jet nebulizers (Pari Respiratory Equipment, Inc., Richmond, Va.), and AEROSONIC (DeVilbiss Medizinische Produkte (Deutschland) GmbH, Heiden, Germany) and ULTRAAIRE (Omron Healthcare, Inc., Vernon Hills, Ill.) ultrasonic nebulizers.

Compounds of the invention may also be formulated for use as topical powders and sprays that can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel. The compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic. Methods to form liposomes are known in the art. See, for example, Prescott (ed.), "Methods in Cell Biology," Volume XIV, Academic Press, New York, 1976, p. 33 et seq.

Effective amounts of the compounds of the invention generally include any amount sufficient to detectably inhibit PI3K activity by any of the assays described herein, by, other PI3K activity assays known to those having ordinary skill in the art, or by detecting an inhibition or alleviation of symptoms of cancer. The amount of active ingredient that may be combined with the carrier materials to produce a single dosage form will vary depending upon the host treated and the particular mode of administration. It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy. The therapeutically effective amount for a given situation can be readily determined by routine experimentation and is within the skill and judgment of the ordinary clinician.

According to the methods of treatment of the present invention, tumor growth is reduced or prevented in a patient such as a human or lower mammal by administering to the patient a therapeutically effective amount of a compound of the invention, in such amounts and for such time as is necessary to achieve the desired result. By a "therapeutically effective amount" of a compound of the invention is meant a sufficient amount of the compound to treat tumor growth, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient, the time of administration, route of administration, and rate of excretion of the specific compound employed; the duration of the treatment; drugs used in combination or coincidental with the specific compound employed; and like factors well known in the medical arts.

For purposes of the present invention, a therapeutically effective dose will generally be a total daily dose administered to a host in single or divided doses may be in amounts, for example, of from 0.001 to 1000 mg/kg body weight daily and more preferred from 1.0 to 30 mg/kg body weight daily. Dosage unit compositions may contain such amounts of submultiples thereof to make up the daily, dose. In general, treatment regimens according to the present invention comprise administration to a patient in need of such treatment from about 10 mg to about 2000 mg of the compound(s) of this invention per day in single or multiple doses.

In another aspect of the invention, kits that include one or more compounds of the invention are provided. Representative kits include a PI3K inhibitor compound of the invention (e.g., a compound of formulas (I)-(III)) and a package insert or other labeling including directions for treating a cellular proliferative disease by administering an PI3K inhibitory amount of the compound.

The term "kit" as used herein comprises a container for containing the pharmaceutical compositions and may also include divided containers such as a divided bottle or a divided foil packet. The container can be in any conventional shape or form as known in the art which is made of a pharmaceutically acceptable material, for example a paper or cardboard box, a glass or plastic bottle or jar, a resealable bag (for example, to hold a "refill" of tablets for placement into a different container), or a blister pack with individual doses for pressing out of the pack according to a therapeutic schedule. The container employed can depend on the exact dosage form involved, for example a conventional cardboard box would not generally be used to hold a liquid suspension. It is feasible that more than one container can be used together in a single package to market a single dosage form. For example, tablets may be contained in a bottle which is in turn contained within a box.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process, recesses are formed in the plastic foil. The recesses have the size and shape of individual tablets or capsules to be packed or may have the size and shape to accommodate multiple tablets and/or capsules to be packed. Next, the tablets or capsules are placed in the recesses accordingly and the sheet of relatively stiff material is sealed against the plastic foil at the face of the foil which is opposite from the direction in which the recesses were formed. As a result, the tablets or capsules are individually sealed or collectively sealed, as desired, in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It maybe desirable to provide a written memory aid, where the written memory aid is of the type containing information and/or instructions for the physician, pharmacist or other health care provider, or subject, e.g., in the form of numbers next to the tablets or capsules whereby the numbers correspond with the days of the regimen which the tablets or capsules so specified should be ingested or a card which contains the same type of information. Another example of such a memory aid is a calendar printed on the card, e.g., as follows "First Week, Monday, Tuesday," "Second Week, Monday, Tuesday, . . . ." Other variations of memory aids will be readily apparent. A "daily dose" can be a single tablet or capsule or several tablets or capsules to be taken on a given day. When the kit contains separate compositions, a daily dose of one or more compositions of the kit can consist of one tablet or capsule while a daily dose of another one or more compositions of the kit can consist of several tablets or capsules.

Another specific embodiment of a kit is a dispenser designed to dispense the daily doses one at a time in the order of their intended use. Preferably, the dispenser is equipped with a memory-aid, so as to further facilitate compliance with the regimen. An example of such a memory-aid is a mechanical counter, which indicates the number of daily doses that has been dispensed. Another example of such a memory-aid is a battery-powered micro-chip memory coupled with a liquid crystal readout, or audible reminder signal which, for example, reads out the date that the last daily dose has been taken and/or reminds one when the next dose is to be taken.

The kits of the present invention may also comprise, in addition to a PI3K inhibitor, one or more additional pharmaceutically active compounds. Preferably, the additional compound is another PI3K inhibitor or another compound useful to treat cancer, angiogenesis, or tumor growth. The additional compounds may be administered in the same dosage form as the PI3K inhibitor or in different dosage forms. Likewise, the additional compounds can be administered at the same time as the PI3K inhibitor or at different times.

The present invention will be understood more readily by reference to the following examples, which are provided by way of illustration and are not intended to be limiting of the present invention.

EXAMPLES

Referring to the examples that follow, compounds of the present invention were synthesized using the methods described herein, or other methods, which are known in the art.

The compounds and/or intermediates were characterized by high performance liquid chromatography (HPLC) using a Waters Millenium chromatography system with a 2695 Separation Module (Milford, Mass.). The analytical columns were Alltima C-18 reversed phase, 4.6×50 mm, flow 2.5 mL/min, from Alltech (Deerfield, Ill.). A gradient elution was used, typically starting with 5% acetonitrile/95% water and progressing to 100% acetonitrile over a period of 40 minutes. All solvents contained 0.1% trifluoroacetic acid (TFA). Compounds were detected by ultraviolet light (UV) absorption at either 220 or 254 rim. HPLC solvents were from Burdick and Jackson (Muskegan, Mich.), or Fisher Scientific (Pittsburgh, Pa.). In some instances, purity was assessed by thin layer chromatography (TLC) using glass or plastic backed silica gel plates, such as, for example, Baker-Flex Silica Gel 1B2-F flexible sheets. TLC results were readily detected visually under ultraviolet light, or by employing well known iodine vapor and other various staining techniques.

Mass spectrometric analysis was performed on one of two LCMS instruments: a Waters System (Alliance HT HPLC and a Micromass ZQ mass spectrometer; Column: Eclipse XDB-C18, 2.1×50 mm; solvent system: 5-95% (or 35-95%, or 65-95% or 95-95%) acetonitrile in water with 0.05% TFA; flow rate 0.8 mL/min; molecular weight range 200-1500; cone Voltage 20 V; column temperature 40° C.) or a Hewlett Packard System (Series 1100 HPLC; Column: Eclipse XDB- C18, 2.1×50 mm; solvent system: 1-95% acetonitrile in water with 0.05% TFA; flow rate 0.8 mL/min; molecular weight range 150-850; cone Voltage 50 V; column temperature 30° C.). All masses were reported as those of the protonated parent ions.

GCMS analysis is performed on a Hewlett Packard instrument (HP6890 Series gas chromatograph with a Mass Selective Detector 5973; injector volume: 1 μL; initial column temperature: 50° C.; final column temperature: 250° C.; ramp time: 20 minutes; gas flow rate: 1 mL/min; column: 5% phenyl methyl siloxane, Model No. HP 190915-443, dimensions: 30.0 m×25 m×0.25 m).

Nuclear magnetic resonance (NMR) analysis was performed on some of the compounds with a Varian 300 MHz NMR (Palo Alto, Calif.). The spectral reference was either TMS or the known chemical shift of the solvent. Some compound samples were run at elevated temperatures (e.g., 75° C.) to promote increased sample solubility.

The purity of some of the invention compounds is assessed by elemental analysis (Desert Analytics, Tucson, Ariz.).

Melting points are determined on a Laboratory Devices Mel-Temp apparatus (Holliston, Mass.).

Preparative separations were carried out using a Flash 40 chromatography system and KP-Sil, 60A (Biotage, Charlottesville, Va.), or by flash column chromatography using silica gel (230-400 mesh) packing material, or by HPLC using a Waters 2767 Sample Manager, C-18 reversed phase column, 30×50 mm, flow 75 mL/min. Typical solvents employed for the Flash 40 Biotage system and flash column chromatography were dichloromethane, methanol, ethyl acetate, hexane, acetone, aqueous ammonia (or ammonium hydroxide), and triethyl amine. Typical solvents employed for the reverse phase HPLC were varying concentrations of acetonitrile and water with 0.1% trifluoroacetic acid.

It should be understood that the organic compounds according to the invention may exhibit the phenomenon of tautomerism. As the chemical structures within this specification can only represent one of the possible tautomeric forms, it should be understood that the invention encompasses any tautomeric form of the drawn structure.

It is understood that the invention is not limited to the embodiments set forth herein for illustration, but embraces all such forms thereof as come within the scope of the above disclosure.

ABBREVIATIONS

| | |
|---|---|
| ACN | Acetonitrile |
| BINAP | 2,2'-bis(diphenylphosphino)-1,1'-binapthyl |
| DIEA | diisopropylethylamine |
| DME | 1,2-dimethoxyethane |
| DMF | N,N-dimethylformamide |
| DPPF | 1,1'-bis(diphenylphosphino)ferrocene |
| EtOAc | ethyl acetate |
| EtOH | ethanol |
| MCPBA | meta-chloroperoxybenzoic acid |
| NBS | N-bromosuccinimide |
| NMP | N-methyl-2-pyrrolidone |
| RT | room temperature |
| THF | tetrahydrofuran |

General Methods for Synthesizing PI3K Inhibitor Compounds

Methods for preparing compounds of Formula I and/or II are provided. The methods include: reacting a 4-halo-2-morpholinopyrimidine with a substituted pyridinyl or pyrimidinyl group containing a reactive boronic ester substituent, in the presence of a palladium catalyst. In one embodiment, the substituted pyridinyl or pyrimidinyl group containing a reactive boronic ester substituent has an —$NH_2$ group positioned para to the boronic ester. In another embodiment, the substituted pyridinyl or pyrimidinyl group containing a reactive boronic ester substituent has an —$NH_2$ group positioned para to the boronic ester and another non-hydrogen substituent positioned ortho to the boronic ester. In certain embodiments, the non-hydrogen substituent is —$CF_3$, —CN, —$NH_2$, halo, or substituted or unsubstituted $C_{1-3}$ alkyl.

In another embodiment, the 4-halo-2-morpholinopyrimidine group is a 4-halo-6-heterocyclyl-2-morpholinopyrimidine group. In another embodiment, the 4-halo-2-morpholinopyrimidine group is a 4-halo-6-heterocyclyloxy-2-morpholinopyrimidine group. In another embodiment, the 4-halo-2-morpholinopyrimidine group is a 4-halo-6-heteroarylamino-2-morpholinopyrimidine group. In another embodiment, the 4-halo-2-morpholinopyrimidine group is 4-chloro-2,6-dimorpholinopyrimidine.

In another embodiment, the pyridinyl boronic ester is 4-(trifluoromethyl)-5-(4,4,5,5-tetramethyl-1,3,2-dioxaborolan-2-yl)pyridin-2-amine. In another embodiment, the palladium catalyst is Pd(dppf)$Cl_2$ dichloromethane adduct.

In another embodiment, the 4-halo-6-heterocyclyl-2-morpholinopyrimidine group is prepared by reacting a heterocyclyl group with a 4,6-dihalo-2-morpholinopyrimidine group. In another embodiment, the 4-chloro-2,6-dimorpholinopyrimidine group is prepared by reacting 4,6-dichloro-2-morpholinopyrimidine with morpholine. In another embodiment, the 4,6-dichloro-2-morpholinopyrimidine group is prepared by reacting 2-morpholinopyrimidine-4,6-diol with $POCl_3$. In another embodiment, the 2-morpholinopyrimidine-4,6-diol is prepared by reacting morpholine-4-carboxamidine with diethyl malonate in the presence of a base, such as sodium ethoxide.

In another embodiment, the substituted pyridinyl or pyrimidinyl group containing a reactive boronic ester substituent is prepared by reacting a substituted pyridinyl or pyrimidinyl group containing a bromo substituent with a diboronic ester, such as 4,4,5,5-tetramethyl-2-(4,4,5,5-tetramethyl-1,3,2-dioxaborolan-2-yl)-1,3,2-dioxaborolane. In another embodiment, the substituted pyridinyl or pyrimidinyl group containing a bromo substituent is prepared by reacting the substituted pyridinyl or pyrimidinyl group with N-bromosuccinimide (NBS).

Another embodiment of the present invention provides a method of preparing a 4-chloro-2,6-dimorpholinopyrimidine comprising reacting morpholine with 2,4,6-trichloropyrimidine in a suitable solvent. In a more particular embodiment, the solvent is a polar aprotic solvent. More particular still the solvent is THF. In another more particular embodiment, the 4-chloro-2,6-dimorpholinopyrimidine is added over a period of at least 10 minutes, or at least 20 minutes, or 30 minutes to a solution comprising morpholine. Alternatively, the morpholine is added to a solution comprising 4-chloro-2,6-dimorpholinopyrimidine. More particular still, the solution is cooled below 20° C., or below 10° C., or below 5° C., or below 0° C. More particularly, during or after addition of the 4-chloro-2,6-dimorpholinopyrimidine, the solution is allowed to warm to greater than 20° C., or greater than 25° C., or greater than 30° C. In another embodiment, after the morpholine and 4-chloro-2,6-dimorpholinopyrimidine are combined, the solution is quenched by addition of an aqueous solution. More particularly, at least 10 hours, or at least 20 hours, or at least 30 hours, or at least 40 hours, or at least 50 hours, or about 64 hours after the morpholine and 4-chloro- 2,6-dimorpholinopyrimidine are combined, the solution is quenched by addition of an aqueous solution. More particularly, after quenching, the solution is purified by column chromatography. More particular still, the column is silica gel. In another embodiment, the 4-chloro-2,6-dimorpholinopyrimidine is reacted with a 2-aminopyridyl or 2-aminopyrimidyl moiety to form a compound of Formula III.

Compounds of the invention containing a pyrimidine core, such as those of Formula I, may be prepared using a number of methods familiar to one of skill in the art. In one method, suitably functionalized amines may be coupled with 4,6-dichloro-2-morpholinopyrimidine by nucleophilic aromatic substitution reactions or by a Buchwald-Hartwig cross-coupling reaction (Hartwig et al., Tetrahedron Letters 36, (1995) 3609), wherein Ar represents aryl or heteroaryl moieties. Subsequently, Suzuki coupling (Suzuki et al., Chem. Commun. (1979) 866) to form the final product may be effected under known conditions such as by treatment with functionalized boronic esters as in the following schemes:

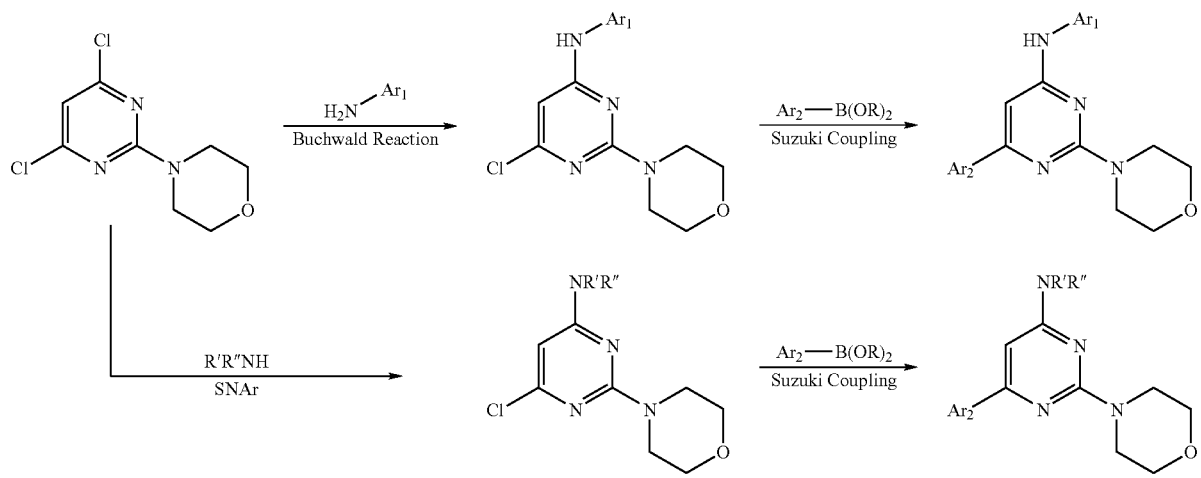

From 2,4,6-tribromopyrimidine: SNAr (or Buchwald) reaction of functionalized arylamines with 2,4,6-tribromopyrimidine gave preferentially 4-substituted products. Morpholine substitution at 2-position followed with Suzuki reaction affords the final pyrimidine analogs:

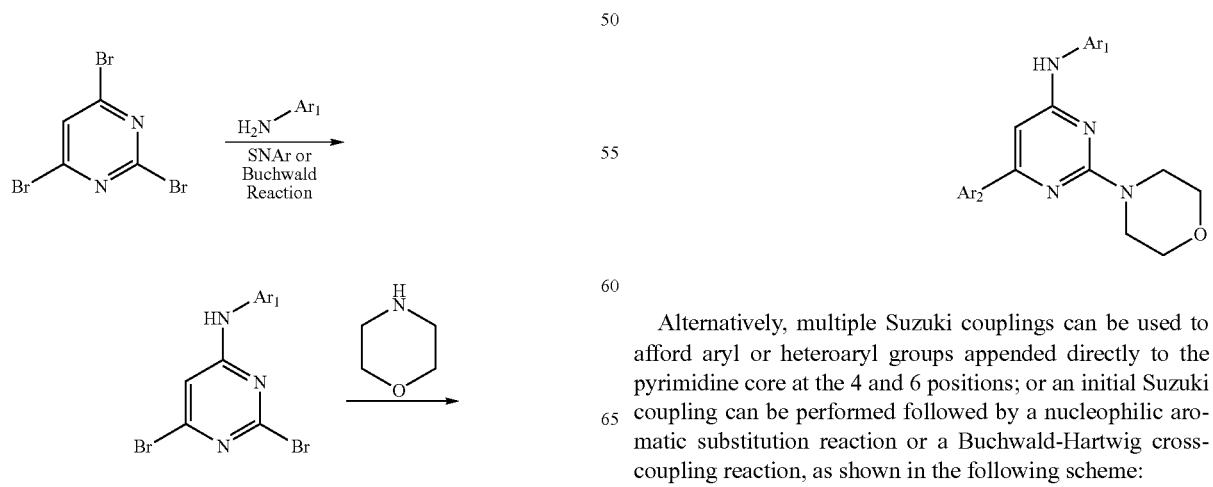

Alternatively, multiple Suzuki couplings can be used to afford aryl or heteroaryl groups appended directly to the pyrimidine core at the 4 and 6 positions; or an initial Suzuki coupling can be performed followed by a nucleophilic aromatic substitution reaction or a Buchwald-Hartwig cross-coupling reaction, as shown in the following scheme:

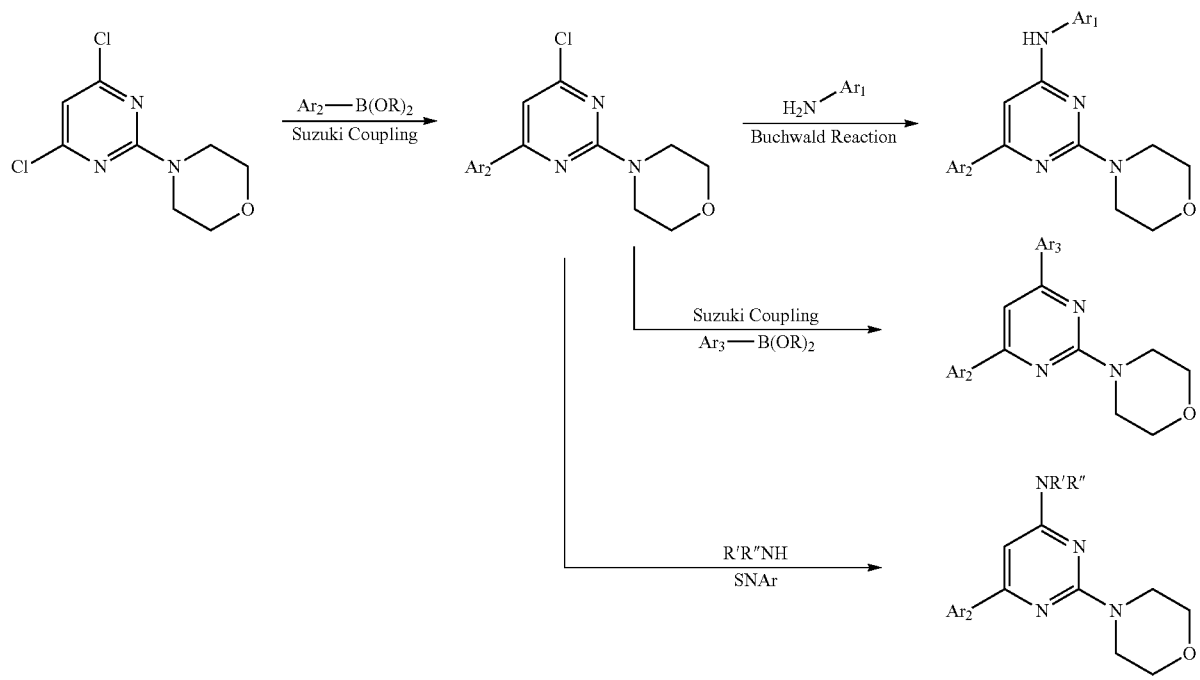

More particular syntheses of compounds of the present invention, particularly those of Formula I, II, and III, are provided in the following Methods and Examples:

Method 1

Synthesis of 5-(4,4,5,5-tetramethyl-1,3,2-dioxaborolan-2-yl)pyrimidine-2-ylamine

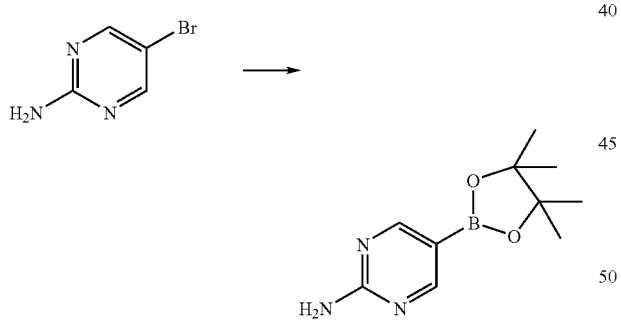

To a dry 500-mL flask was added 2-amino-5-bromopyrimidine (10 g, 57.5 mmol), potassium acetate (16.9 g, 172 mmol), 4,4,5,5-tetramethyl-2-(4,4,5,5-tetramethyl-1,3,2-dioxaborolan-2yl)-1,3,2-dioxaborolane (16.1 g, 63.0 mmol) and dioxane (300 mL). Argon was bubbled through the solution for 15 minutes, at which time dichloro[1,1'-bis(diphenylphosphino)ferrocene]palladium (II) dichloromethane adduct (Pd(dppf)Cl$_2$ CH$_2$Cl$_2$) (2.34 g, 2.87 mmol) was added. The reaction mixture was refluxed in a 115° C. oil bath for 4 hours under argon. After cooling to room temperature, EtOAc (500 mL) was added and the resulting slurry was sonicated and filtered. Additional EtOAc (500 mL) was used to wash the solid. The combined organic extracts were washed with H$_2$O (2×300 mL), NaCl$_{(sat.)}$ (300 mL), dried over Na$_2$SO$_4$, and filtered through a 5 cm pad of silica gel. Additional EtOAc was used to flush product. After the solvent was concentrated, the crude was treated with a mixture of 1:3 dichloromethane and hexane (40 mL), filtered and washed with hexane yielding a light yellow solid (8.5 g, 75%). LCMS (m/z): 140 (MH$^+$ of boronic acid, deriving from product hydrolysis on LC). $^1$H NMR (CDCl$_3$): δ 8.58 (s, 2H), 5.74 (s, 2H), 1.32 (s, 12H).

Method 2

Synthesis of 2-Aminomethyl-5-bromopyrimidine

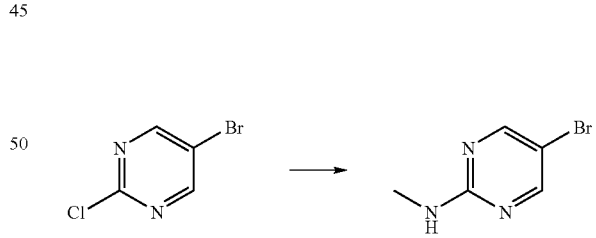

Methylamine (2.0 M in methanol, 40 mL, 80 mmol) was added to 5-bromo-2-chloropyrimidine (5.6 g, 29.0 mmol) in a sealable reaction vessel. After allowing to vent for a few minutes, the vessel was sealed, placed behind a safety shield and heated in a 115° C. oil bath for 48 hours. Upon cooling the volatiles were removed in vacuo. The material was dissolved in CH$_2$Cl$_2$ (200 mL) and washed with 1M NaOH (40 mL). The aqueous layer was extracted further with CH$_2$Cl$_2$ (2×50 mL). The combined organics were dried over MgSO$_4$, filtered and concentrated yielding an off white solid (5.1 g, 93%). LCMS (m/z): 188.0/190.0 (MH$^+$).

Synthesis of methyl[5-(4,4,5,5-tetramethyl(1,3,2-dioxaborolan-2-yl))pyrimidin-2-yl]amine Synthesis of 4-methyl-5-(4,4,5,5-tetramethyl(1,3,2-dioxaborolan-2-yl))pyrimidine-2-ylamine

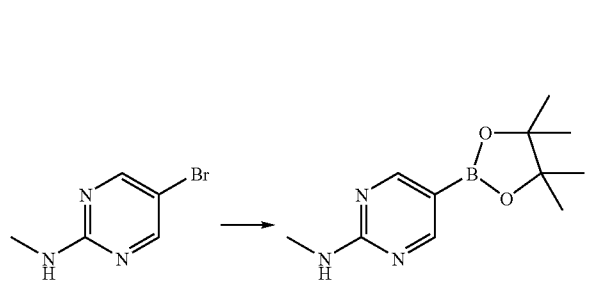

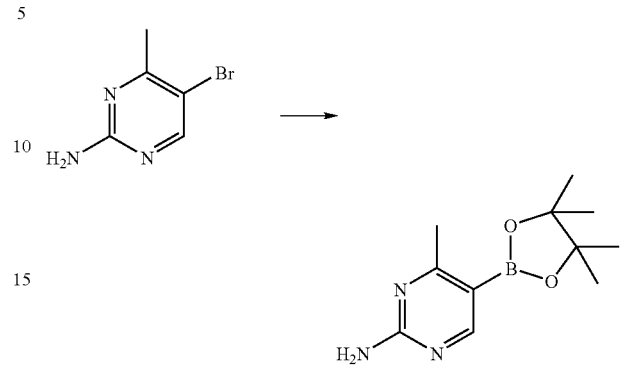

To a dry 500 mL flask was added 2-methylamino-5-bromopyrimidine (9.5 g, 50.5 mmol), potassium acetate (15.1 g, 154.4 mmol), 4,4,5,5,-tetramethyl-2-(4,4,5,5,-tetramethyl-1,3,2-dioxaborolan-2-yl)-1,3,2-dioxaborolane (14.1 g, 55.5 mmol) and dioxane (280 mL). Argon was bubbled through the solution for 15 minutes, at which time 1,1'-bis(diphenylphosphino)ferrocene palladium(II) chloride dichloromethane adduct (2.05 g, 2.51 mmol) was added. The reaction was refluxed in a 115° C. oil bath for 4 hours under argon. After cooling to room temperature, EtOAc (500 mL) was added and the resulting slurry was sonicated and filtered. Additional EtOAc (500 mL) was used to wash the solid. The combined organics were washed with $H_2O$ (2×300 mL), $NaCl_{(sat.)}$, (300 mL), dried over $Na_2SO_4$, filtered and the solvents were removed in vacuo. Purification by $SiO_2$ chromatography (50% EtOAc/hexanes) yielded an off white solid (7.66 g, 64%). LCMS (m/z): 154 ($MH^+$ of boronic acid, deriving from in situ product hydrolysis on LC). $^1H$ NMR ($CDCl_3$): δ 8.58 (s, 2H), 5.56 (s, 1H), 3.02 (d, 3H), 1.32 (s, 12H).

Method 3

Synthesis of 5-bromo-4-methylpyrimidine-2-ylamine

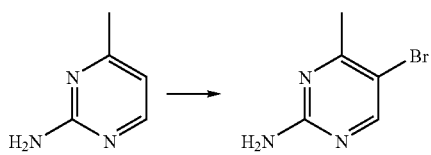

To a solution of 4-methylpyrimidine-2-ylamine (10.9 g, 100 mmol) in chloroform (400 mL) was added N-bromosuccinimide (17.8 g, 100 mmol). The solution was stirred in the dark for 15 hours, at which time it was added to $CH_2Cl_2$ (1400 mL), washed with 1N NaOH (3×200 mL) and $NaCl_{(sat.)}$ (100 mL), dried over $Na_2SO_4$, filtered and concentrated, yielding 5-bromo-4-methylpyrimidine-2-ylamine (18.8 g, 99%). LCMS (m/z): 188.0/190.0 ($MH^+$). $^1H$ NMR ($CDCl_3$): δ 8.22 (s, 1H), 5.02 (bs, 2H), 2.44 (s, 3H).

To a dry 1 L flask was added 5-bromo-4-methylpyrimidine-2-ylamine (18.8 g, 100 mmol), potassium acetate (29.45 g, 300 mmol), 4,4,5,5-tetramethyl-2-(4,4,5,5-tetramethyl-1,3,2-dioxaborolan-2-yl)-1,3,2-dioxaborolane (26.7 g, 105 mmol) and dioxane (500 mL). Argon was bubbled through the solution for 15 minutes, at which time 1,1'-bis(diphenylphosphino)ferrocene palladium(II) chloride dichloromethane adduct (4.07 g, 5 mmol) was added. The reaction was refluxed in a 115° C. oil bath for 18 hours under argon. After cooling to room temperature, EtOAc (500 mL) was added and the resulting slurry was sonicated and filtered. Additional EtOAc (500 mL) was used to wash the solid. The combined organic extracts were washed with $H_2O$ (2×300 mL), $NaCl_{(sat.)}$ (300 mL), dried over $Na_2SO_4$, concentrated and purified by $SiO_2$ chromatography (EtOAc eluent) yielding 18.1 g of an off-white solid. By $^1H$ NMR the material was a 5:1 mixture of boronate ester and 4-methylpyrimidine-2-ylamine as a byproduct. The material was used as is in subsequent Suzuki reactions. LCMS (m/z): 154 ($MH^+$ of boronic acid, deriving from in situ product hydrolysis on LC). $^1H$ NMR ($CDCl_3$): δ 8.52 (s, 1H), 5.14 (bs, 2H), 2.56 (d, 3H), 1.32 (s, 12H).

Method 4

Synthesis of 5-bromo-4-(trifluoromethyl)-2-pyridylamine

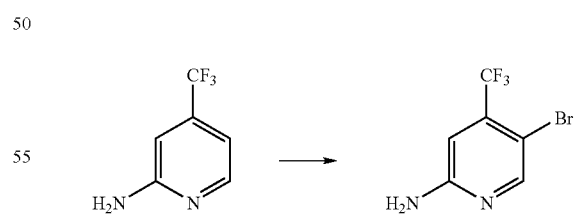

To a solution of 2-amino-4-trifluoromethylpyridine (10.0 g, 62.1 mmol) in chloroform (200 mL) was added N-bromosuccinimide (12.0 g, 67.4 mmol). The solution was stirred in the dark for 2 hours, at which time it was added to $CH_2Cl_2$ (200 mL) and 1N NaOH (200 mL). Upon mixing, the layers were separated and the organic layer was washed with $NaCl_{(sat.)}$ (100 mL), dried over $Na_2SO_4$, filtered and concentrated. The crude material was purified by $SiO_2$ chromatography (0-5% EtOAc/CH₂Cl₂) yielding 12.0 g (80%) of 5-bromo-4-(trifluoromethyl)-2-pyridylamine LCMS (m/z): 241/243 (MH⁺). ¹H NMR (CDCl₃): δ 8.28 (s, 1H), 6.77 (s, 1H), 4.78 (bs, 2H).

Synthesis of 5-(4,4,5,5-tetramethyl(1,3,2-dioxaborolan-2-yl))-4-(trifluoromethyl)-2-pyridylamine

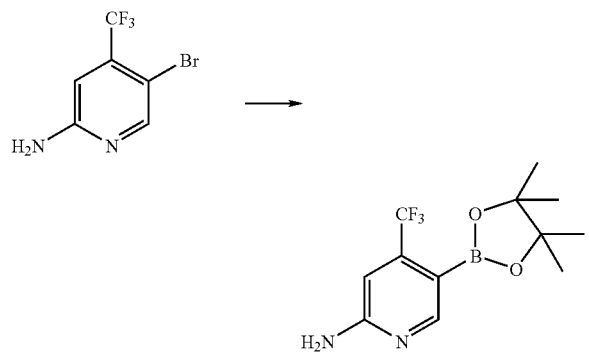

To a dry 500 mL flask was added 5-bromo-4-(trifluoromethyl)-2-pyridylamine (11.8 g, 49.0 mmol), potassium acetate (14.4 g, 146.9 mmol), 4,4,5,5-tetramethyl-2-(4,4,5,5-tetramethyl-1,3,2-dioxaborolan-2-yl)-1,3,2-dioxaborolane (13.6 g, 53.9 mmol) and dioxane (300 mL). Argon was bubbled through the solution for 15 minutes, at which time 1,1'-bis(diphenylphosphino)ferrocene palladium(II) chloride dichloromethane adduct (2.0 g, 2.45 mmol) was added. The reaction was refluxed in a 115° C. oil bath for 8 hours under argon. After cooling to room temperature, the dioxane was removed in vacuo. EtOAc (500 mL) was added, and the resulting slurry was sonicated and filtered. Additional EtOAc (500 mL) was used to wash the solid. The combined organic extracts were concentrated and the crude material was partially purified by SiO₂ chromatography (30-40% EtOAc/Hexanes). Upon removal of solvent, hexanes (75 mL) was added; after sonication, the resulting solid was filtered and dried on a high vacuum for 3 days yielding 2.4 g of an off-white solid. By ¹H NMR the material was a 5:1 mixture of boronate ester and 2-amino-4-trifluoromethyl pyridine byproduct. The material was used as is in subsequent Suzuki reactions. LCMS (m/z): 207 (MH⁺ of boronic acid, deriving from in situ product hydrolysis on LC). ¹H NMR (CDCl₃): δ 8.50 (s, 1H), 6.72 (s, 1H), 4.80 (bs, 2H), 1.34 (s, 12H).

Method 5

Synthesis of 5-bromo-4-(trifluoromethyl)pyrimidin-2-amine

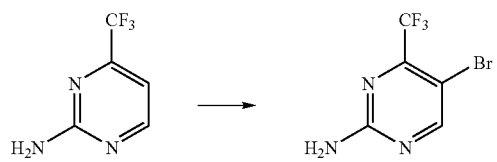

To a solution of 2-amino-4-trifluoromethylpyrimidine (8.0 g, 49.1 mmol) in chloroform (300 mL) was added N-bromosuccinimide (8.9 g, 50 mmol). The solution was stirred in the dark for 16 hours, at which time additional N-bromosuccinimide (4.0 g, 22.5 mmol) was added. After stirring for an additional 4 hours the solution was added to CH₂Cl₂ (200 mL) and 1N NaOH (200 mL). Upon mixing, the layers were separated and the organic layer was washed with NaCl$_{(sat.)}$ (100 mL), dried over Na₂SO₄, filtered and concentrated, yielding 10.9 g (82%) of 5-bromo-4-(trifluoromethyl)-2-pyrimidylamine. LCMS (m/z): 242/244 (MH⁺). ¹H NMR (CDCl₃): δ 8.52 (s, 1H), 5.38 (bs, 2H).

Synthesis of 5-(4,4,5,5-tetramethyl(1,3,2-dioxaborolan-2-yl))-4-(trifluoromethyl)pyrimidine-2-ylamine

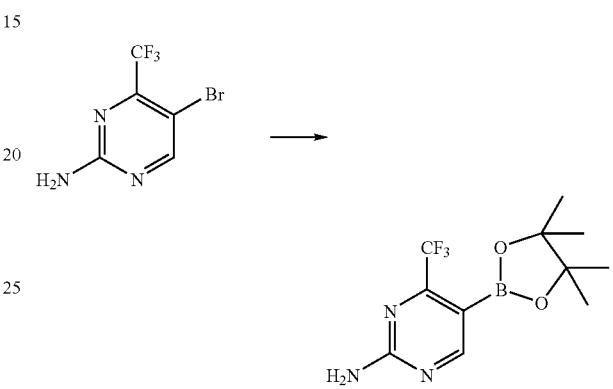

To a dry 500 mL flask was added 5-bromo-4-(trifluoromethyl)-2-pyrimidylamine (10.1 g, 41.7 mmol), potassium acetate (12.3 g, 125.2 mmol), 4,4,5,5-tetramethyl-2-(4,4,5,5-tetramethyl-1,3,2-dioxaborolan-2-yl)-1,3,2-dioxaborolane (11.6 g, 45.9 mmol) and dioxane (150 mL). Argon was bubbled through the solution for 15 minutes, at which time 1,1'-bis(diphenylphosphino)ferrocene palladium (II) chloride (1.7 g, 2.1 mmol) was added. The reaction was refluxed in a 115° C. oil bath for 6 hours under argon. After cooling to room temperature, the dioxane was removed in vacuo. EtOAc (500 mL) was added and the resulting slurry was sonicated and filtered. Additional EtOAc (500 mL) was used to wash the solid. The combined organic extracts were concentrated and the crude material was purified by SiO₂ chromatography (30-40% EtOAc/hexanes) yielding 4.40 g of an off white solid. By ¹H NMR the material was a 1:1 mixture of boronate ester and 2-amino-4-trifluoromethylpyrimidine byproduct. The material was used as is in subsequent Suzuki reactions. LCMS (m/z): 208 (MH⁺ of boronic acid, deriving from in situ product hydrolysis on LC). ¹H NMR (CDCl₃): δ 8.72 (s, 1H), 5.50 (bs, 2H), 1.34 (s, 12H).

Method 6

Synthesis of 5-bromo-4-chloro-2-pyridylamine

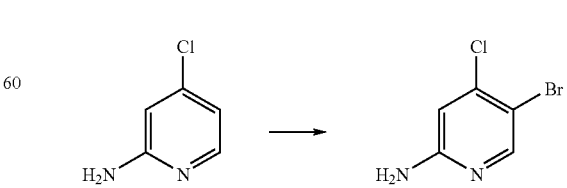

To a solution of 4-chloro-2-pyridylamine (6.0 g, 46.7 mmol) in chloroform (180 mL) was added N-bromosuccinimide (8.3 g, 46.7 mmol). The solution was stirred in the dark for 2 hours, at which time it was added to $CH_2Cl_2$ (800 mL) and 1N NaOH (100 mL). Upon mixing, the layers were separated and the organic layer was washed with $NaCl_{(sat.)}$ (100 mL), dried over $Na_2SO_4$, filtered and concentrated. The crude material was purified by $SiO_2$ chromatography (25-35% EtOAc/hexanes) yielding 3.63 g (38%) of 5-bromo-4-chloro-2-pyridylamine. LCMS (m/z): 206.9/208.9 (MH+). $^1$H NMR ($CDCl_3$): δ 8.18 (s, 1H), 6.62 (s, 1H), 4.52 (bs, 2H).

Synthesis of 4-chloro-5-(4,4,5,5-tetramethyl(1,3,2-dioxaborolan-2-yl))-2-pyridylamine

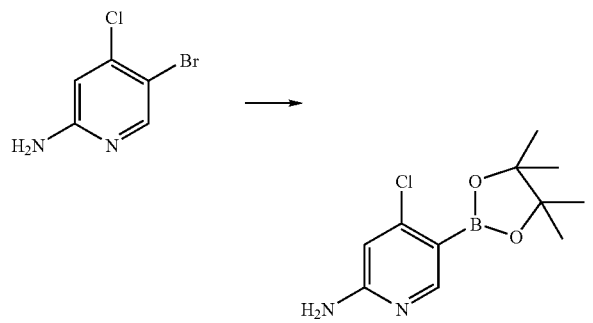

To a dry 500-mL flask was added 5-bromo-4-chloro 2-pyridylamine (7.3 g, 35.8 mmol), potassium acetate (10.3 g, 105 mmol), 4,4,5,5-tetramethyl-2-(4,4,5,5-tetramethyl-1,3,2-dioxaborolan-2-yl)-1,3,2-dioxaborolane (10.1 g, 39.8 mmol) and dioxane (150 mL). Argon was bubbled through the solution for 15 minutes, at which time 1,1'-bis(diphenylphosphino)ferrocene palladium(II) chloride dichloromethane adduct (0.85 g, 1.04 mmol) was added. The reaction was refluxed in a 115° C. oil bath for 6 hours under argon. After cooling to room temperature, the dioxane was removed in vacuo. EtOAc (500 mL) was then added and the resulting slurry was sonicated and filtered. Additional EtOAc (500 mL) was used to wash the solid. The combined organic extracts were concentrated and the crude material was purified by $SiO_2$ chromatography (EtOAc as eluent). Upon removal of solvent, 3:1 hexanes/$CH_2Cl_2$ was added (100 mL). After sonication, the resulting solid was filtered and concentrated in vacuo yielding 2.8 g of a white solid. By $^1$H NMR the material was a 10:1 mixture of boronate ester and 2-amino-4-chloropyridine byproduct. The material was used as is in subsequent Suzuki reactions. LCMS (m/z): 173 (MH+ of boronic acid, deriving from in situ product hydrolysis on LC). $^1$H NMR ($CDCl_3$): δ 8.36 (s, 1H), 6.46 (s, 1H), 4.70 (bs, 2H), 1.38 (s, 12H).

Method 7

Synthesis of 5-bromopyrimidine-2,4-diamine

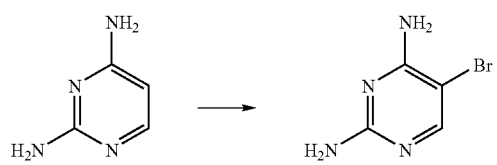

To a solution of 2,4-diaminopyrimidine (1.0 g, 9.1 mmol) in chloroform (30 mL) was added N-bromosuccinimide (1.62 g, 9.08 mmol). The solution was stirred in the dark for 12 hours, at which time it was added to $CH_2Cl_2$ (150 mL) and 1N NaOH (50 mL). The solid that formed was filtered, rinsed with water and concentrated in vacuo, yielding 1.4 g (74%) of 5-bromopyrimidine-2,4-diamine. LCMS (m/z): 189/191 (MH+). $^1$H NMR (DMSO-$d_6$): δ 7.78 (s, 1H), 6.58 (bs, 2H), 6.08 (bs, 2H).

Synthesis of 5-(4,4,5,5-tetramethyl-1,3,2-dioxaborolan-2-yl)pyrimidine-2,4-diamine

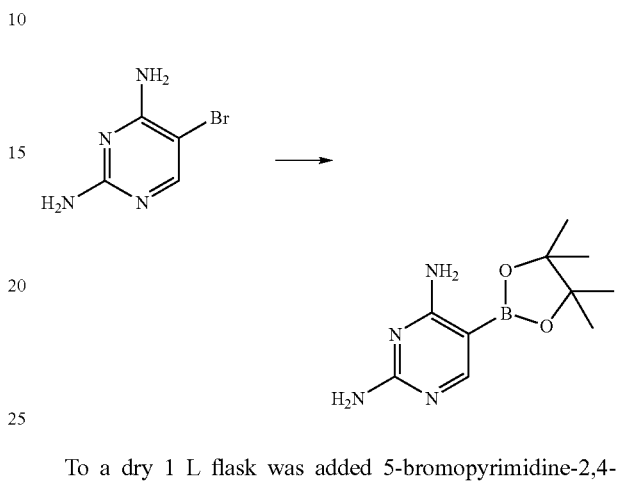

To a dry 1 L flask was added 5-bromopyrimidine-2,4-diamine (30.0 g, 158.7 mmol), potassium acetate (45.8 g, 466.7 mmol), 4,4,5,5-tetramethyl-2-(4,4,5,5-tetramethyl-1,3,2-dioxaborolan-2-yl)-1,3,2-dioxaborolane (51.2 g, 202.2 mmol) and dioxane (500 mL). Argon was bubbled through the solution for 15 minutes, at which time 1,1'-bis(diphenylphosphino)ferrocene palladium(II) chloride (2.5 g, 3.11 mmol) was added. The reaction was refluxed in a 115° C. oil bath for 16 hours under argon. After cooling to room temperature, the solid inorganic material was filtered, rinsed with EtOAc (1 L). The organic filtrate was concentrated in vacuo and to the resulting solid was added dichloromethane (1 L). After sonication the solid was filtered. The solid was the debrominated 2,4-diaminopyrimidine. The filtrate containing desired boronate ester was concentrated in vacuo. To this residue was added diethyl ether (100 mL). After sonication, the solution was filtered, rinsed with additional diethyl ether (50 mL) and the solid obtained was dried under high vacuum to yield the desired 2,4-diaminopyrimidyl-5-boronate ester (10.13 g, 27%). By $^1$H NMR the material was a 4:1 mixture of 2,4-diaminopyrimidyl-5-boronate ester and 2,4-diaminopyrimidine byproduct. The material was used as is in subsequent Suzuki reactions. LCMS (m/z): 155 (MH+ of boronic acid, deriving from in situ product hydrolysis on LC). $^1$H NMR ($CDCl_3$+$CD_3OD$): δ 8.16 (s, 1H), 1.34 (s, 12H).

Method 8

Synthesis of 4-methoxypyrimidine-2-ylamine

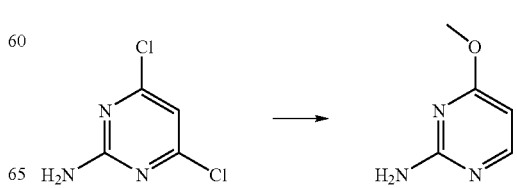

To a solution of 4,6-dichloro-2-amino pyrimidine (5.0 g, 30.5 mmol) in methanol (100 mL) was added 25% sodium methoxide (6.59 g, 30.5 mmol). The solution was refluxed for 20 hours, at which time the methanol was removed in vacuo. The residue was dissolved in EtOAc (350 mL), washed with H$_2$O (100 mL) and with NaCl$_{(sat.)}$ (100 mL), dried over Na$_2$SO$_4$, filtered and concentrated yielding 4.4 g (90%) of 4-chloro-6-methoxypyrimidine-2-ylamine.

To a solution of 4-chloro-6-methoxypyrimidine-2-ylamine (4.4 g, 27.7 mmol) in EtOAc (200 mL) and ethanol (150 mL), was added diisopropylethylamine (9.6 mL, 55.3 mmol) and 10% palladium on carbon (2.9 g, 2.77 mmol). The heterogeneous solution was stirred under a balloon atmosphere of H$_2$ for 14 hours, at which time the solution was filtered through a Celite pad and the volatiles were removed in vacuo. The residue was dissolved in EtOAc (200 mL), washed with Na$_2$CO$_{3(sat.)}$ (100 mL) and with NaCl$_{(sat.)}$ (100 mL), dried over Na$_2$SO$_4$, filtered and concentrated yielding 3.1 g (90%) of 4-methoxypyrimidine-2-ylamine. LCMS (m/z): 126 (MH$^+$). $^1$H NMR (CDCl$_3$): δ 8.00 (d, J=5.7 Hz, 1H), 6.08 (d, J=5.7 Hz, 1H), 4.98 (bs, 2H), 3.84 (s, 3H).

Synthesis of 5-bromo-4-methoxypyrimidine-2-ylamine

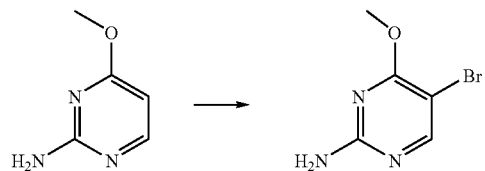

To a solution of 4-methoxypyrimidine-2-ylamine (1.84 g, 14.7 mmol) in chloroform (600 mL) was added N-bromosuccinimide (2.62 g, 14.7 mmol). After stirring in the dark for 5 hours, the solution was added to CH$_2$Cl$_2$ (200 mL) and 1N NaOH (100 mL). Upon mixing, the layers were separated and the organic layer was washed with NaCl$_{(sat.)}$ (100 mL), dried over Na$_2$SO$_4$, filtered and concentrated yielding 2.88 g (96%) of 5-bromo-4-methoxypyrimidine-2-ylamine. LCMS (m/z): 204/206 (MH$^+$). $^1$H NMR (CDCl$_3$): δ 8.10 (s, 1H), 4.93 (bs, 2H), 3.96 (s, 3H).

Synthesis of 4-methoxy-5-(4,4,5,5-tetramethyl(1,3,2-dioxaborolan-2-yl))pyrimidine-2-ylamine

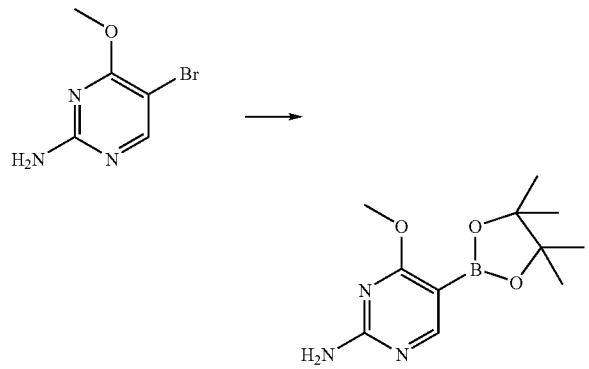

To a dry 200-mL flask was added 5-bromo-4-methoxypyrimidine-2-ylamine (2.88 g, 14.1 mmol), potassium acetate (4.16 g, 42.4 mmol), 4,4,5,5-tetramethyl-2-(4,4,5,5-tetramethyl-1,3,2-dioxaborolan-2-yl)-1,3,2-dioxaborolane (3.76 g, 14.8 mmol) and dioxane (75 mL). Argon was bubbled through the solution for 15 minutes, at which time 1,1'-bis(diphenylphosphino)ferrocene palladium(II) chloride dichloromethane adduct (0.58 g, 0.71 mmol). The reaction was refluxed in a 115° C. oil bath for 21 hours under argon. After cooling to room temperature, the dioxane was removed in vacuo. EtOAc (500 mL) was added and the resulting slurry was sonicated and filtered. Additional EtOAc (500 mL) was used to wash the solid. The combined organics were concentrated and the crude material was purified by SiO$_2$ chromatography (EtOAc as eluent) yielding 2.4 g of an off white solid. By $^1$H NMR the material was a 1:1 mixture of boronate ester and 4-methoxypyrimidine-2-ylamine. The material was used as is in subsequent Suzuki reactions. LCMS (m/z): 170 (MH$^+$ of boronic acid, deriving from in situ product hydrolysis on LC). $^1$H NMR (CDCl$_3$): δ 8.42 (s, 1H), 5.22 (bs, 2H), 3.90 (s, 3H), 1.34 (s, 12H).

Method 9

Synthesis of 5-bromo-6-fluoro-2-pyridylamine

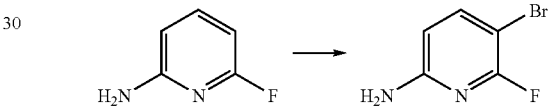

To a solution of 6-fluoro-2-pyridylamine (1.0 g, 8.93 mmol) in chloroform (55 mL) was added N-bromosuccinimide (1.59 g, 8.93 mmol). The solution was stirred in the dark for 15 hours, at which time it was added to CH$_2$Cl$_2$ (200 mL) and 1N NaOH (50 mL). Upon mixing, the layers were separated and the organic layer was washed with NaCl$_{(sat.)}$ (50 mL), dried over Na$_2$SO$_4$, filtered and concentrated. The crude material was purified by SiO$_2$ chromatography (25% EtOAc/hexanes) yielding 5-bromo-6-fluoro-2-pyridylamine (386 mg, 22%). LCMS (m/z): 190.9/192.9 (MH$^+$); $^1$H NMR (CDCl$_3$): δ 7.59 (t, J=8.7 Hz, 1H), 6.25 (dd, J=8.1, 1.2 Hz, 1H), 4.58 (bs, 1H).

Synthesis of 6-fluoro-5-(4,4,5,5-tetramethyl(1,3,2-dioxaborolan-2-yl))-2-pyridylamine

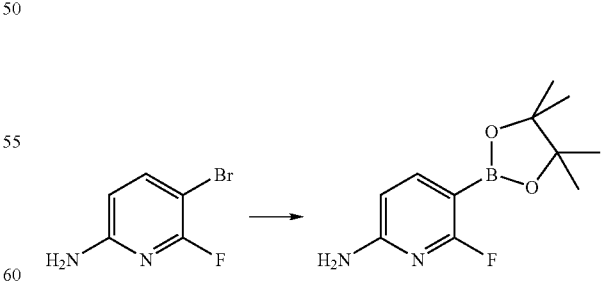

To a dry 50-mL flask was added 5-bromo-6-fluoro-2-pyridylamine (370 mg, 1.93 mmol), potassium acetate (569 mg, 5.8 mmol), 4,4,5,5-tetramethyl-2-(4,4,5,5-tetramethyl-1,3,2-dioxaborolan-2-yl)-1,3,2-dioxaborolane (538 mg, 2.12 mmol) and dioxane (15 mL). Argon was bubbled through the solution for 15 minutes, at which time 1,1'-bis(diphenylphosphino)ferrocene palladium(II) chloride dichloromethane adduct (79 mg, 0.09 mmol). The reaction was refluxed in a 115° C. oil bath for 4 hours under argon. After removal of the volatiles in vacuo, EtOAc (150 mL) was added and the solution was washed with H₂O (3×40 mL), with NaCl$_{(sat.)}$ (300 mL), dried over Na₂SO₄, filtered and concentrated. Purification by SiO₂ chromatography (30% EtOAc/hexanes) yielded boronate ester (161 mg, 35%). LCMS (m/z): 157 (MH⁺ of boronic acid, deriving from in situ product hydrolysis on LC) ¹H NMR (CDCl₃): δ 7.86 (t, J=8.4 Hz, 1H), 6.29 (dd, J=8.1, 2.7 Hz, 1H), 4.70 (bs, 1H), 1.32 (s, 12H).

Method 10

Synthesis of 5-bromo-4-fluoropyridin-2-amine

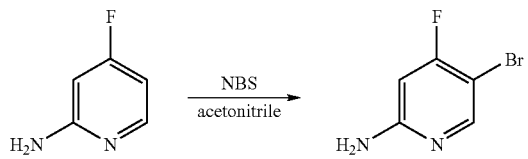

N-Bromosuccinimide (126 mg, 0.71 mmol) was added to a solution of 4-fluoropyridin-2-amine TFA salt (162 mg, 0.72 mmol) in acetonitrile (4 mL) in an aluminum foil-wrapped flask in a darkened hood. The reaction solution was stirred at room temperature in darkness for 2 hours. After evaporation of the solvent, the crude product was purified on a silica gel column eluting with EtOAc to give 5-bromo-4-fluoropyridin-2-amine as an ivory solid (92 mg, 67%). LC/MS (m/z): 190.9/192.9 (MH⁺), R$_t$ 1.02 minutes.

Synthesis of 4-fluoro-5-(4,4,5,5-tetramethyl-1,3,2-dioxaborolan-2-yl)pyridin-2-amine

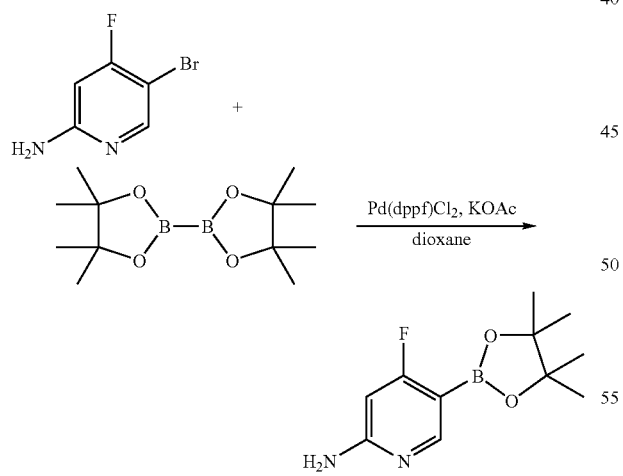

In a sealable Pyrex pressure vessel, a mixture of 5-bromo-4-fluoropyridin-2-amine (25 mg, 0.13 mmol), 4,4,5,5-tetramethyl-2-(4,4,5,5-tetramethyl-1,3,2-dioxaborolan-2-yl)-1,3,2-dioxaborolane (40 mg, 0.16 mmol), potassium acetate (51 mg, 0.52 mmol) and dichloro[1,1'-bis(diphenylphosphino)ferrocene]palladium(II)-dichloromethane adduct (16 mg, 0.019 mmol) was suspended in dioxane (1.7 mL) under argon. The pressure vessel was sealed and the reaction mixture was stirred at 110° C. for 2 hours. After the reaction was complete as judged by LCMS, the reaction mixture was cooled to room temperature and the 4-fluoro-5-(4,4,5,5-tetramethyl-1,3,2-dioxaborolan-2-yl)pyridin-2-amine was used in subsequent reactions without further purification, assuming a quantitative yield (0.13 mmol). LC/MS (m/z): 157.0 (MH⁺ of the boronic acid formed by product hydrolysis on LC), R$_t$ 0.34 minutes.

Method 11

Synthesis of 2-amino-5-bromo-isonicotinonitrile

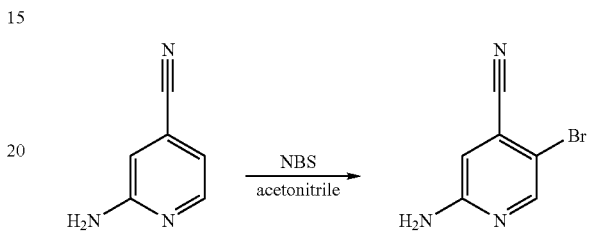

In an aluminum foil-covered flask in a darkened hood, 2-amino-isonicotinonitrile TFA salt (125 mg, 0.54 mmol) was dissolved in acetonitrile (3.5 mL). Solid N-bromosuccinimide (89.2 mg, 0.501 mmol) was added to the stirred solution in one portion at RT. The reaction solution was stirred at room temperature in darkness for 90 minutes. After evaporation of the solvent, the crude material was further purified by silica gel chromatography to give 2-amino-5-bromo-isonicotinonitrile (53 mg, 49%). LC/MS (m/z): 197.9 (MH⁺), R$_t$ 2.92 minutes.

Synthesis of 2-amino-5-boronic ester-isonicotinonitrile

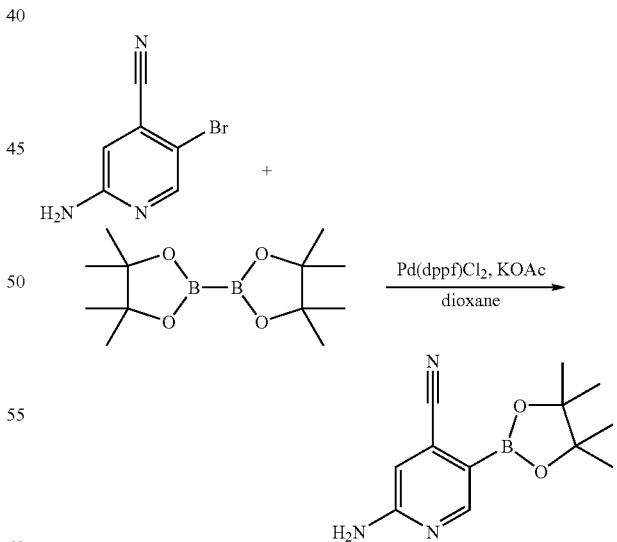

In a glass pressure vessel, a mixture of 2-amino-5-bromo-isonicotinonitrile (25 mg, 0.126 mmol), 4,4,5,5-tetramethyl-2-(4,4,5,5-tetramethyl-1,3,2-dioxaborolan-2-yl)-1,3,2-dioxaborolane (38 mg, 0.151 mmol) and potassium acetate (49 mg, 0.504 mmol) were suspended in dioxane (1.8 mL). After purging the mixture with argon for 1-2 min, dichloro[1,1'-bis (diphenylphosphino)ferrocene]palladium(II) dichloromethane adduct (16 mg, 0.019 mmol) was added in one portion. The reaction vessel was sealed and heated at 120° C. with stirring for 2 hours. The crude reaction solution was cooled to room temperature and used without further purification assuming a quantitative yield of the boronic ester (0.126 mmol). LC/MS (m/z): 164.0 (MH$^+$ of the boronic acid formed by product hydrolysis on LC), R$_t$ 0.37 minutes.

Method 12

Synthesis of 3-fluoro-5-(4,4,5,5-tetramethyl-1,3,2-dioxaborolan-2-yl)pyridin-2-amine Synthesis of N-allyl-3-fluoropyridin-2-amine

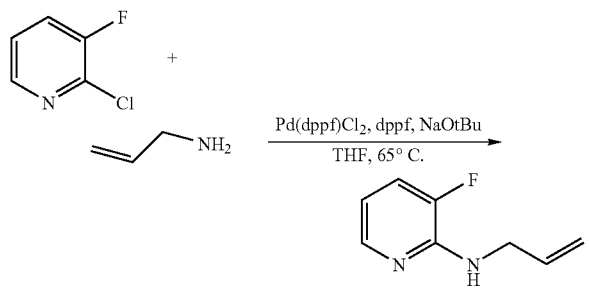

To a preformed bright-yellow complex of Pd(dppf)Cl$_2$ CH$_2$Cl$_2$ (41 mg, 0.05 mmol), dppf (83 mg, 0.15 mmol) and NaOt-Bu (1.4 g, 15 mmol) in THF (20 mL) was added 2-chloro-3-fluoropyridine (1.32 g, 10 mmol) and allylamine (1.2 mL, 15 mmol). The mixture was sparged with nitrogen and the pressure vessel was capped and sealed. The reaction was heated at 65-70° C. for 16 hours. The cooled reaction was filtered through a plug of Celite and the pad was washed with EtOAc (30 mL). The solvent was removed under reduced pressure to give a brown thick oil. The crude product was purified by silica gel chromatography eluting with 5% MeOH in EtOAc. The product-containing fractions were diluted with EtOAc (100 mL) and extracted with 1 M HCl (2×50 mL). The aqueous acidic product was lyophilized to a light brown solid giving N-allyl-3-fluoropyridin-2-amine as an HCl salt (1.6 g, 85%). LC/MS (m/z): 153.1 (MH$^+$), R$_t$ 0.5 minutes.

Synthesis of 3-fluoropyridin-2-amine

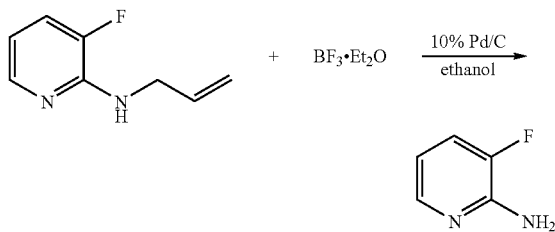

In one portion, 10% Pd/C (1.23 g) was added to a solution of N-allyl-3-fluoropyridin-2-amine (1.62 g, 7.18 mmol) and BF$_3$·Et$_2$O (900 uL, 7.18 mmol) in EtOH (20 mL) at RT under nitrogen. After stirring at 80° C. for 2 days, the reaction mixture was filtered through a plug of Celite and the pad was washed with EtOH (20 mL). 6 N HCl was added to the light yellow filtrate until the solution was acidic. The HCl salt of 3-fluoropyridin-2-amine is much less volatile than the free base. The filtrate was concentrated under reduced pressure. The salt residue was dried in vacuo to give 3-fluoropyridin-2-amine as a light yellow glassy solid (1.66 g, quant. yield). LC/MS (m/z): 113.0 (MH$^+$), R$_t$ 0.41 minutes.

Synthesis of 5-bromo-3-fluoropyridin-2-amine and 3-fluoro-5-(4,4,5,5-tetramethyl-1,3,2-dioxaborolan-2-yl)pyridin-2-amine

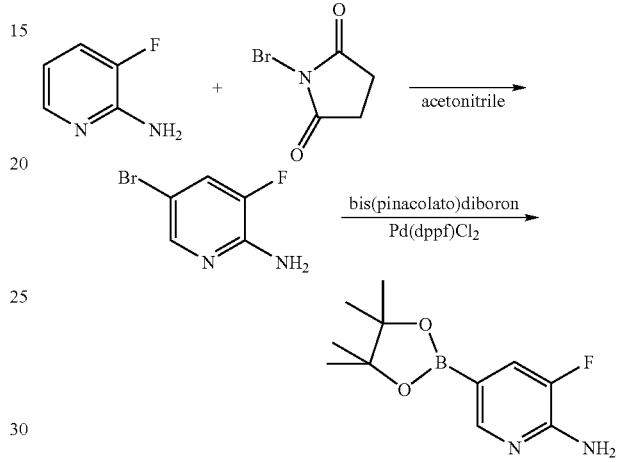

Solid NBS (750 mg, 4.2 mmol) was added to a solution of 3-fluoropyridin-2-amine HCl salt (1.66 g, 7.18 mmol) in ACN (30 mL) at RT with stirring. The reaction was shielded from light and stirred under nitrogen. After 1 h, an additional amount of NBS (250 mg, 1.4 mmol) was added to the reaction. After 1 h, the solvent was removed under reduced pressure and the residue purified by silica gel flash chromatography eluting with 70% EtOAc/hexane followed by 100% EtOAc to afford 5-bromo-3-fluoropyridin-2-amine as a yellow-brown solid (1.26 g, 92% yield). LC/MS (m/z): 191.0/193.0 (MH$^+$), R$_t$ 1.18 minutes.

The bromide was converted to the pinacolborane ester under conditions described in Method 1. LC/MS (m/z): 157.0 (MH$^+$), R$_t$ 0.36 minutes.

Method 13

Synthesis of 4-fluoro-5-(4,4,5,5-tetramethyl-1,3,2-dioxaborolan-2-yl)pyridin-2-amine Synthesis of N-allyl-4-fluoropyridin-2-amine

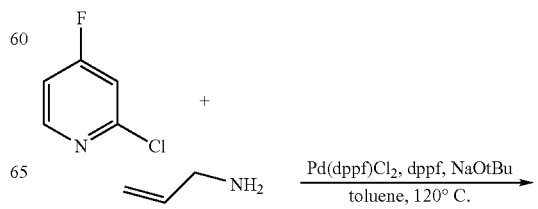

-continued

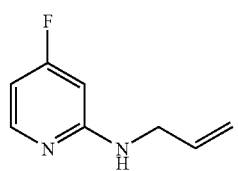

To a preformed red-brown complex of Pd(dppf)Cl₂ (817 mg, 1.0 mmol), dppf (1.66 g, 3.0 mmol) and NaOtBu (2.9 g, 30 mmol) in toluene (30 mL) was added 2-chloro-4-fluoropyridine (2.16 g, 20 mmol) and allylamine (1.2 mL, 15 mmol). The mixture was sparged with nitrogen and the pressure vessel was capped and sealed. The reaction was heated at 120-125° C. for 18 hours. The cooled dark brown reaction was filtered through a plug of Celite and the pad was washed with EtOAc (60 mL). The solvent was gently removed under reduced pressure to give a brown thick oil which can sublime under vacuum. The crude mixture was acidified with 6 N HCl (10 mL) and lyophilized to dryness to give a brown powder as the HCl salt. The crude product was partitioned between EtOAc (100 mL) and sat. NaHCO₃ (80 mL) The layers were separated and the aqueous layer was extracted again with EtOAc (100 mL). The combined organic layers are washed with brine (100 mL), dried over sodium sulfate, filtered and concentrated under reduced pressure to give a brown solid N-allyl-4-fluoropyridin-2-amine (690 mg, 25%). LC/MS (m/z): 153.0 (MH⁺), $R_t$ 1.13 minutes.

Synthesis of N-allyl-4-fluoropyridin-2-amine

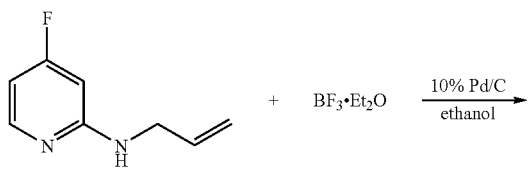

In one portion, 10% Pd/C (552 mg) was added to a solution of N-allyl-4-fluoropyridin-2-amine (690 mg, 3.07 mmol) and BF₃·Et₂O (0.386 mL, 3.07 mmol) in abs. EtOH (12 mL) at RT under nitrogen. After stirring at 80° C. for 24 h, reaction mixture was filtered through a plug of Celite and the pad was washed with MeOH (100 mL). 6 N HCl (2 mL) was added to the dark filtrate until the solution was acidic. The HCl salt of 4-fluoropyridin-2-amine is much less volatile than the free base. The filtrate was concentrated under reduced pressure and dried in vacuo. The crude product was purified by preparative HPLC to give 4-fluoropyridin-2-amine as a brown powder TFA salt (162 mg, 23%). LC/MS (m/z): 113.0 (MH⁺), $R_t$ 0.40 minutes.

Synthesis of 5-bromo-4-fluoropyridin-2-amine and 4-fluoro-5-(4,4,5,5-tetramethyl-1,3,2-dioxaborolan-2-yl)pyridin-2-amine

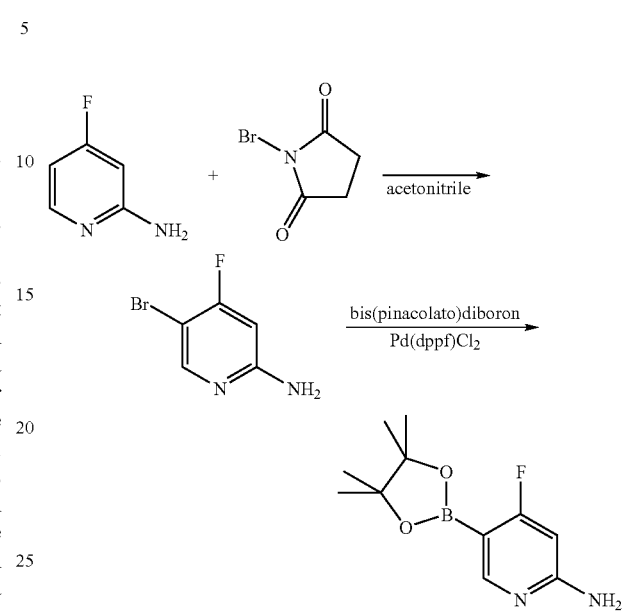

Solid NBS (78 mg, 0.43 mmol) was added to a solution of 3-fluoropyridin-2-amine HCl salt (162 mg, 0.72 mmol) in ACN (4 mL) at RT with stirring. The reaction was shielded from light and stirred under nitrogen. After 1.5 h, an additional amount of NBS (15 mg, 0.084 mmol) was added to the reaction. Checking the reaction again after 1.5 h, an additional amount of NBS (15 mg, 0.084 mmol) was added to the reaction until the starting material had been consumed by LCMS. After 1 h, the solvent was removed under reduced pressure and the residue purified by silica flash chromatography eluting with 50% ethyl acetate/hexane to afford 5-bromo-4-fluoropyridin-2-amine as a ivory solid (92 mg, 68%). LC/MS (m/z): 190.9/192.9 (MH⁺), $R_t$ 1.02 minutes.

The bromide was converted to the pinacolborane under conditions described in Method 1. LC/MS (m/z): 157.0 (MH⁺), $R_t$ 0.34 minutes.

Method 14

Synthesis of 2-(5-nitropyridin-2-yloxy)-N,N-dimethylethanamine

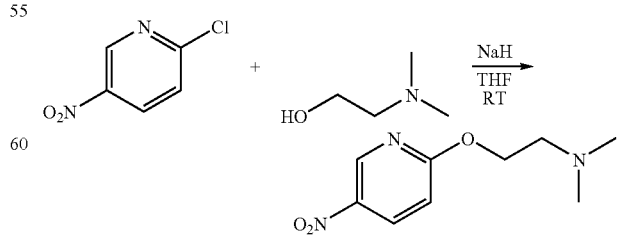

Microwave heating. To a solution of 2-(dimethylamino)ethanol (339 mg, 3.80 mmol) in DMF (5 mL) was added sodium bis(trimethylsilyl)amide (4.75 mL, 1M solution in THF, 4.75 mmol). The mixture was stirred at room temperature for 15 min. 2-Chloro-5-nitropyridine (500 mg, 3.16 mmol) was then added. The vial was capped and subjected to microwave irradiation (150° C. for 10 minutes). The mixture was diluted with water (250 mL) and EtOAc (250 mL). The two layers were separated, and the aqueous layer extracted two more times with EtOAc. The organic extracts were combined, washed with water and brine, dried over sodium sulfate and evaporated to give the crude material as brown oil. Purification by column chromatography on silica gel using 5% methanol/methylene chloride yielded 2-(5-nitropyridin-2-yloxy)-N,N-dimethylethanamine as a light yellow solid (295 mg, 44%).

Sodium hydride and oil bath heating. To a mixture of sodium hydride (189 mg, 4.73 mmol) in anhydrous tetrahydrofuran (2 mL) at 0° C. a solution of 2-chloro-5-nitropyridine (500 mg, 3.16 mmol) and 2-(dimethylamino)ethanol (353 mg, 3.96 mmol) in anhydrous tetrahydrofuran (4 mL) was added dropwise. The reaction was warmed to room temperature and stirred for 16 h. The THF was evaporated, and water (100 mL) and EtOAc (200 mL) were added. The aqueous layer was extracted with EtOAc (200 mL), and the organic layers combined, washed with brine, dried over sodium sulfate and concentrated to give a brown oil. Purification column chromatography on silica gel using 5% methanol/methylene chloride yielded 2-(5-nitropyridin-2-yloxy)-N,N-dimethylethanamine as a light yellow solid (233=mg, 35%). LC/MS (m/z): 212.2 (MH+), R$_t$ 1.28 minutes.

Synthesis of 6-(2-(dimethylamino)ethoxy)pyridin-3-amine

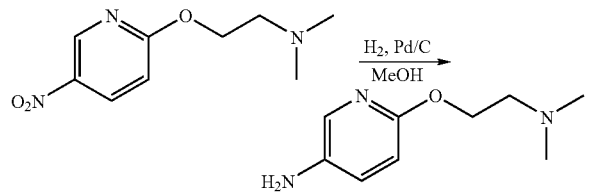

2-(5-Nitropyridin-2-yloxy)-N,N-dimethylethanamine (295 mg, 1.40 mmol) was dissolved in 5 mL of methanol and placed under a nitrogen atmosphere. A catalytic amount of 10% palladium on carbon was added and a hydrogen balloon was connected to the reaction flask. The flask was flushed five times with hydrogen and stirred at room temperature under hydrogen atmosphere for 16 hours. The solid was filtered and washed with methanol. The filtrate was evaporated under reduced pressure yielding 6-[2-(dimethylamino)ethoxy]pyridin-3-amine as a brown oil (250 mg, 99%). LC/MS (m/z): 182.1 (MH+), R$_t$ 0.36 minutes.

Method 15

Synthesis of 2-(1-methylpiperidin-4-yloxy)-5-nitropyridine

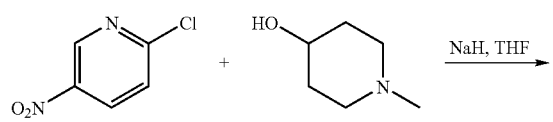

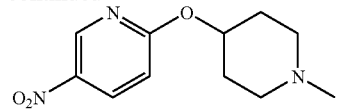

To a mixture of sodium hydride (189 mg, 4.73 mmol) in anhydrous tetrahydrofuran (2 mL) at 0° C., a solution of 2-chloro-5-nitropyridine (500 mg, 3.16 mmol) and 1-methylpiperidin-4-ol (455 mg, 3.96 mmol) in anhydrous tetrahydrofuran (4 mL) was added dropwise. The reaction was heated reflux for 16 h. The THF was evaporated and water (100 mL) and EtOAc (200 mL) were added. The aqueous layer was extracted with EtOAc (200 mL). The organic layers were combined, washed with brine, dried over sodium sulfate and concentrated to give a brown oil. Purification by silica gel column chromatography using 3% methanol/methylene chloride yielded 2-(1-methylpiperidin-4-yloxy)-5-nitropyridine as a yellow solid, (367 mg, 49%). LC/MS (m/z): 238.0 (MH+), R$_t$ 1.59 minutes.

Synthesis of 6-(1-methylpiperidin-4-yloxy)pyridin-3-amine

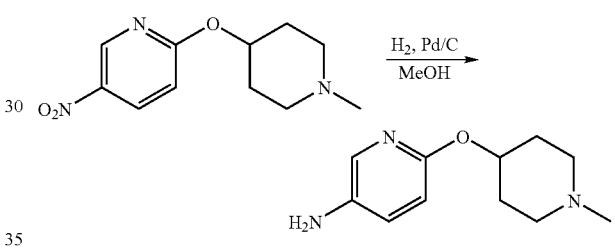

2-(1-Methylpiperidin-4-yloxy)-5-nitropyridine (100 mg, 0.42 mmol) was dissolved in 5 mL of methanol and placed under a nitrogen atmosphere. A catalytic amount of 10% palladium on carbon was added and a hydrogen balloon connected to the reaction flask. The flask was flushed five times with hydrogen and stirred at room temperature under hydrogen atmosphere. The solid was filtered and washed with methanol. The filtrate was evaporated under reduced pressure to yield 6-(1-methylpiperidin-4-yloxy)pyridin-3-amine as a brown solid (85 mg, 98%). LC/MS (m/z): 208.2 (MH+), R$_t$ 0.34 minutes.

Method 16

Synthesis of tert-butyl 4-(5-nitropyridin-2-yloxy)piperidine-1-carboxylate

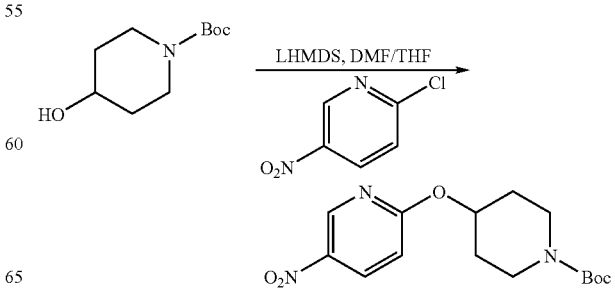

To a solution of tert-butyl 4-hydroxypiperidine-1-carboxylate (1 eq) in DMF was added potassium bis-trimethylsilylamide (1.5 eq, 1M solution in tetrahydrofuran). The solution was stirred at room temperature for 10 minutes, and 2-chloro-5-nitropyridine (1.2 eq) was added. The reaction mixture was submitted to microwave irradiation for 600 seconds at 145° C. EtOAc and water were added to the reaction and the layers separated. The organic layer was washed with water, brine, dried over sodium sulfate and evaporated to give brown crude material. Purification by silica gel column chromatography using 10% EtOAc/hexane afforded the product as a light yellow solid. LC/MS (m/z): 324.3 (MH$^+$) R$_t$ 3.33 minutes Synthesis of 5-nitro-2-(piperidin-4-yloxy)pyridine

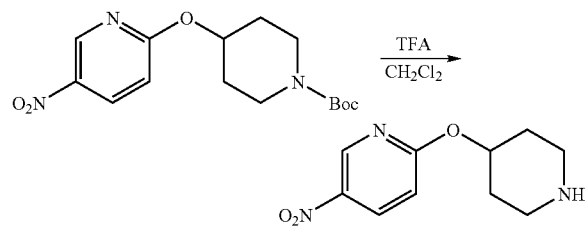

Trifluoroacetic acid (5 eq) was added to a solution of tert-butyl 4-(5-nitropyridin-2-yloxy)piperidine-1-carboxylate (1 eq) in dichloromethane, stirring at room temperature for 1 hour. The solvent was then evaporated, the residue brought to pH=10 with sat. aq. Na$_2$CO$_3$ solution and extracted with EtOAc. The organic layer was washed with brine, dried over sodium sulfate and evaporated to afford the product as a light yellow crystalline solid. LC/MS (m/z): 224.3 (MH$^+$), R$_t$ 1.64 minutes Synthesis of 2-(1-isopropylpiperidin-4-yloxy)-5-nitropyridine

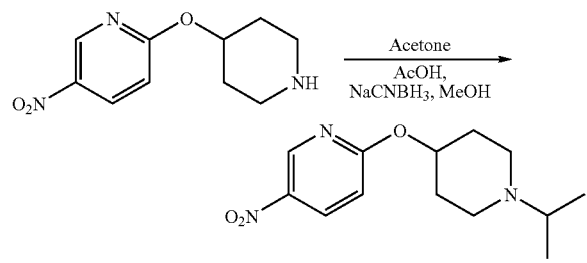

To a solution of 10% acetic acid in methanol was added 5-nitro-2-(piperidin-4-yloxy)pyridine (1 eq) and anhydrous acetone (5 eq). The solution was stirred at room temperature for 1 hour. The reaction mixture was cooled to 0° C. on an ice bath and sodium cyanoborohydride (1.5 eq) was added. The reaction mixture was then warmed to room temperature and stirred for 5 hours. The solvent was evaporated, the residue brought to pH=10 with sodium carbonate and extracted with EtOAc. The organic layer was washed with water, brine, dried over sodium sulfate, and evaporated to give the crude material. Purification by silica gel column chromatography using 2% methanol/dichloromethane afforded the product as a yellow solid. LC/MS (m/z): 266.3 (MH$^+$), R$_t$ 1.85 minutes.

Synthesis of 6-(1-isopropylpiperidin-4-yloxy)pyridin-3-amine

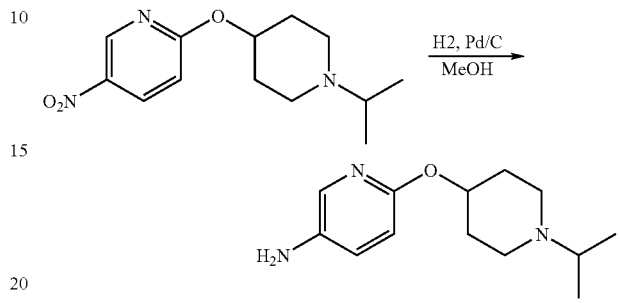

2-(1-Isopropylpiperidin-4-yloxy)-5-nitropyridine (1 eq) was dissolved in methanol and laced under a nitrogen atmosphere. A catalytic amount of 10% palladium on carbon was added and a hydrogen balloon connected to the reaction flask. The flask was flushed five times with hydrogen and stirred at room temperature for 4 hours under hydrogen atmosphere. The solid was filtered and washed with methanol. The filtrate was evaporated under reduced pressure yielding the product as a brown oil. LC/MS (m/z): 236.3 (MH$^+$), R$_t$ 0.38 minutes.

Method 17

Synthesis of 7-methylthio-3-nitroquinoline

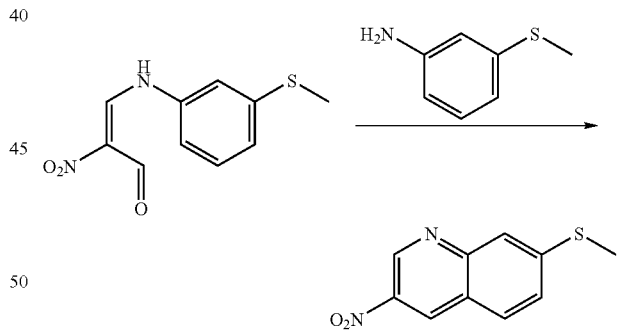

To a refluxing mixture of 3-[(3-methylthiophenyl)amino]-2-nitroprop-2-enal (2.3 g, 9.6 mmol) and the HCl salt of 3-methylthiophenylamine (2.7 g, 19.3 mmol) in acetic acid (25 mL) was added thiophenol (0.2 g, 1.9 mmol). After being refluxed for 18 h, the mixture was cooled to room temperature and the acetic acid was removed under reduced pressure. To the remaining dark colored solid EtOAc (50 mL) was added with stirring. Filtration gave a yellow/green solid and a dark filtrate. The product crystallized from the EtOAc solution upon standing. Filtration and rinsing with cold EtOAc gave 330 mg crystalline product. The yellow/green solid was washed with 3×250 mL portions of dichloromethane. The dichloromethane washes were concentrated to give an additional 150 mg of product (23%). LC/MS (m/z): 221.1 (MH$^+$), R$_t$ 2.54 minutes.

Synthesis of 7-(methylsulfonyl)-3-nitroquinoline

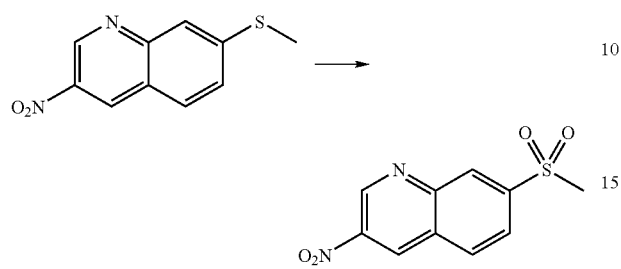

To an ice-bath chilled solution of 7-methylthio-3-nitroquinoline (141 mg, 0.6 mmol) in dichloromethane (6 mL) was added MCPBA (221 mg, 1.3 mmol) in dichloromethane (3 mL). After warming to room temperature, the white precipitate formed was filtered and rinsed with an additional 10 mL of dichloromethane to yield the pure product (85 mg, 53%). LC/MS (m/z): 252.9 (MH$^+$), R$_t$ 1.82 minutes.

Synthesis of 7-(methylsulfonyl)-3-quinolylamine

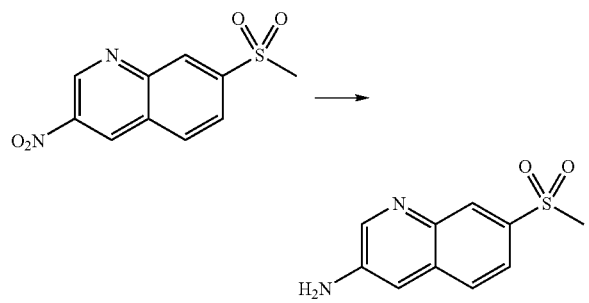

To a suspension of 7-(methylsulfonyl)-3-nitroquinoline (85 mg, 0.4 mmol) in EtOAc (6 mL,) under argon, was added 10% Pd/C (22 mg, 0.04 mmol). A H$_2$ balloon was connected to the reaction flask, the flask was purged with H$_2$ three times and the reaction mixture was allowed to stir under H$_2$ atmosphere for 18 h. Unreacted starting material could be seen settling to the bottom of the flask together with the catalyst. The solids were removed from the EtOAc solution by filtration. Evaporation of EtOAc under reduced pressure yielded 7-(methylsulfonyl)-3-quinolylamine (22 mg, 30%). LC/MS (m/z): 223.0 (MH$^+$), R$_t$ 1.10 minutes.

Method 18

Synthesis of 6-methoxyquinolin-3-amine

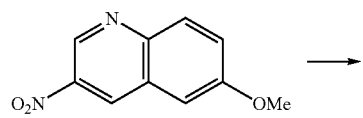

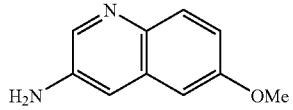

A mixture of 6-methoxy-3-nitroquinoline (Magnus, P. et al., *J. Am. Chem. Soc.* 119, 5591, 1997; 0.17 g, 0.83 mmol) and Pd/C (10%, 80 mg) in EtOAc (15 mL) was hydrogenated with a hydrogen balloon to give 6-methoxyquinolin-3-amine in quantitative yield. LC/MS (m/z): 175.1 (MH+), R$_t$ 1.54 minutes.

Method 19

Synthesis 6-hydroxy-3-nitroquinoline

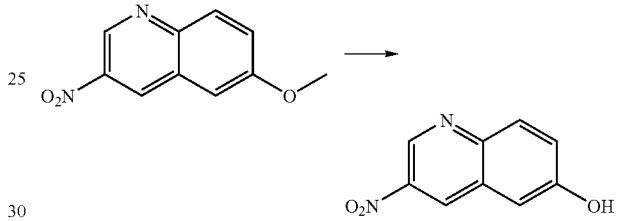

6-Methoxy-3-nitroquinoline (Magnus, P. et al., *J. Am. Chem. Soc.* 119, 5591, 1997; 100 mg, 0.49 mmol) was dissolved in hydrogen bromide solution (47% aq, 2.5 mL, 0.2 M), heated and stirred at 120° C. for 16 hours. The reaction mixture was cooled to room temperature, neutralized with 6N NaOH, then extracted with EtOAc (150 mL). The organic layer was dried over Na$_2$SO$_4$ and purified by flash chromatography (SiO$_2$, 40-50% EtOAc/hexanes), obtaining 73 mg (78%) of 6-hydroxy-3-nitroquinoline. LC/MS (m/z): 190.9 (MH$^+$), R$_t$ 1.97 minutes.

Synthesis of 3-nitro-6-(2-(pyrrolidin-1-yl)ethoxy)quinoline

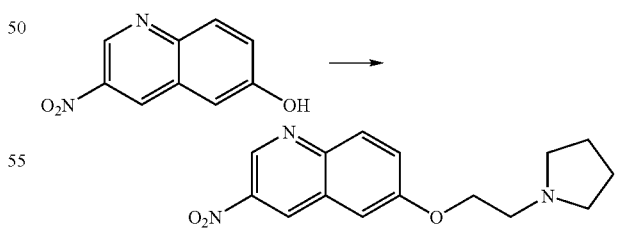

6-Hydroxy-3-nitroquinoline (148 mg, 0.78 mmol) was dissolved in THF (18 mL). 2-(Pyrrolidin-1-yl)ethanol (0.091 mL, 0.78 mmol) and triphenylphosphine (306 mg, 1.17 mmol) were added. Lastly, diethyl azodicarboxylate (0.184 mL, 1.17 mmol) was added and the reaction mixture was allowed to stir at room temperature for 2 hours. The solvent was then concentrated in vacuo and the residue was purified by flash chromatography (SiO$_2$) to yield 134 mg (60%) of 3-nitro-6-(2-(pyrrolidin-1-yl)ethoxy)quinoline. LC/MS (m/z): 288.1 (MH$^+$), R$_t$ 1.80 minutes.

Synthesis of 3-amino-6-(2-(pyrrolidin-1-yl)ethoxy)quinoline

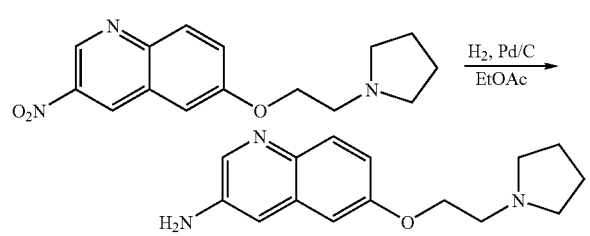

3-Nitro-6-(2-(pyrrolidin-1-yl)ethoxy)quinoline (134 mg, 0.46 mmol) was dissolved in EtOAc (10 mL) and the solution was sparged with N$_2$ for several minutes. Triethylamine (0.065 mL, 0.46 mmol) was then added followed by a catalytic amount of 10% Pd/C. Sparging with N$_2$ was repeated after each addition. A balloon of H$_2$ was connected to the reaction flask and the reaction mixture was stirred at room temperature under H$_2$ atmosphere for 48 hours. The mixture was then filtered through a Celite pad and concentrated to obtain crude 3-amino-6-(2-(pyrrolidin-1-yl)ethoxy)quinoline, which was used as is in the next reaction. LC/MS (m/z): 258.1 (MH$^+$), R$_t$ 0.33 minutes.

Method 20

Synthesis of 5-methoxy-3-nitro-quinoline

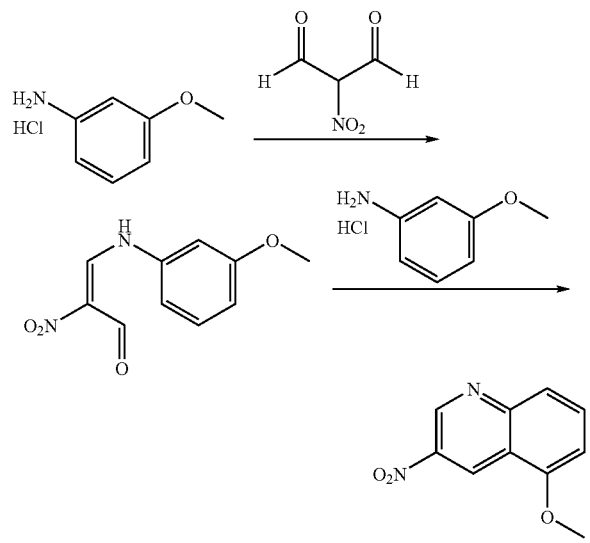

Synthesis of 3-(3-methoxy-phenylamino)-2-nitro-propenal

To the HCl salt of 3-methoxy-phenylamine (4.6 g, 28.9 mmol) in 1N HCl (300 mL) was added a solution of 2-nitromalonaldehyde (2.7 g, 19.3 mmol) in 150 mL water. After 30 min, the precipitate was filtered and rinsed with 0.1 N HCl. Air-drying in a Büchner funnel for 18 h gave 3.36 g (78%) of a light yellow/green powder. LC/MS (m/z): 245.1 (MH$^+$+Na), R$_t$ 2.21 minutes.

Synthesis of 5-methoxy-3-nitroquinoline and 7-methoxy-3-nitroquinoline

To the HCl salt of 3-methoxy-phenylamine (4.7 g, 29.7 mmol) in 30 mL acetic acid was added 3-(3-methoxy-phenylamino)-2-nitro-propenal (3.3 g, 14.9 mmol). The reaction mixture was heated to reflux, and thiophenol (0.3 mL, 2.98 mmol) was added. After 22 h, the reaction mixture was cooled to room temperature and the solvent was removed in vacuo. Addition of 70 mL EtOAc and filtration gave solid byproduct, 7-methoxy-3-nitro-quinoline, and a filtrate, which contained impure 5-methoxy-3-nitro-quinoline. The filtrate was loaded on to silica column and eluted from 5% to 25% EtOAc in hexanes at 85 mL/min for 30 minutes. The product-enriched fractions were concentrated and taken on to the next step as a mixture of 5- and 7-methoxy substituted 3-nitroquinolines. LC/MS (m/z): 205.1 (MH$^+$), R$_t$ 2.26 minutes.

Synthesis of 5-methoxyquinolin-3-amine

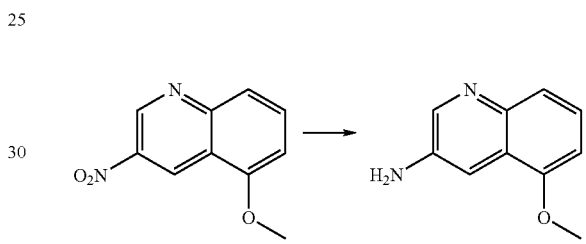

A mixture of 5- and 7-methoxy substituted 3-nitroquinolines (780 mg, 3.82 mmol) was dissolved in EtOAc (75 mL) and the reaction mixture sparged with N$_2$ for several minutes. 10% Pd/C (54 mg) was then added and a H$_2$ balloon was connected to the reaction flask. The reaction mixture was sparged with H$_2$ and stirred at room temperature under H$_2$ atmosphere overnight. Solvent removal in vacuo and purification by column chromatography on silica gel (100% EtOAc) afforded the two separated isomers 5-methoxyquinolin-3-amine and 7-methoxyquinolin-3-amine. The desired product 5-methoxyquinolin-3-amine (80 mg, 12%) was obtained as a yellow powder. The structure was assigned by $^1$H NMR (CD$_3$OD): δ 8.40 (d, 1H), 7.69 (d, 1H), 7.40 (d, 1H), 7.30 (t, 1H), 6.85 (d, 1H). LC/MS (desired isomer) (m/z): 175.0 (MH$^+$), R$_t$ 1.54 minutes; LC/MS (undesired isomer) (m/z): 175.0 (MH$^+$), R$_t$ 1.53 minutes.

Method 21

Synthesis of 2-(methylsulfonyl)pyridin-4-amine

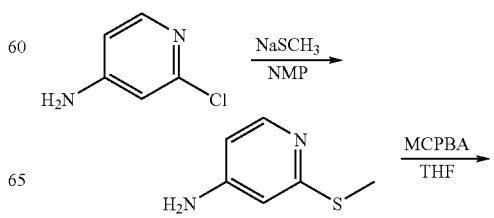

-continued

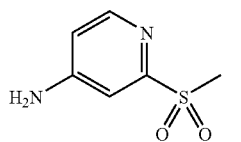

Synthesis of 2-(methylthio)pyridin-4-amine

Sodium thiomethoxide (140 mg, 1.98 mmol) was added to a solution of 2-chloropyridin-4-amine (150 mg, 1.17 mmol) in NMP (0.65 mL) in a pressure vessel. The vessel was sealed and heated in a microwave to 200° C. for 800 sec. Purification by silica flash chromatography eluting with 8% MeOH/DCM afforded 2-(methylthio)pyridin-4-amine (435 mg, 50% yield). LC/MS (m/z): 140.9 (MH$^+$), R$_t$ 0.59 minutes.

Solid MCPBA (780 mg, 2-3 mmol) was slowly added in small portions to a solution of 2-(methylthio)pyridin-4-amine (435 mg, 1.17 mmol) in THF (7 mL) at RT, with stirring. The reaction was followed by LCMS as the starting material was consumed by titrating with MCPBA. Silica was added to the reaction mixture, which was then concentrated to dryness under reduced pressure. Silica supported crude was purified by silica flash chromatography, eluting with 5% MeOH/DCM, to afford 2-(methylsulfonyl)pyridin-4-amine (220 mg, quant. yield). LC/MS (m/z): 173.0 (MH$^+$), R$_t$ 0.34 minutes.

Method 22

Synthesis of 2-morpholinopyrimidine-4,6-diol

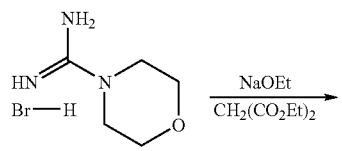

Sodium (17.25 g, 150 mmol) was cut into small pieces and slowly added to EtOH (500 mL) in a 1-L round bottom flask under N$_2$ and cooled with water. After all the sodium was dissolved, morpholinoformamidine hydrobromide (52.5 g, 50 mmol) and diethyl malonate (40 g, 50 mmol) were added. The mixture was heated to reflux for three hours. The reaction mixture was cooled to room temperature, and the ethanol was removed in vacuo. Aqueous HCl (1N, 800 mL) was added, to the white solid, at room temperature. The solid initially dissolved, giving a clear solution, then the product crashed out as a white solid. After 1 h at room temperature, the solid was filtered, washed with water (3×), dried (air and then over P$_2$O$_5$) to give 2-morpholinopyrimidine-4,6-diol (42.5 g, 86%). LC/MS (m/z): 198.1 (MH$^+$), R$_t$ 0.51 minutes.

Synthesis of 4,6-dichloro-2-morpholinopyrimidine

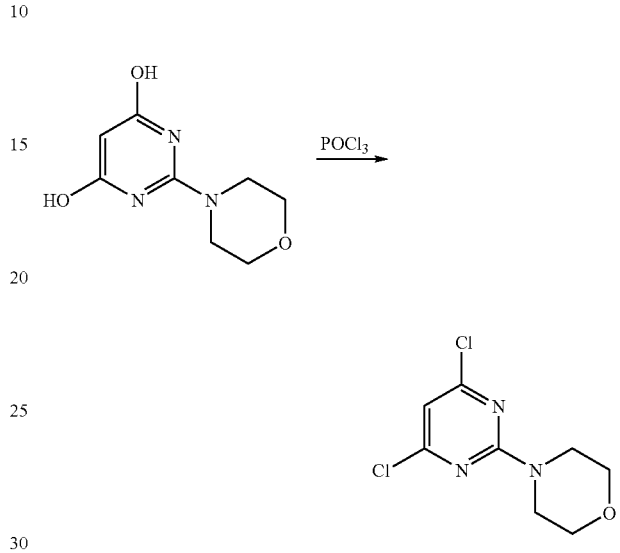

A mixture of 2-morpholinopyrimidine-4,6-diol (30 g, 0.15 mol) and POCl$_3$ (150 mL, 1.61 mol) was heated at 120° C. for 16 h, then cooled to RT. Excess POCl$_3$ was removed to give a semi-solid. The solid was gradually transferred to a stirring solution of water (700 mL) and EtOH (100 mL) occasionally cooled with water. White solid formed and was subsequently filtered, washed with water, 10% EtOH in water, and dried over P$_2$O$_5$ to give 4,6-dichloro-2-morpholinopyrimidine (17.82 g, 50%). LC/MS (m/z): 233.9 (MH$^+$), R$_t$ 2.95 minutes.

Method 23

Synthesis of 4,6-dichloro-5-methyl-2-morpholinopyrimidine 4,6-Dichloro-5-methyl-2-morpholinopyrimidine was prepared by similar procedure as 4,6-dichloro-2-morpholinopyrimidine (in Method 22) using dimethyl 2-methylmalonate in place of diethyl malonate. LC/MS (m/z): 248.1 (MH$^+$).

Method 24

Synthesis of 4,6-dichloro-5-ethyl-2-morpholinopyrimidine

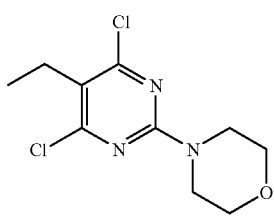

4,6-Dichloro-5-ethyl-2-morpholinopyrimidine was prepared by similar procedure as 4,6-dichloro-2-morpholinopyrimidine (in Method 22) using dimethyl 2-ethylmalonate in place of diethyl malonate. LC/MS (m/z): 262.1 (MH$^+$), R$_t$ 3.59 minutes.

Method 25

Synthesis of 5-fluoro-2-morpholinopyrimidine-4,6-diol

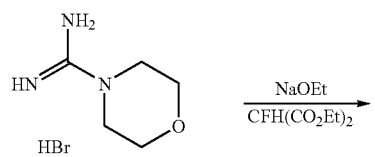

Sodium hydride (60% in oil, 3.9 g, 96.5 mmol) was washed with hexanes in a round bottom flask under argon and cooled with an ice water bath. EtOH (100 mL) was slowly added. The resulting mixture was warmed to RT and stirred for 30 minutes. To the base mixture, diethyl 2-fluoromalonate (5.7 g, 32.2 mmol) was added, followed by morpholinoformamidine hydrobromide (6.8 g, 32.2 mmol). The mixture was heated to 90-95° C. with stirring under argon. After 12 hours, the reaction was cooled to room temperature and the EtOH was removed in vacuo. The resulting white solid was dissolved in water (25 mL) and acidified with conc. HCl to pH=3-4. A white precipitate formed which was collected on a Büchner filter, washed with water (2×50 mL), air dried on the filter, and dried in vacuo to give 5-fluoro-2-morpholinopyrimidine-4,6-diol (0.87 g, 12%). LC/MS (m/z): 216.0 (MH$^+$), R$_t$ 0.63 minutes.

Synthesis of 4-(4,6-dichloro-5-fluoropyrimidin-2-yl)morpholine

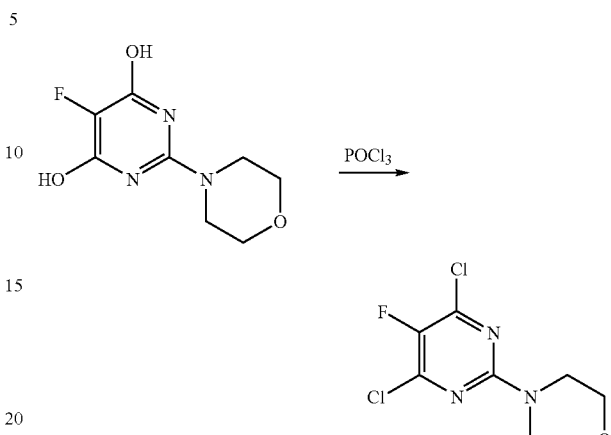

A mixture of 5-fluoro-2-morpholinopyrimidine-4,6-diol (0.87 g, 4.0 mmol) and POCl$_3$ (10 mL) was heated at 120° C. for 16 hours, then cooled to RT. Excess of POCl$_3$ was removed under reduced pressure to give a semi-solid which was dried further in vacuo. After 12 h of vacuum drying, the solid was diluted in EtOAc (150 mL) and washed with sat. NaHCO$_3$ (60 mL). A solid formed during the wash and was discarded with the aqueous layer. The organic layer was washed again with sat. NaHCO$_3$ (2×30 mL), brine (30 mL), dried with Na$_2$SO$_4$, filtered and evaporated under reduced pressure to give a crude product. The product was purified by flash chromatography eluting with 25% EtOAc/hexane to give 4-(4,6-dichloro-5-fluoropyrimidin-2-yl)morpholine (418 mg, 42%). LC/MS (m/z): 251.9 (MH$^+$), R$_t$ 3.22 minutes.

Method 26

Synthesis of 2,4,6-tribromopyrimidine

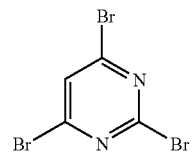

To a mixture of pyrimidine-2,4,6(1H,3H,5H)-trione (2.66 g, 20.87 mmol) and POBr$_3$ (25 g, 87.2 mmol) in toluene (35 mL) in a 200 mL flask, N,N-dimethylaniline (4.52 mL, 35.7 mmol) was added. The brick-red slurry was heated to reflux for 3 hours. During the process a biphasic solution formed with a red gum at the bottom of the flask and a clear yellow liquid above. The reaction mixture was cooled to room temperature and the yellow organic layer decanted off. The red gum was rinsed once with EtOAc. The combined organic extracts were washed with saturated NaHCO$_3$ (3×, or until CO$_2$ evolution ceased), H$_2$O (3×), brine (2×) and dried over Na$_2$SO$_4$. The solution was then concentrated and dried under high vacuum to yield 2,4,6-tribromopyrimidine (5.40 g, 82%), which was used without further purification. LC/MS (m/z): 316.8/318.7 (MH+), $R_t$ 2.78 minutes.

Method 27

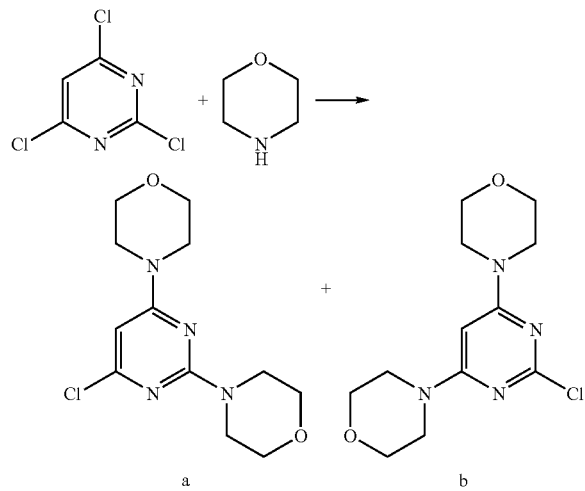

A solution of morpholine (100 g; 1.15 moles; 5.3 equivalents) in THF (450 mL) was cooled with an ice bath. A solution of 2,4,6-trichloropyrimidine (39.9 g; 217 mmoles; 1.0 equivalents) in THF (100 mL) was added over a period of 30 minutes. A copious white precipitate formed upon addition of 2,4,6-trichloropyrimidine and the reaction mixture rapidly thickened. The mixture was allowed to warm to ambient temperature and mechanically stirred for 64 hours (heating the reaction mixture at reflux following the addition of 2,4,6-trichloropyrimidine leads to complete reaction in 60 min. The ratio of a to b was unchanged). The mixture was then filtered and the filter cake washed with additional THF (2×100 mL). The filtrate was concentrated on the rotavap. Water (600 mL) was added and the resulting slurry was stirred for 30 minutes. The solids were isolated by filtration, washed with additional water (2×100 mL) and dried overnight under vacuum. Yield a+b: 61.3 g (99%). Product was 87% a by hplc area percent; remainder is b.

31 g of the crude solid was dissolved in 200 mL of $CH_2Cl_2$ and applied to 600 g of dry silica in a fritted glass funnel. The silica was eluted with 1:1 hexane:EtOAc and 300 mL fractions were collected. TLC analysis shows a to be present in fractions 1-7 and 4,6-dimorpholino-2-chloropyrimidine in fractions 6-10. Fractions 1-5 were pooled and concentrated to provide a white solid. Yield: 28.2 g (Product was 98% a by hplc area percent).

Method 28

Synthesis of 4-(1-isopropylpiperidin-4-yloxy)aniline
Synthesis of T-butyl 4-(2-methoxy-4-nitrophenoxy) piperidine-1-carboxylate

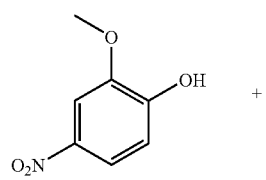

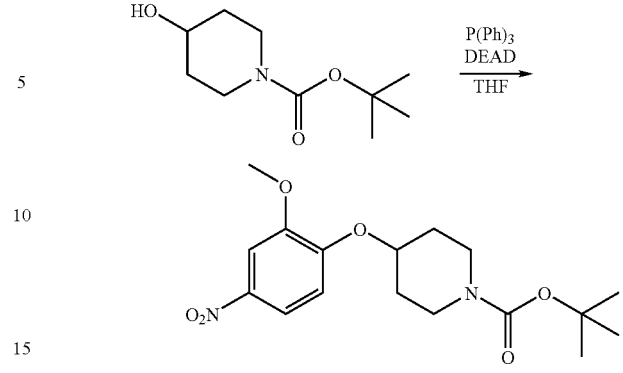

To a mixture of triphenylphosphine (3.10 g, 11.8 mmol) and diethylazodicarboxylate (2.06 g, 11.8 mmol) under $N_2$ in THF (40 mL) was added t-butyl 4-hydroxypiperidine-1-carboxylate (2.00 g, 9.94 mmol). After stirring 10 min, 2-methoxy-4-nitrophenol (1.00 g, 5.91 mmol) was added. The reaction was stirred for 16 h and the solvent was evaporated under reduced pressure to give orange oil. The crude product was purified by column chromatography on silica gel using 25% EtOAc/hexane yielding t-butyl 4-(2-methoxy-4-nitrophenoxy)piperidine-1-carboxylate as a beige solid (1.70 g, 82%). LC/MS (m/z): 353.2 (MH+), $R_t$ 3.23 minutes Synthesis of
4-(2-methoxy-4-nitrophenoxy)piperidine

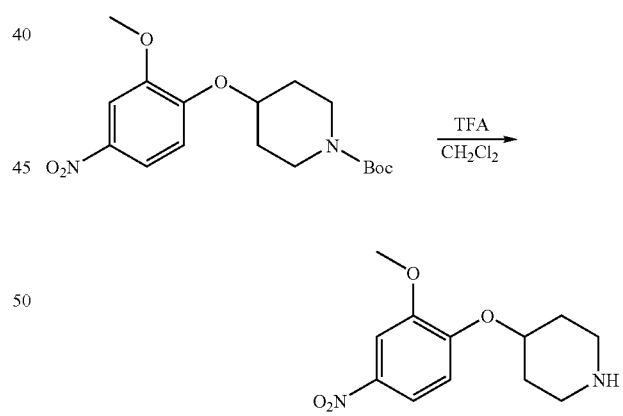

Trifluoroacetic acid (5 eq) was added to a solution of tert-butyl 4-(2-methoxy-4-nitrophenoxy)piperidine-1-carboxylate (200 mg, 0.57 mmol, 1 eq) in dichloromethane, stirring at room temperature for 1 hour. The solvent was then evaporated, the residue was brought to pH 10 with sat. aq. Na2CO3 solution and extracted with EtOAc. The organic layer was washed with brine, dried over sodium sulfate and evaporated to afford the product 4-(2-methoxy-4-nitrophenoxy)piperidine as a light yellow solid (137.3 mg, 96%). LC/MS (m/z): 253.2 (MH+), Rt 1.81 minutes.

Synthesis of 1-isopropyl-4-(2-methoxy-4-nitrophenoxy)piperidine

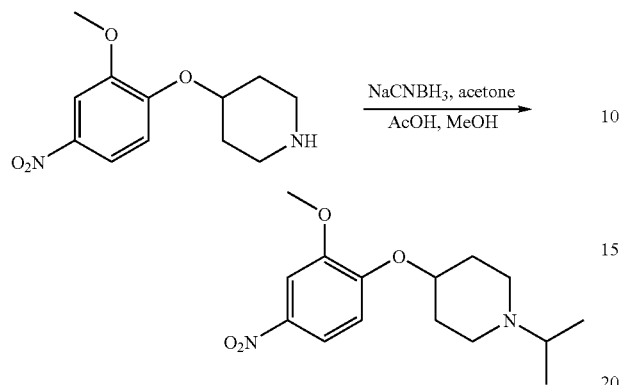

To a solution of 10% acetic acid in methanol was added 4-(2-methoxy-4-nitrophenoxy)piperidine (148 mg, 0.59 mmol, 1 eq), anhydrous acetone (5 eq), and sodium cyanoborohydride (1.5 eq). The solution was stirred at room temperature for 24 h. Additional anhydrous acetone (5 eq) and sodium cyanoborohydride (1.5 eq) were added and the reaction was stirred for 24 h. The solvent was evaporated, the residue was brought to pH 10 with aqueous sodium carbonate and extracted with EtOAc. The organic layer was washed with water, brine, dried with magnesium sulfate and evaporated to afford 1-isopropyl-4-(2-methoxy-4-nitrophenoxy)piperidine as a yellow oil (163 mg, 97%). LC/MS (m/z): 295.2 (MH$^+$), R$_t$ 1.96 minutes.

Synthesis of 4-(1-isopropylpiperidin-4-yloxy)-3-methoxyaniline

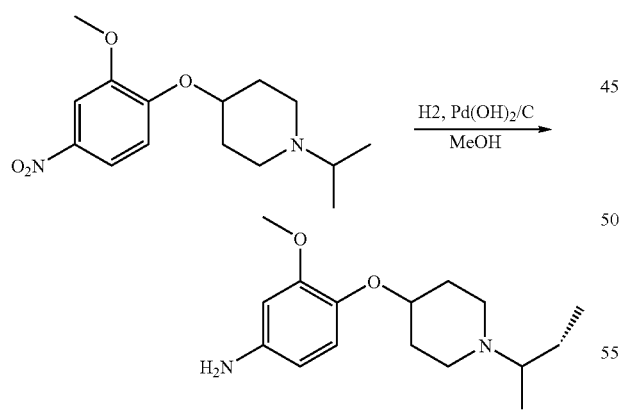

1-isopropyl-4-(2-methoxy-4-nitrophenoxy)piperidine (167 mg, 0.57 mmol) was dissolved in methanol (20 mL) and placed under a nitrogen atmosphere. A catalytic amount of 20% palladium hydroxide on carbon was added and a hydrogen balloon was connected to the reaction flask. The flask was flushed five times with hydrogen and stirred at room temperature under hydrogen atmosphere for 16 hours. The reaction mixture was filtered and washed with methanol. The filtrate was evaporated under reduced pressure. Acetonitrile (10 mL) was added to the residue, swirled for 10 min, and decanted away from white film. The acetonitrile layer was evaporated under reduced pressure yielding 4-(1-isopropylpiperidin-4-yloxy)aniline as a brown oil (131 mg, 87%). LC/MS (m/z): 265.2 (MH$^+$), R$_t$ 0.33 minutes.

Method 29

Synthesis of 4-(1-isopropylpiperidin-4-yloxy)-3-methoxyaniline; Synthesis of Tert-butyl 4-(2-methoxy-4-nitrophenoxy)piperidine-1-carboxylate

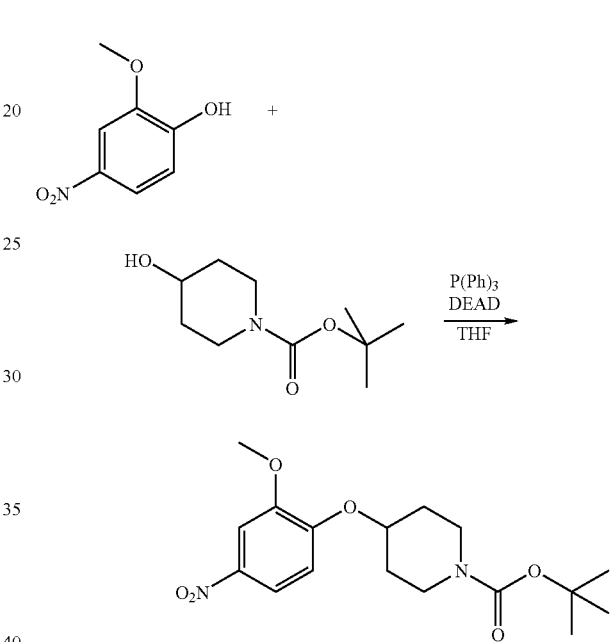

To a mixture under N$_2$ of triphenylphosphine (3.10 g, 11.825 mmol) and diethylazodicarboxylate (2.06 g, 11.825 mmol) in THF (40 mL) was added tert-butyl 4-hydroxypiperidine-1-carboxylate (2.00 g, 9.937 mmol). After stirring 10 min, 2-methoxy-4-nitrophenol (1.00 g, 5.912 mmol) was added. The reaction stirred 16 h and evaporated under reduced pressure to give an orange oil. The crude product was purified by column chromatography on silica gel using 25% EtOAc/hexane yielding tert-butyl 4-(2-methoxy-4-nitrophenoxy)piperidine-1-carboxylate as a beige solid (1.70 g, 82%). LC/MS (m/z): 353.2 (MH$^+$), R$_t$ 3.23 minutes

Synthesis of 4-(2-methoxy-4-nitrophenoxy)piperidine

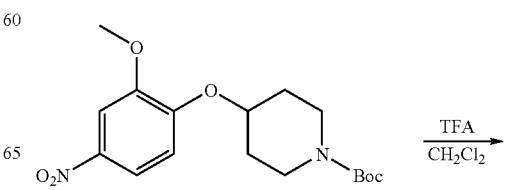

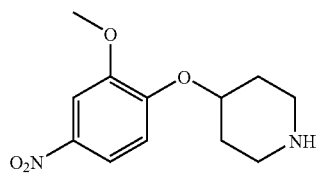

Trifluoroacetic acid (5 eq) was added to a solution of tert-butyl 4-(2-methoxy-4-nitrophenoxy)piperidine-1-carboxylate (200 mg, 0.5676 mmol, 1 eq) in dichloromethane, stirring at room temperature for 1 hour. The solvent was then evaporated, the residue brought to pH=10 with sat. aq. $Na_2CO_3$ solution and extracted with EtOAc. The organic layer was washed with brine, dried over sodium sulfate and evaporated to afford the product 4-(2-methoxy-4-nitrophenoxy)piperidine as a light yellow solid (137.3 mg, 96%). LC/MS (m/z): 253.2 (MH$^+$), R$_t$ 1.81 minutes.

Synthesis of
1-isopropyl-4-(2-methoxy-4-nitrophenoxy)piperidine

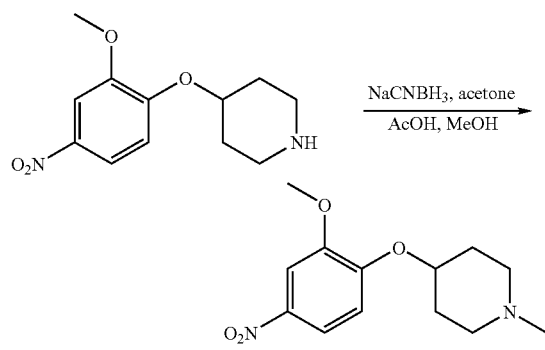

To a solution of 10% acetic acid in methanol was added 4-(2-methoxy-4-nitrophenoxy)piperidine (148 mg, 0.59 mmol, 1 eq), anhydrous acetone (5 eq), and sodium cyanoborohydride (1.5 eq). The solution was stirred at room temperature for 24 h. Reaction is 85% complete. Charged additional anhydrous acetone (5 eq) and sodium cyanoborohydride (1.5 eq) and stirred for 24 h. The solvent was evaporated, the residue brought to pH=10 with sodium carbonate and extracted with EtOAc. The organic layer was washed with water, brine, dried with magnesium sulfate and evaporated to afford 1-isopropyl-4-(2-methoxy-4-nitrophenoxy)piperidine as a yellow oil (163 mg, 97%). LC/MS (m/z): 295.2 (MH$^+$), R$_t$ 1.96 minutes.

Synthesis of
4-(1-isopropylpiperidin-4-yloxy)-3-methoxyaniline

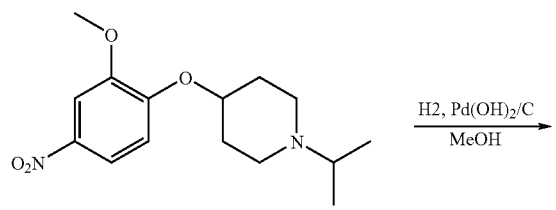

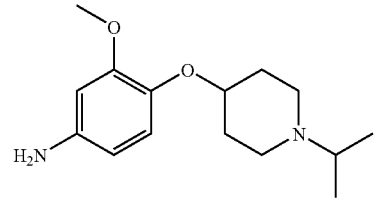

1-isopropyl-4-(2-methoxy-4-nitrophenoxy)piperidine (167 mg, 0.57 mmol) was dissolved in 20 mL of methanol and placed under a nitrogen atmosphere. A catalytic amount of 20% palladium hydroxide on carbon was added and a hydrogen balloon was connected to the reaction flask. The flask was flushed five times with hydrogen and stirred at room temperature under hydrogen atmosphere for 16 hours. The reaction mixture was filtered and washed with methanol. The filtrate was evaporated under reduced pressure. Acetonitrile (10 mL) was added to the residue, swirled for 10 min, and decanted away from white film. The acetonitrile layer was evaporated under reduced pressure yielding 4-(1-isopropylpiperidin-4-yloxy)aniline as a brown oil (131 mg, 87%). LC/MS (m/z): 265.2 (MH$^+$), R$_t$ 0.33 minutes.

Method 30

Synthesis of N-(6-chloro-2-morpholinopyrimidin-4-yl)-4-phenylthiazol-2-amine

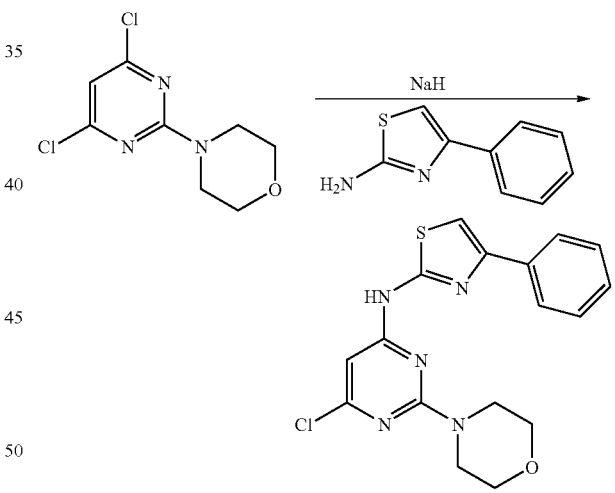

To a solution of the 4-phenylthiazol-2-amine (374 mg, 2.1 mmol) in 10 mL of N,N-dimethylacetamide was added sodium hydride (50 mg, 2.1 mmol) at room temperature. After the mixture was stirred at that temperature for 10 minutes, the dichloride (470 mg, 2.0 mmol) was added to the reaction mixture. After being stirred at room temperature for 1 hour, additional sodium hydride (50 mg, 2.1 mmol) was added to the reaction mixture. The mixture was stirred for 1 hour and quenched with 5 mL of aq. ammonium chloride. The resulting mixture was extracted with ethyl acetate (2×10 mL). The combined organic layers were washed with water (10 mL), brine (10 mL), then dried over MgSO4, filtered, and evaporated under reduced pressure to give crude product, which was purified by silica gel column eluted with ethyl acetate and hexane to give N-(6-chloro-2-morpholinopyrimidin-4-yl)-4-phenylthiazol-2-amine. LC/MS (m/z): 374 and 376 (MH+), Rt 3.40 minutes.

Example 1

Preparation of N-(6-(2-aminopyrimidin-5-yl)-2-morpholinopyrimidin-4-yl)quinolin-3-amine

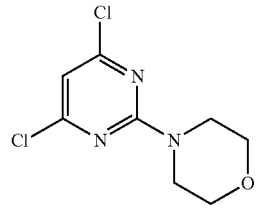

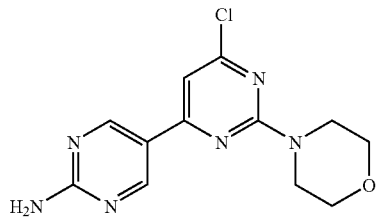

4,6-Dichloro-2-morpholinopyrimidine (prepared as in Method 22; 3.0 g, 12.9 mmol) and 5-(4,4,5,5-tetramethyl-1,3,2-dioxaborolan-2-yl)pyrimidin-2-amine (3.43 g, 15.5 mmol) were dissolved in DME (130 mL). Aqueous $Na_2CO_3$ (2 M, 32 mL, 64 mmol) was then added and the reaction mixture was sparged with $N_2$ for several minutes. $Pd(OAc)_2$ (145 mg, 0.65 mmol) and $PPh_3$ (339 mg, 1.29 mmol) were then added and the reaction mixture was heated at 95° C. for 1 h. The reaction mixture was allowed to cool to room temperature, the solution was decanted away from the solid residue and concentrated. The solid thus formed was separated from the water phase. The water extracted with EtOAc and this organic layer was combined with the precipitate. Removal of the solvent in vacuo gave a solid residue which was triturated with about 20 mL of EtOAc, filtered and evaporated under reduced pressure to give the desired product. Additional product was obtained by concentrating the mother liquor and purifying the solid crash out by trituration with EtOAc. The two crops were combined obtaining 1.98 g (52%) of the desired product. LC/MS (m/z): 293.1 (MH$^+$), $R_t$ 1.92 minutes N-(6-(2-aminopyrimidin-5-yl)-2-morpholinopyrimidin-4-yl)quinolin-3-amine

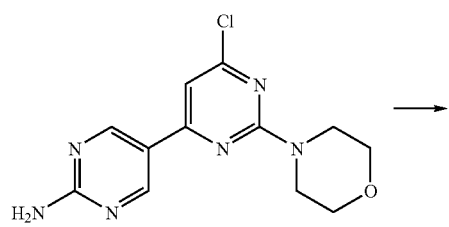

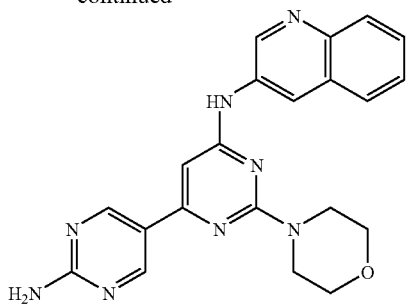

$Pd(OAc)_2$, BINAP, cesium carbonate, THF (0.8 mL) were mixed with 5-(6-chloro-2-morpholinopyrimidin-4-yl)pyrimidin-2-amine (1 eq) and quinolin-3-amine (2 eq). The mixture was heated under microwave irradiation for 10 minutes at 110° C. The solution was filtered and concentrated under reduced pressure. LC/MS (m/z): 401.4 (MH$^+$).

Example 2

Preparation of N-(6-(6-aminopyridin-3-yl)-2-morpholinopyrimidin-4-yl)quinolin-3-amine 5-(6-Chloro-2-morpholin-4-yl-pyrimidin-4-yl)pyridin-2-ylamine

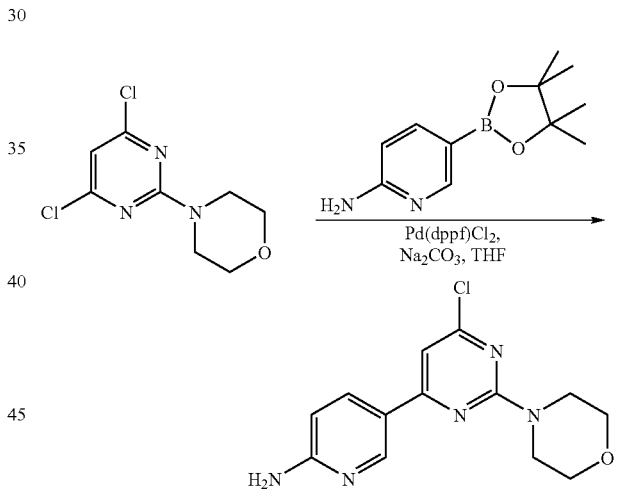

THF (130 mL) and aq. $Na_2CO_3$ (2M, 40 mL, 80 mmol) were added to a glass pressure vessel containing 4,6-dichloro-2-morpholinopyrimidine (prepared as in Method 22; 4.5 g, 19.2 mmol) and 5-(4,4,5,5-tetramethyl-1,3,2-dioxaborolan-2-yl)pyridin-2-amine (4.7 g, 21.2 mmol). The resulting mixture was stirred and sparged with argon for 1-2 minutes. The catalyst, dichloro[1,1'-bis(diphenylphosphino)ferrocene] palladium (II) dichloromethane adduct (1.26 g, 1.54 mmol), was then added in one portion. After sealing the reaction vessel, the reaction was heated at 85° C. for 1 hour with stirring. Upon cooling to RT, the THF was removed under reduced pressure to leave a viscous residue. EtOAc (450 mL) and water (50 mL) were added. After vigorously stirring for 1-2 minutes, the solids were filtered off and washed with EtOAc (100 mL). The organic layer was separated and the aqueous layer was extracted with EtOAc (100 mL). The combined organic layers were washed with saturated NaCl solution (1×50 mL), dried with $Na_2SO_4$, filtered and evaporated under reduced pressure. The crude material was further purified by silica gel chromatography to give 5-(6-chloro-2-morpholin-4-yl-pyrimidin-4-yl)-pyridin-2-ylamine (2.48 g, 44%). LC/MS (m/z): 292.1 (MH$^+$), R$_t$ 2.06 minutes.

[6-(6-amino-pyridin-3-yl)-2-morpholin-4-yl-pyrimidin-4-yl]-(6-methoxy-pyridin-3-yl)-amine

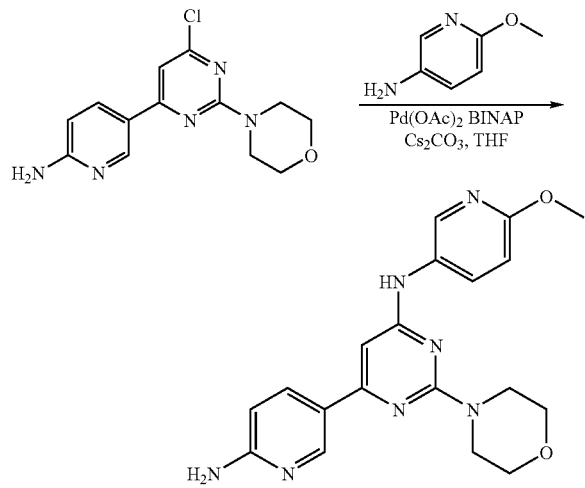

In a glass pressure vessel, Pd(OAc)$_2$ (2.0 mg, 0.0082 mmol), BINAP (6.4 mg, 0.0102 mmol), cesium carbonate (20.0 mg, 0.0615 mmol) and THF (0.8 mL) were mixed and stirred at room temperature for 1-3 minutes. To the resulting mixture was added 5-(6-chloro-2-morpholin-4-yl-pyrimidin-4-yl)-pyridin-2-ylamine (12.0 mg, 0.041 mmol) followed by 6-methoxypyridin-3-ylamine (10.2 mg, 0.082 mmol). The glass pressure vessel was sealed and stirred at 95° C. for 90 minutes. The reaction mixture was filtered and concentrated under reduced pressure. The product was purified by preparative reverse phase HPLC to give [6-(6-amino-pyridin-3-yl)-2-morpholin-4-yl-pyrimidin-4-yl]-(6-methoxy-pyridin-3-yl)-amine (5.0 mg, 32%). LC/MS (m/z): 380.1 (MH$^+$), R$_t$ 1.82 minutes.

Example 3

Preparation of 5-(6-[2-(methylsulfonamide)pyridin]-3-yl)-2-morpholino-pyrimidin-4-yl)pyridin-2-amine 5-[6-(2-fluoro-pyridin-3-yl)-2-morpholin-4-yl-pyrimidin-4-yl]-pyridin-2-ylamine

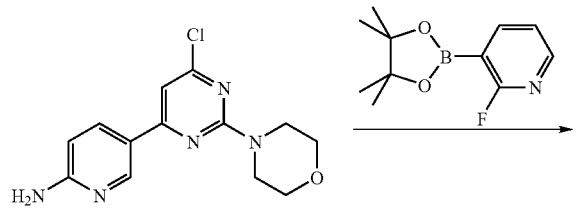

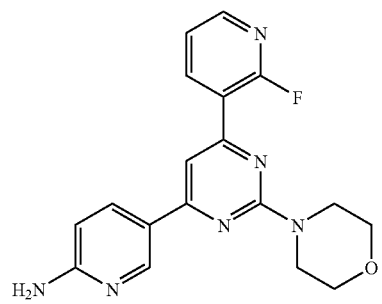

To a solution of 5-(6-chloro-2-morpholin-4-yl-pyrimidin-4-yl)pyridin-2-ylamine, prepared as in Example 2, (252 mg, 0.87 mmol) and 2-fluoro-3-(4,4,5,5-tetramethyl-[1,3,2]dioxaborolan-2-yl)pyridine (183 mg, 1.30 mmol) in DME (4 mL) was added an aqueous solution of Na$_2$CO$_3$ (2 M, 1 mL), followed by dichloro[1,1'-bis(diphenylphosphino)ferrocene]palladium(II)-dichloromethane (71 mg, 0.087 mmol). The mixture was heated in a microwave for 20 min at 120° C. The aqueous phase was separated from DME, and extracted with EtOAc. The combined organic phases were washed with brine, dried, filtered, and concentrated to give crude desired product which was carried on to the next step without further purification. LC/MS (m/z): 353.3 (MH$^+$), 1.84 minutes.

N-{3-[6-(6-Amino-pyridin-3-yl)-2-morpholin-4-yl-pyrimidin-4-yl]pyridin-2-yl}-methanesulfonamide

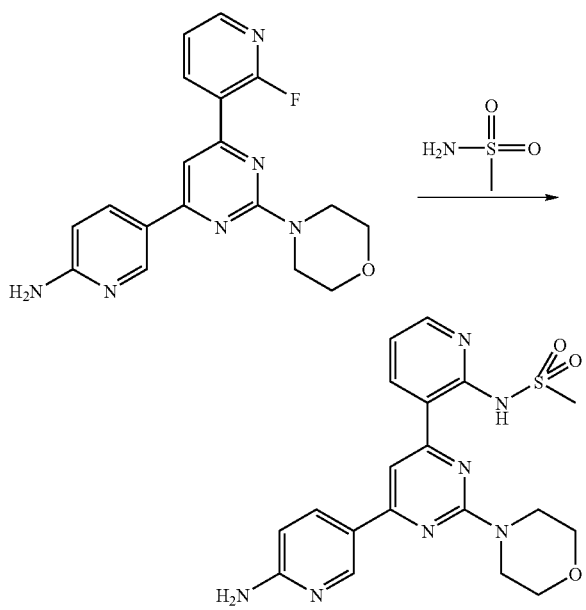

To a solution of 5-[6-(2-fluoro-pyridin-3-yl)-2-morpholin-4-yl-pyrimidin-4-yl]-pyridin-2-ylamine (200 mg, 0.57 mmol) and methanesulfonamide (216 mg, 2.3 mmol) in NMP (8 mL) was added Cs$_2$CO$_3$ (372 mg, 1.1 mmol). The solution was heated at 125° C. for 4 hours. The reaction mixture was cooled to room temperature, filtered and purified by reverse phase preparatory HPLC to give the title compound. LC/MS (m/z): 428.3 (MH⁺), $R_t$ 1.80 minutes.

Example 4

Preparation of N-(6-(6-amino-4-fluoropyridin-3-yl)-2-morpholinopyrimidin-4-yl)quinolin-3-amine N-(6-bromo-2-morpholinopyrimidin-4-yl)quinolin-3-amine

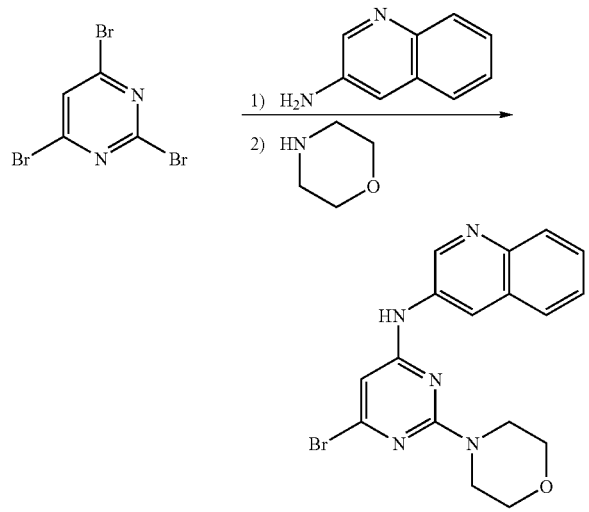

To a solution of 2,4,6-tribromopyrimidine (5.40 g, 17.2 mmol) in acetonitrile (60 mL) was added quinolin-3-amine, followed by DIEA (8.99 mL, 51.6 mmol). The reaction mixture was heated to 45° C. overnight. Morpholine (1.50 mL, 17.2 mmol) was then added, and the reaction mixture continued heating for 4 h. The reaction mixture was then cooled to room temperature, concentrated and dissolved in EtOAc (about 500 mL), the organic solution was washed with saturated NaHCO₃ (3×), H₂O (2×), brine (1×) and dried over Na₂SO₄. The solution was then evaporated in the presence of silica gel and purified by column chromatography (SiO₂, 15-25% EtOAc/Hexanes) to yield N-(6-bromo-2-morpholinopyrimidin-4-yl)quinolin-3-amine. LC/MS (m/z): 386.1 (MH⁺).

N-(6-(6-amino-4-fluoropyridin-3-yl)-2-morpholinopyrimidin-4-yl)quinolin-3-amine

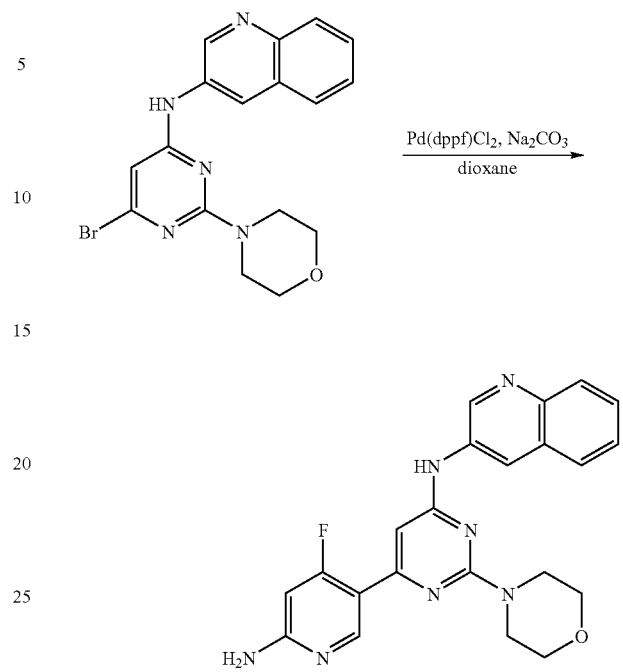

To a solution of 4-fluoro-5-(4,4,5,5-tetramethyl-1,3,2-dioxaborolan-2-yl)pyridin-2-amine (prepared as shown in Method 10) in dioxane (1.7 mL, 0.13 mmol), N-(6-bromo-2-morpholinopyrimidin-yl)quinolin-3-amine (20 mg, 0.052 mmol), dichloro[1,1'-bis(diphenylphosphino)ferrocene]palladium(II)-dichloromethane adduct (11 mg, 0.013 mmol) and 2 M aqueous sodium carbonate solution (0.6 mL, 1.2 mmol) were added under argon. The pressure vessel was sealed and the reaction mixture was heated in a microwave reactor at 120° C. for 15 minutes. The crude product was partitioned between EtOAc (30 mL) and saturated sodium bicarbonate (10 mL). The organic layer was separated, dried over sodium sulfate, filtered and concentrated under reduced pressure. The product was purified by reverse phase preparative HPLC to give N-(6-(6-amino-4-fluoropyridin-3-yl)-2-morpholinopyrimidin-4-yl)quinolin-3-amine as yellow powder (14 mg, 26%). LC/MS (m/z): 418.0 (MH⁺), $R_t$ 2.31 minutes.

Example 5

Preparation of 2-amino-5-[2-morpholin-4-yl-6-(quinolin-3-ylamino)-pyrimidin-4-yl]-isonicotinonitrile

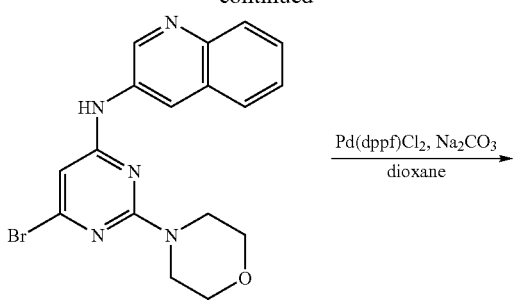

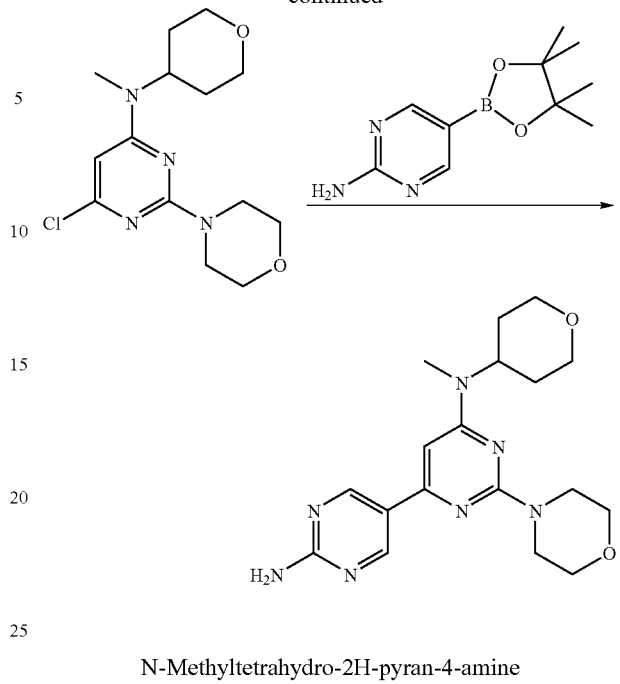

To the crude 2-amino-5-(4,4,5,5-tetramethyl-1,3,2-dioxaborolan-2-yl)pyridine-4-carbonitrile (prepared as in Method 11) (25 mg, 0.13 mmol) solution in dioxane (1.8 mL) in a pressure vessel, was added (6-bromo-2-morpholin-4-yl-pyrimidin-4-yl)-quinolin-3-yl-amine (19.4 mg, 0.05 mmol) and aq. Na$_2$CO$_3$ (2 M, 0.6 mL, 1.2 mmol). After purging the reaction mixture with argon, dichloro[1,1'-bis(diphenylphosphino)ferrocene]palladium(II) dichloromethane adduct (10.3 mg, 0.01 mmol) was added in one portion. The pressure vessel was sealed and the mixture was heated in a microwave at 120° C. for 900 seconds. The crude mixture was filtered and concentrated under reduced pressure. The crude product was purified by reverse phase preparative HPLC to give 2-amino-5-[2-morpholin-4-yl-6-(quinolin-3-ylamino)-pyrimidin-4-yl]-isonicotinonitrile (4.5 mg, 20%). LC/MS (m/z): 425.0 (MH$^+$), R$_t$ 2.03 minutes.

Example 6

Preparation of N$^6$-methyl-2-morpholino-N$^6$-(tetrahydro-2H-pyran-4-yl)-4,5'-bipyrimidine-2',6-diamine

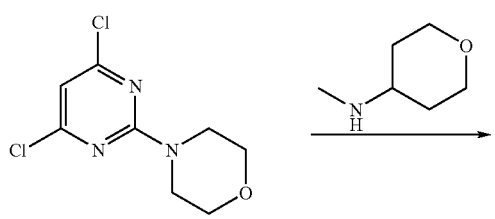

N-Methyltetrahydro-2H-pyran-4-amine

Tetrahydro-2H-pyran-4-amine (90 mg, 0.9 mmol) was added to a solution of formaldehyde (37% solution in water, 0.091 mL, 1.13 mmol) and acetic acid (0.162 mL) in ACN (0.8 mL). After stirring for 5 minutes, Na(CN)BH$_3$ (60 mg, 1.13 mmol) was added in one portion at RT. After 1 hour, excess Cs$_2$CO$_3$ was added to the reaction until made alkaline. After stirring for 15 minutes, the reaction was filtered to remove solids and the solvent evaporated under reduced pressure. The crude product, N-methyltetrahydro-2H-pyran-4-amine, was used for the following displacement without further purification. LC/MS (m/z): 116.1 (MH$^+$), R$_t$ 0.34 minutes.

6-chloro-N-methyl-2-morpholino-N-(tetrahydro-2H-pyran-4-yl)pyrimidin-4-amine

The crude N-methyltetrahydro-2H-pyran-4-amine (104 mg, 0.9 mmol) was dissolved in NMP (0.8 mL). To the solution, Cs$_2$CO$_3$ (366 mg, 1.13 mmol) and 4-(4,6-dichloropyrimidin-2-yl)morpholine (prepared as in Method 22) (80 mg, 0.34 mmol) were added at room temperature. The reaction mixture was heated to 95° C. After 90 minutes, the reaction mixture was cooled to room temperature, filtered and purified by reverse phase preparative HPLC yielding 24 mg (23%) of pure 6-chloro-N-methyl-2-morpholino-N-(tetrahydro-2H-pyran-4-yl)pyrimidin-4-amine. LC/MS (m/z): 313.2 (MH$^+$), R$_t$ 2.61 minutes.

N$^6$-methyl-2-morpholino-N$^6$-(tetrahydro-2H-pyran-4-yl)-4,5'-bipyrimidine-2',6-diamine To an argon flushed mixture of 5-(4,4,5,5-tetramethyl-1,3,2-dioxaborolan-2-yl)pyrimidin-2-amine (42 mg, 0.19 mmol), 6-chloro-N-methyl-2-morpholino-N-(tetrahydro-2H-pyran-4-yl)pyrimidin-4-amine (12 mg, 0.038 mmol) in THF (0.8 mL), and aq. Na$_2$CO$_3$ (2M, 0.27 mL) in a pressure vessel, was added dichloro[1,1'-bis(diphenylphosphino)ferrocene]palladium (II) dichloromethane adduct (8 mg, 0.0095 mmol) in one portion. The pressure vessel was sealed and the mixture was heated in a microwave at 120° C. for 600 seconds. The crude mixture was filtered, concentrated under reduced pressure and purified by reverse phase preparative HPLC to give N[6]-methyl-2-morpholino-N[6]-(tetrahydro-2H-pyran-4-yl)-4,5'-bipyrimidine-2',6-diamine (4.6 mg, 32%). LC/MS (m/z): 372.2 (MH$^+$), R$_t$ 1.76 minutes.

Example 7

Preparation of N-(6-(2-aminopyrimidin-5-yl)-2-morpholinopyrimidin-4-yl)-5-methoxyquinolin-3-amine

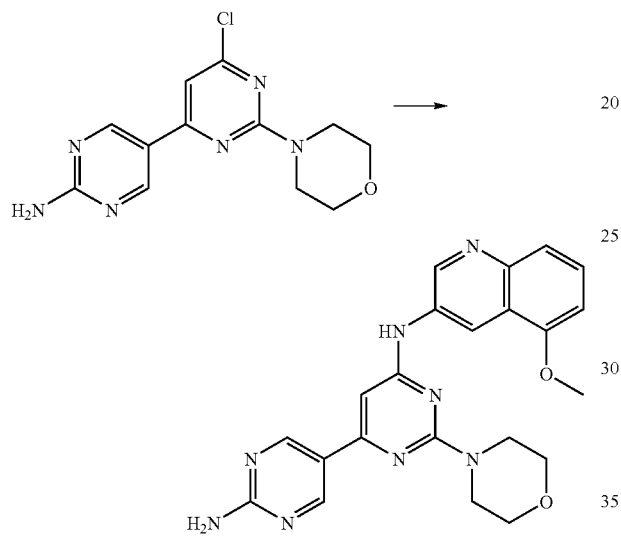

The desired compound was prepared as described in Example 2: Pd(OAc)$_2$, BINAP, cesium carbonate, THF (0.8 mL) were mixed with 5-(6-chloro-2-morpholinopyrimidin-4-yl)pyrimidin-2-amine (1 eq.) and 5-methoxyquinolin-3-amine (2 eq), which was prepared as shown in Method 20. The mixture was heated under microwave irradiation for 10 minutes at 110° C. The solution was filtered and concentrated under reduced pressure. The crude product was purified by preparative reverse phase HPLC. LC/MS (m/z): 431.2 (MH$^+$), R$_t$ 2.03 minutes.

Example 8

Preparation of 5-(2-morpholino-6-(pyridin-3-yloxy)pyrimidin-4-yl)pyrimidin-2-amine

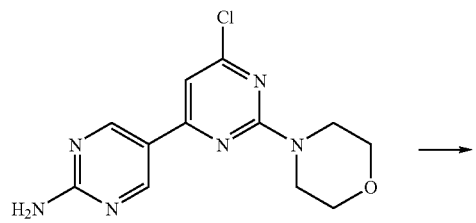

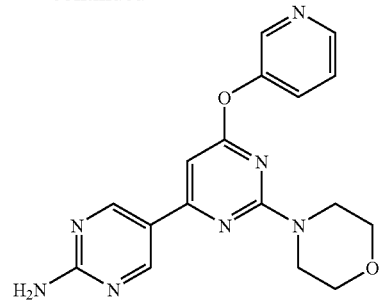

5-(6-chloro-2-morpholinopyrimidin-4-yl)pyrimidin-2-amine (10 mg, 0.034 mmol, prepared as in example 1), potassium tert-butoxide (6 mg, 0.051 mmol), pyridin-3-ol (5 mg, 0.051 mmol) and DMSO (0.5 mL) were all combined together and heated at 110° C. for 2 days. The crude product was purified directly by preparative reverse phase HPLC to give 5-(2-morpholino-6-(pyridin-3-yloxy)pyrimidin-4-yl)pyrimidin-2-amine (5.1 mg, 32%). LC/MS (m/z): 352.1 (MH$^+$), R$_t$ 1.83 minutes.

Example 9

Preparation of 6-(2-aminopyrimidin-5-yl)-2-morpholino-N-(6-(piperazin-1-yl)pyridin-3-yl)pyrimidin-4-amine

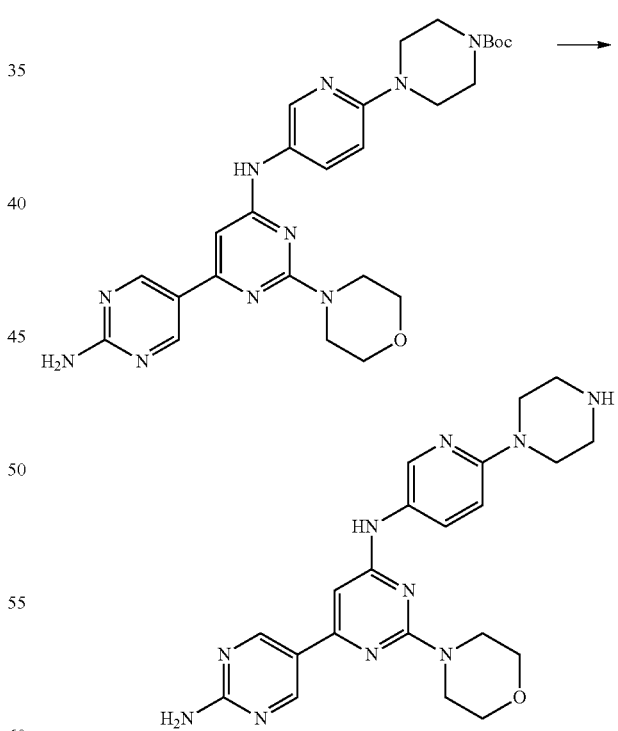

To tert-butyl 4-(5-(6-(2-aminopyrimidin-5-yl)-2-morpholinopyrimidin-4-ylamino)pyridin-2-yl)piperazine-1-carboxylate (prepared as described in Example 1 from 5-(6-chloro-2-morpholinopyrimidin-4-yl)pyrimidin-2-amine and commercially available tert-butyl 4-(5-aminopyridin-2-yl)piperazine-1-carboxylate, 30 mg, 0.06 mmol) were added 5 mL of 4N HCl in dioxane. After stirring for one hour, the solution was concentrated in vacuo. The residue was dissolved in a 3:1 acetonitrile and water and lyophilized to afford the desired product LC/MS (m/z): 435.2 (MH+), R$_t$ 1.52 minutes.

Example 10

Preparation of 4-(trifluoromethyl)-5-(2,6-dimorpholinopyrimidin-4-yl)pyridin-2-amine

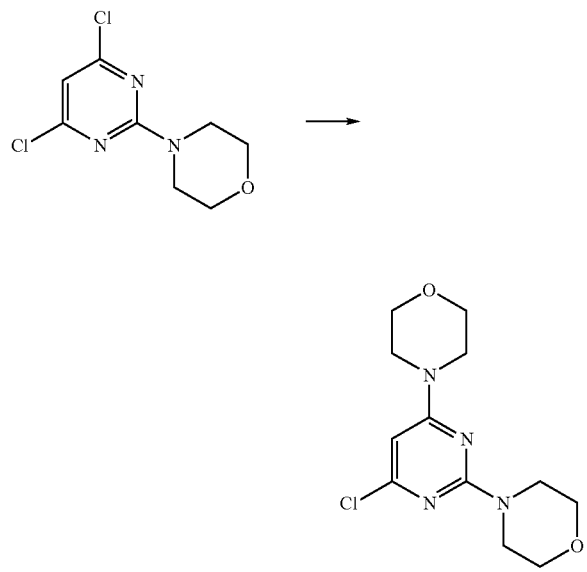

To a slurry of 2-morpholino-4,6-dichloropyrimidine (prepared as in Method 22, 2.0 g, 8.54 mmol) in NMP (14 mL), triethylamine (1.43 mL, 10.25 mmol) was added. The heterogeneous mixture was stirred for 15 minutes, then treated with morpholine (0.75 mL, 8.54 mmol). Upon refluxing at 85° C. under argon for 2 hours, the solution was cooled, then added to EtOAc (160 mL). The organic solution was washed with 25 mL of NaHCO$_{3(sat.)}$ (2×), water (2×) and brine, dried over Na$_2$SO$_4$, filtered and concentrated. The crude material was dissolved in 200 mL EtOAc and filtered through a SiO$_2$ pad, further eluting with EtOAc, yielding 2.2 g (93%) of 2,4-dimorpholino-6-chloropyrimidine as an off-white solid. LCMS (m/z): 285.0 (MH+), $^1$H NMR (CDCl$_3$): δ 5.86 (s, 1H), 3.71-3.76 (m, 12H), 3.52-3.56 (m, 4H).

4-(trifluoromethyl)-5-(2,6-dimorpholinopyrimidin-4-yl)pyridin-2-amine

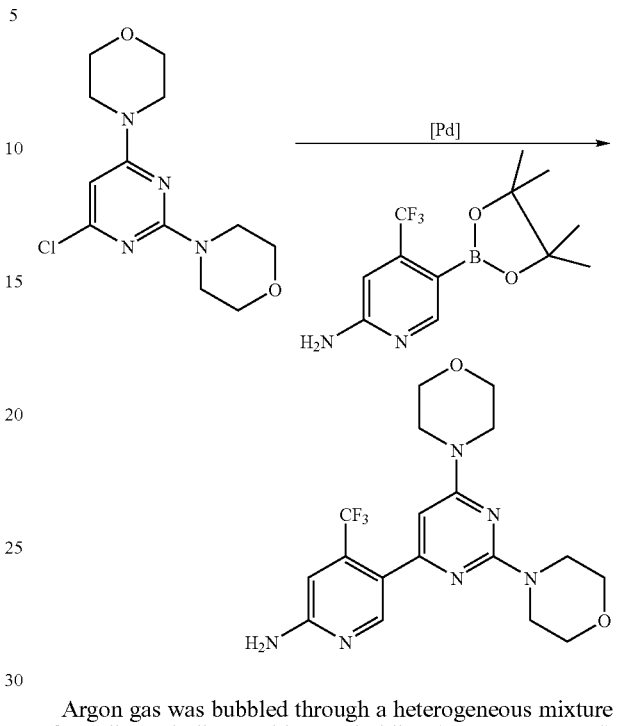

Argon gas was bubbled through a heterogeneous mixture of 2,4-dimorpholino-6-chloropyrimidine (4.1 g, 14.3 mmol) and 4-(trifluoromethyl)-5-(4,4,5,5-tetramethyl-1,3,2-dioxaborolan-2-yl)pyridin-2-amine (16.5 g, 57.3 mmol) in 1,2-dimethoxyethane and 2M Na$_2$CO$_3$ (3:1) for 20 minutes. 1,1'-Bis(diphenylphosphino)ferrocene palladium(II) chloride (292 mg, 0.36 mmol) was added and the high pressure glass vessel containing the mixture was sealed. The reaction mixture was then heated at 90° C. for 15 hours, cooled and diluted with EtOAc (300 mL). The organic solution was washed with 300 mL of a mixture of water: Na$_2$CO$_{3(sat.)}$:NH$_4$OH$_{(conc.)}$=5:4:1, then NH$_4$Cl$_{(sat)}$, and brine (2×), dried over Na$_2$SO$_4$, filtered and concentrated. The crude material was purified by SiO$_2$ chromatography (50-90% EtOAc/hexanes with 0.1% TEA) resulting in 5.62 g (95%) of 4-(trifluoromethyl)-5-(2,6-dimorpholinopyrimidin-4-yl)pyridin-2-amine as an off-white solid. LCMS (m/z): 411.3 (MH+); $^1$H NMR (CDCl$_3$): δ 8.27 (s, 1H), 6.78 (s, 1H), 5.97 (s, 1H), 4.77 (bs, 2H), 3.59-3.80 (m, 12H), 3.58-3.61 (m, 4H).

Example 11

Preparation of N-(6-(1-isopropylpiperidin-4-yloxy)pyridin-3-yl)-6-(6-amino-4-(trifluoromethyl)pyridin-3-yl)-2-morpholinopyrimidin-4-amine

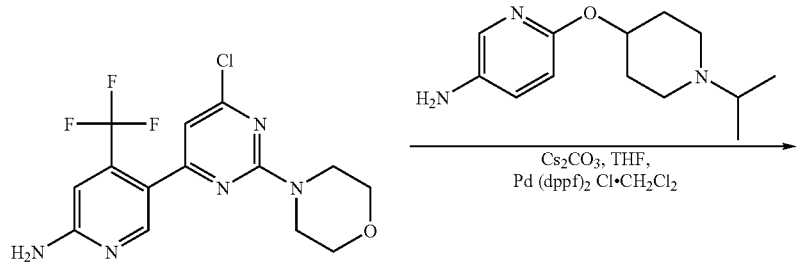

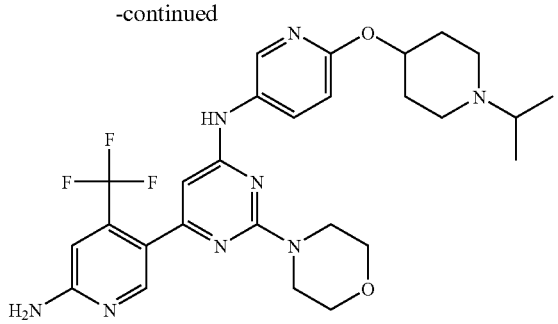

N-(6-(1-isopropylpiperidin-4-yloxy)pyridin-3-yl)-6-(6-amino-4-(trifluoromethyl)-pyridin-3-yl)-2-morpholinopyrimidin-4-amine was synthesized according to the general procedure for the Buchwald reaction in Example 2 by reacting 6-(1-isopropylpiperidin-4-yloxy)pyridin-3-amine (prepared as in Method 16) with 5-(6-chloro-2-morpholinopyrimidin-4-yl)-4-(trifluoromethyl)pyridin-2-amine. LC/MS (m/z): 559.2 (MH$^+$), R$_t$ 1.92 minutes. $^1$H NMR (DMSO): δ 10.27 (1H, bs, NH); 8.41 (1H, bs); 8.17 (1H, s); 7.98 and 7.94 (1H, 2 b doublets, J=9.0 Hz, 2 conformers); 6.97 (1H, s); 6.90 and 6.84 (1H, 2 doublets, J=9.0 Hz, 2 conformers); 6.23 (1H, bs); 5.25 and 5.15 (1H, 2 multiplets, 2 conformers); 3.66 (8H, bs); 3.44 (1H, m); 3.35 (2H, m); 3.10 (2H, m); 2.22 (2H, m); 2.03 (2H, m); 1.27 (6H, overlapping doublets because of conformers, app. triplet, J=5.7 Hz).

Example 12

Preparation of N-(5-((diethylamino)methyl)thiazol-2-yl)-6-(6-amino-4-(trifluoromethyl)pyridin-3-yl)-2-morpholinopyrimidin-4-amine 5-((diethylamino)methyl)thiazol-2-amine

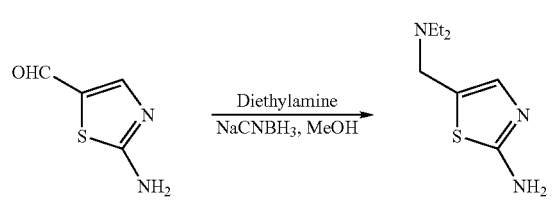

2-Aminothiazole-5-carbaldehyde (1 eq) was added to a stirring solution of diethylamine (4 eq) in anhydrous MeOH at 0° C. Sodium cyanoborohydride (1.5 eq) was then added in portions at 0° C. The reaction mixture was stirred at 70° C. for 10 hours. After this time, the solution was quenched with H$_2$O and extracted with EtOAc. The combined organic extracts were dried over Na$_2$SO$_4$ and concentrated to afford a viscous brown oil. LC/MS (m/z): 186.2 (MH$^+$), R$_t$ 0.33 minutes.

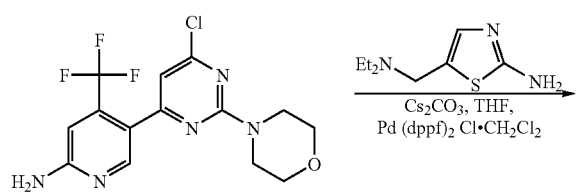

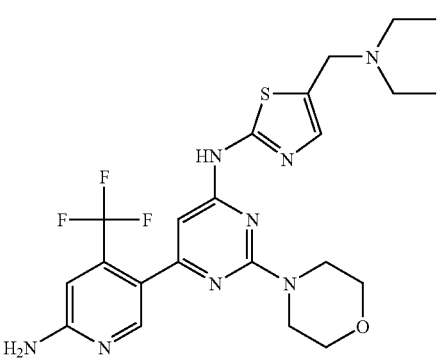

The title compound was synthesized according to the general procedure shown in Example 2. LC/MS (m/z): 509.2 (MH$^+$), R$_t$ 1.98 minutes. $^1$H NMR (DMSO): δ 11.0, (2H, bs, NH2), 8.17 (1H, s); 7.63 (1H, s); 7.08 (1H, bs), 6.40 (1H, s); 4.48 (2H, bd, J=4.2 Hz); 3.80 (4H, m); 168 (4H, m); 3.03 (4H, bq, J=6.9 Hz); 1.30 (6H, t, J=6.9 Hz).

Example 13

Synthesis of 6-(6-amino-4-(trifluoromethyl)pyridin-3-yl)-N-(4-(2-(diethylamino)ethyl)thiazol-2-yl)-2-morpholinopyrimidin-4-amine 2-(2-aminothiazol-4-yl)-N,N-diethylacetamide

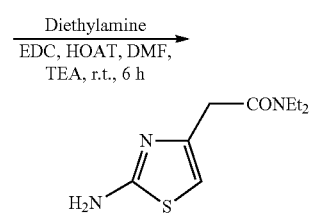

A mixture of 2-(2-aminothiazol-4-yl)acetic acid (1 eq), HOAT (1 eq), EDC (1.1 eq), TEA (1 eq) and HNEt$_2$ (1 eq) in DMA was stirred at room temperature for 6 hours. The reaction mixture was then quenched with H$_2$O and concentrated.

The residue was dissolved in a stirred 4:1 mixture of EtOAc and NaHCO$_{3(sat.)}$. The two phases were separated and the organic solution was washed with brine, dried over Na$_2$SO$_4$ and concentrated to dryness. The resulting solid was washed twice with Et$_2$O and dried to yield the desired product as a white solid. LC/MS (m/z): 214.0 (MH$^+$), R$_t$ 1.13 minutes.

4-(2-(diethylamino)ethyl)thiazol-2-amine

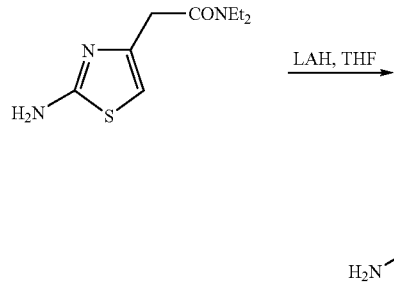

A suspension of 2-(2-aminothiazol-4-yl)-N,N-diethylacetamide (1 eq) in THF was added dropwise to a vigorously stirred suspension of LAH (1 eq) in THF at 0° C. The mixture was stirred at room temperature for 2 hours. At this time, the resulting mixture was cooled to 0° C. and 1 part H$_2$O, followed by 1 part 10% NaOH and lastly 3 parts H$_2$O, were added dropwise. The mixture was stirred for 10 minutes, filtered, and the solid residue washed with THF. The filtrate was collected and concentrated to dryness. The resulting crude material was washed with Et$_2$O twice and dried to afford a viscous brown oil. LC/MS (m/z): 200.1, (MH$^+$), R$_t$ 0.34 minutes.

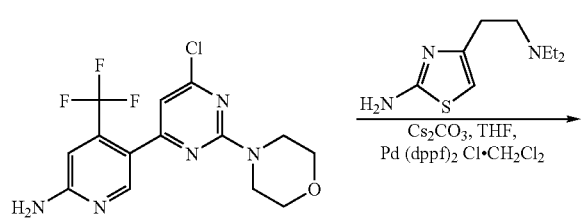

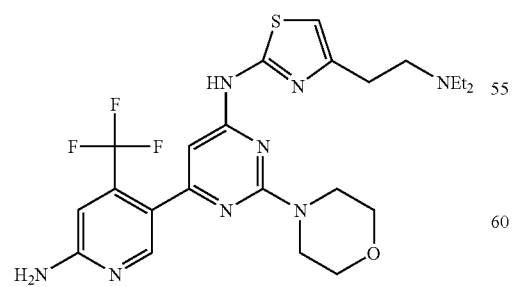

The title compound was synthesized according to the general procedure shown in Example 2. LC/MS (m/z): 523.1 (MH$^+$), R$_t$ 2.11 minutes. $^1$H-NMR (DMSO): δ 8.15 (1H, s); 7.08 (1H, s); 6.96 (1H, s); 6.38 (1H, s); 3.78 (4H, m); 3.65 (4H, m); 3.31 (2H, m); 3.13 (4H, q, J=7.2 Hz); 3.02 (2H, m); 1.20 (6H, t, J=7.2 Hz).

Example 14

Preparation of N$^6$-(2-methoxyethyl)-2-morpholino-4, 5'-bipyrimidine-2',6-diamine

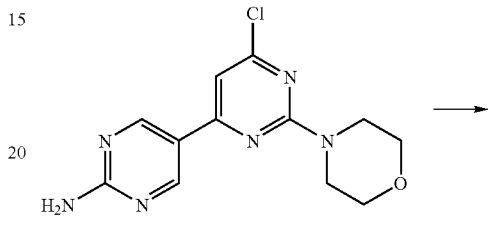

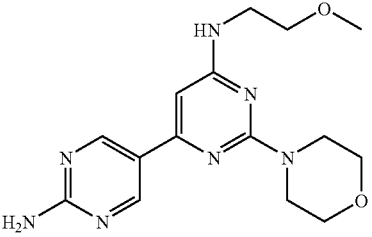

An argon sparged mixture of 6-chloro-2-morpholino-4,5'-bipyrimidin-2'-amine (10 mg, 0.03 mmol) and 2-methoxyethanamine (0.018 mL, 0.20 mmol) in NMP (0.8 mL) contained in a sealed pressure vessel was heated in a microwave at 155° C. for 1000 seconds. The reaction mixture was filtered and purified by reverse phase preparative HPLC to give N$^6$-(2-methoxyethyl)-2-morpholino-4,5'-bipyrimidine-2',6-diamine as the TFA salt (4.0 mg, 30%). LC/MS (m/z): 332.2 (MH$^+$), R$_t$ 1.44 minutes.

Example 15

Preparation of 2-morpholino-6-(2-phenylmorpholino)-4,5'-bipyrimidin-2'-amine

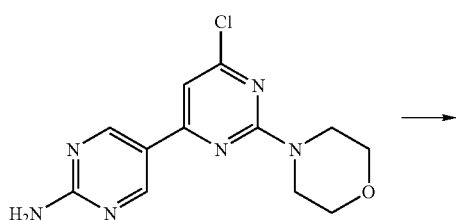

give N⁶-tert-butyl-2-morpholino-4,5'-bipyrimidine-2',6-diamine as the TFA salt (0.9 mg, 7%). LC/MS (m/z): 330.2 (MH⁺), R$_t$ 1.96 minutes.

Example 17

Preparation of 1-(2-(6-amino-4-(trifluoromethyl)pyridin-3-yl)-6-morpholino-pyrimidin-4-yl)piperidin-2-one 5-(2-chloro-6-morpholinopyrimidin-4-ylamino)pentanoic acid

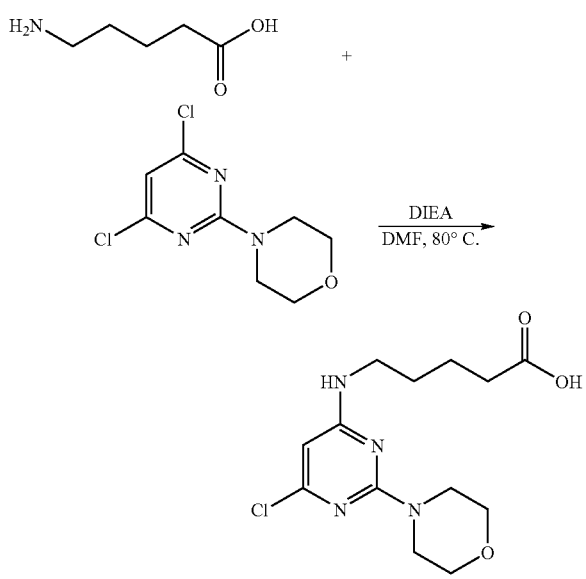

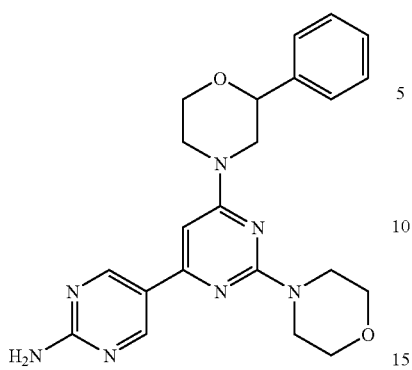

An argon sparged mixture of 6-chloro-2-morpholino-4,5'-bipyrimidin-2'-amine (10 mg, 0.03 mmol), Cs₂CO₃ (27 mg, 0.09 mmol) and 2-phenylmorpholine (11 mg, 0.068 mmol) in NMP (0.5 mL) contained in a sealed pressure vessel, was heated in a microwave at 170° C. for 600 seconds. The reaction mixture was filtered and purified by reverse phase preparative HPLC to give 2-morpholino-6-(2-phenylmorpholino)-4,5'-bipyrimidin-2'-amine as the TFA salt (7.2 mg, 45%). LC/MS (m/z): 420.1 (MH⁺), R$_t$ 2.20 minutes.

Example 16

Preparation of N⁶-tert-butyl-2-morpholino-4,5'-bipyrimidine-2',6'-diamine

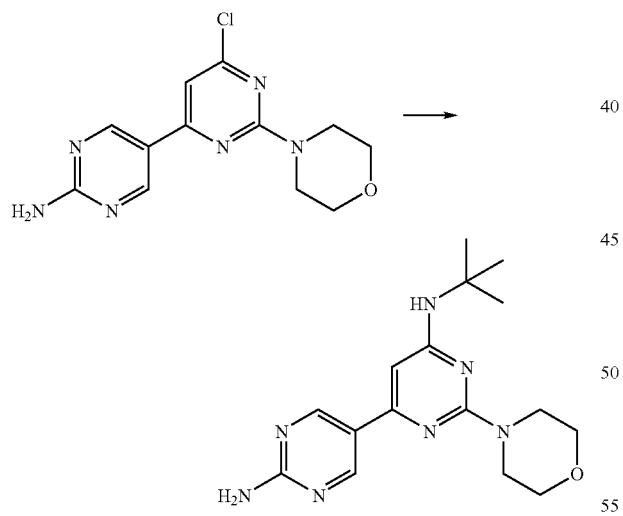

An argon sparged mixture of 6-chloro-2-morpholino-4,5'-bipyrimidin-2'-amine (10 mg, 0.03 mmol) and tert-butylamine (12.5 mg, 0.17 mmol) in NMP (0.5 mL) contained in a sealed pressure vessel, was heated in a microwave at 175° C. for 800 seconds. An additional amount of tert-butylamine (50 mg, 0.68 mmol) was added to the reaction. The reaction was again heated in a microwave at 175° C. for 800 seconds and again at 175° C. for 800 seconds until disappearance of the starting material. The crude mixture was filtered. The crude product was purified by reverse phase preparative HPLC to 5-Aminopentanoic acid (140 mg, 1.19 mmol), 4-(2,6-dichloropyrimidin-4-yl)morpholine (prepared as in Method 22; 234 mg, 1.0 mmol) and DIEA (0.530 mL, 3.0 mmol) were dissolved in N,N-dimethylformamide (6 mL). The reaction solution was stirred at 40° C. for 40 hours. The reaction was diluted with EtOAc (100 mL) and washed with 0.5 M HCl (40 mL), water (40 mL), brine (40 mL), dried with Na₂SO₄, filtered and evaporated to give a solid. The crude product was chromatographed on a silica gel column by eluting with 80% EtOAc in hexane to give 5-(2-chloro-6-morpholinopyrimidin-4-ylamino)pentanoic acid as a white solid (190 mg, 60%). LC/MS (m/z): 315.0 (MH⁺), R$_f$ 1.79 minutes.

1-(2-chloro-6-morpholinopyrimidin-4-yl)piperidin-2-one

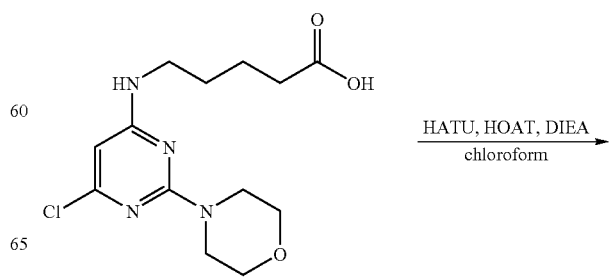

105

-continued

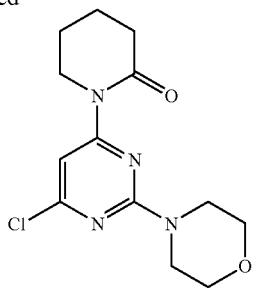

To a solution of HATU (304 mg, 0.8 mmol), HOAT (82 mg, 0.6 mmol) and DIEA (0.209 mL, 1.2 mmol) in chloroform (20 mL) under argon, a solution of 5-(2-chloro-6-morpholinopyrimidin-4-ylamino)pentanoic acid (190 mg, 0.6 mmol) in chloroform (10 mL) was slowly added. The reaction solution was stirred at room temperature for 5 hours. After the reaction was complete, the solution was evaporated to dryness to give a white solid which was chromatographed on a silica gel column by eluting with 40% EtOAc/hexane to give 1-(2-chloro-6-morpholinopyrimidin-4-yl)piperidin-2-one as a white solid (62 mg, 35%). LC/MS (m/z): 297.0 (MH$^+$), R$_t$ 2.74 minutes.

1-(2-(6-amino-4-(trifluoromethyl)pyridin-3-yl)-6-morpholinopyrimidin-4-yl)piperidin-2-one

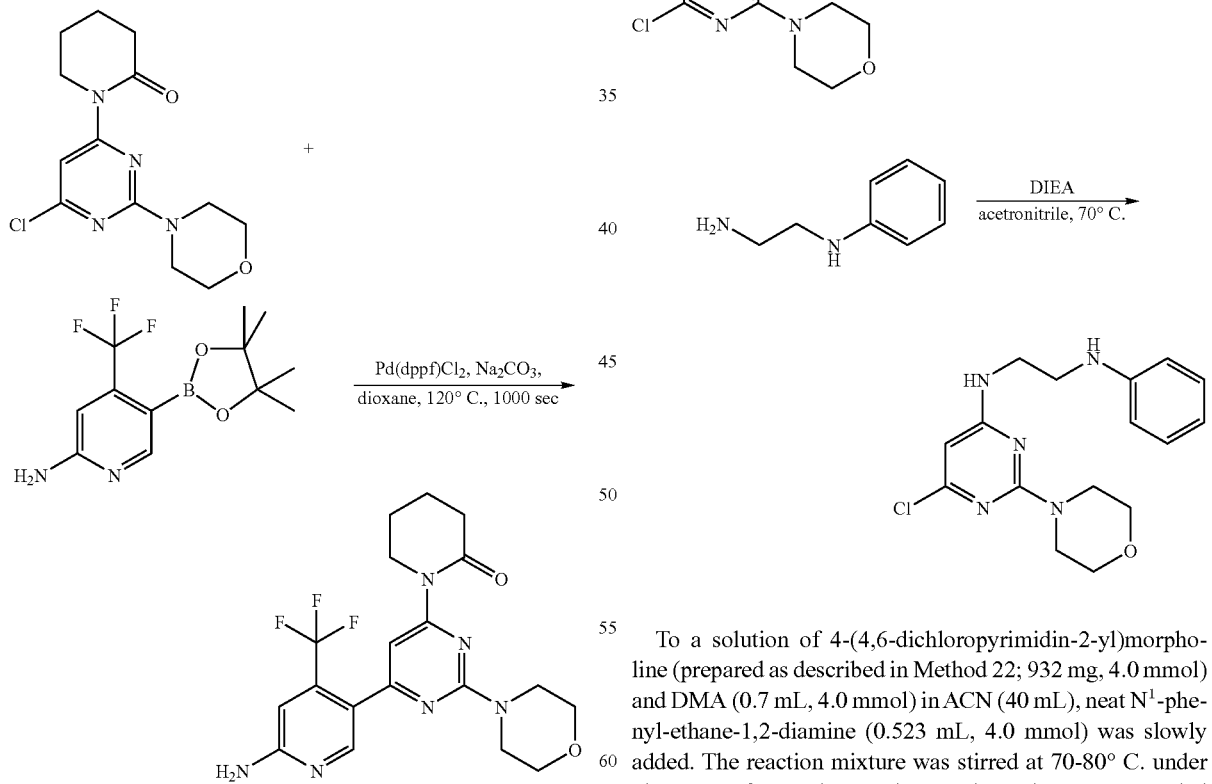

To a suspension of 1-(2-chloro-6-morpholinopyrimidin-4-yl)piperidin-2-one (16 mg, 0.05 mmol), 5-(4,4,5,5-tetramethyl-1,3,2-dioxaborolan-2-yl)-4-(trifluoromethyl)pyridin-2-amine (prepared as in Method 4; 23 mg, 0.08 mmol) and dichloro[1,1'-bis(diphenylphosphino)ferrocene]palladium

106

(II) dichloromethane adduct (8 mg, 0.009 mmol) in dioxane (1.1 mL), 2 M aqueous sodium carbonate solution (0.4 mL, 0.8 mmol) was added under argon. The reaction mixture was heated in a microwave at 120° C. for 1000 seconds. The crude product was partitioned between EtOAc (30 mL) and saturated sodium bicarbonate (10 mL). The organic layer was separated, dried over sodium sulfate, filtered and concentrated under reduced pressure. The crude product was purified by preparative reverse phase HPLC to give 1-(2-(6-amino-4-(trifluoromethyl)pyridin-3-yl)-6-morpholinopyrimidin-4-yl)piperidin-2-one as a yellow powder (8.8 mg, 42%). LC/MS (m/z): 423.0 (MH$^+$), R$_t$ 2.25 minutes.

Example 18

Preparation of 1-(6-(6-amino-4-(trifluoromethyl)pyridin-3-yl)-2-morpholinopyrimidin-4-yl)-3-phenylimidazolidin-2-one $N^1$-(6-chloro-2-morpholinopyrimidin-4-yl)-$N^2$-phenylethane-1,2-diamine

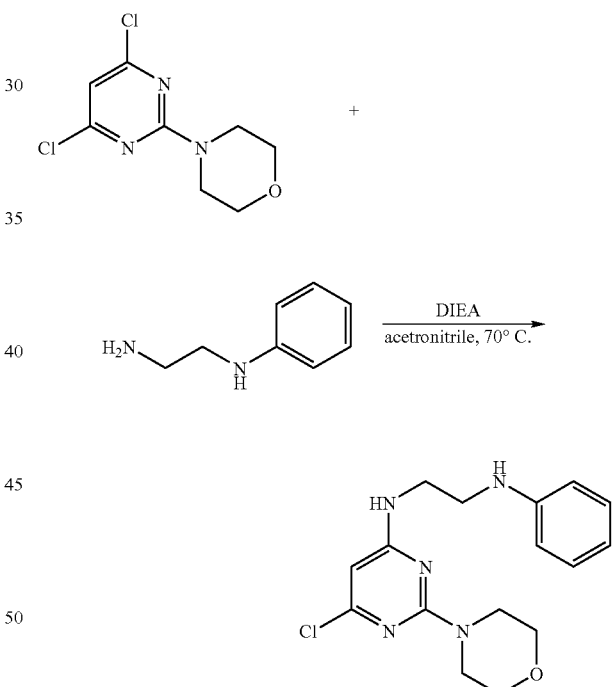

To a solution of 4-(4,6-dichloropyrimidin-2-yl)morpholine (prepared as described in Method 22; 932 mg, 4.0 mmol) and DMA (0.7 mL, 4.0 mmol) in ACN (40 mL), neat $N^1$-phenyl-ethane-1,2-diamine (0.523 mL, 4.0 mmol) was slowly added. The reaction mixture was stirred at 70-80° C. under nitrogen. After 20 hours, the reaction mixture was cooled down, and the solvent was removed under reduced pressure. The crude product was partitioned between EtOAc (120 mL) and 0.1 M NaHCO$_3$ (50 mL). The organic layer was washed with additional 0.1 M NaHCO$_3$ (2×50 mL), brine (50 mL), dried, filtered and concentrated to give $N^1$-(6-chloro-2-morpholinopyrimidin-4-yl)-N²-phenylethane-1,2-diamine, as an off-white solid (1.29 g, 96%). LC/MS (m/z): 334.0 (MH⁺), R$_t$ 1.94 minutes.

1-(6-chloro-2-morpholinopyrimidin-4-yl)-3-phenylimidazolidin-2-one

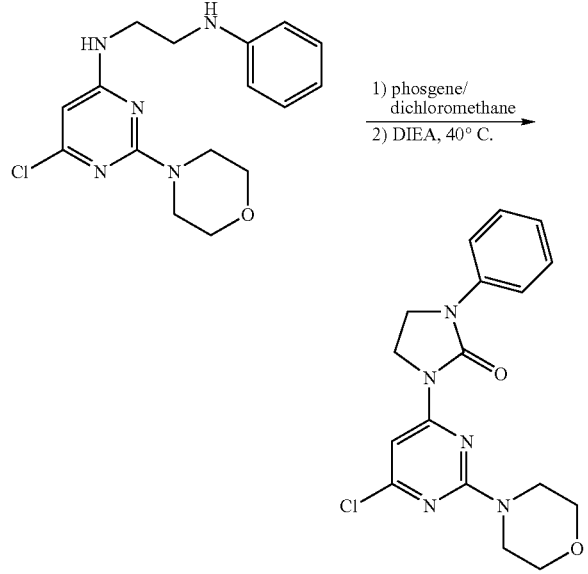

To a solution of N¹-(6-chloro-2-morpholinopyrimidin-4-yl)-N²-phenylethane-1,2-diamine (100 mg, 0.3 mmol) in DCM (15 mL) at 0° C. under nitrogen, a solution of phosgene in toluene (1.89 M, 0.32 mL, 0.6 mmol) was slowly added. After 20 minutes, the reaction was allowed to warm to RT. After 18 hours, DIEA (0.42 mL, 2.4 mmol) was added and the reaction solution was heated to 40-50° C. for 40 hours. The reaction mixture was evaporated under reduced pressure and the crude product was purified by silica gel chromatography eluting with 70% EtOAc/hexane to give 1-(6-chloro-2-morpholinopyrimidin-4-yl)-3-phenylimidazolidin-2-one as a white solid (94 mg, 87%). LC/MS (m/z): 360.1 (MH⁺), R$_t$ 3.41 minutes.

1-(6-(6-amino-4-(trifluoromethyl)pyridin-3-yl)-2-morpholinopyrimidin-4-yl)-3-phenylimidazolidin-2-one

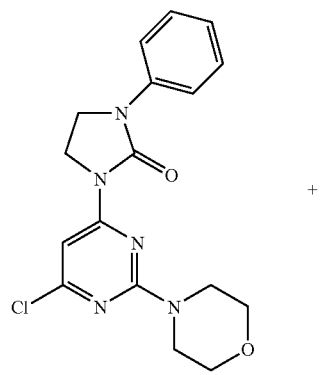

+

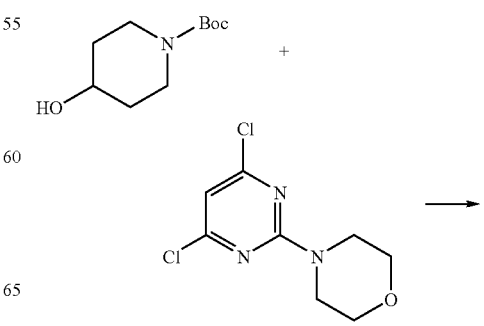

To a suspension of 1-(6-chloro-2-morpholinopyrimidin-4-yl)-3-phenylimidazolidin-2-one (18 mg, 0.05 mmol), 5-(4,4,5,5-tetramethyl-1,3,2-dioxaborolan-2-yl)-4-(trifluoromethyl)pyridin-2-amine (prepared as described in Method 4; 18 mg, 0.06 mmol) and dichloro[1,1'-bis(diphenylphosphino)ferrocene]palladium (II) dichloromethane adduct (3.2 mg, 0.004 mmol) in DME (1.2 mL), 2 M aqueous sodium carbonate solution (0.4 mL, 0.8 mmol) was added under argon. The reaction mixture was stirred at 95° C. for 5 hours. The crude product was partitioned between EtOAc (30 mL) and saturated sodium bicarbonate (10 mL). The organic layer was separated, dried over sodium sulfate, filtered and concentrated under reduced pressure. The crude product was purified by preparative HPLC to give 1-(6-(6-amino-4-(trifluoromethyl)pyridin-3-yl)-2-morpholinopyrimidin-4-yl)-3-phenylimidazolidin-2-one as a pale yellow powder (8.4 mg, 35% overall yield). LC/MS (m/z): 448.1 (MH⁺), R$_t$ 3.29 minutes.

Example 19

Preparation of 1-(4-(6-(6-amino-4-(trifluoromethyl)pyridin-3-yl)-2-morpholinopyrimidin-4-yloxy)piperidin-1-yl)ethanone Step 1: Alkoxylation of 2-morpholino-4,6-dichloropyrimidine

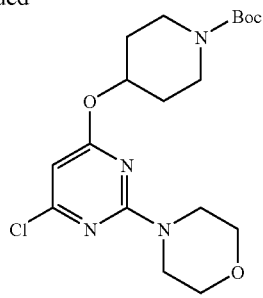

To a solution of N-Boc-4-hydroxy piperidine (2.58 g, 12.81 mmol) in tetrahydrofuran at 0° C. under argon, was added sodium hydride (60%, 512 mg, 12.81 mmol). After stirring for 20 minutes, a solution of 2-morpholino-4,6-dichloropyrimidine (2.0 g, 8.54 mmol) in tetrahydrofuran (20 mL) was added through a syringe. The solution was stirred for 14 hours as the ice bath warmed to room temperature. At this time, the reaction mixture was quenched with water (2 mL), and was partitioned between EtOAc (350 mL) and Na$_2$CO$_3$ (sat.) (75 mL). The organic layer was separated, washed with brine (50 mL), dried over Na$_2$SO$_4$, filtered, concentrated and the residue was purified by SiO$_2$ chromatography (15-20% EtOAc in hexanes) to yield tert-butyl 4-(6-chloro-2-morpholinopyrimidin-4-yloxy)piperidine-1-carboxylate as a white solid (2.64 g, 77%). LCMS (m/z): 399.1 (MH$^+$). $^1$H NMR (CDCl$_3$): δ 6.00 (s, 1H), 5.18 (m, 1H), 3.74 (s, 8H), 3.64-3.74 (m, 2H), 3.28-3.38 (m, 2H), 1.86-1.96 (m, 2H), 1.68-1.78 (m, 2H), 1.44 (s, 9H).

Step 2: Suzuki Reaction of 2-morpholino-4-alkoxy-substituted-6-chloropyrimidine

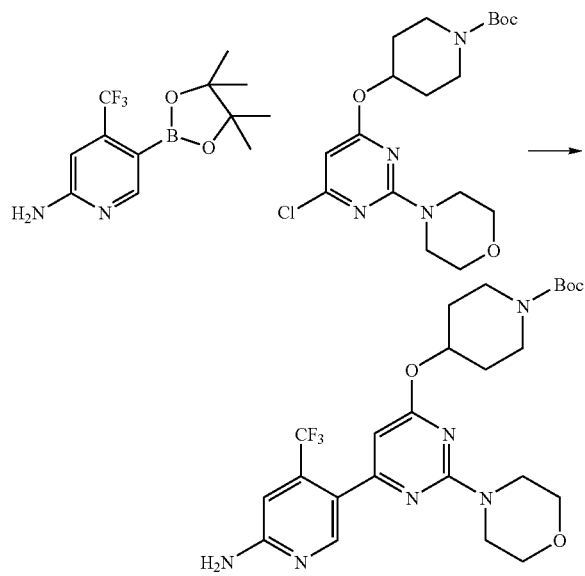

A mixture of tent-butyl 4-(6-chloro-2-morpholinopyrimidin-4-yloxy)piperidine-1-carboxylate (250 mg, 0.63 mmol), 5-(4,4,5,5-tetramethyl-1,3,2-dioxaborolan-2-yl)-4-(trifluoromethyl)pyridine-2-amine (prepared as in method 4, 325 mg, 1.13 mmol) and Pd(dppf)Cl$_2$—CH$_2$Cl$_2$ (25.6 mg, 0.031 mmol) in dimethoxyethane/2 M Na$_2$CO$_3$ (3:1, 8 mL) was heated under microwave irradiation for 15 minutes at 120° C. The reaction mixture was partitioned between EtOAc (200 mL) and Na$_2$CO$_{3(sat.)}$ (50 mL), the organic layer was separated, washed with brine (50 mL), dried over Na$_2$SO$_4$, filtered, concentrated and purified by SiO$_2$ chromatography (50-75% EtOAc/hexanes) to yield the product as a white solid (207 mg, 63%). LCMS (m/z): 525.2 (MH$^+$).

Step 3: Hydrolysis of N-Boc Protecting Group

A mixture of tert-butyl 4-(6-(6-amino-4-(trifluoromethyl)pyridin-3-yl)-2-morpholinopyrimidin-4-yloxy)piperidine-1-carboxylate (649 mg, 1.24 mmol) and 4 M HCl/dioxane (15 mL, 60 mmol) was allowed to stand at room temperature for 14 hours. Upon removal of volatiles in vacuo, diethyl ether (50 mL) was added, the material was sonicated and concentrated yielding the bis HCl salt of the desired product as an off white solid. LCMS (m/z): 425.1 (MH$^+$).

Step 4: Acylation

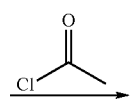

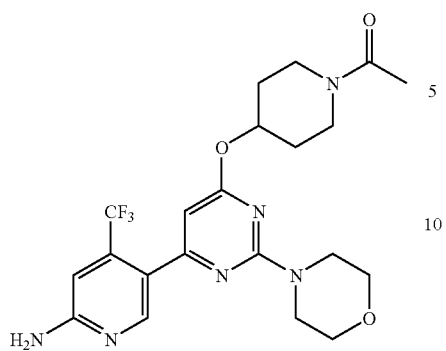

To a solution of 4-(trifluoromethyl)-5-(2-morpholino-6-(piperidin-4-yloxy)pyrimidin-4-yl)pyridin-2-amine in NMP, was added diisopropylethylamine (5 eq) and acetyl chloride (1.5 eq). The reaction mixture was stirred at room temperature for 2 h and then was purified directly by reverse-phase HPLC and lyophilized yielding the TFA salt of the product. Alternatively, after reverse phase HPLC the free base of the product could be isolated after extraction into EtOAc upon basifying, followed by drying over $Na_2SO_4$ and removal of volatiles in vacuo. LCMS (m/z): 467.1 (MH$^+$).

Example 20

Preparation of 5-(6-((S)-piperidin-3-yloxy)-2-morpholinopyrimidin-4-yl)-4-(trifluoromethyl)pyridin-2-amine

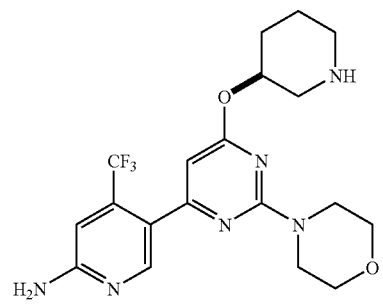

(S)-tert-butyl 3-(6-chloro-2-morpholinopyrimidin-4-yloxy)piperidine-1-carboxylate was prepared as in Example 19, Step 1, for the alkoxylation of 2-morpholino-4,6-dichloropyrimidine (87%). LCMS (m/z): 399.1 (MH$^+$). The Boc protected intermediate was prepared by Suzuki reaction as shown in Step 2 of Example 19 and was purified by $SiO_2$ chromatography (30-60% EtOAc/hexanes; 78%). LCMS (m/z): 526.0 (MH$^+$). The title compound was prepared by cleaving the N-Boc protecting group as shown in Step 3 of Example 19. LCMS (m/z): 425.1 (MH$^+$).

Example 21

Preparation of 5-(6-((R)-piperidin-3-yloxy)-2-morpholino pyrimidin-4-yl)-4-(trifluoromethyl)pyridin-2-amine

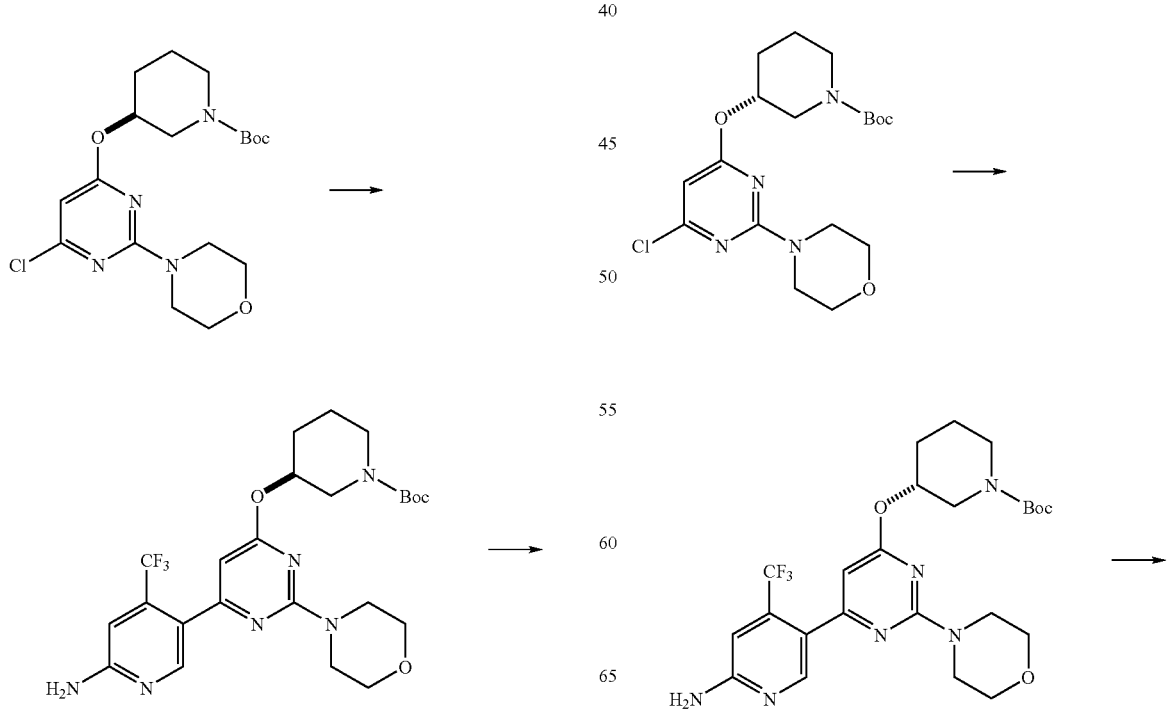

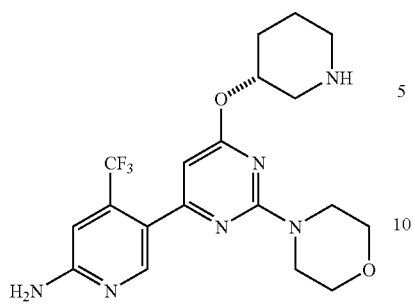

(R)-tert-butyl 3-(6-chloro-2-morpholinopyrimidin-4-yloxy)piperidine-1-carboxylate was prepared as in Example 19, Step 1, for the alkoxylation of 2-morpholino-4,6-dichloropyrimidine (82%). LCMS (m/z): 399.1 (MH+). The Boc protected intermediate was prepared by Suzuki reaction as shown in Step 2 of Example 19 and was purified by silica gel chromatography (30-60% EtOAc/hexanes, 54%). LCMS (m/z): 526.0 (MH+). The title compound was prepared by cleaving the N-Boc protecting group as shown in Step 3 of Example 19. LCMS (m/z): 425.1 (MH+).

Example 22

Preparation of 1-((R)-3-(6-(6-amino-4-(trifluoromethyl)pyridin-3-yl)-2-morpholinopyrimidin-4-yloxy)pyrrolidin-1-yl)ethanone

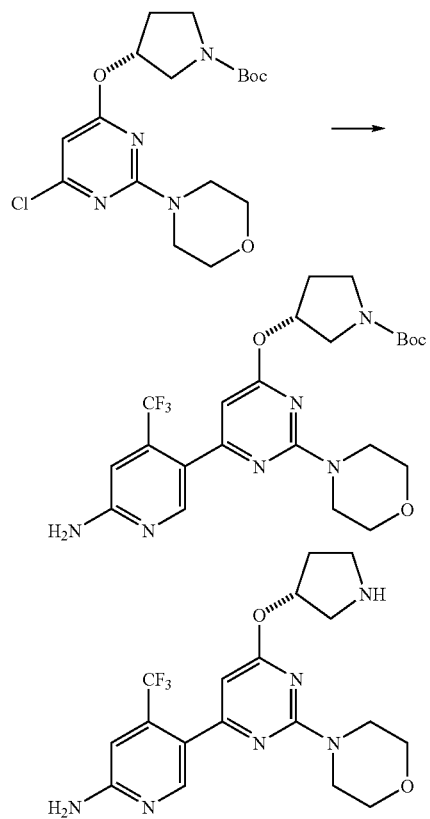

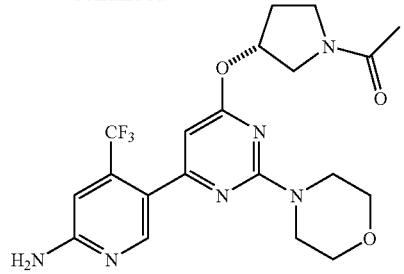

(R)-tert-butyl 3-(6-chloro-2-morpholinopyrimidin-4-yloxy)pyrrolidine-1-carboxylate was prepared as in Example 19, Step 1, for the alkoxylation of 2-morpholino-4,6-dichloropyrimidine (41%). LCMS (m/z): 385.0 (MH+).

The Boc protected intermediate was prepared by Suzuki reaction as shown in Step 2 of Example 19 and was purified by reverse phase HPLC and isolated as free base after extraction into EtOAc upon basifying (71%). LCMS (m/z): 511.0 (MH+). Cleavage of the N-Boc protecting group was performed as shown in Step 3 of Example 19. LCMS (m/z): 411.0 (MH+). The title compound was prepared as in Step 4 of Example 19. LCMS (m/z): 453.1 (MH+), $R_t$ 2.18.

Example 23

Preparation of 1-((S)-3-(6-(6-amino-4-(trifluoromethyl)pyridin-3-yl)-2-morpholinopyrimidin-4-yloxy)pyrrolidin-1-yl)ethanone

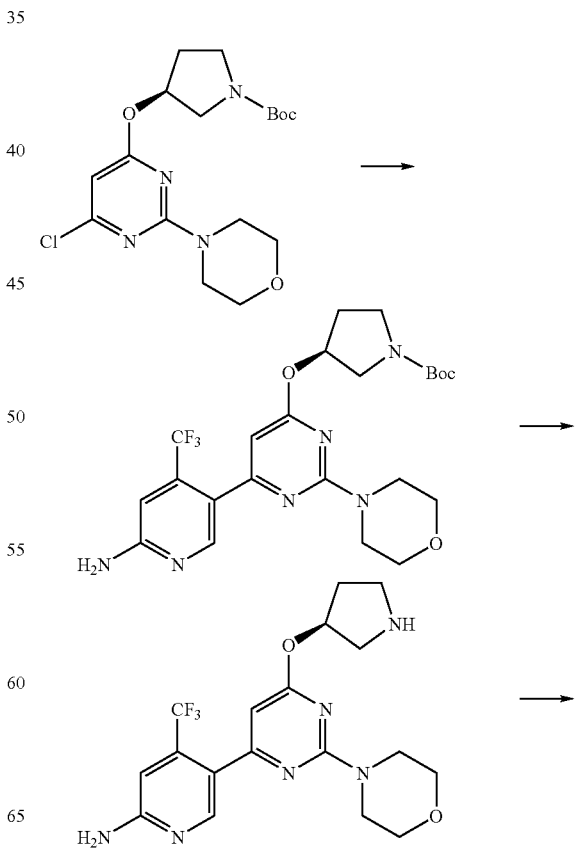

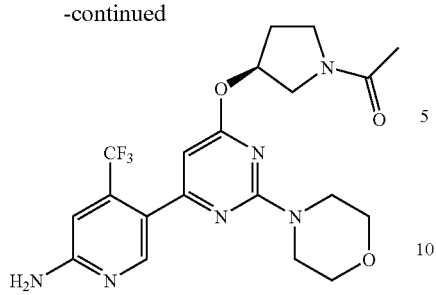

(S)-tert-butyl 3-(6-chloro-2-morpholinopyrimidin-4-yloxy)pyrrolidine-1-carboxylate was prepared according to Example 19, Step 1, for the alkoxylation of 2-morpholino-4,6-dichloropyrimidine (99%). LCMS (m/z): 385.0 (MH+). The Boc protected intermediate was prepared by Suzuki reaction as shown in Step 2 of Example 19, purified by reverse phase HPLC and isolated as free base after extraction into EtOAc upon basifying (72%). LCMS (m/z): 511.0 (MH+). The N-Boc protecting group was cleaved as shown in Step 3 of Example 19. LCMS (m/z): 411.0 (MH+). The title compound was prepared as in step 4 of Example 19. LCMS (m/z): 453.1 (MH+), $R_t$ 2.18.

Example 24

Preparation of 4-(trifluoromethyl)-5-(2-morpholino-6-(tetrahydro-2H-pyran-4-yloxy)pyrimidin-4-yl)pyridin-2-amine

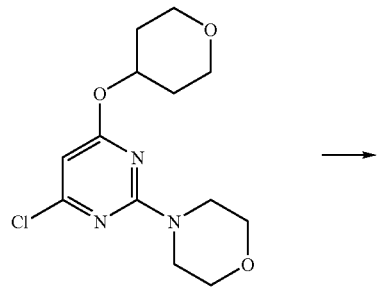

4-(4-chloro-6-(tetrahydro-2H-pyran-4-yloxy)pyrimidin-2-yl)morpholine was prepared according to Example 19, Step 1, for the alkoxylation of 2-morpholino-4,6-dichloropyrimidine with 4-hydroxytetrahydropyran (80%). LCMS (m/z): 300.1 (MH+). The title compound was prepared by Suzuki reaction as shown in Step 2 of Example 19. LC/MS (m/z): 426.1 (MH+), $R_t$ 2.26 minutes.

Example 25

Preparation 5-(6-((R)-tetrahydrofuran-3-yloxy)-2-morpholino pyrimidin-4-yl)-4-(trifluoromethyl)pyridin-2-amine

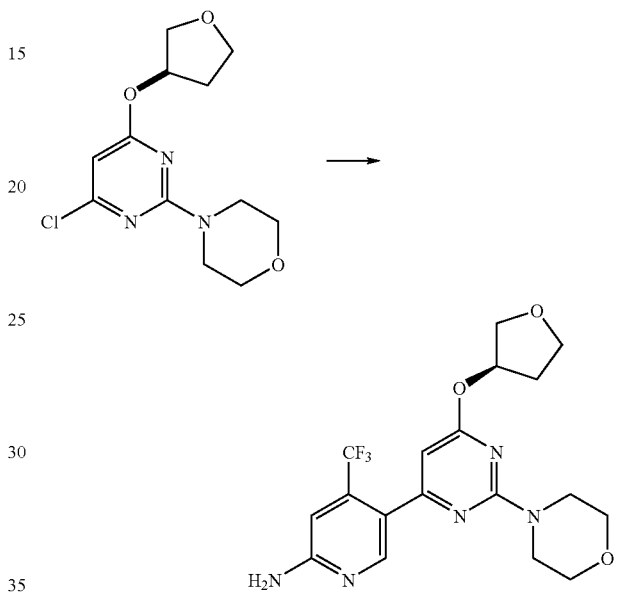

(R)-4-(4-chloro-6-(tetrahydrofuran-3-yloxy)pyrimidin-2-yl)morpholine was prepared according to Example 19, Step 1, for the alkoxylation of 2-morpholino-4,6-dichloropyrimidine with (R)-3-hydroxytetrahydrofuran (81%). LCMS (m/z): 286.1 (MH+). The title compound was prepared by Suzuki reaction as shown in Step 2 of Example 19. LC/MS (m/z): 412.1 (MH+).

Example 26

Preparation of 5-(6-((S)-tetrahydrofuran-3-yloxy)-2-morpholino pyrimidin-4-yl)-4-(trifluoromethyl)pyridin-2-amine

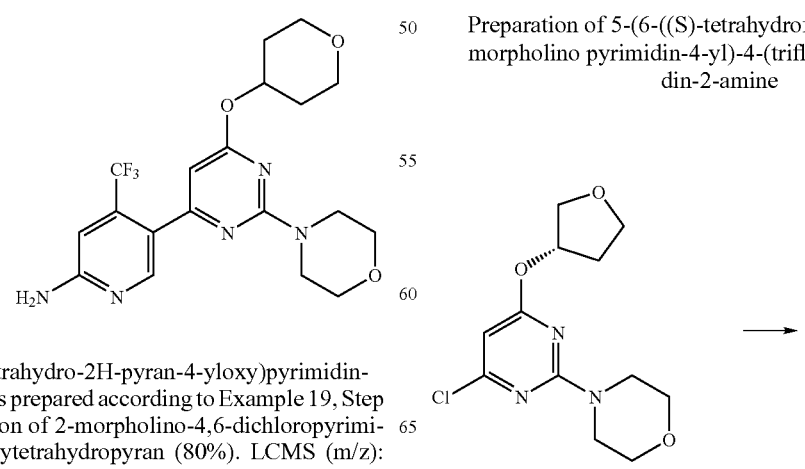

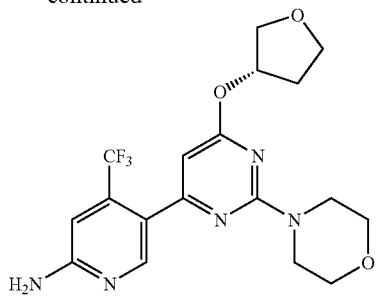

(S)-4-(4-chloro-6-(tetrahydrofuran-3-yloxy)pyrimidin-2-yl)morpholine was prepared according to Example 19, Step 1, for alkoxylation of 2-morpholino-4,6-dichloropyrimidine with (S)-3-hydroxytetrahydrofuran (85%). LCMS (m/z): 286.1 (MH⁺). The title compound was prepared by Suzuki reaction as shown in Step 2 of Example 19. LC/MS (m/z): 412.1 (MH⁺).

Example 27

Preparation of 4-(trifluoromethyl)-5-(2-morpholino-6-(piperidin-4-yloxy)pyrimidin-4-yl)pyrimidin-2-amine

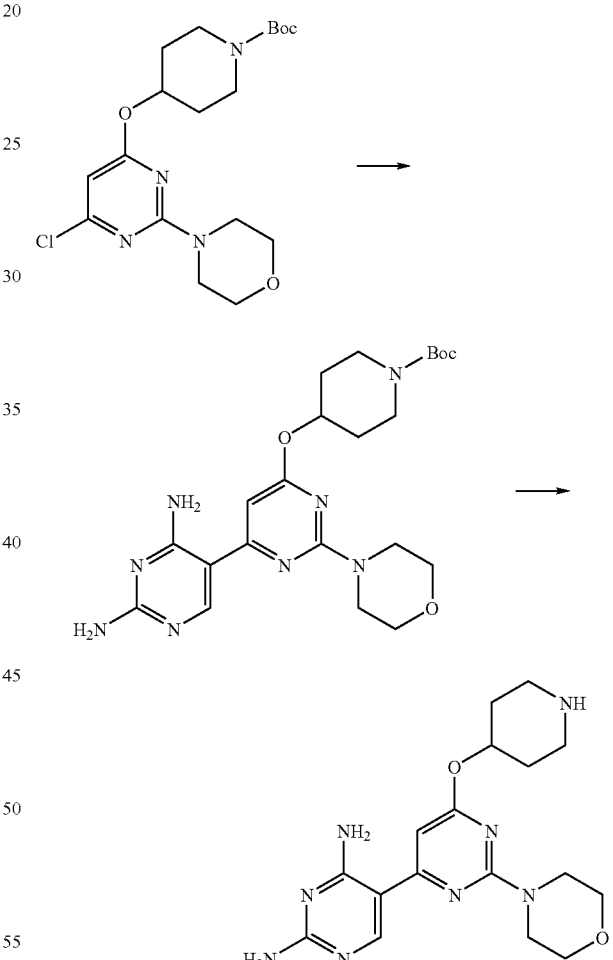

tert-butyl 4-(6-(2-amino-4-(trifluoromethyl)pyrimidin-5-yl)-2-morpholinopyrimidin-4-yloxy)piperidine-1-carboxylate was prepared by Suzuki reaction of tert-butyl 4-(6-chloro-2-morpholinopyrimidin-4-yloxy)piperidine-1-carboxylate, as shown in Step 2 of Example 19, with 5-(4,4,5,5-tetramethyl(1,3,2-dioxaborolan-2-yl))-4-(trifluoromethyl)pyrimidine-2-ylamine (prepared as in Method 5). The crude product was purified by silica gel chromatography (30-50% EtOAc/hexanes) (63%). LCMS (m/z): 526.0 (MH⁺). The title compound was prepared by cleaving the N-Boc protecting group as shown in Step 3 of Example 19. LCMS (m/z): 426.0 (MH⁺).

Example 28

Preparation of 5-(2-morpholino-6-(piperidin-4-yloxy)pyrimidin-4-yl)pyrimidine-2,4-diamine

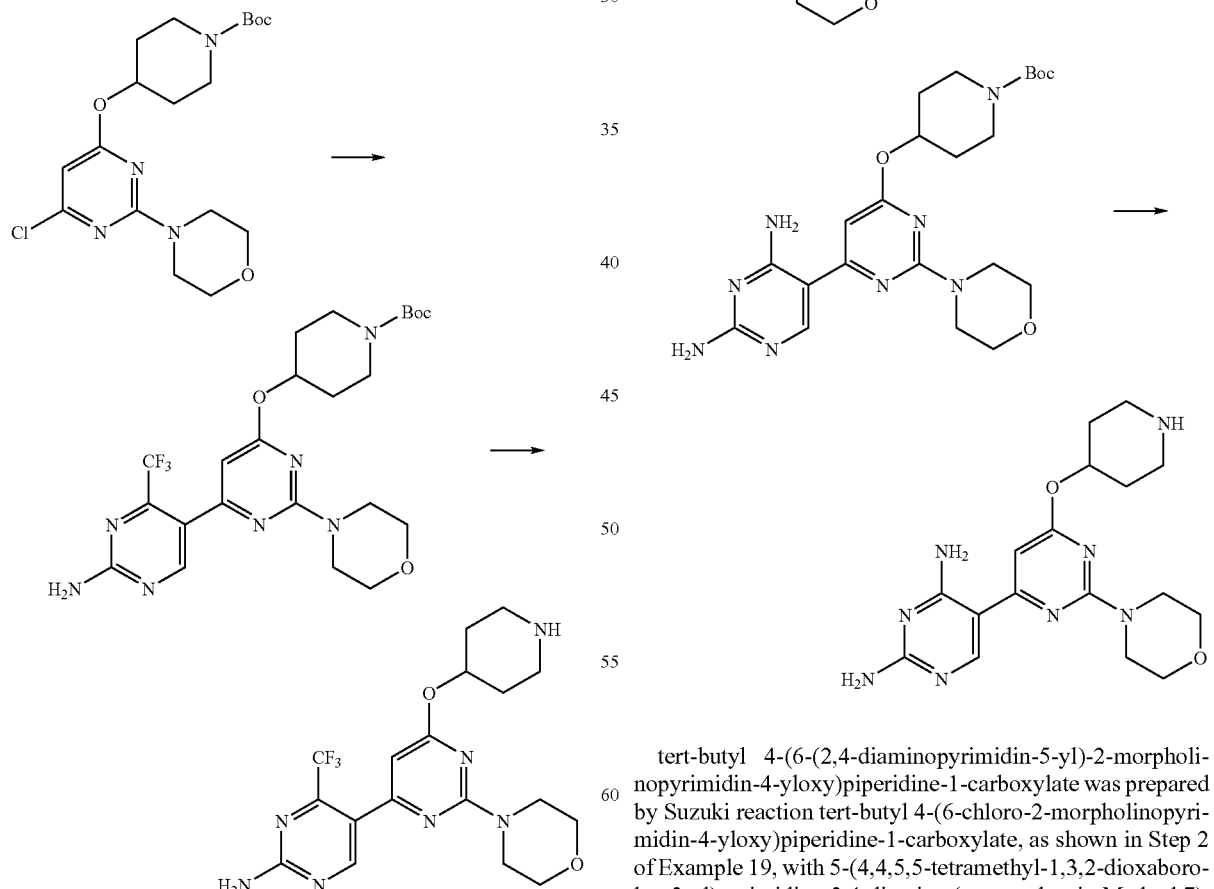

tert-butyl 4-(6-(2,4-diaminopyrimidin-5-yl)-2-morpholinopyrimidin-4-yloxy)piperidine-1-carboxylate was prepared by Suzuki reaction tert-butyl 4-(6-chloro-2-morpholinopyrimidin-4-yloxy)piperidine-1-carboxylate, as shown in Step 2 of Example 19, with 5-(4,4,5,5-tetramethyl-1,3,2-dioxaborolan-2-yl)pyrimidine-2,4-diamine (prepared as in Method 7). The crude product was purified by reverse phase HPLC and isolated as the free base after extraction into EtOAc upon basifying (70%). LCMS (m/z): 473.1 (MH⁺). The title compound was prepared by cleaving the N-Boc protecting group as shown in Step 3 of Example 19. LCMS (m/z): 373.0 (MH+).

Example 29

Preparation of 1-((R)-3-(6-(2,4-diaminopyrimidin-5-yl)-2-morpholinopyrimidin-4-yloxy)piperidin-1-yl)ethanone

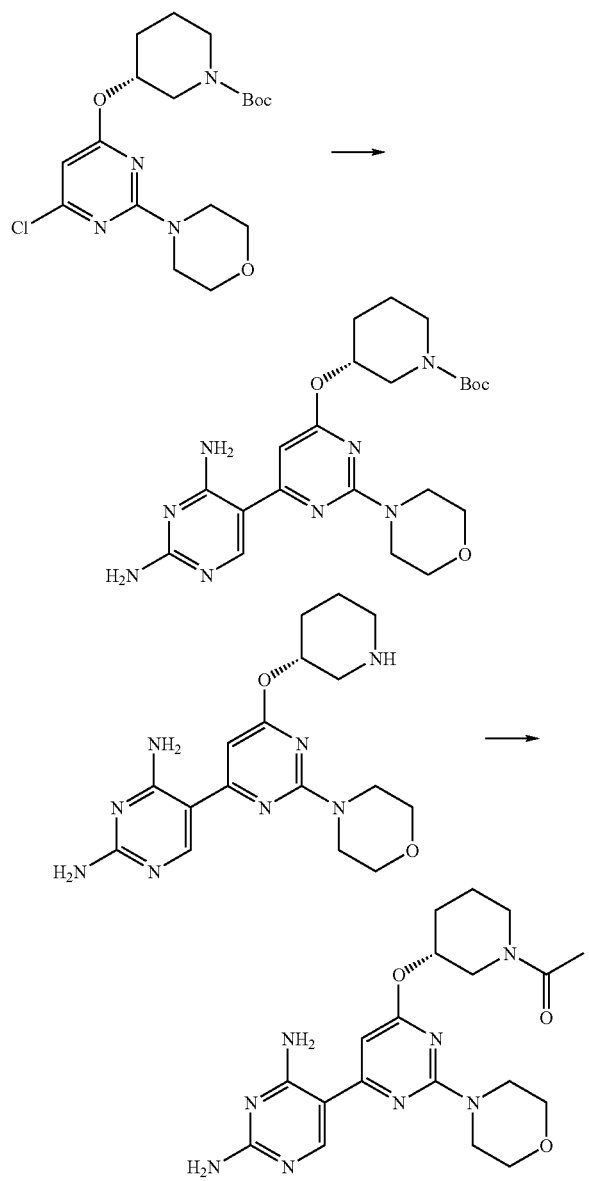

(R)-tert-butyl 3-(6-(2,4-diaminopyrimidin-5-yl)-2-morpholinopyrimidin-4-yloxy)piperidine-1-carboxylate was prepared by Suzuki reaction of 4-(6-chloro-2-morpholinopyrimidin-4-yloxy)piperidine-1-carboxylate, as shown in Step 2 of Example 19, with 5-(4,4,5,5-tetramethyl-1,3,2-dioxaborolan-2-yl)pyrimidine-2,4-diamine. The crude product was purified by reverse phase HPLC and isolated as the free base after extraction into EtOAc upon basifying (77%). LCMS (m/z): 473.1 (MH+). The N-Boc protecting group was cleaved as shown in Step 3 of Example 19. LCMS (m/z): 373.0 (MH+). The title compound was synthesized as shown in step 4 of Example 19. LCMS (m/z): 460.1 (MH+), $R_t$ 2.51.

Example 30

Preparation of 2-amino-5-(2-morpholino-6-(N-acyl-piperidin-4-yloxy)pyrimidin-4-yl)pyrimidin-4(3H)-one

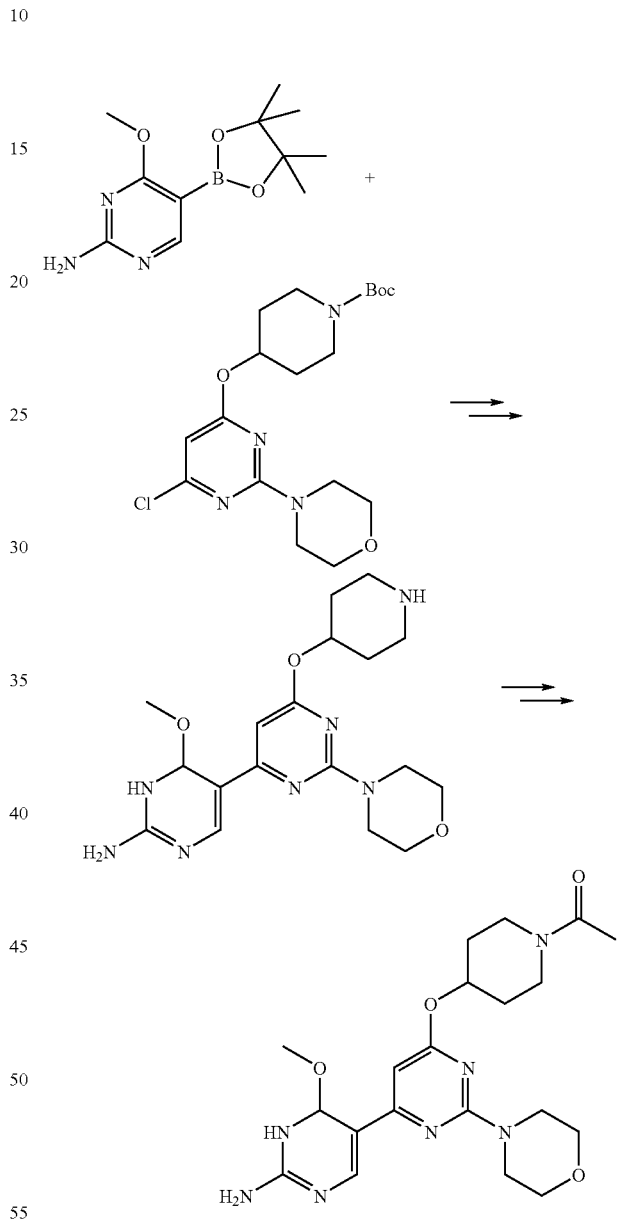

A mixture of tert-butyl 4-(6-chloro-2-morpholinopyrimidin-4-yloxy)piperidine-1-carboxylate (500 mg, 1.26 mmol), 4-methoxy-2-aminopyrimidyl boronate ester (prepared as in Method 8, 630 mg, 2.51 mmol) and Pd(dppf)Cl$_2$—CH$_2$Cl$_2$ (51 mg, 0.063 mmol) in dimethoxyethane and 2 M Na$_2$CO$_3$ (3:1, 12 mL) was heated under microwave irradiation for 15 minutes at 120° C. The reaction mixture was partitioned between EtOAc (200 mL) and Na$_2$CO$_{3(sat.)}$ (50 mL), the organic layer was separated and washed with brine (50 mL). The combined aqueous layers were extracted further with EtOAc (2×100 mL), and the combined organic layers were dried over Na₂SO₄, filtered and concentrated. To this material was added 4 M HCl/dioxane (20 mL) to remove the Boc group. After standing for 12 hours, the volatiles were removed in vacuo, and the residue was partitioned between CH₂Cl₂ (200 mL) and 1N NaOH (50 mL). Upon separating, the aqueous layer was extracted further with CH₂Cl₂ (200 mL) and then CHCl₃ (2×150 mL). The combined organic layers were concentrated yielding 1,6-dihydro-6-methoxy-5-(2-morpholino-6-(piperidin-4-yloxy)pyrimidin-4-yl)pyrimidin-2-amine (464 mg). The crude compound and morpholine (0.9 mL, 10.45 mmol) in NMP (10 mL) were heated under microwave irradiation for 15 minutes at 200° C. to convert the methoxy pyrimidine to the pyrimidone. Additional morpholine (0.9 mL, 10.45 mmol) was added and the solution was heated under microwave irradiation for 15 minutes and than 10 minutes at 200° C. Upon cooling the material was directly purified by reverse-phase HPLC. After lyophilization, the bis TFA salt of the 2-amino-5-(2-morpholino-6-(piperidin-4-yloxy)pyrimidin-4-yl)pyrimidin-4(3H)-one was isolated as an off-white solid (325 mg, 45%). LCMS (m/z): 374.1 (MH⁺). The title compound was prepared by acylation of the secondary amino group as shown in Example 19, step 4. LCMS (m/z): 416.0 (MH⁺), R$_t$ 1.67.

Example 31

Preparation of 2-amino-5-(2-morpholino-6-(N-methoxycarbonyl-piperidin-4-yloxy)pyrimidin-4-yl)pyrimidin-4(3H)-one

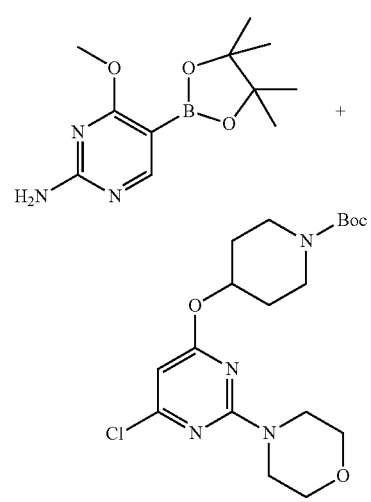

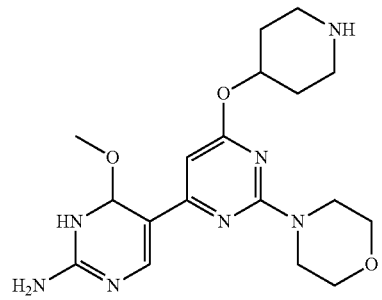

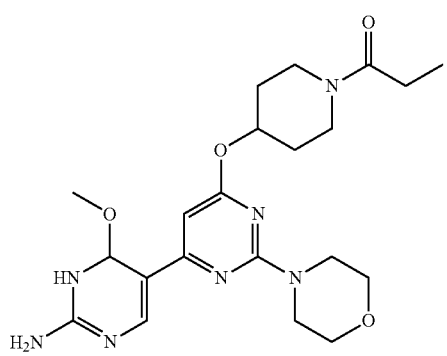

The title compound was prepared as in Example 30, except utilizing methylchloroformate instead of acetyl chloride in the last step. LCMS (m/z): 432.0 (MH⁺), R$_t$ 2.05.

Example 32

Preparation of 6-[6-amino-4-(trifluoromethyl)pyridin-3-yl]-N-[4-(1-isopropylpiperidin-4-yloxy)phenyl]-2-morpholinopyrimidin-4-amine

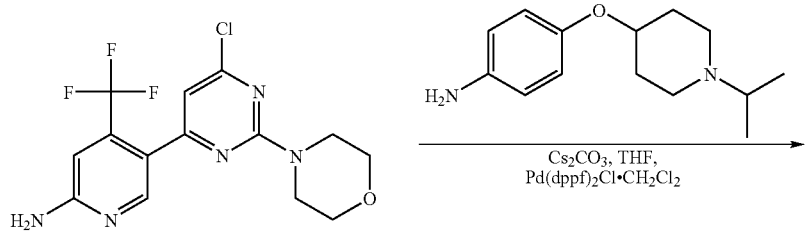

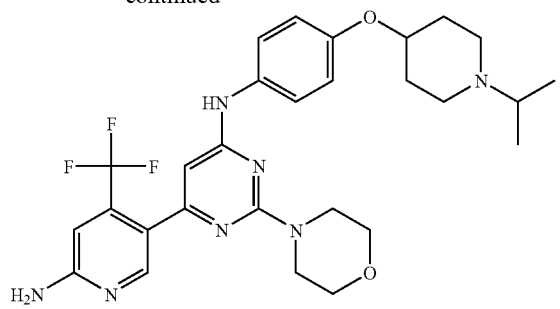

In a glass pressure vessel, Pd(OAc)$_2$ (5.0 mg, 0.022 mmol), BINAP (17.0 mg, 0.028 mmol), cesium carbonate (72.0 mg, 0.22 mmol) and THF (2.0 mL) were mixed and stirred at room temperature for 1-3 minutes. To the resulting mixture was added 5-(6-chloro-2-morpholin-4-yl-pyrimidin-4-yl)-pyridin-2-ylamine (40.0 mg, 0.11 mmol) followed by 4-(1-isopropylpiperidin-4-yloxy) aniline (37.0 mg, 0.16 mmol). The glass pressure vessel was sealed, stirred, and heated in microwave under irradiation at 110° C. for 10 minutes. The reaction mixture was filtered and concentrated under reduced pressure. The product was purified by preparative reverse phase HPLC to give 6-[6-amino-4-(trifluoromethyl)pyridin-3-yl]-N-[4-(1-isopropylpiperidin-4-yloxy)phenyl]-2-morpholinopyrimidin-4-amine (3.0 mg, 5%). LC/MS (m/z): 558.3 (MH$^+$), R$_t$ 1.90 minutes.

Example 33

Preparation of 6-(6-amino-4-(trifluoromethyl)pyridin-3-yl)-N-(4-(1-isopropylpiperidin-4-yloxy)-3-methoxyphenyl)-2-morpholinopyrimidin-4-amine

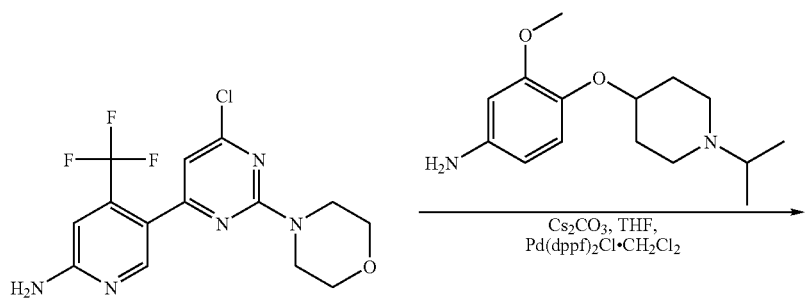

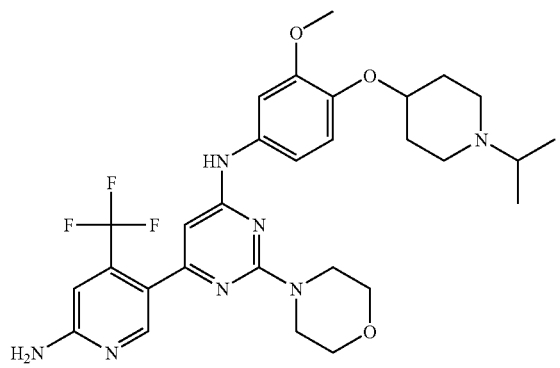

In a glass pressure vessel, Pd(OAc)$_2$ (5.0 mg, 0.02 mmol), BINAP (17.0 mg, 0.028 mmol), cesium carbonate (72.0 mg, 0.22 mmol) and THF (2.0 mL) were mixed and stirred at room temperature for 1-3 minutes. To the resulting mixture was added 5-(6-chloro-2-morpholin-4-yl-pyrimidin-4-yl)-pyridin-2-ylamine (40.0 mg, 0.11 mmol) followed by 4-(1-isopropylpiperidin-4-yloxy)-3-methoxyaniline (46.6 mg, 0.16 mmol). The glass pressure vessel was sealed, stirred, and heated in microwave under irradiation at 120° C. for 10 minutes. The reaction mixture was filtered and concentrated under reduced pressure. The residue was purified by preparative reverse phase HPLC to give 6-(6-amino-4-(trifluoromethyl)pyridin-3-yl)-N-(4-(1-isopropylpiperidin-4-yloxy)-3-methoxyphenyl)-2-morpholinopyrimidin-4-amine (6.6 mg, 10%). LC/MS (m/z): 588.3 (MH$^+$), R$_t$ 1.92 minutes.

A solution of N-(6-chloro-2-morpholinopyrimidin-4-yl)-4-phenylthiazol-2-amine (15 mg, 0.040 mmol), 5-(4,4,5,5-tetramethyl-1,3,2-dioxaborolan-2-yl)-4-(trifluoromethyl)pyridin-2-amine (23 mg, 0.080 mmol) and 1,1'-bis(diphenylphosphino)ferrocene palladium (II) chloride (6.6 mg, 0.0080 mmol) in 0.5 mL of 1,4-dioxane and 0.05 mL of 2 M aq. sodium carbonate was heated in the microwave at 120° C. for 600 seconds. The crude product was purified by reverse phase prep HPLC to give N-(6-(6-amino-4-(trifluoromethyl)pyridin-3-yl)-2-morpholinopyrimidin-4-yl)-4-phenylthiazol-2-amine. LC/MS (m/z): 500 (MH$^+$), R$_t$ 2.46 minutes.

Example 34

Synthesis of N-(6-(6-amino-4-(trifluoromethyl)pyridin-3-yl)-2-morpholinopyrimidin-4-yl)-4-phenylthiazol-2-amine Examples 35

Preparation of N-6-(6-amino-4-(trifluoromethyl)pyridin-3-yl)-5-methyl-2-morpholinopyrimidin-4-yl)-4-phenylthiazol-2-amine

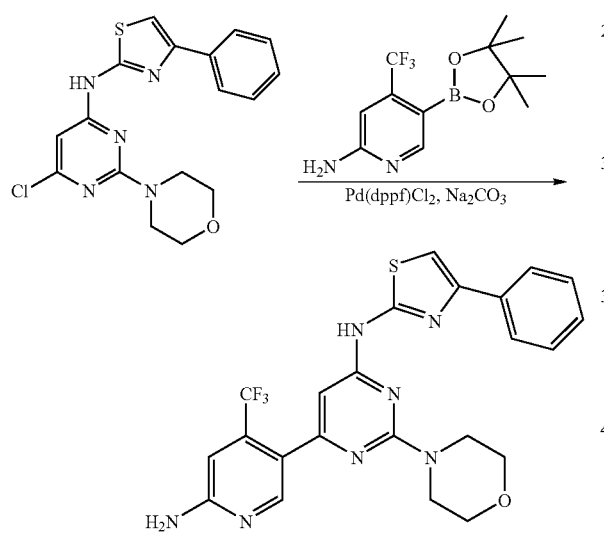

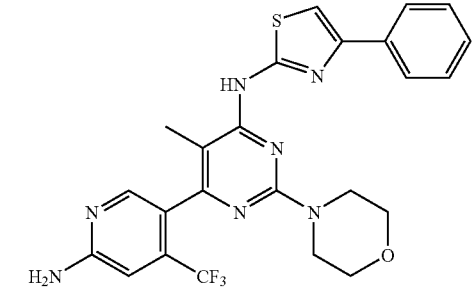

N-(6-(6-amino-4-(trifluoromethyl)pyridin-3-yl)-5-methyl-2-morpholinopyrimidin-4-yl)-4-phenylthiazol-2-amine was prepared according to Example 35. LC/MS (m/z): 514 (MH$^+$), R$_t$ 2.62 minutes.

TABLE 1

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 1 | 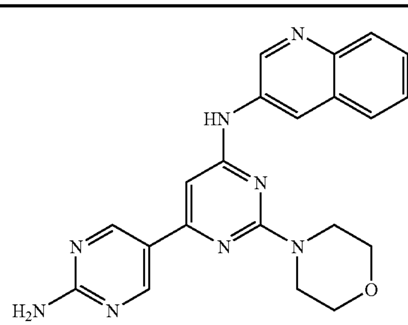 | 401.4, 2.00 | | ++++ | ++++ | ++++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 2 | 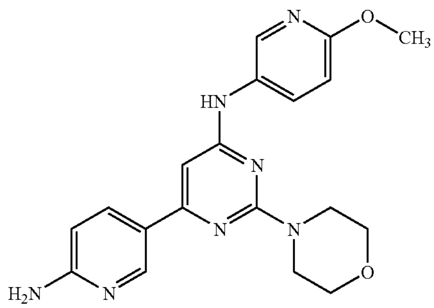 | 380.1, 1.82 | 9.67 L | ++++ | N/D | N/D |
| 3 | 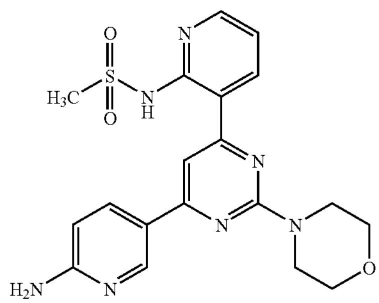 | 428.2, 2.09 | 11.50 L | ++++ | ++++ | ++++ |
| 4 | 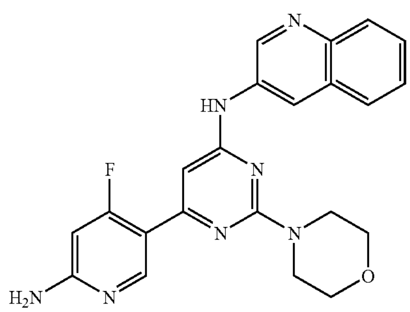 | 418.0 | 1.99 | ++++ | ++++ | ++++ |
| 5 | 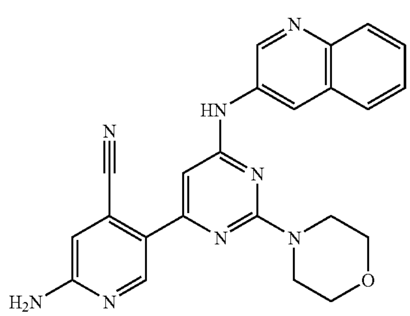 | 425.0 | 11.16 L | ++++ | +++ | ++++ |
| 6 | 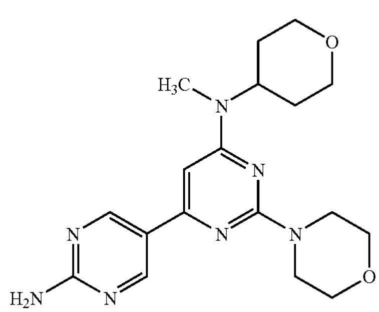 | 372.2 | | ++++ | N/D | +++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 7 | 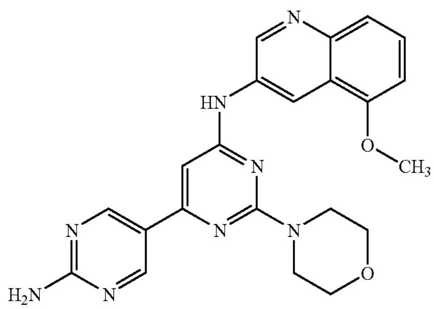 | 431.2, 2.03 | | ++++ | ++++ | ++++ |
| 8 | 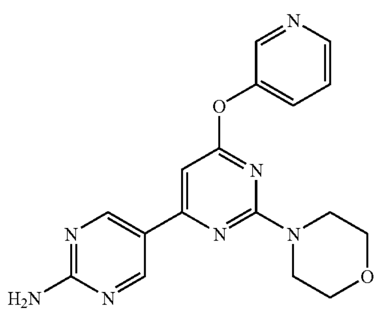 | 352.1, 1.83 | | ++++ | ++++ | ++++ |
| 9 | 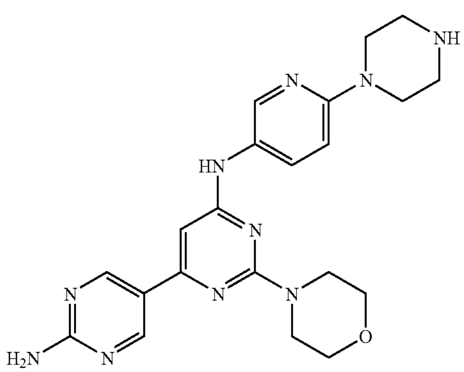 | 435.2, 1.52 | | ++++ | ++++ | ++++ |
| 10 | 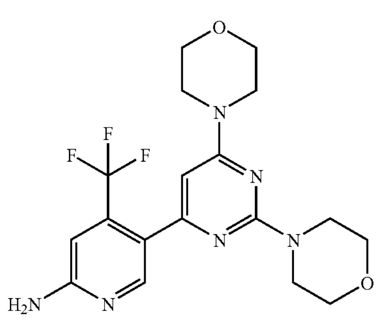 | 411.3, 1.86 | | ++++ | ++++ | ++++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 11 | 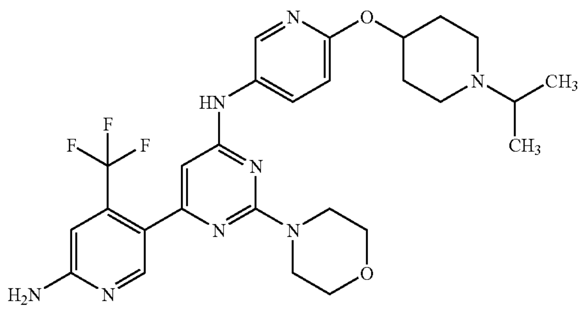 | 559.2, 1.92 | | ++++ | ++++ | ++++ |
| 12 | 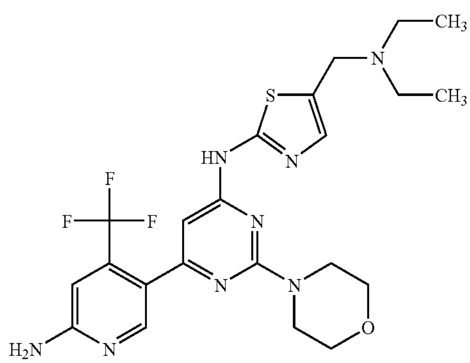 | 509.0, 1.72 | | ++++ | ++++ | +++ |
| 13 | 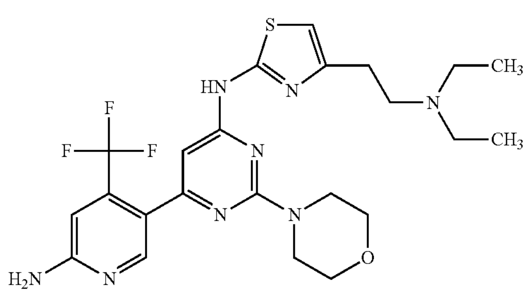 | 523.1, 2.02 | 2.11 | ++++ | ++++ | ++++ |
| 14 | 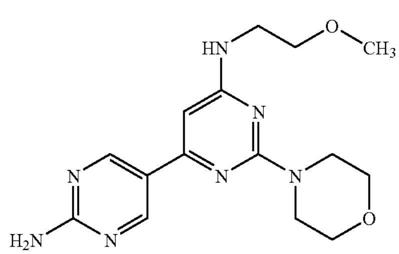 | 332.2 | 7.50 L | ++++ | N/D | ++++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 15 | 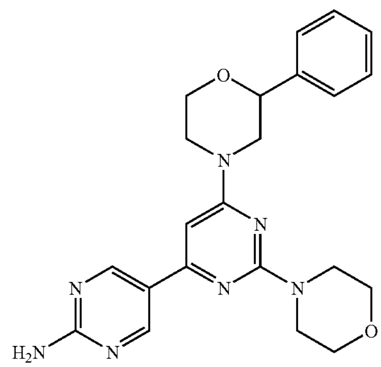 | 420.1 | 13.14 L | ++++ | ++++ | ++++ |
| 16 | 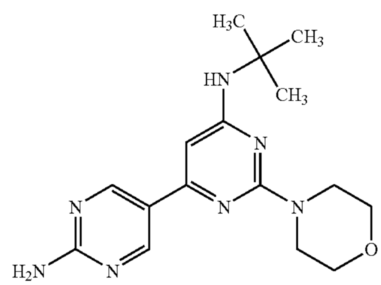 | 330.2 | 10.83 L | ++++ | N/D | ++++ |
| 17 | 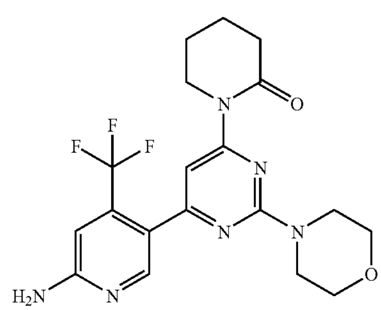 | 423.1 | 2.57 | ++++ | N/D | ++++ |
| 18 | 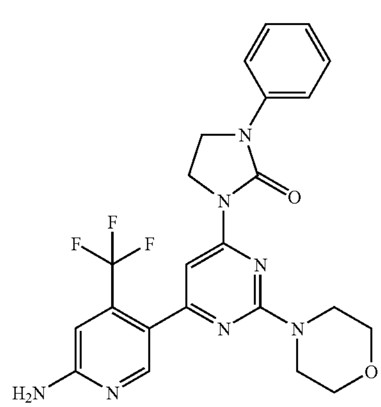 | 486 | 3.23 | ++++ | N/D | ++++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 19 | 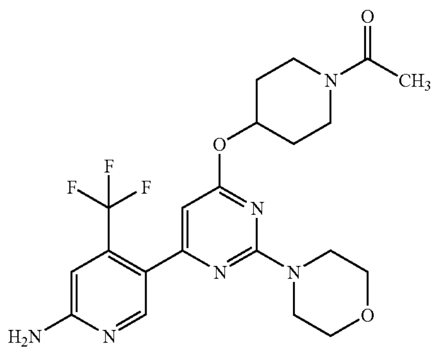 | 467.1, 2.36 | | ++++ | N/D | ++++ |
| 20 | Chiral | 525.0, 3.42 | | ++++ | N/D | ++++ |
| 21 | Chiral | 525.0, 3.42 | | ++++ | N/D | N/D |
| 22 | Chiral | 453.1, 2.18 | | ++++ | N/D | +++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 23 | Chiral | 453.1, 2.18 | | ++++ | N/D | N/D |
| 24 | 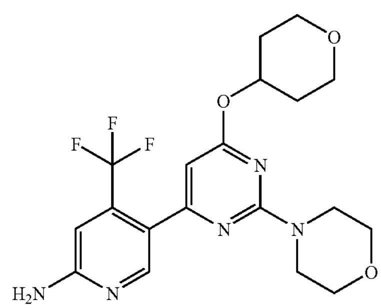 | 426.1, 2.26 | 2.54 | ++++ | ++++ | ++++ |
| 25 | Chiral | 412.1, 2.47 | | ++++ | ++++ | +++ |
| 26 | Chiral | 412.1, 2.19 | 2.47, (12.34) | ++++ | N/D | +++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 27 | 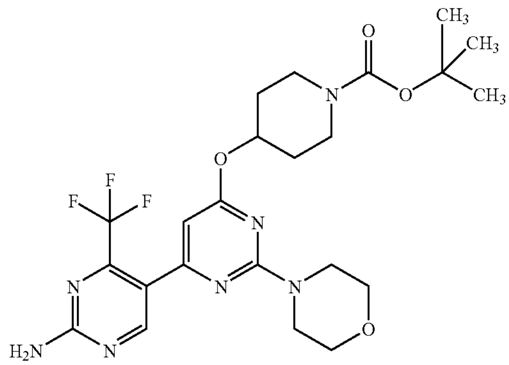 | 526.0, 4.30 | | ++++ | ++++ | ++++ |
| 28 | 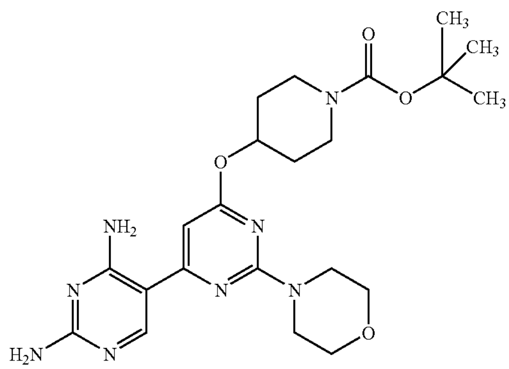 | 473.1, 3.02 | | ++++ | ++++ | ++++ |
| 29 | Chiral | 415.1, 2.06 | | ++++ | ++++ | ++++ |
| 30 | 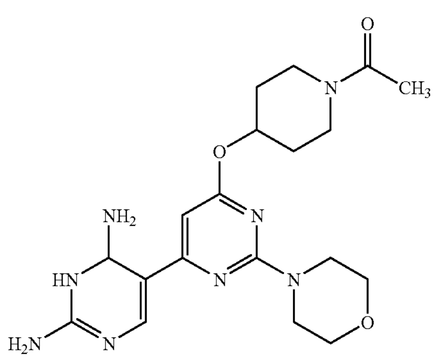 | 416.0, 1.67 | | ++++ | ++++ | ++++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 31 | 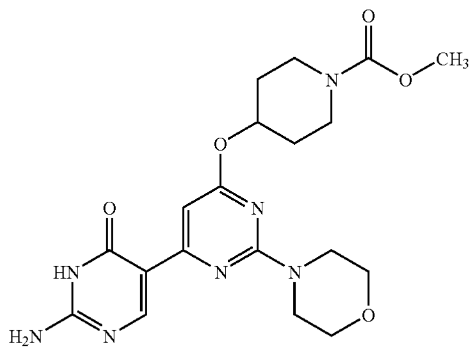 | 432.0, 2.05 | | ++++ | ++++ | ++++ |
| 32 | 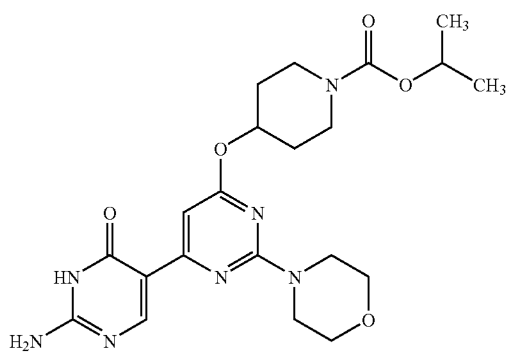 | 460.1, 2.51 | | ++++ | ++++ | ++++ |
| 33 | 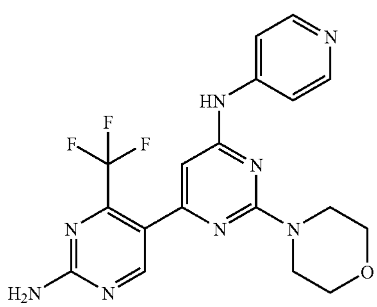 | 419.0, 2.17 | | ++++ | ++++ | ++++ |
| 34 | 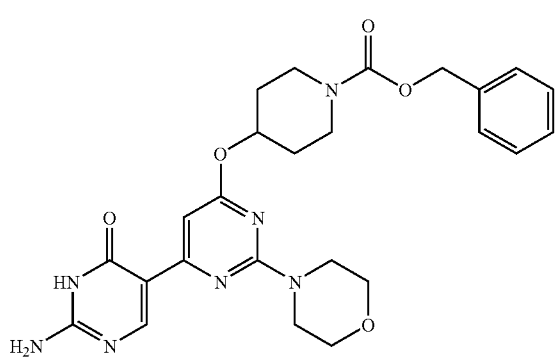 | 508.0, 2.17 | 2.96, (14.82) | ++++ | ++++ | ++++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 35 | 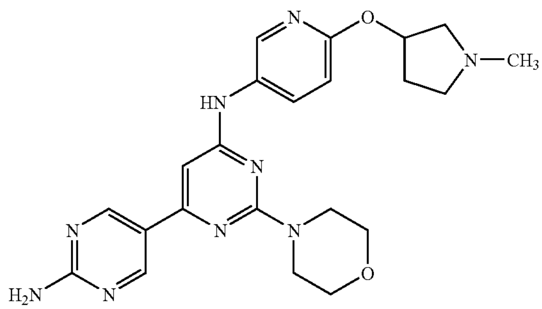 | 450.2, 1.61 | | ++++ | ++++ | ++++ |
| 36 | 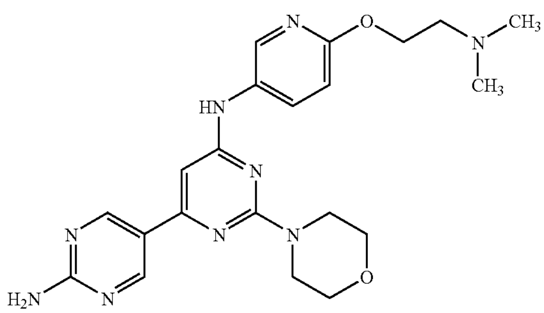 | 438.1, 1.61 | | ++++ | ++++ | ++++ |
| 37 | 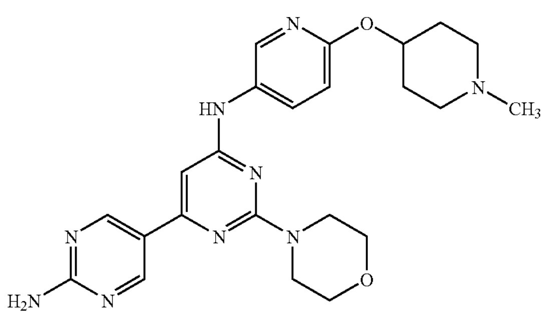 | 464.4, 1.53 | | ++++ | ++++ | ++++ |
| 38 | 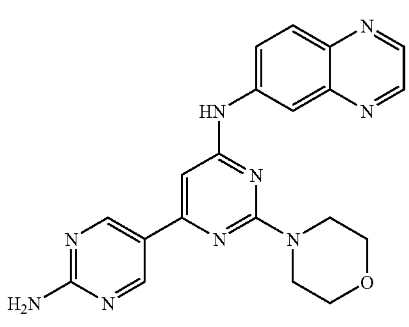 | 402.2, 1.88 min | | ++++ | ++++ | ++++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 39 | Chiral | 361.0, 1.44 | 1.73, (8.13) | ++++ | ++++ | ++++ |
| 40 | 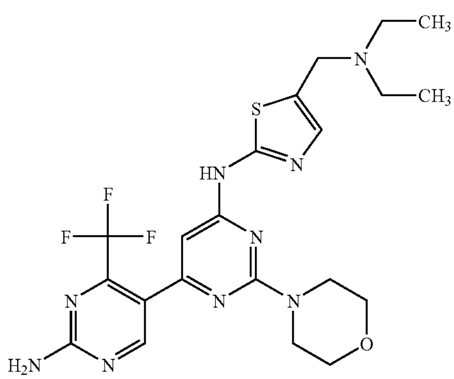 | 510.1, 1.98 | 2.18 | ++++ | ++++ | ++++ |
| 41 | 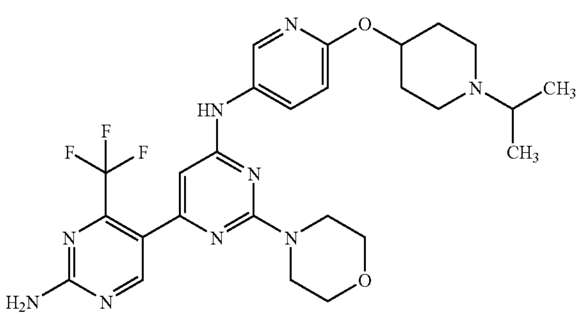 | 560.2, 1.93 | 1.98 | ++++ | ++++ | ++++ |
| 42 | 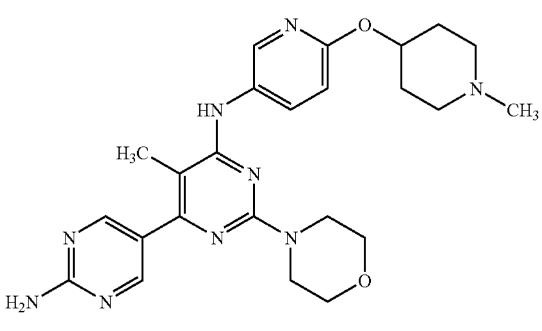 | 478.4, 1.59 | | ++++ | ++++ | ++++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 43 | 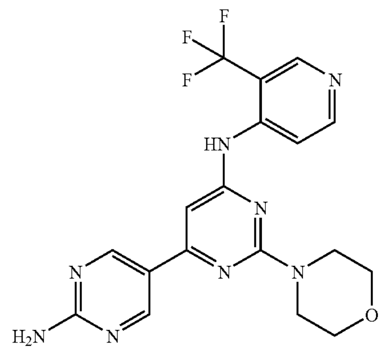 | 4.19 | 9.23 L | ++++ | ++++ | ++++ |
| 44 | 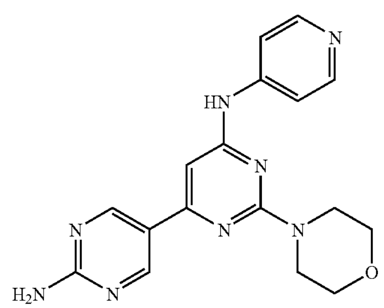 | 351.1 | 8.23 L | ++++ | ++++ | ++++ |
| 45 | 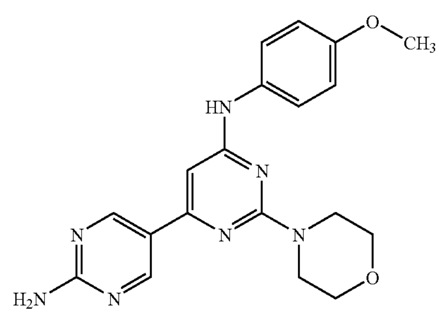 | 375.0, 2.11 | 2.41 | ++++ | ++++ | ++++ |
| 46 | 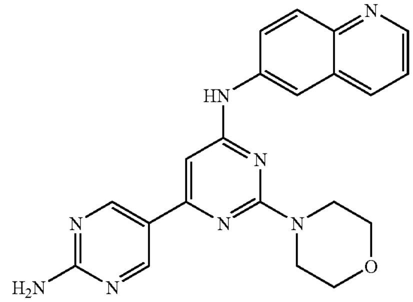 | 401.1, 1.70 | 1.70 | ++++ | ++++ | ++++ |

TABLE 1-continued
| Compound | Structure | LC/MS (M + H, Rt min) | hplc 10 min (L = 45 min) | PI3 Kinase Alpha, IC50 | PSer473 AKT, EC50 | Cellular Proliferation, EC50 |
|---|---|---|---|---|---|---|
| 47 | 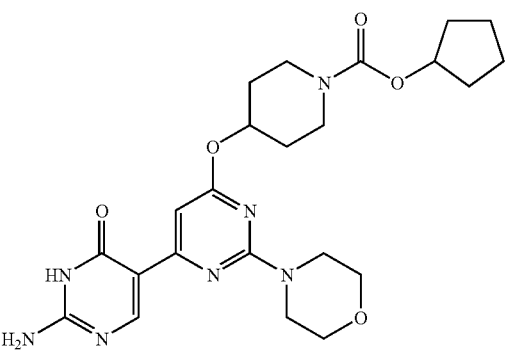 | 486.1, 2.11 | 2.76, (14.49) | ++++ | ++++ | ++++ |
| 48 | 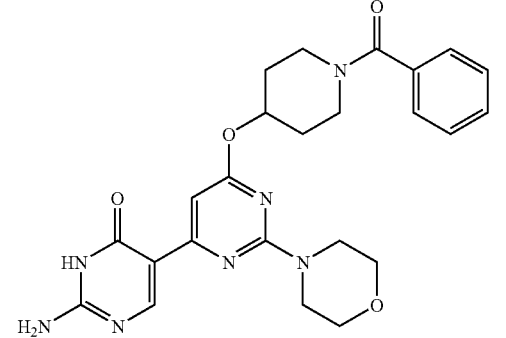 | 478.0, 1.79 | 2.23, (11.48) | ++++ | ++++ | ++++ |
| 49 | 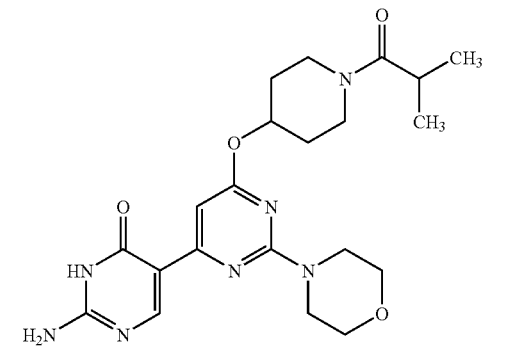 | 444.1, 1.70 | 2.06, (10.23) | ++++ | ++++ | ++++ |
| 50 | 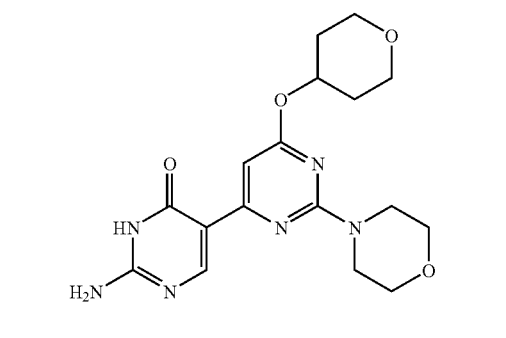 | 375.1, 1.80 | 1.82, (8.95) | ++++ | ++++ | ++++ |

TABLE 1-continued
| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 51 | 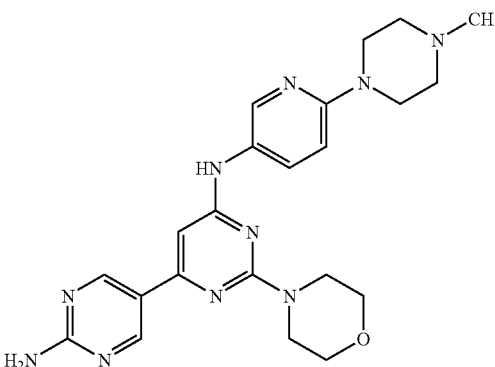 | 449.1, 1.51 | 6.56 L | ++++ | ++++ | ++++ |
| 52 | 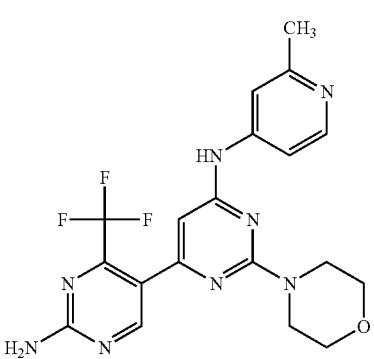 | 433.0, 2.30 | | ++++ | ++++ | ++++ |
| 53 | 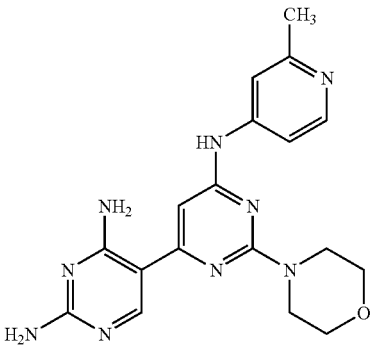 | 380.1, 1.65 | | ++++ | ++++ | ++++ |
| 54 | 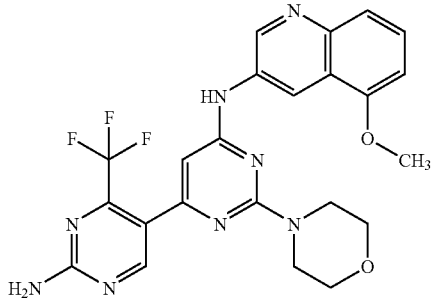 | 498.9, 2.55 | | ++++ | ++++ | ++++ |

TABLE 1-continued
| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 55 | 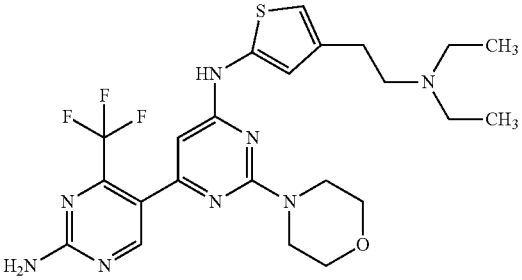 | 524.1, 2.10 | 2.37 | ++++ | ++++ | ++++ |
| 56 | 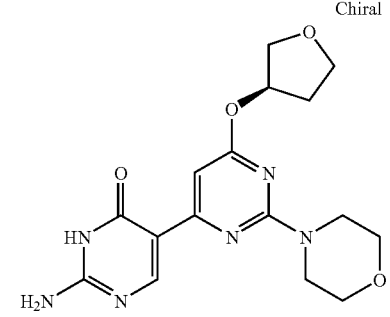 | 361.0, 1.45 | 1.64, (8.18) | ++++ | ++++ | ++++ |
| 57 | 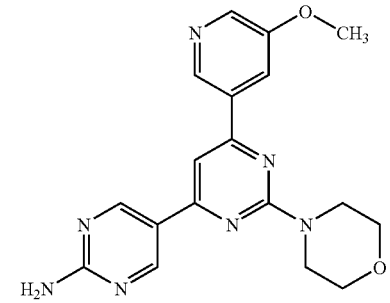 | 366.1, 1.85 | 1.95 | ++++ | ++++ | ++++ |
| 58 | 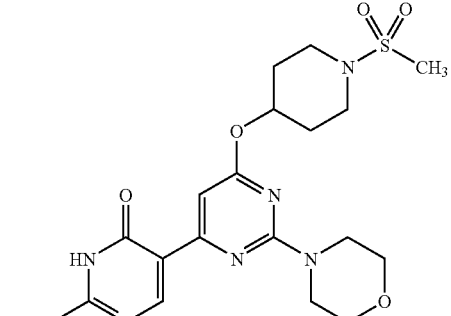 | 452.0, 1.65 | | ++++ | ++++ | ++++ |

TABLE 1-continued
| Compound | Structure | LC/MS (M + H, Rt min) | hplc 10 min (L = 45 min) | PI3 Kinase Alpha, IC50 | PSer473 AKT, EC50 | Cellular Proliferation, EC50 |
| --- | --- | --- | --- | --- | --- | --- |
| 59 | 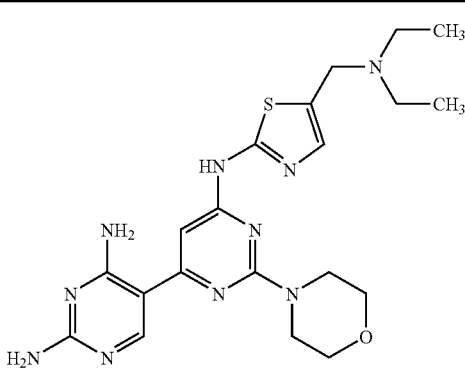 | 457.2, 1.72 | 1.71 | ++++ | ++++ | ++++ |
| 60 | 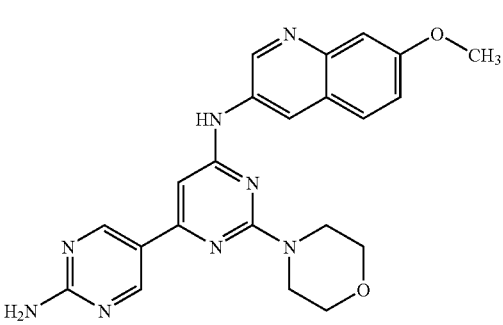 | 431.2, 1.95 | 10.48 L | ++++ | ++++ | ++++ |
| 61 | 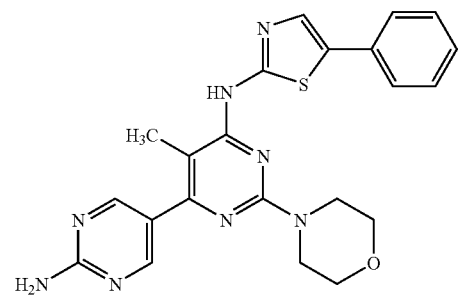 | 247.4, 2.85 | | ++++ | ++++ | ++++ |
| 62 | 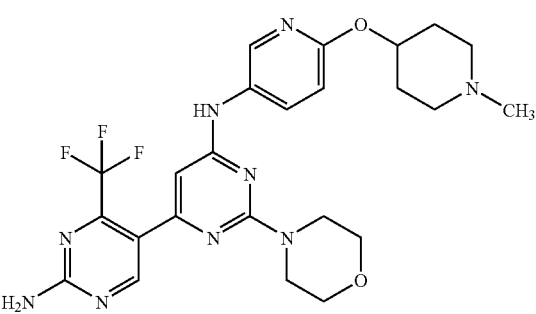 | 532.0, 1.85 | | ++++ | ++++ | ++++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 63 | Chiral | 431.2, 2.43 | | ++++ | ++++ | ++++ |
| 64 | 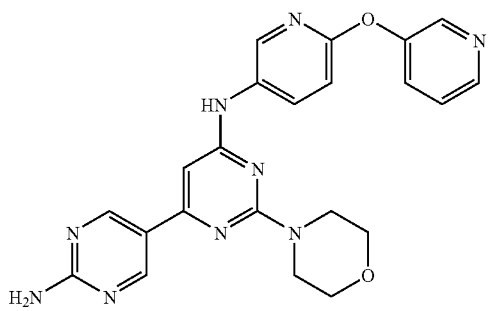 | 444.4, 1.66 | | ++++ | ++++ | ++++ |
| 65 | 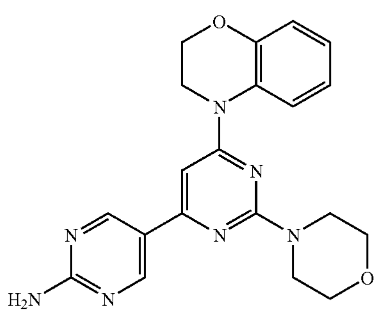 | 392.3, 2.55 | | ++++ | ++++ | ++++ |
| 66 | 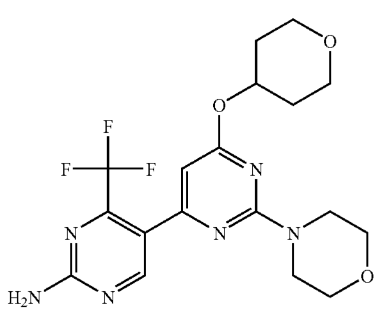 | 427.1, 3.21 | | ++++ | ++++ | +++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 67 | 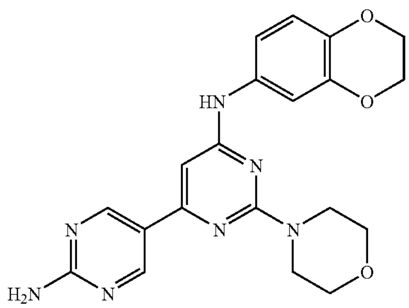 | 408.1, 1.98 | 2.16 | ++++ | ++++ | ++++ |
| 68 | 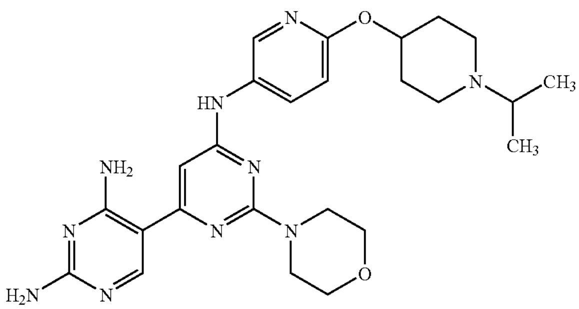 | 507.2, 1.79 | 1.78 | ++++ | ++++ | ++++ |
| 69 | 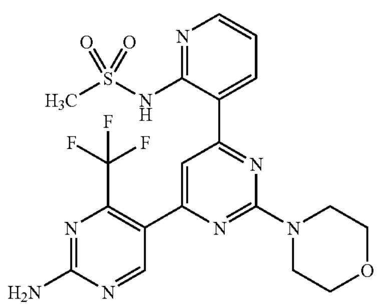 | 496.9, 2.40 | 3.39, (16.57) | ++++ | ++++ | ++++ |
| 70 | 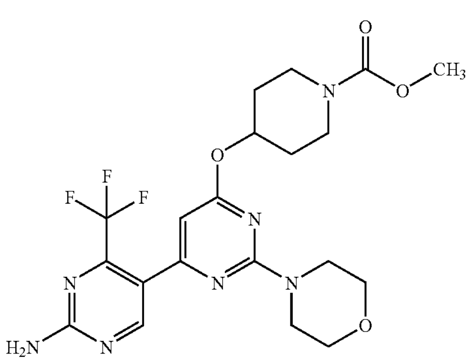 | 484.0, 3.36 | | ++++ | ++++ | ++++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 71 | 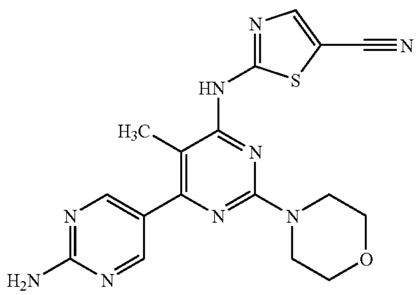 | 396.3, 2.32 | | ++++ | ++++ | ++++ |
| 72 | 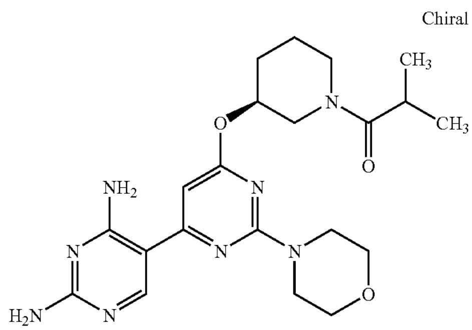 | 443.2, 2.45 | | ++++ | ++++ | +++ |
| 73 | 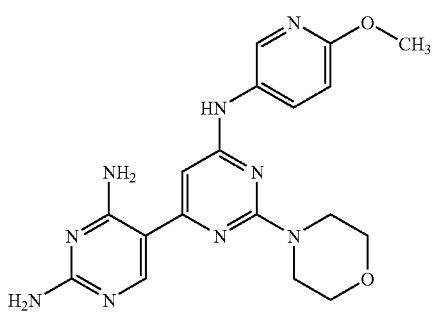 | 396.1, 1.58 | 1.89, (9.53) | ++++ | ++++ | +++ |
| 74 | 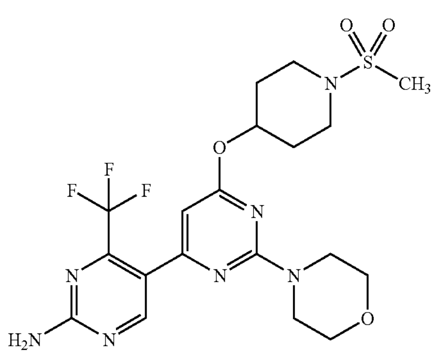 | 504.0, 3.19 | | ++++ | ++++ | ++++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 75 | Chiral | 431.2, 2.38 | | ++++ | ++++ | +++ |
| 76 | 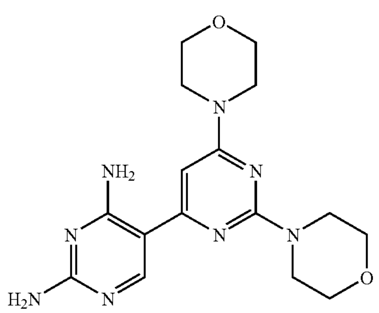 | 359.1, 1.42 | | ++++ | ++++ | +++ |
| 77 | 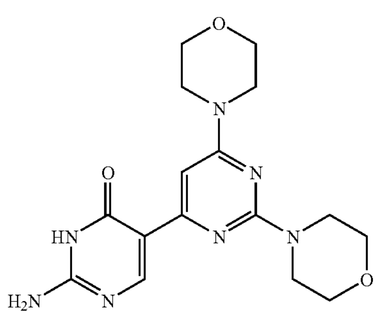 | 360.0, 1.47 | 1.79, (8.61) | ++++ | ++++ | ++++ |
| 78 | 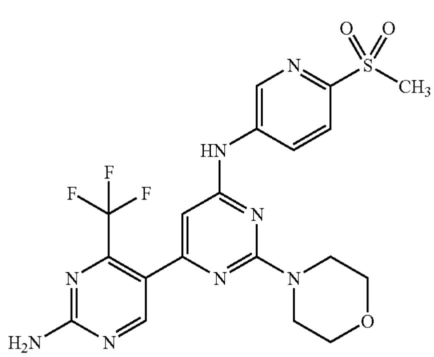 | 496.9, 2.42 | | ++++ | ++++ | ++++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 79 | 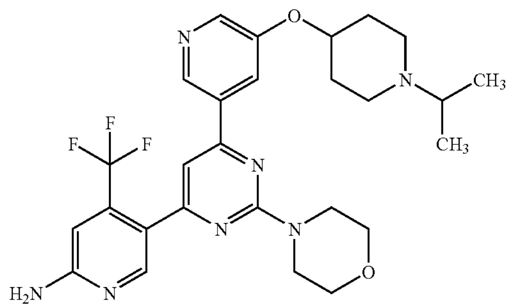 | 544.2, 1.97 | 2.04 | ++++ | ++++ | +++ |
| 80 | 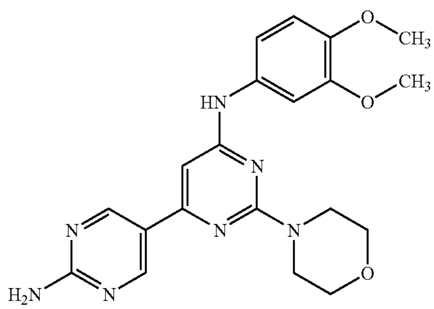 | 410.1, 1.91 | 10.36 L | ++++ | ++++ | ++++ |
| 81 | 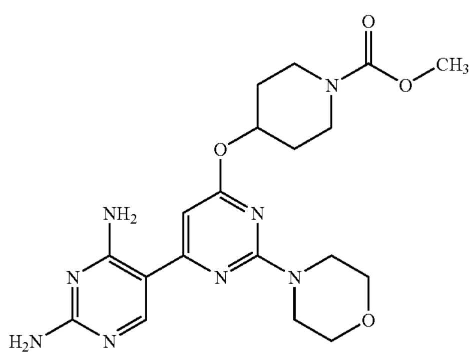 | 431.0, 2.45 | | ++++ | ++++ | ++++ |
| 82 | 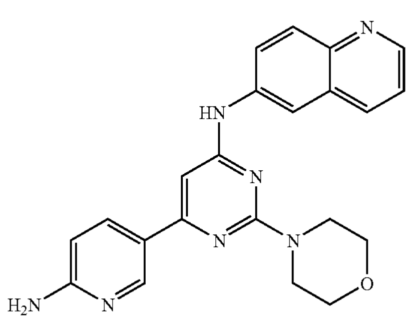 | 400.0, 1.74 | 1.76 | ++++ | ++++ | ++++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 83 | 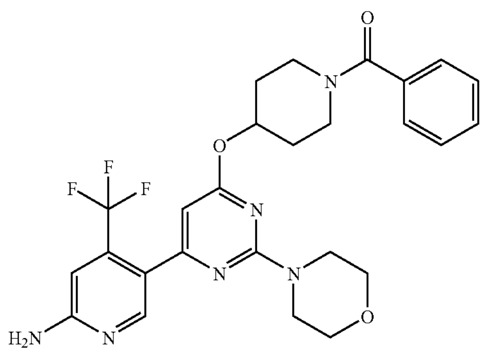 | 529.2, 2.98 | | ++++ | ++++ | +++ |
| 84 | 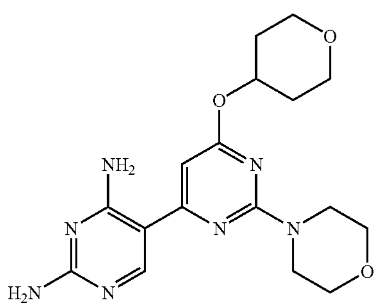 | 374.1, 2.13 | | ++++ | ++++ | ++++ |
| 85 | 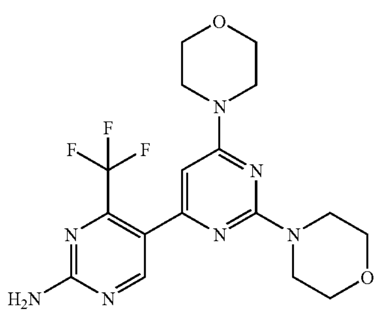 | 412.0, 2.03 | | ++++ | ++++ | ++++ |
| 86 | 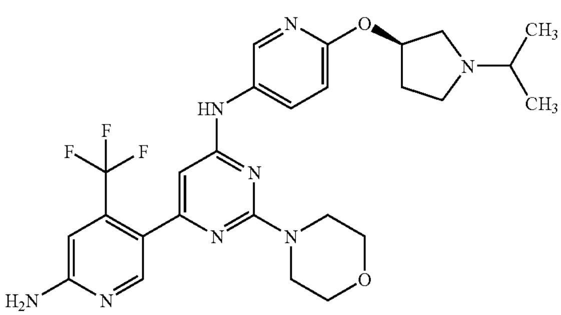 | 545.6, 1.78 | | ++++ | ++++ | ++++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 87 | 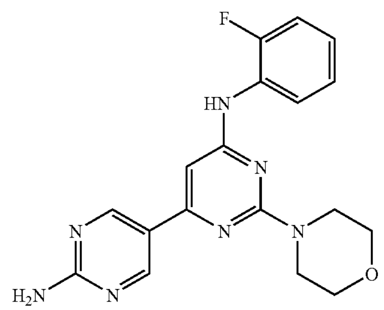 | 368.1, 2.05 | 2.26 | ++++ | ++++ | +++ |
| 88 | 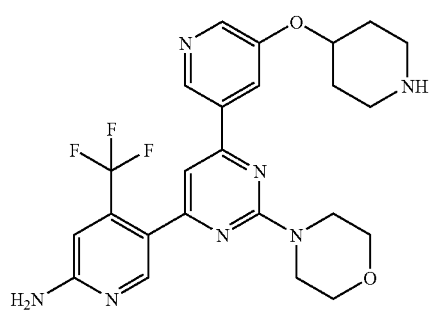 | 502.1, 1.89 | 1.95 | ++++ | ++++ | +++ |
| 89 | Chiral | 451.1, 2.30 | | ++++ | ++++ | ++++ |
| 90 | 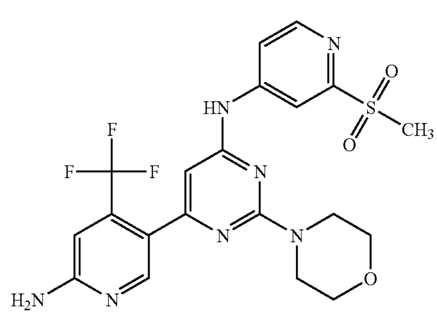 | 496 | 2.29 | ++++ | ++++ | ++++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 91 | 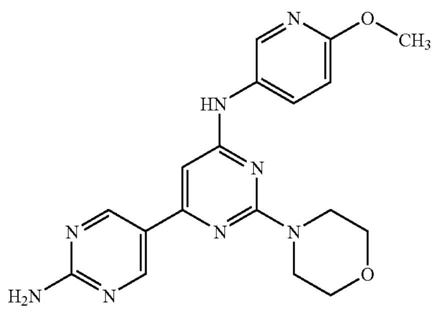 | 381.4, 1.95 | | ++++ | ++++ | ++++ |
| 92 | 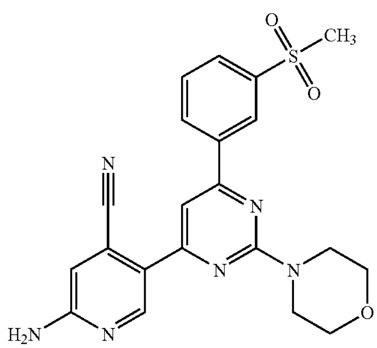 | 437.1, 2.33 | 2.8 | ++++ | ++++ | ++++ |
| 93 | 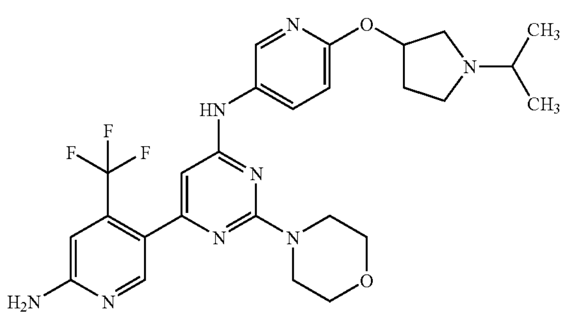 | 545.6, 1.78 | | ++++ | ++++ | ++++ |
| 94 | 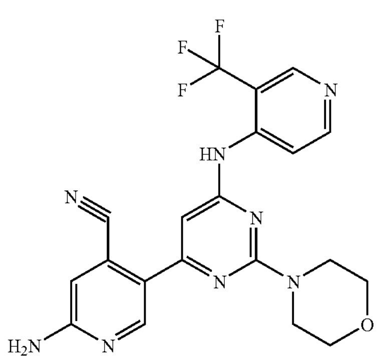 | 443.1 | 2.07 | ++++ | ++++ | ++++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 95 | 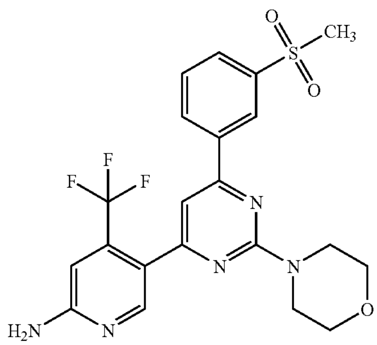 | 480.4, 2.13 | 2.85, (14.41) | ++++ | ++++ | ++++ |
| 96 | 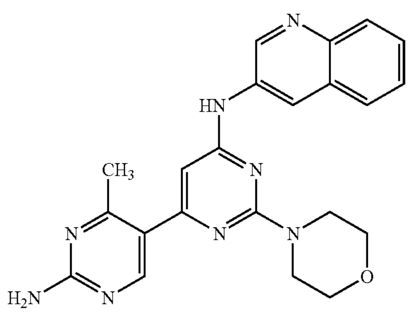 | 415.3, 1.90 | | ++++ | ++++ | ++++ |
| 97 | 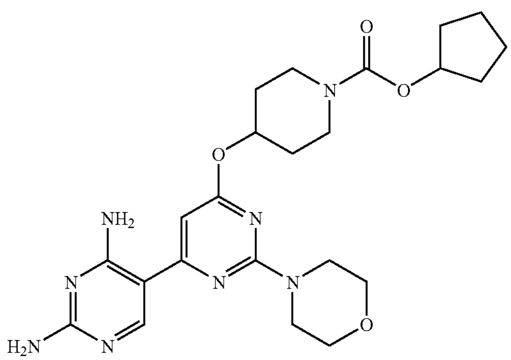 | 485.1, 3.04 | | ++++ | ++++ | ++++ |
| 98 | 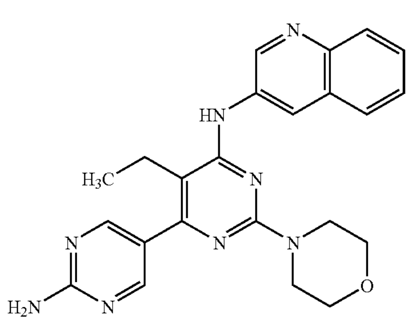 | 429.2 | 8.99 L | ++++ | ++++ | ++++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 99 | 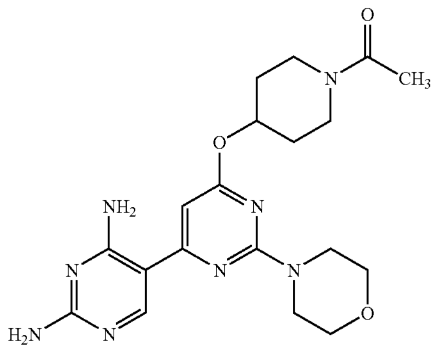 | 415.1, 1.97 | | ++++ | ++++ | ++++ |
| 100 | 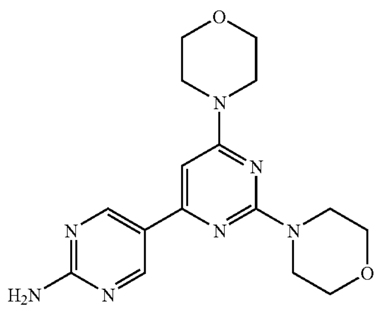 | 344.1 | 7.58 L | ++++ | ++++ | ++++ |
| 101 | 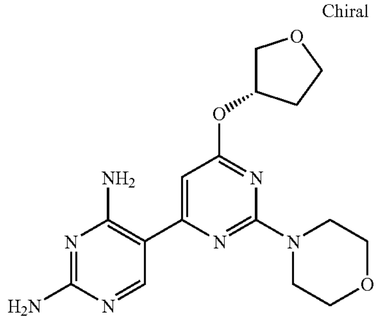 | 360.1, 2.05 | | ++++ | ++++ | +++ |
| 102 | 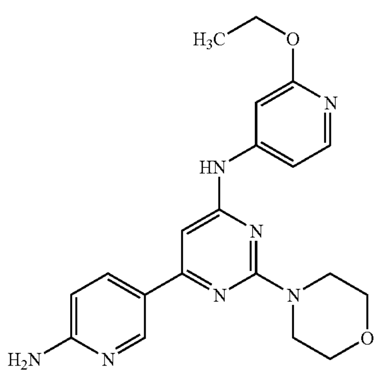 | 394.2, 1.85 | 1.92 | ++++ | ++++ | ++++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 103 | 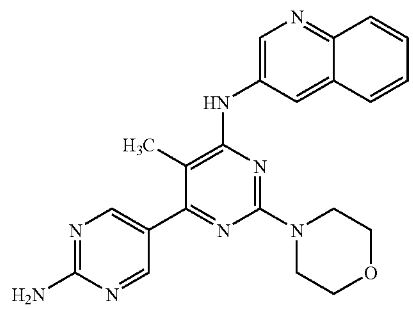 | 415.3, 1.68 | | ++++ | ++++ | ++++ |
| 104 | 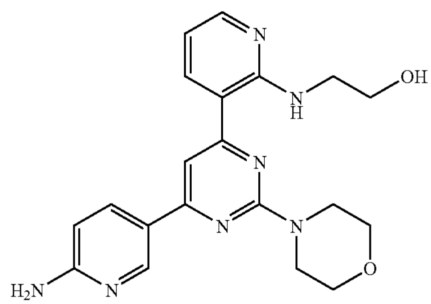 | 394.4, 1.62 | | ++++ | ++++ | +++ |
| 105 | 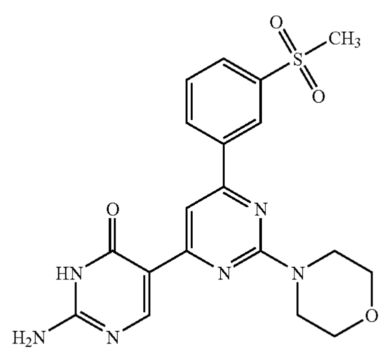 | 428.9, 1.72 | 2.25, (10.78) | ++++ | ++++ | ++++ |
| 106 | 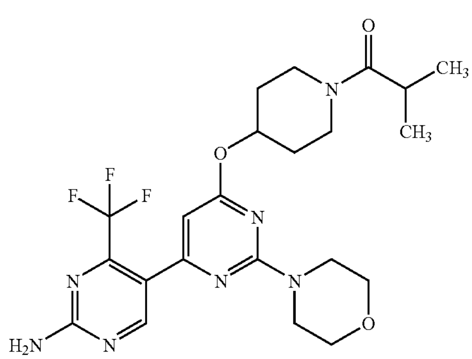 | 496.0, 3.28 | | ++++ | ++++ | ++++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 107 | 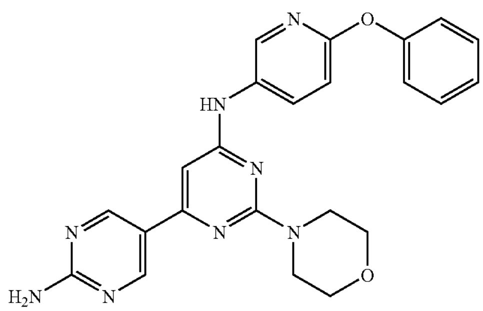 | 443.4, 270 | | ++++ | ++++ | +++ |
| 108 | Chiral | 360.1, 2.05 | | ++++ | ++++ | ++++ |
| 109 | 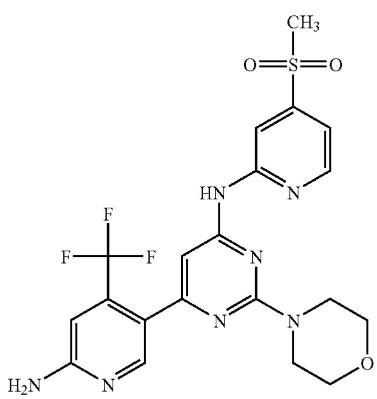 | 496.0, 2.07 | 2.39 | ++++ | ++++ | +++ |
| 110 | 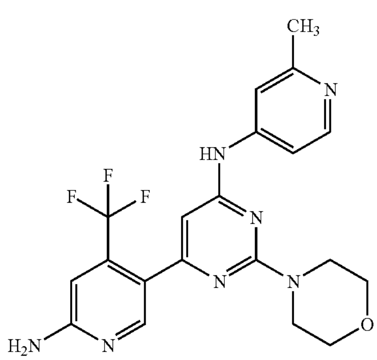 | 432.1 | 1.97 | ++++ | ++++ | ++++ |

TABLE 1-continued
| Compound | Structure | LC/MS (M + H, Rt min) | hplc 10 min (L = 45 min) | PI3 Kinase Alpha, IC50 | PSer473 AKT, EC50 | Cellular Proliferation, EC50 |
|---|---|---|---|---|---|---|
| 111 | 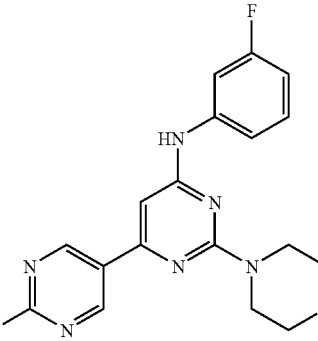 | 368.0; 2.15 | 2.48 | ++++ | ++++ | +++ |
| 112 | 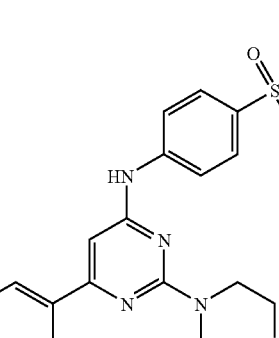 | 427.1 | 2.08 | ++++ | ++++ | +++ |
| 113 | 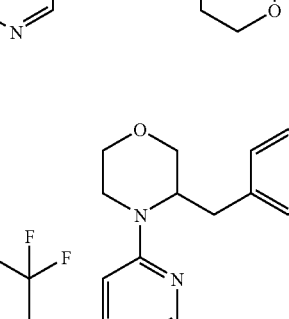 | 501.1, 2.34 | 14.12 L | ++++ | ++++ | +++ |
| 114 | 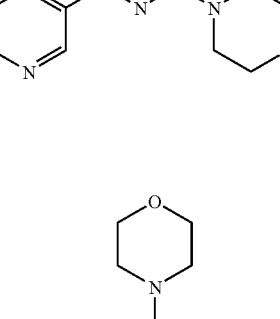 | 3.77.0, 1.54 | | ++++ | ++++ | +++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 115 | 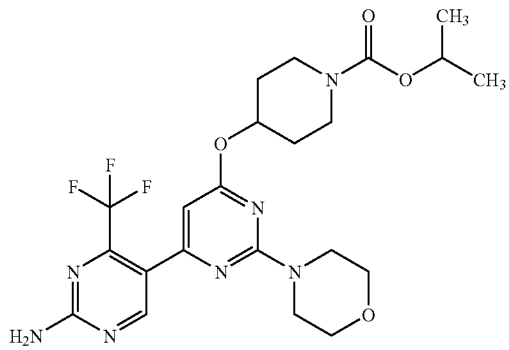 | 512.0, 3.96 | | ++++ | ++++ | +++ |
| 116 | 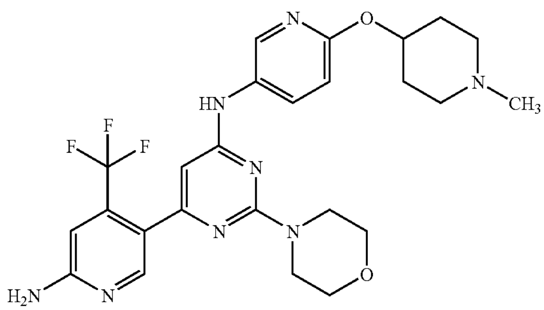 | 531.5, 1.77 | | ++++ | ++++ | +++ |
| 117 | 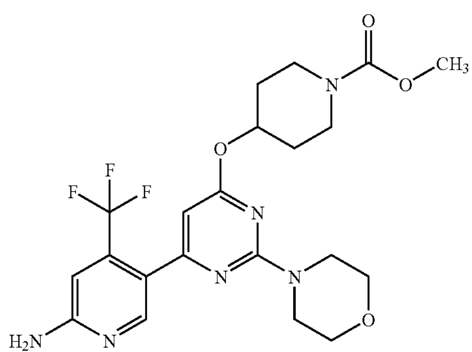 | 483.1, 2.37 | 2.82, (14.09) | ++++ | ++++ | +++ |
| 118 | 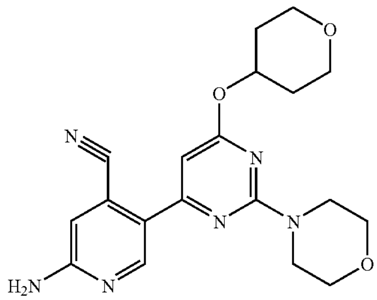 | 383.0, 2.76 | 2.53 | ++++ | ++++ | ++++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 119 | 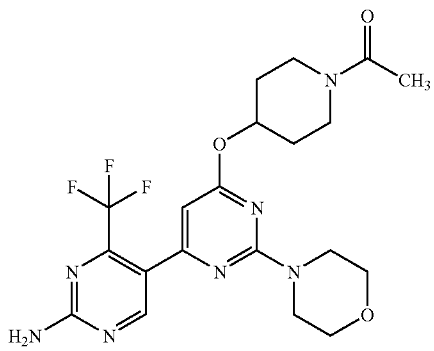 | 468.0, 2.70 | | ++++ | ++++ | ++++ |
| 120 | 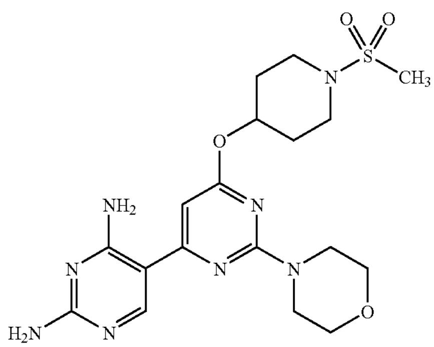 | 451.0, 2.28 | | ++++ | ++++ | +++ |
| 121 | 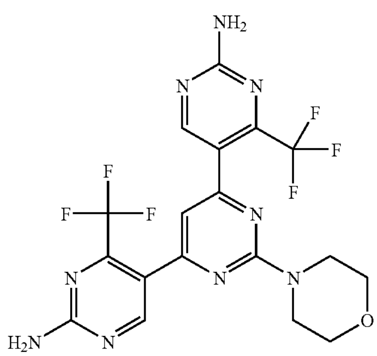 | 487.9 | 3.45 | ++++ | ++++ | ++++ |
| 122 | 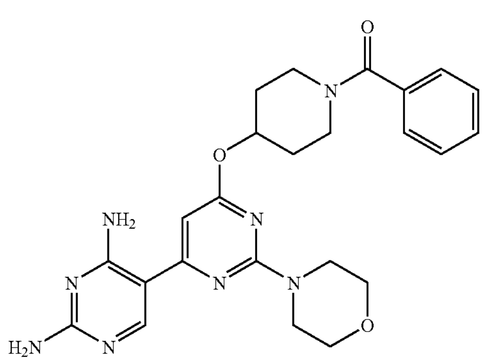 | 477.1, 2.60 | | ++++ | ++++ | ++++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 123 | 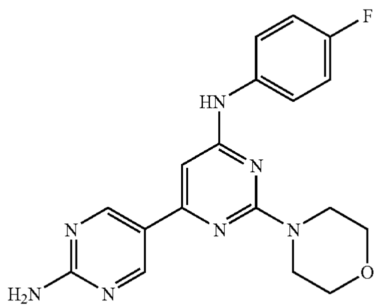 | 368.1, 2.09 | 2.34 | ++++ | ++++ | +++ |
| 124 | 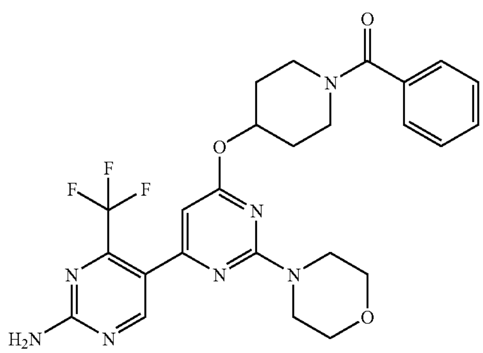 | 530.0, 3.53 | | ++++ | ++++ | ++++ |
| 125 | 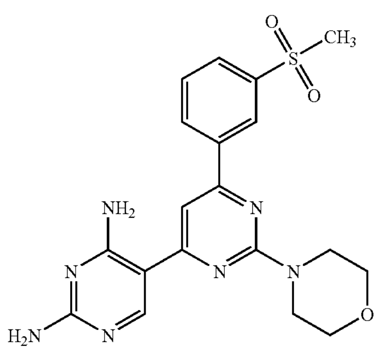 | 428.0, 2.38 | | ++++ | ++++ | ++++ |
| 126 | 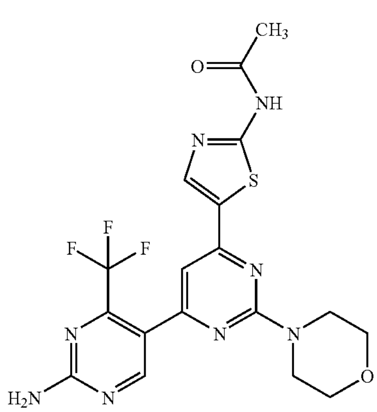 | 466.1, 2.25 | 2.62 | ++++ | ++++ | +++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 127 | Chiral | 451.1, 2.25 | | ++++ | ++++ | +++ |
| 128 | 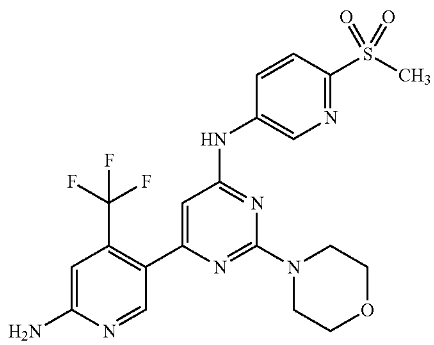 | 496.1 | 2.26 | ++++ | ++++ | +++ |
| 129 | 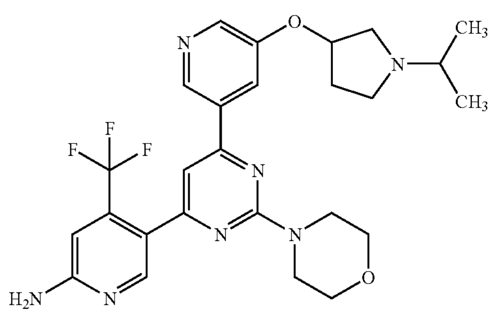 | 530.1, 1.93 | 1.99 | ++++ | ++++ | +++ |
| 130 | 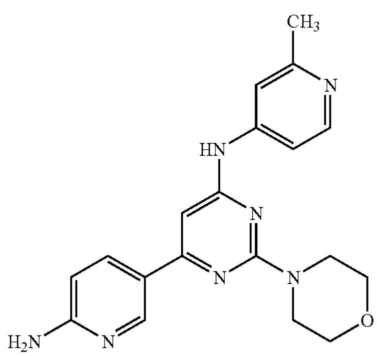 | 364.1, 1.69 | 1.76 | ++++ | ++++ | ++++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 131 | 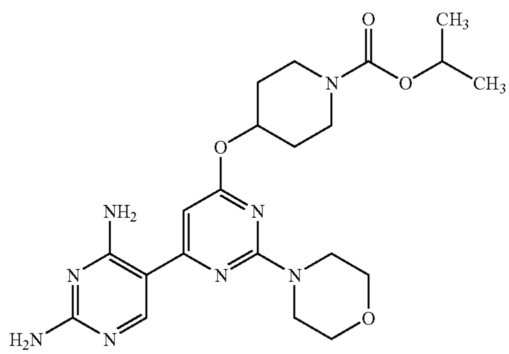 | 459.1, 2.82 | | ++++ | ++++ | ++++ |
| 132 | 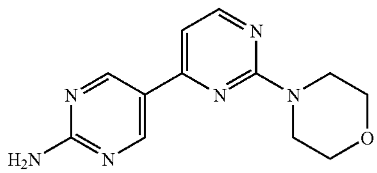 | 259.2, 1.27 | 1.34, (6.23) | ++++ | ++++ | +++ |
| 133 | 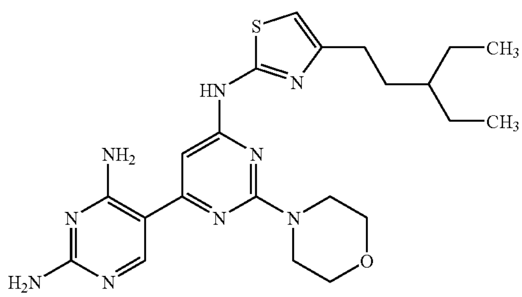 | 471.2, 1.79 | 1.88 | ++++ | ++++ | ++++ |
| 134 | 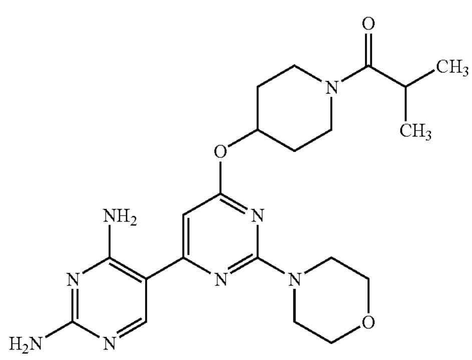 | 443.2, 2.37 | | ++++ | ++++ | ++++ |
| 135 | 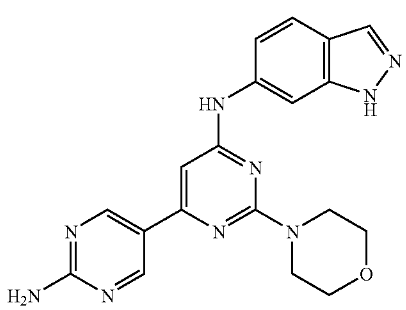 | 390.1, 1.85 | 9.52 L | ++++ | ++++ | ++++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 136 | 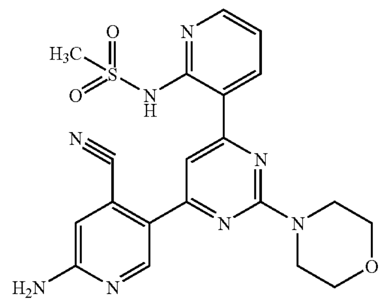 | 453.0, 2.29 | 2.76 | ++++ | ++++ | ++++ |
| 137 | Chiral | 443.2, 2.38 | | ++++ | ++++ | +++ |
| 138 | 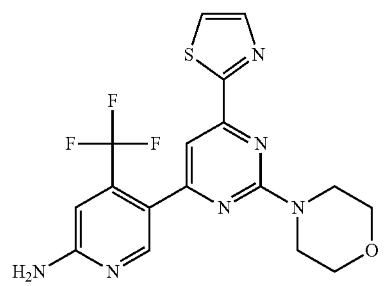 | 409.0, 2.95 | | ++++ | ++++ | +++ |
| 139 | 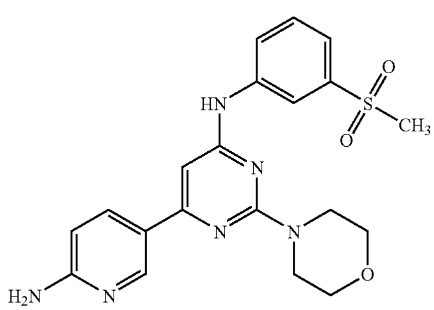 | 427.1 | 2.03 | ++++ | ++++ | +++ |
| 140 | 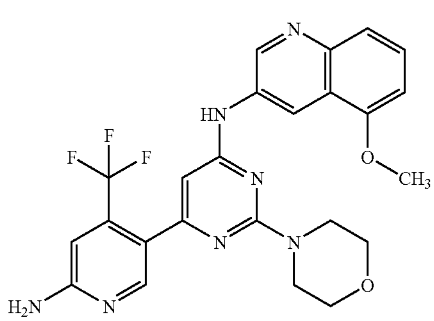 | 498.5, 2.36 | | ++++ | ++++ | +++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 141 | 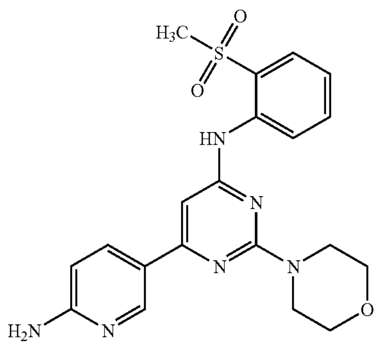 | 427 | 2.38 | ++++ | ++++ | +++ |
| 142 | 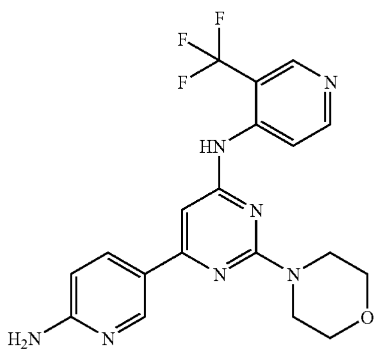 | 418.1, 1.78 | 8.81 L | ++++ | ++++ | ++++ |
| 143 | 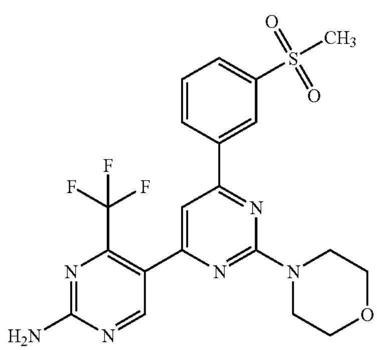 | 480.9, 2.46 | 3.50, (17.16) | ++++ | ++++ | ++++ |
| 144 | 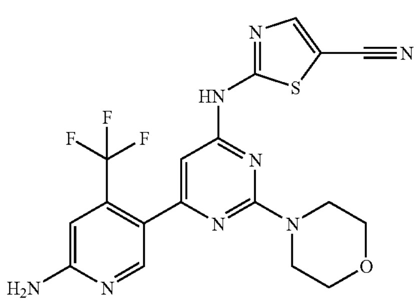 | 448.9, 2.76 | | ++++ | ++++ | +++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 145 | 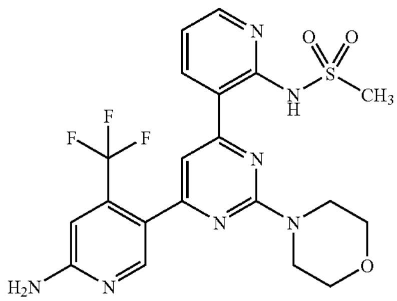 | 496.0, 2.35 | 2.75 | ++++ | ++++ | +++ |
| 146 | 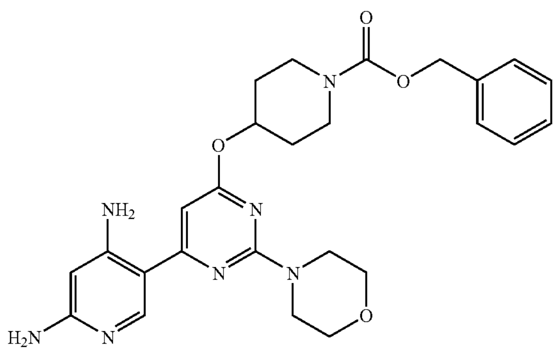 | 507.2, 3.12 | | ++++ | ++++ | ++++ |
| 147 | 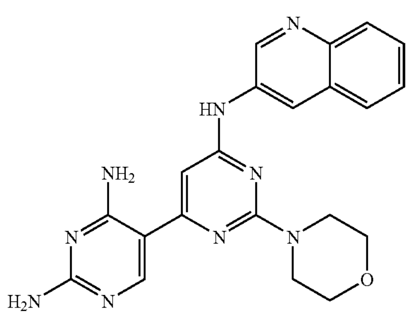 | 416.0, 1.98 | | ++++ | ++++ | ++++ |
| 148 | 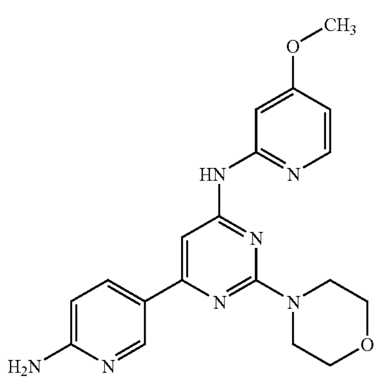 | 380.1 | 1.78 | ++++ | ++++ | ++ |

TABLE 1-continued
| Compound | Structure | LC/MS (M + H, Rt min) | hplc 10 min (L = 45 min) | PI3 Kinase Alpha, IC50 | PSer473 AKT, EC50 | Cellular Proliferation, EC50 |
|---|---|---|---|---|---|---|
| 149 | 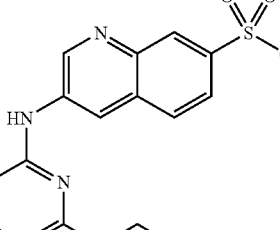 | 478.9, 1.75 | | ++++ | ++++ | +++ |
| 150 | 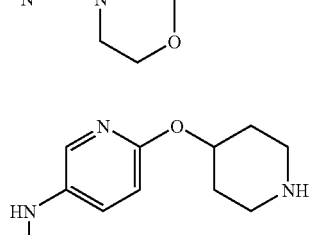 | 517.5, 1.78 | | ++++ | ++++ | ++++ |
| 151 | 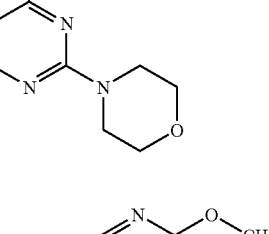 | 449.0, 2.42 | | ++++ | ++++ | +++ |
| 152 | 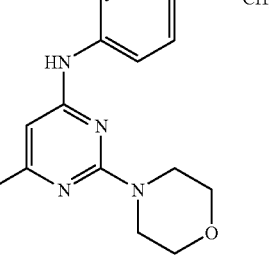 | 375.0 | 2.22 | ++++ | ++++ | +++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 153 | 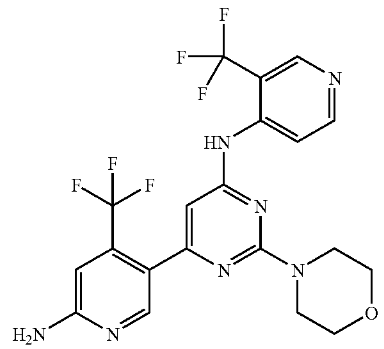 | 486.4, 2.12 | | ++++ | ++++ | ++++ |
| 154 | 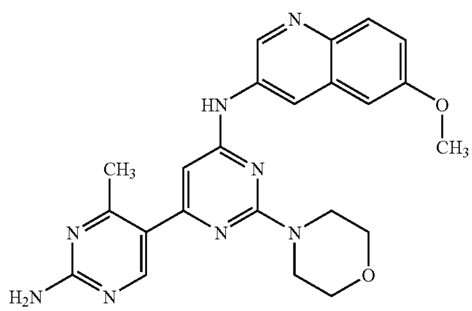 | 445.3, 2.02 | | ++++ | ++++ | ++++ |
| 155 | 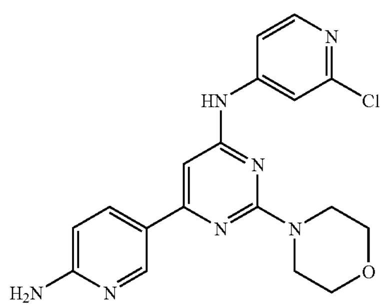 | 384.0, 2.04 | 2.28 | ++++ | ++++ | +++ |
| 156 | 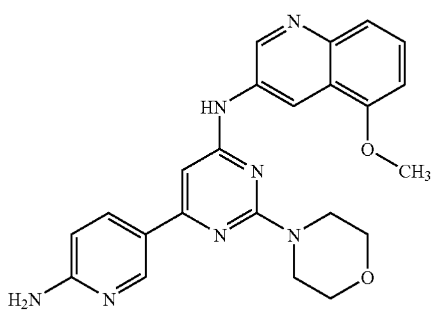 | 430.2, 2.05 | 11.18 L | ++++ | ++++ | ++++ |

TABLE 1-continued

| Compound | Structure | LC/MS (M + H, Rt min) | hplc 10 min (L = 45 min) | PI3 Kinase Alpha, IC50 | PSer473 AKT, EC50 | Cellular Proliferation, EC50 |
|---|---|---|---|---|---|---|
| 157 | 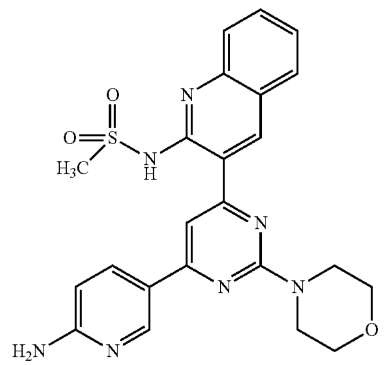 | 478.1, 2.40 | 14.67 L | ++++ | ++++ | ++ |
| 158 | 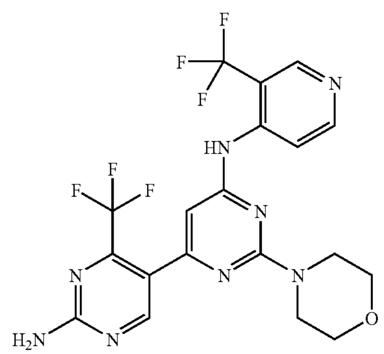 | 486.9, 2.48 | | ++++ | ++++ | ++++ |
| 159 | 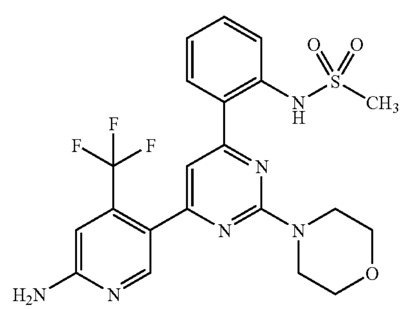 | 495.0, 2.57 | 3.13 | ++++ | ++++ | +++ |
| 160 | 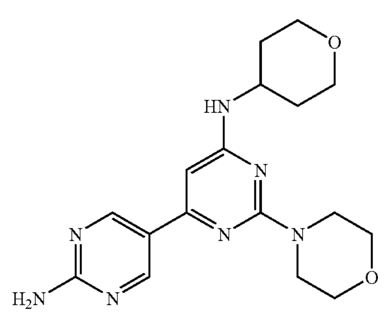 | 358.1 | 8.00 L | ++++ | ++++ | +++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 161 | 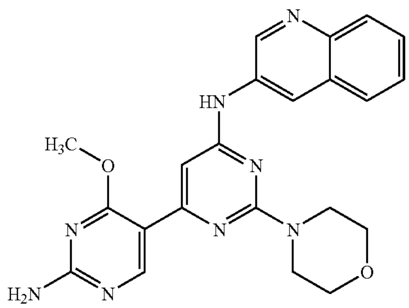 | 431.4, 1.96 | | ++++ | ++++ | ++++ |
| 162 | 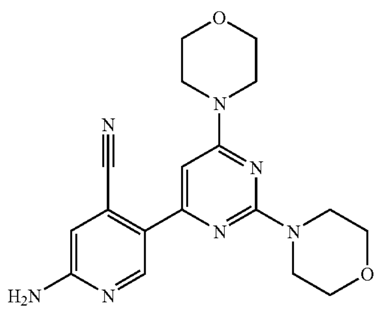 | 368.2 | 1.84 | ++++ | ++++ | ++++ |
| 163 | 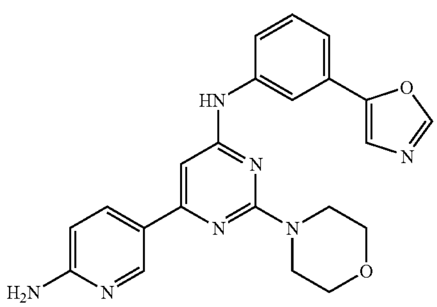 | 416.1 | 2.23 | ++++ | ++++ | +++ |
| 164 | 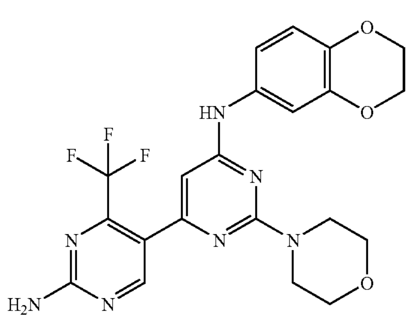 | 475.9, 2.69 | | ++++ | ++++ | ++++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 165 | 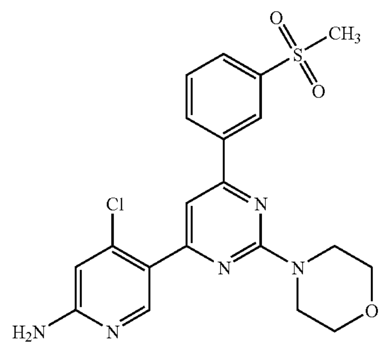 | 445.9, 1.95 | 2.57, (12.84) | ++++ | ++++ | ++++ |
| 166 | 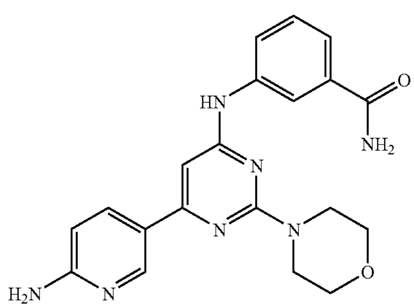 | 392.1 | 1.62 | ++++ | ++++ | +++ |
| 167 | Chiral | 459.2, 2.71 | | ++++ | ++++ | +++ |
| 168 | 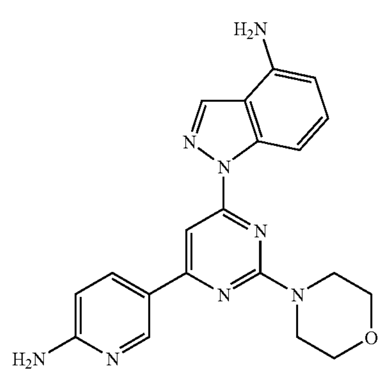 | 389.1 | 2.38 | ++++ | ++++ | ++++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 169 | 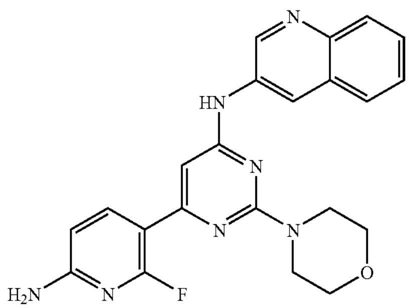 | 418.3, 1.70 | 2.16, (10.66) | ++++ | ++++ | ++++ |
| 170 | 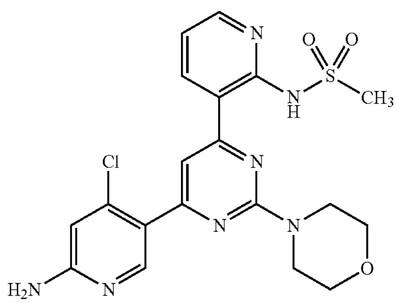 | 462.9, 2.41 | | ++++ | ++++ | ++++ |
| 171 | 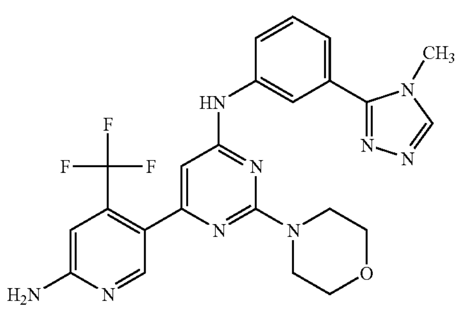 | 498.1 | 1.92 | ++++ | ++++ | ++++ |
| 172 | 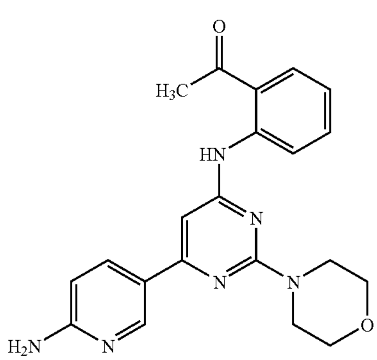 | 391.2 | 2.62 | ++++ | ++++ | +++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 173 | 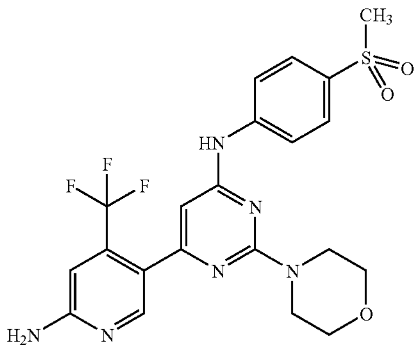 | 495.0 | 2.32 | ++++ | ++++ | +++ |
| 174 | 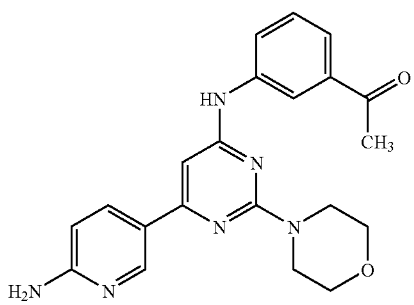 | 391.1 | 2.14 | ++++ | ++++ | +++ |
| 175 | 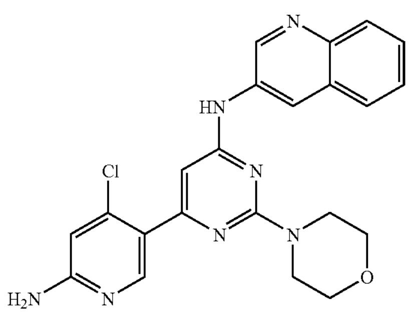 | 434.3, 1.95 | | ++++ | ++++ | ++++ |
| 176 | 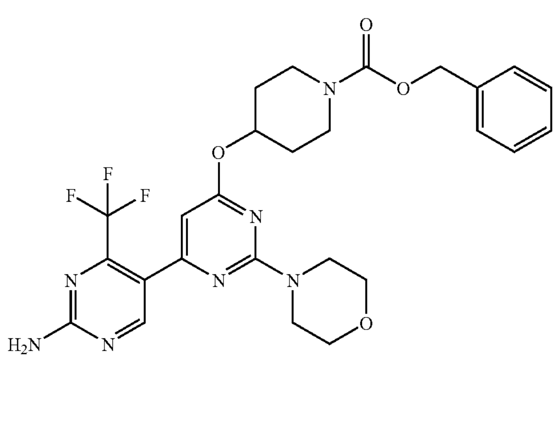 | 560.0, 4.28 | | ++++ | ++++ | +++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 177 | 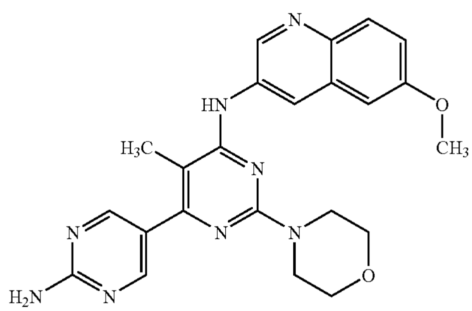 | 445.3, 1.79 | | ++++ | ++++ | ++++ |
| 178 | 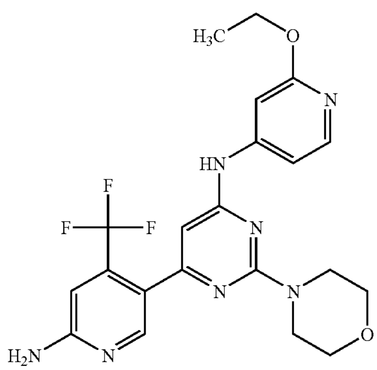 | 462.0, 1.98 | 2.19 | ++++ | ++++ | +++ |
| 179 | 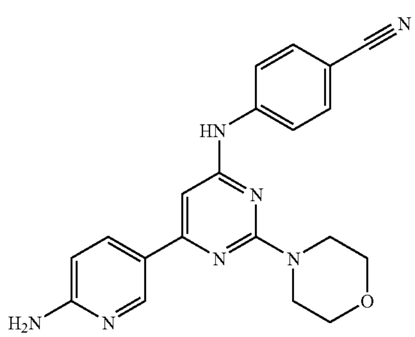 | 374.0, 2.16 | 2.48 | ++++ | ++++ | +++ |
| 180 | 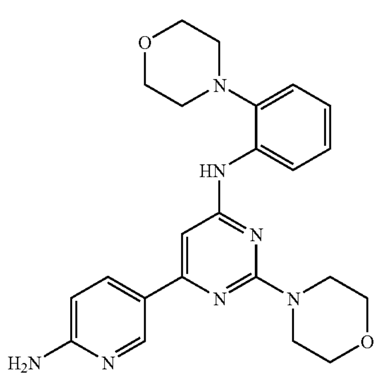 | 434.1 | 2.4 | ++++ | ++++ | +++ |

TABLE 1-continued

| Compound | Structure | LC/MS (M + H, Rt min) | hplc 10 min (L = 45 min) | PI3 Kinase Alpha, IC50 | PSer473 AKT, EC50 | Cellular Proliferation, EC50 |
|---|---|---|---|---|---|---|
| 181 | 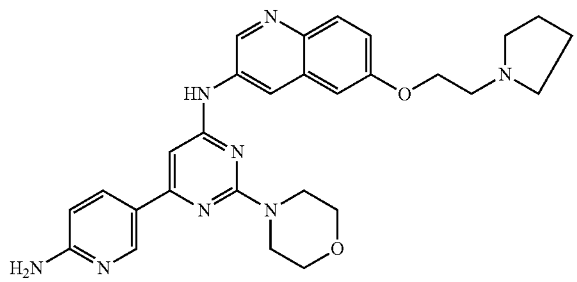 | 513.1, 1.76 | 1.72 | ++++ | ++++ | ++++ |
| 182 | 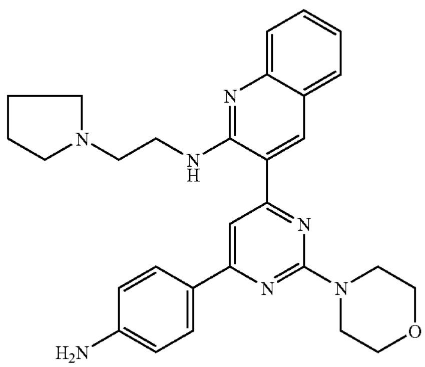 | 497.2, 1.90 | 9.89 L | ++++ | ++++ | ++++ |
| 183 | 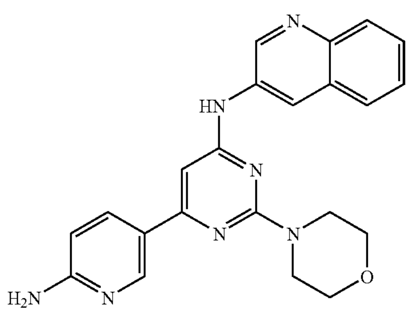 | 400.4, 2.03 | | ++++ | ++++ | ++++ |
| 184 | 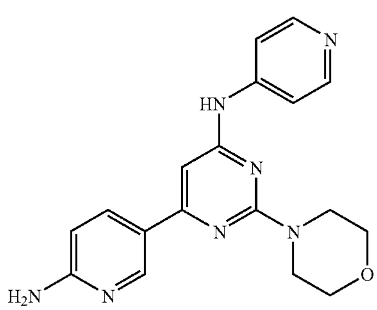 | 350.1 | 7.65 L | ++++ | ++++ | ++++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 185 | 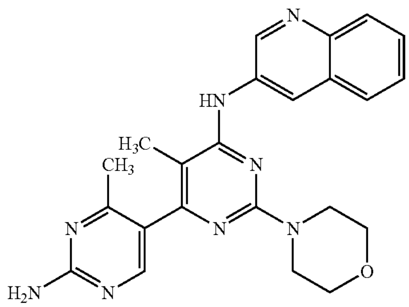 | 429.4, 1.67 | | ++++ | ++++ | ++++ |
| 186 | Chiral | 485.1, 2.91 | | ++++ | ++++ | +++ |
| 187 | 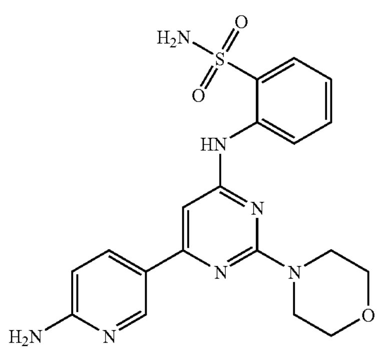 | 428.1 | 2.17 | ++++ | ++++ | +++ |
| 188 | Chiral | 545.2, 1.84 | 1.89 | ++++ | ++++ | +++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 189 | 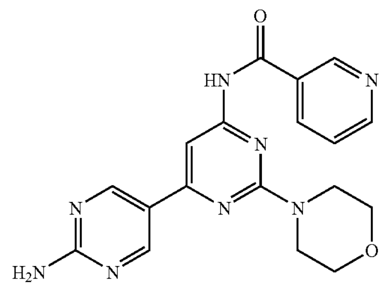 | 379.4, 1.42 | | ++++ | ++++ | +++ |
| 190 | 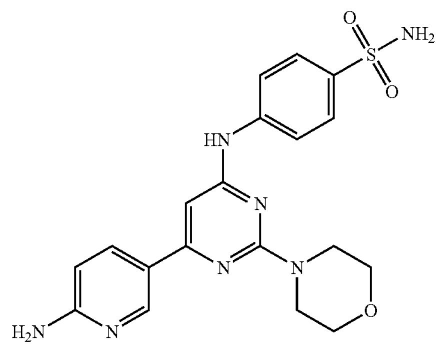 | 428.1 | 1.85 | ++++ | ++++ | +++ |
| 191 | 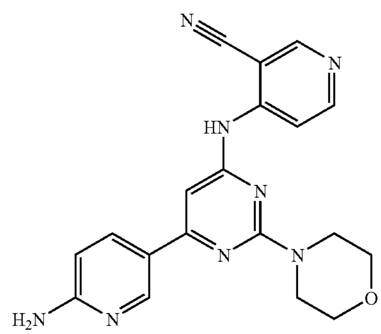 | 375.1, 1.75 | 1.74 | ++++ | ++++ | +++ |
| 192 | 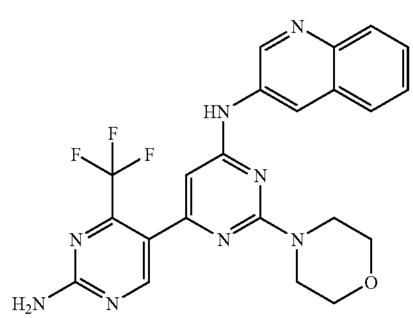 | 469.4, 2.44 | | ++++ | ++++ | ++++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 193 | 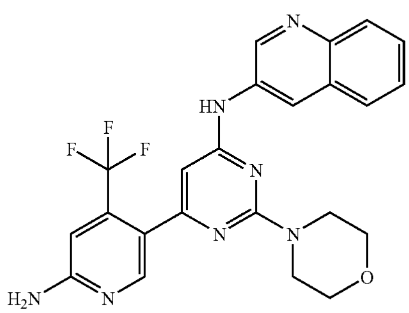 | 468.4, 2.26 | | ++++ | ++++ | ++++ |
| 194 | 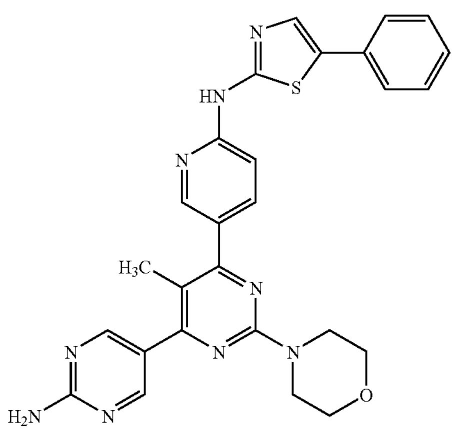 | 524.5, 2.44 | 3.44 | ++++ | ++++ | +++ |
| 195 | 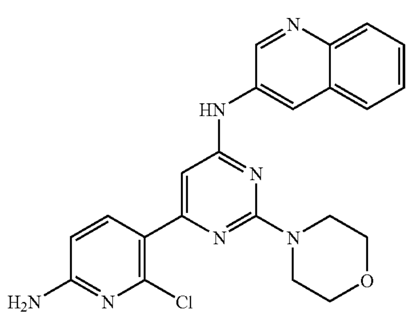 | 434.3, 2.06 | | ++++ | ++++ | ++++ |
| 196 | 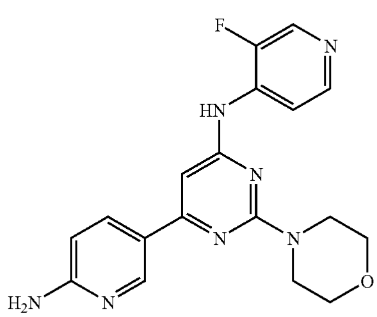 | 368.1, 1.69 | 1.63 | ++++ | ++++ | ++++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 197 | 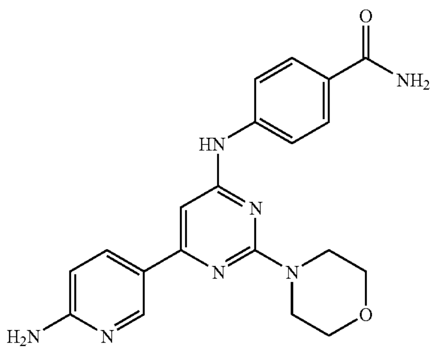 | 392.1 | 1.68 | ++++ | ++++ | +++ |
| 198 | 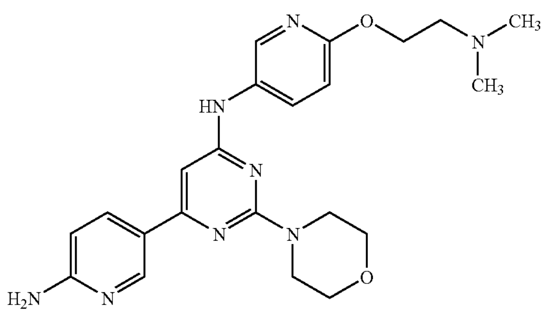 | 437.2, 1.60 | 1.45 | ++++ | ++++ | N/D |
| 199 | 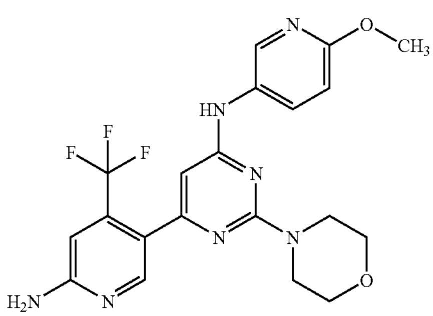 | 448.4, 2.24 | | ++++ | ++++ | +++ |
| 200 | 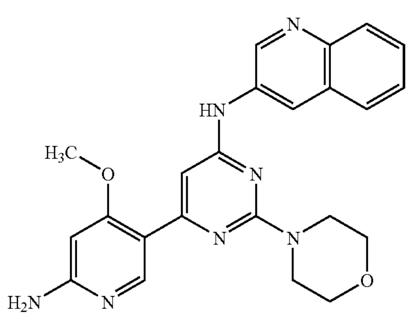 | 430.1, 1.84 | 9.55 L | ++++ | ++++ | ++++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
| --- | --- | --- | --- | --- | --- | --- |
| 201 | 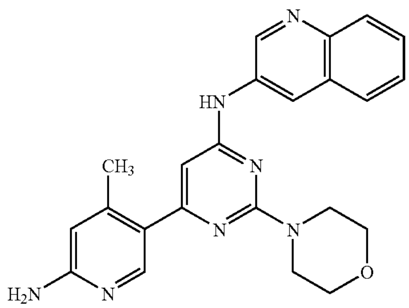 | 414.1, 1.85 | 9.53 L | ++++ | ++++ | ++++ |
| 202 | 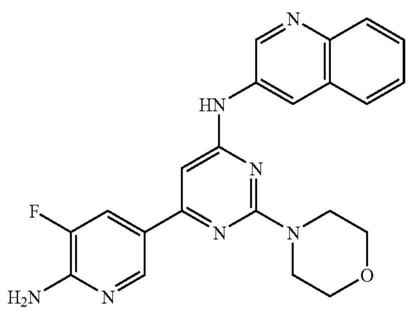 | 418.3 | 2.16 | ++++ | ++++ | ++++ |
| 203 | 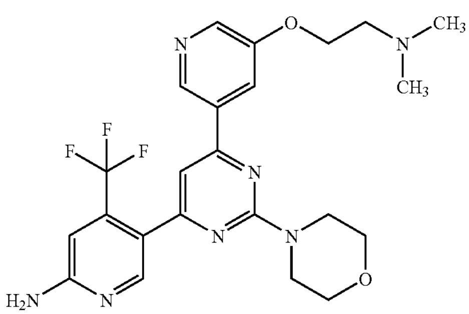 | 491.1, 1.85 | 1.83 | ++++ | ++++ | +++ |
| 204 | 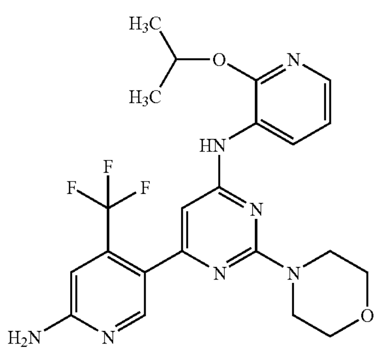 | 476.1, 2.42 | 2.86 | ++++ | ++++ | ++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 205 | 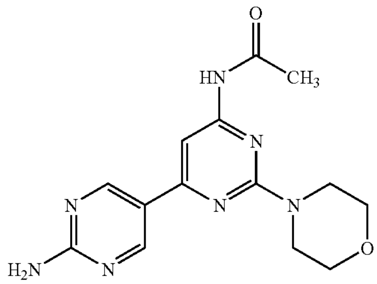 | 316.2, 1.45 | | ++++ | ++++ | +++ |
| 206 | 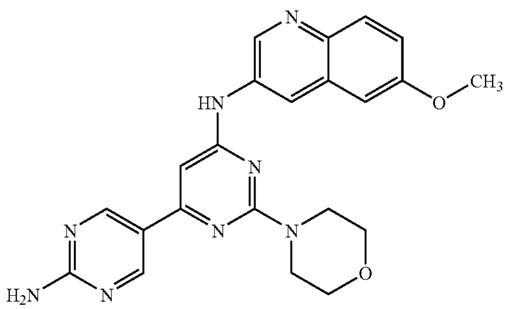 | 431.0, 1.91 | 2.16 | ++++ | ++++ | ++++ |
| 207 | 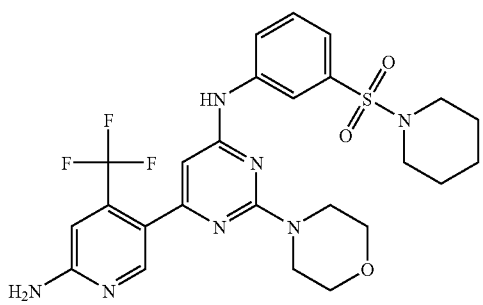 | 564.1 | 3.08 | ++++ | +++ | ++++ |
| 208 | 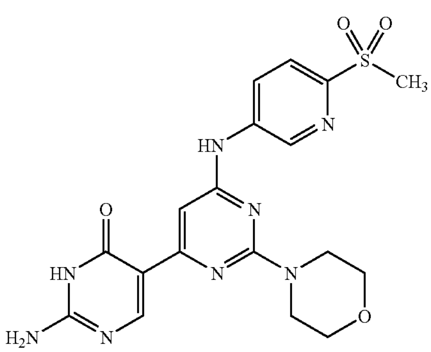 | 445.0, 1.50 | 1.78 (8.91) | ++++ | +++ | ++ |
| 209 | 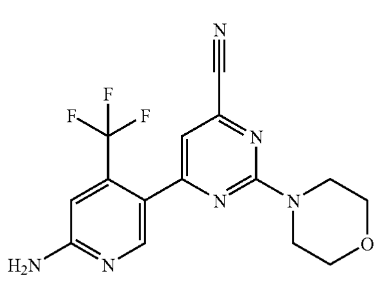 | 351.0, 2.12 | 2.88, (14.36) | ++++ | +++ | +++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 210 | 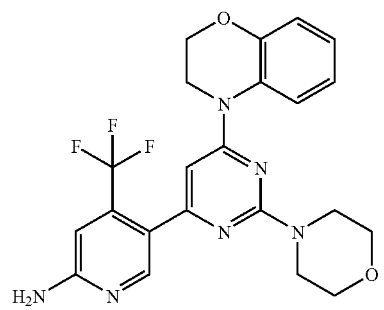 | 459.4, 2.80 | | ++++ | +++ | +++ |
| 211 | 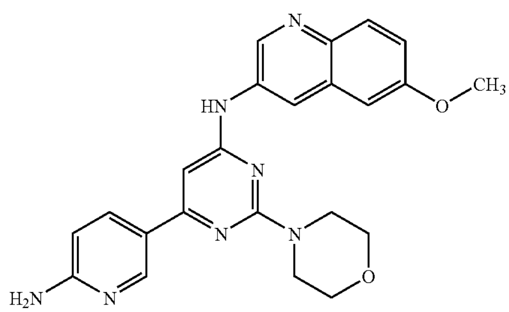 | 430.2, 2.02 | 2.14 | ++++ | +++ | ++++ |
| 212 | 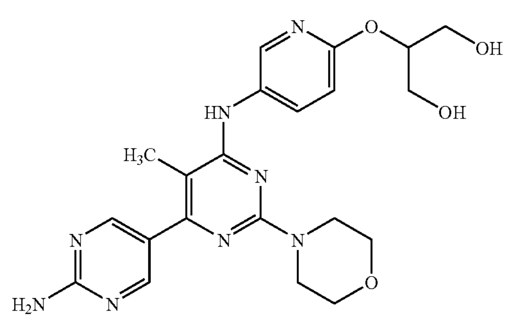 | 455.5, 1.53 | | ++++ | +++ | ++ |
| 213 | 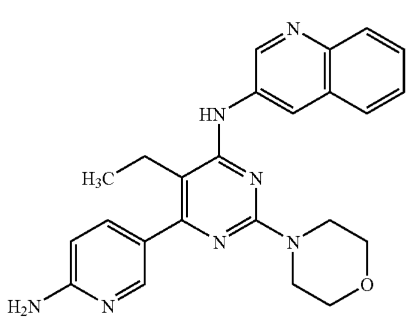 | 428.2, 1.74 | 8.55 L | ++++ | +++ | ++++ |

TABLE 1-continued
| Compound | Structure | LC/MS (M + H, Rt min) | hplc 10 min (L = 45 min) | PI3 Kinase Alpha, IC50 | PSer473 AKT, EC50 | Cellular Proliferation, EC50 |
|---|---|---|---|---|---|---|
| 214 | 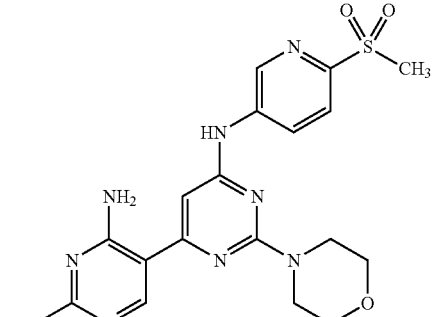 | 444.0, 2.06 | | ++++ | +++ | ++ |
| 215 | 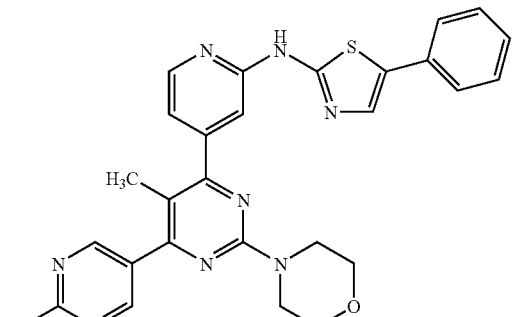 | 524.5, 2.44 | 3.36 | ++++ | +++ | +++ |
| 216 | 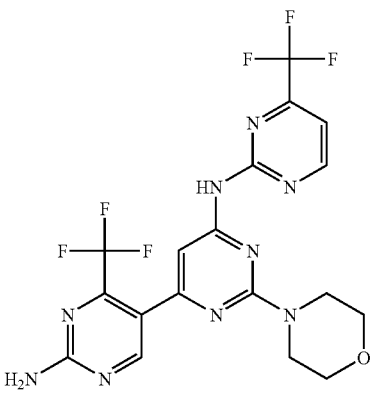 | 487.9, 3.60 | | ++++ | N/D | +++ |
| 217 | 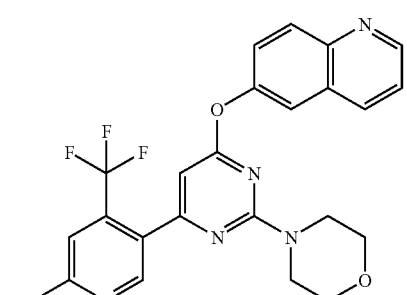 | 469.1, 2.01 | 2.13 | ++++ | N/D | +++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 218 | 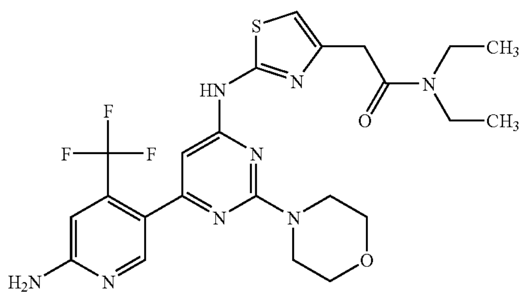 | 537.1, 2.27 | 2.53 | ++++ | N/D | +++ |
| 219 | 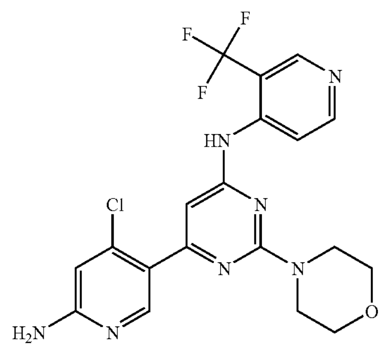 | 452.0, 1.85 | 1.89 | ++++ | N/D | +++ |
| 220 | 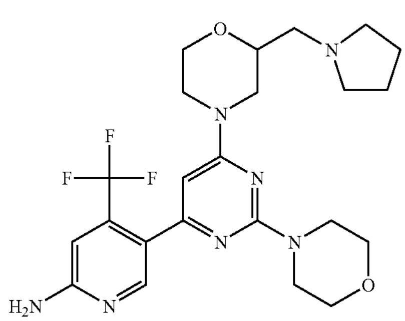 | 494.1, 1.67 | 1.59 | +++ | N/D | ++ |
| 221 | 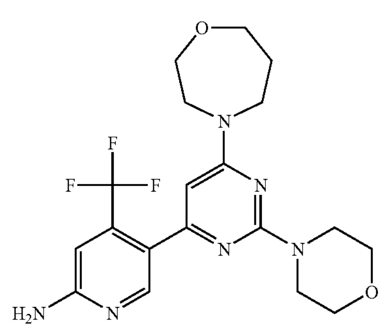 | 425.0, 1.66 | 1.98 | ++++ | N/D | +++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
| --- | --- | --- | --- | --- | --- | --- |
| 222 | 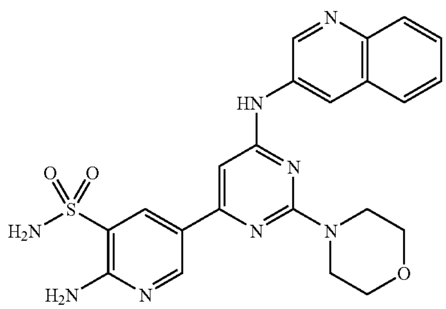 | 479.1, 1.98 | 2.20 | +++ | N/D | N/D |
| 223 | 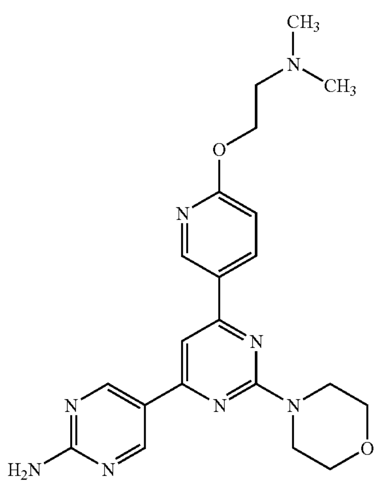 | 423.2, 1.83 | 1.99 | ++++ | N/D | +++ |
| 224 | 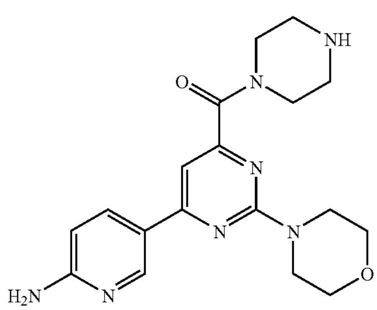 | 370.3, 1.25 | 1.39 | +++ | N/D | N/D |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 225 | 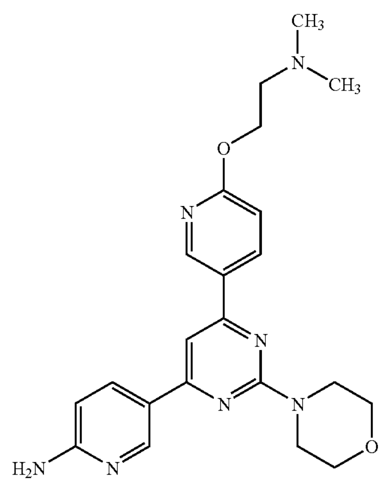 | 422.2, 1.84 | 1.86 | ++++ | N/D | N/D |
| 226 | 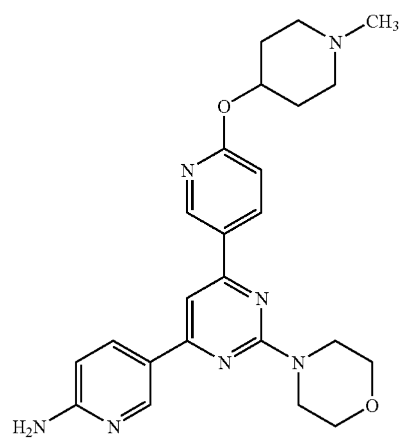 | 448.3, 1.93 | 1.94 | ++++ | N/D | N/D |
| 227 | 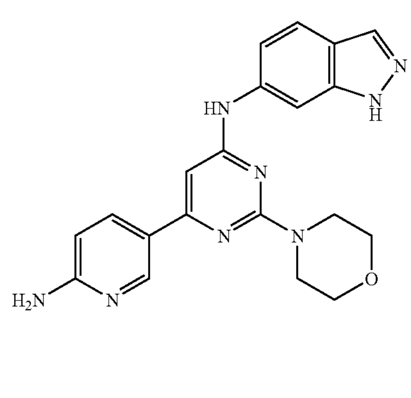 | 389.2, 1.93 | 1.93 | ++++ | N/D | +++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 228 | 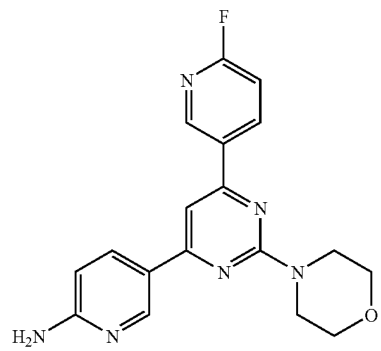 | 353.1, 2.25 | 2.55 | ++++ | N/D | N/D |
| 229 | 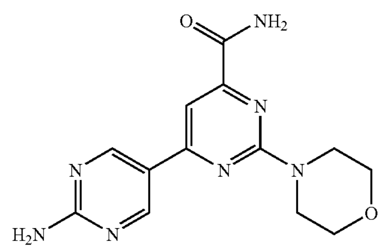 | 302.1, 1.68 | 1.74 | ++++ | N/D | N/D |
| 230 | 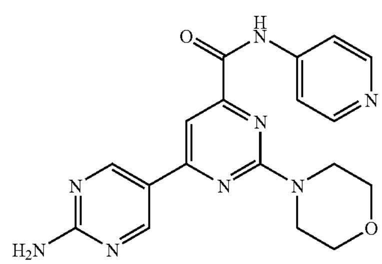 | 379.1, 1.73 | 1.74 | ++++ | N/D | +++ |
| 231 | 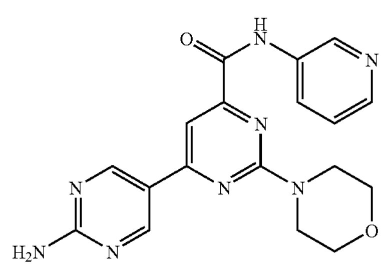 | 379.1, 1.75 | 1.78 | ++++ | N/D | +++ |
| 232 | 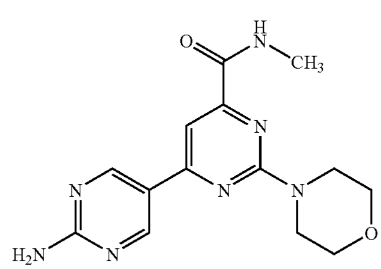 | 316.1, 1.84 | 2.24 | ++++ | N/D | ++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 233 | 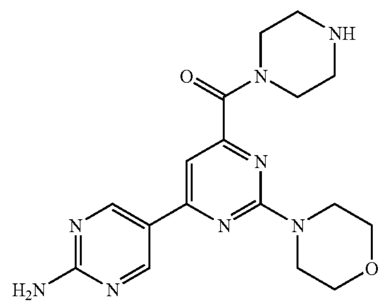 | 371.2, 1.49 | 1.39 | ++++ | N/D | +++ |
| 234 | 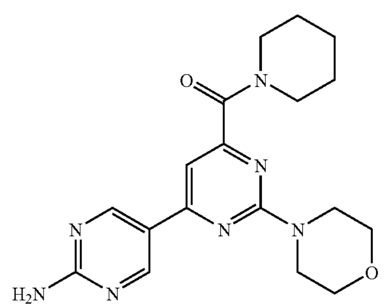 | 370.0, 2.12 | 2.37 | ++++ | N/D | ++ |
| 235 | 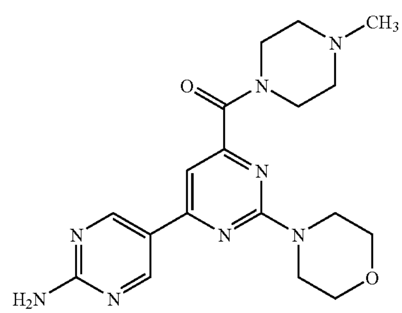 | 385.2, 1.50 | 1.40 | ++++ | N/D | +++ |
| 236 | 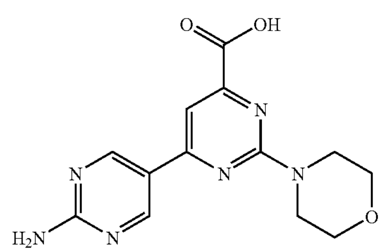 | 303.1, 1.65 | 1.70 | ++++ | N/D | N/D |
| 237 | 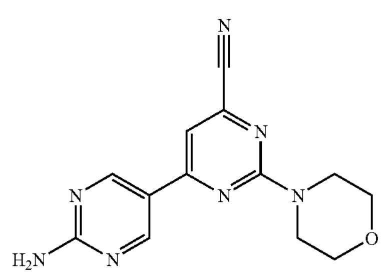 | 284.1, 2.12 | 2.56 | ++++ | N/D | +++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 238 | 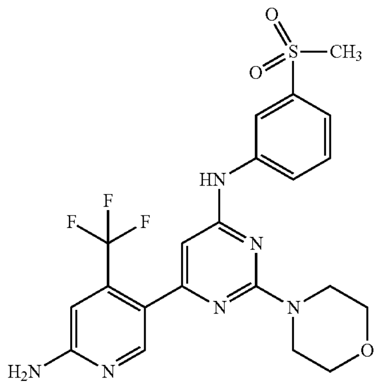 | 495.0 | 2.3 | ++++ | N/D | +++ |
| 239 | 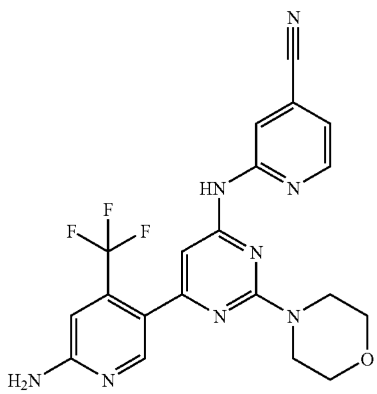 | 443.1 | 2.63 | ++++ | N/D | +++ |
| 240 | 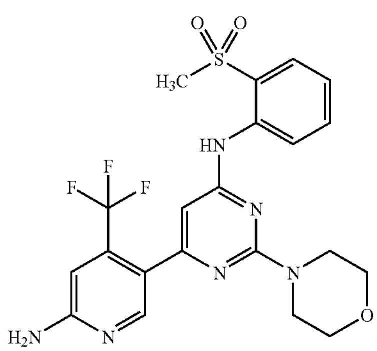 | 495, 2.20 | 3.29 | ++++ | N/D | N/D |
| 241 | 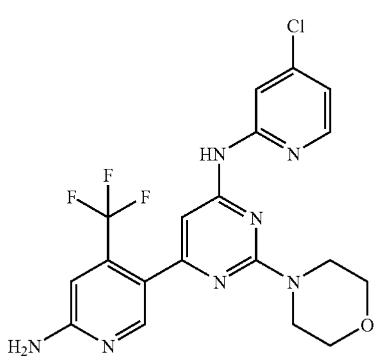 | 452.0 | 2.57 | ++++ | N/D | +++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 242 | 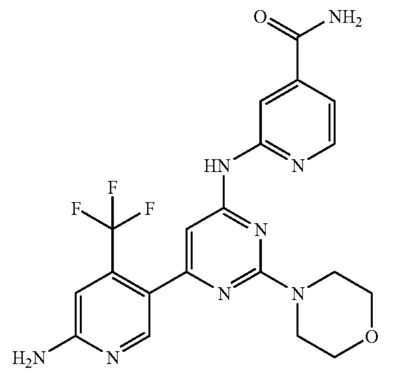 | 461.1 | 1.85 | ++++ | N/D | +++ |
| 243 | 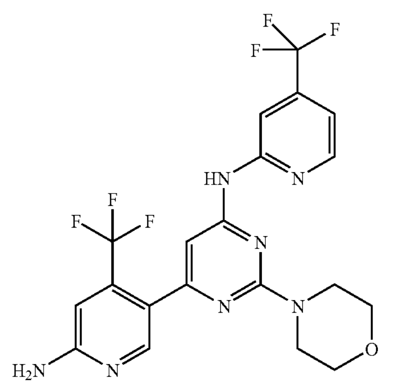 | 486, 2.01 | 2.26 | ++++ | N/D | N/D |
| 244 | 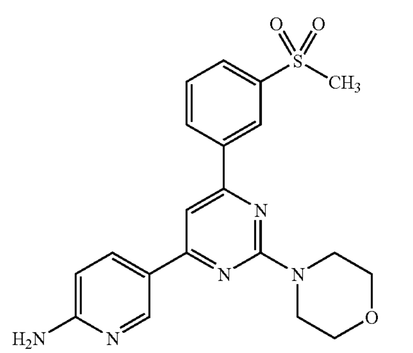 | 413, 2.13 | 2.41 | ++++ | N/D | +++ |
| 245 | 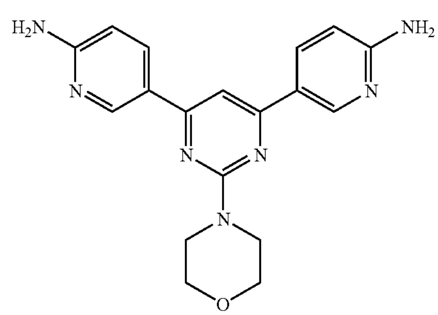 | 350, 1.72 | 1.66 | ++++ | N/D | +++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 246 | 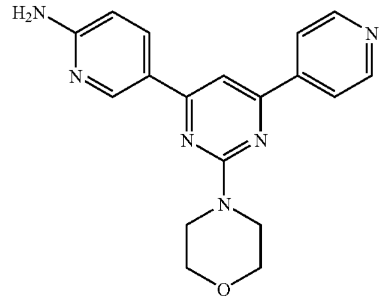 | 335, 1.66 | 1.57 | ++++ | N/D | +++ |
| 247 | 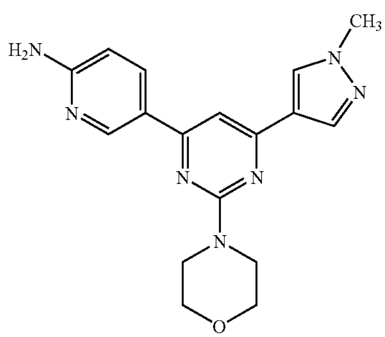 | 338, 1.92 | 2.02 | ++++ | N/D | +++ |
| 248 | 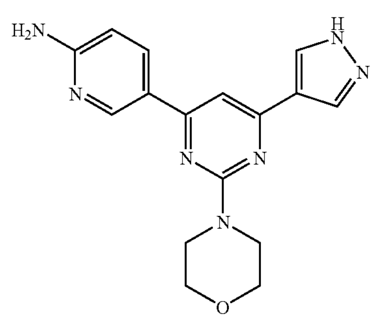 | 324, 1.79 | 1.82 | ++++ | N/D | +++ |
| 249 | 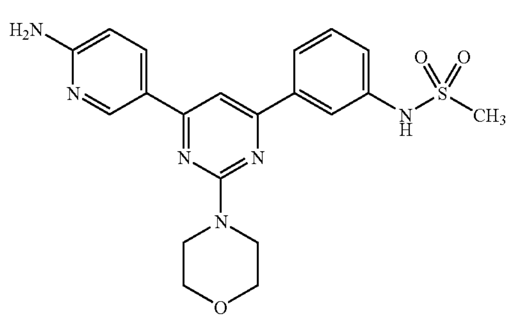 | 427, 2.15 | 2.40 | ++++ | N/D | +++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 250 | 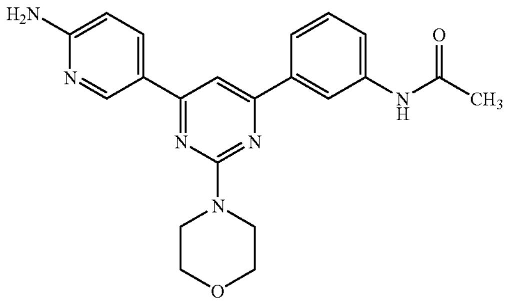 | 391, 2.07 | 2.30 | ++++ | N/D | +++ |
| 251 | 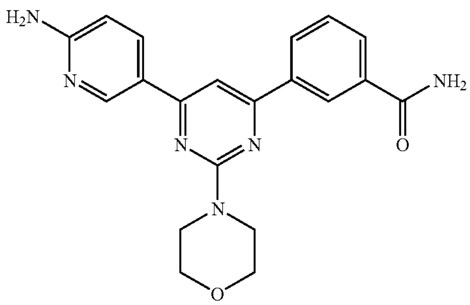 | 377, 1.98 | 2.14 | ++++ | N/D | +++ |
| 252 | 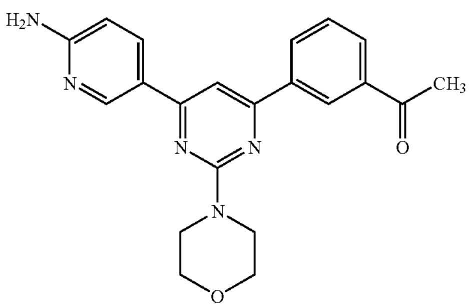 | 376, 2.31 | 2.66 | ++++ | N/D | +++ |
| 253 | 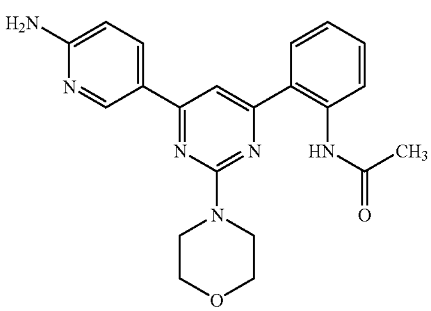 | 391, 2.13 | 2.56 | ++++ | N/D | +++ |
| 254 | 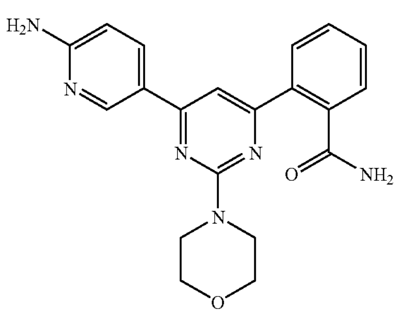 | 377, 1.76 | 1.81 | ++++ | N/D | ++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 255 | 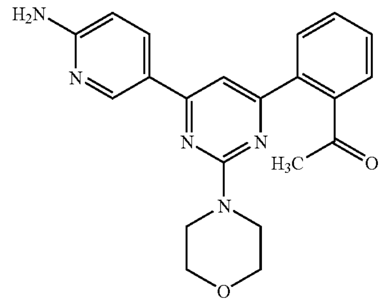 | 376, 2.14 | 2.39 | ++++ | N/D | ++ |
| 256 | 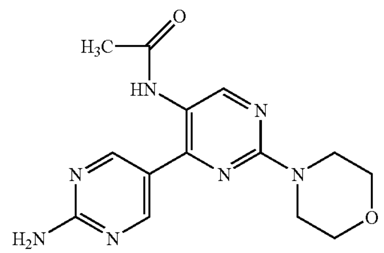 | 316, 1.44 | 1.32 | ++++ | N/D | N/D |
| 257 | 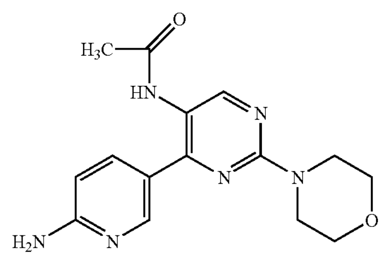 | 315, 1.46 | 1.30 | +++ | N/D | N/D |
| 258 | 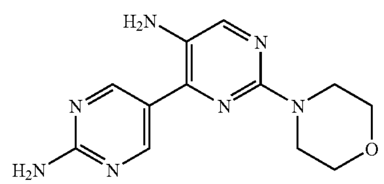 | 274, 1.40 | 1.22 | ++++ | N/D | ++ |
| 259 | 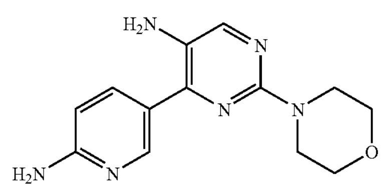 | 273, 1.40 | 1.23 | +++ | N/D | ++ |
| 260 | 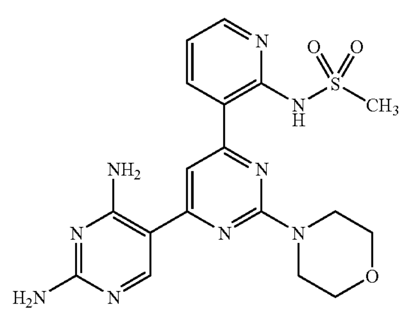 | 444.1, 2.02 | 2.24 | ++++ | N/D | +++ |

TABLE 1-continued
| Compound | Structure | LC/MS (M + H, Rt min) | hplc 10 min (L = 45 min) | PI3 Kinase Alpha, IC50 | PSer473 AKT, EC50 | Cellular Proliferation, EC50 |
|---|---|---|---|---|---|---|
| 261 | 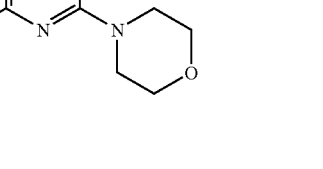 | 507.2, 1.92 | 1.98 | ++++ | N/D | +++ |
| 262 | 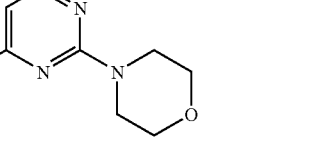 | 559.2, 2.07 | 2.25 | ++++ | N/D | +++ |
| 263 | 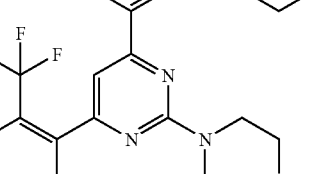 | 500.2, 1.66 | 2.03 | ++++ | N/D | +++ |
| 264 | 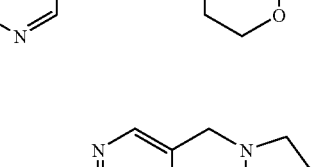 | 486.1, 1.61 | 1.94 | ++++ | N/D | +++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 265 | 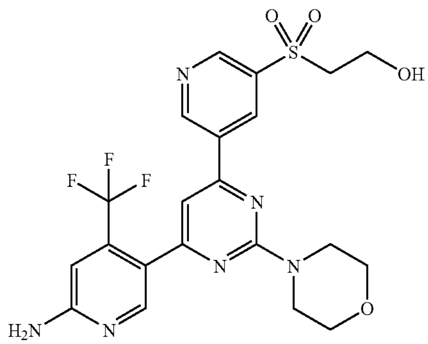 | 511.1, 2.09 | 2.44 | ++++ | N/D | +++ |
| 266 | 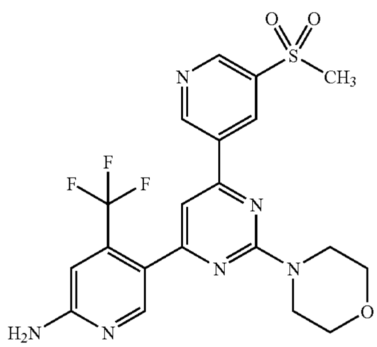 | 481.1, 2.23 | 2.59 | ++++ | N/D | +++ |
| 267 | 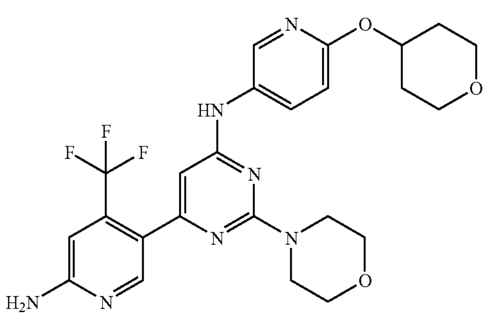 | 518.2, 2.18 | | ++++ | N/D | +++ |
| 268 | 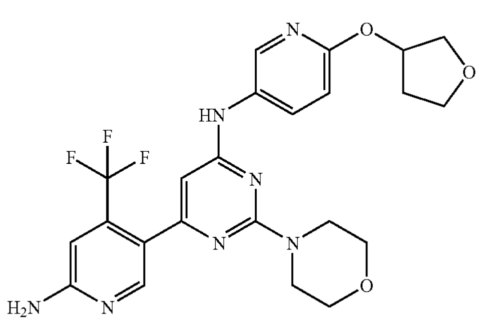 | 504.1, 2.13 | | ++++ | N/D | +++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 269 | 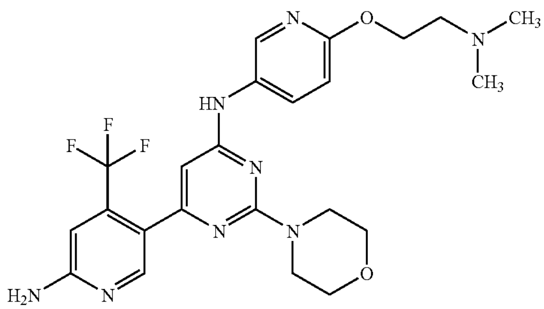 | 505.2, 1.76 | | ++++ | N/D | +++ |
| 270 | 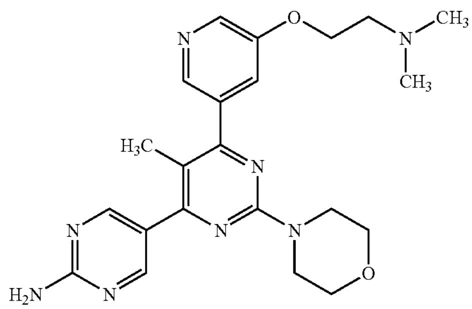 | 437.1, 1.56 | 1.44 | ++++ | N/D | ++ |
| 271 | 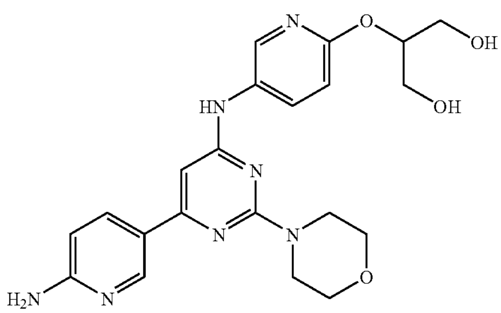 | 440.1, 1.59 | 1.45 | ++++ | N/D | ++ |
| 272 | 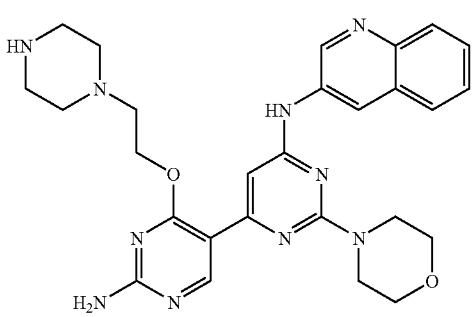 | 529.1, 1.64 | 1.72 | ++++ | N/D | N/D |
| 273 | 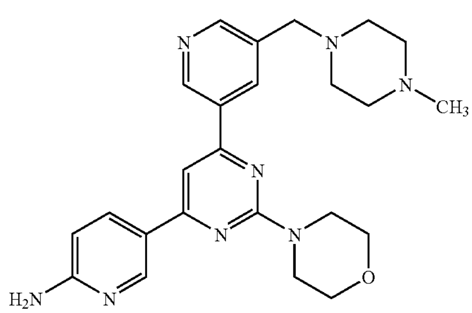 | 447.2, 1.61 | 1.54 | ++++ | N/D | +++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 274 | 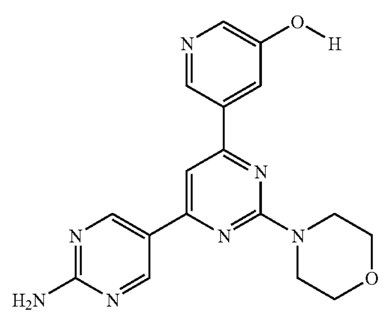 | 352.2, 1.81 | 1.77 | ++++ | N/D | ++++ |
| 275 | 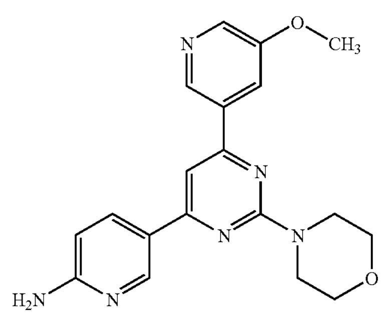 | 365.2, 1.88 | 1.90 | ++++ | N/D | ++++ |
| 276 | 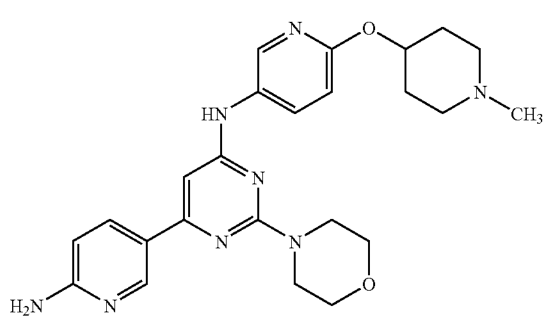 | 463.3, 1.72 | | ++++ | N/D | +++ |
| 277 | 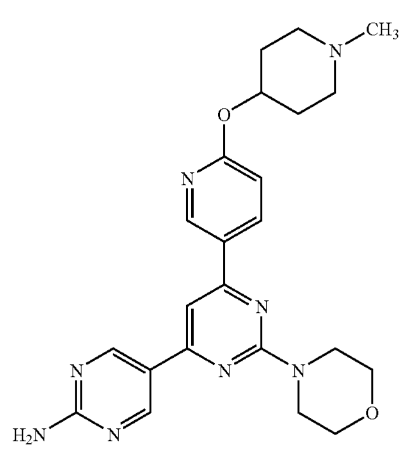 | 449.2, 2.00 | 2.11 | ++++ | N/D | +++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 278 | 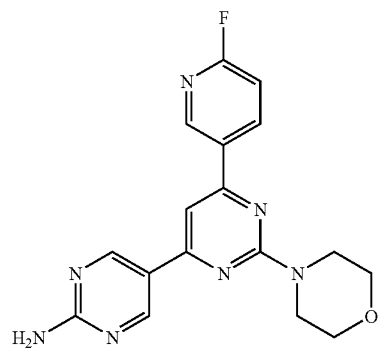 | 354.2, 2.32 | 2.12 | ++++ | N/D | +++ |
| 279 | 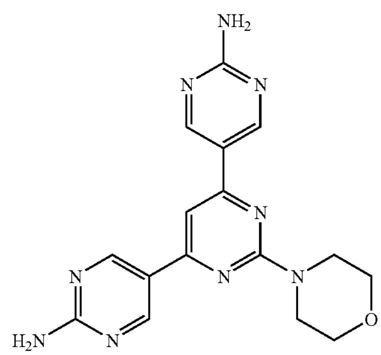 | 352.1, 1.81 | 1.48 | ++++ | N/D | +++ |
| 280 | 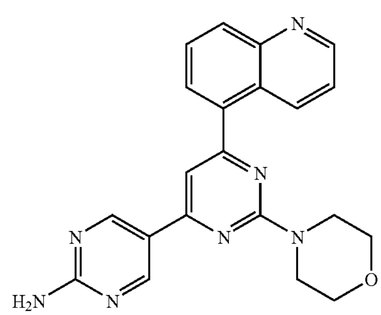 | 386.1, 1.83 | 1.91 | ++++ | N/D | +++ |
| 281 | 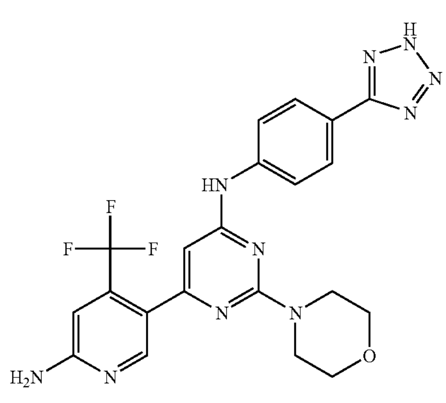 | 485.1, 2.17 | | ++++ | N/D | ++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
| --- | --- | --- | --- | --- | --- | --- |
| 282 | 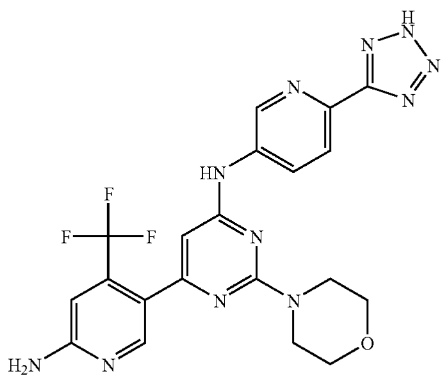 | 486.0, 1.69 | | ++++ | N/D | ++ |
| 283 | 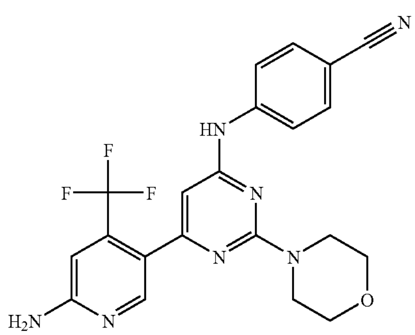 | 442.0, 2.02 | | ++++ | N/D | +++ |
| 284 | 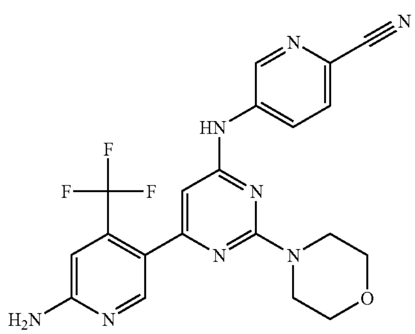 | 443.1, 2.22 | | ++++ | N/D | +++ |
| 285 | 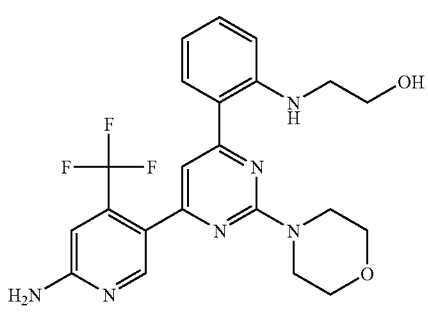 | 462.1, 1.95 | | ++++ | N/D | +++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 286 | 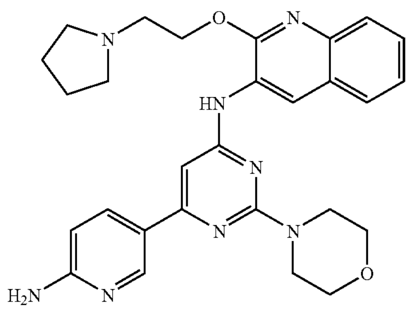 | 513.1, 2.46 | | +++ | N/D | N/D |
| 287 | 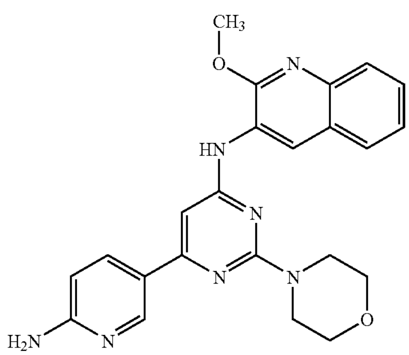 | 430.1, 2.98 | | ++++ | N/D | +++ |
| 288 | 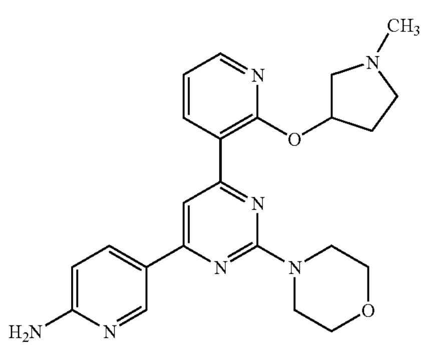 | 434.4, 1.97 | | +++ | N/D | N/D |
| 289 | 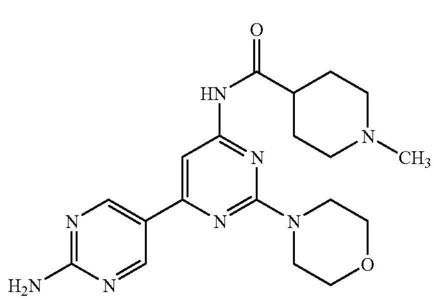 | 399.4, 1.50 | | ++++ | N/D | +++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 290 | Chiral | 372.3, 1.74 | | ++++ | N/D | +++ |
| 291 | 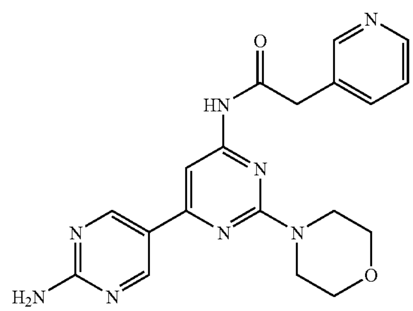 | 393.4, 1.32 | | ++++ | N/D | ++ |
| 292 | 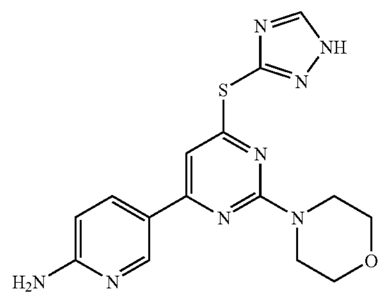 | 357.2, 1.78 | | +++ | N/D | N/D |
| 293 | 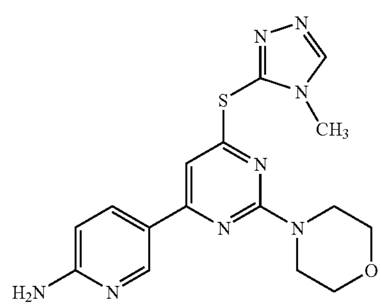 | 371.4, 1.68 | | +++ | N/D | N/D |
| 294 | 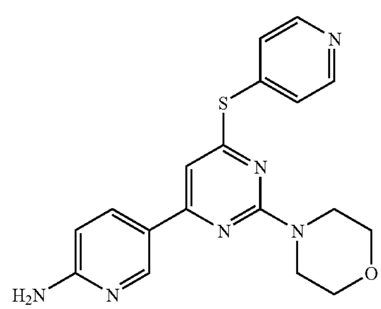 | 367.3, 1.65 | | ++++ | N/D | +++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 295 | 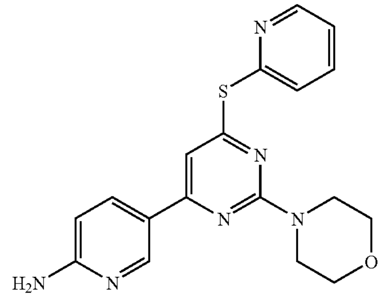 | 367.3, 2.17 | | ++++ | N/D | +++ |
| 296 | 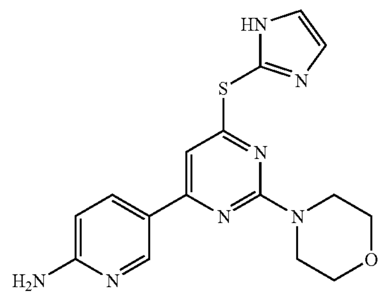 | 356.3, 1.22 | | +++ | N/D | N/D |
| 297 | 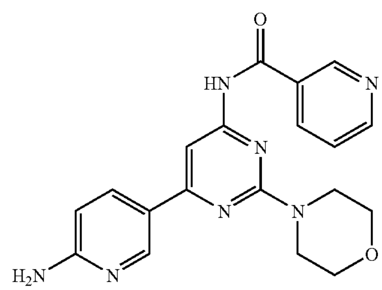 | 378.4, 1.72 | | ++++ | N/D | N/D |
| 298 | 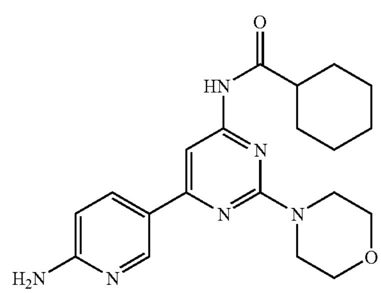 | 383.4, 2.69 | | ++++ | N/D | N/D |
| 299 | 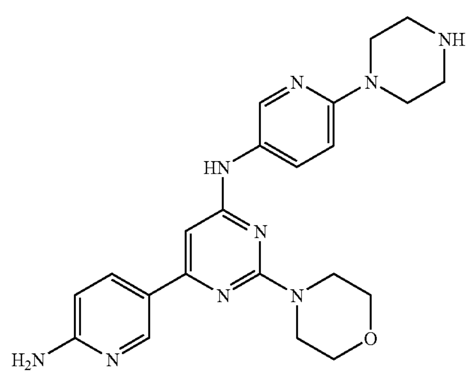 | 434.5, 1.41 | | ++++ | N/D | +++ |

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 300 | 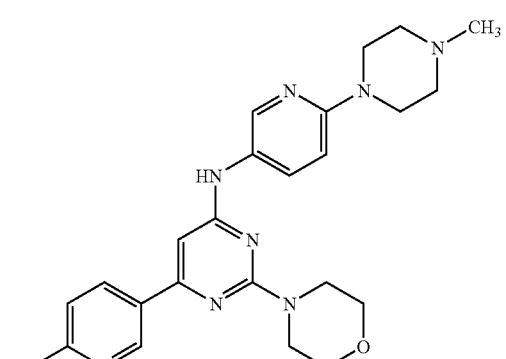 | 448.4, 1.44 | | ++++ | N/D | +++ |
| 301 | 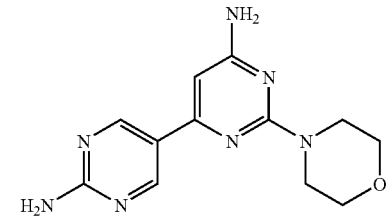 | 274.2, 0.46 | | ++++ | N/D | ++ |
| 302 | 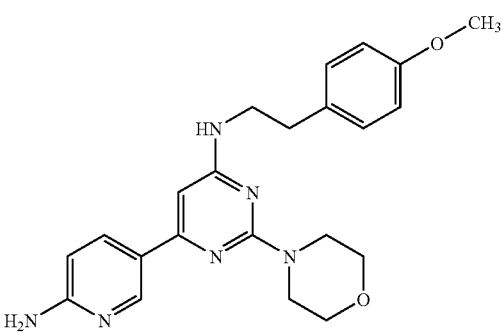 | 407.2, 2.04 | 3.73 | +++ | N/D | ++ |
| 303 | 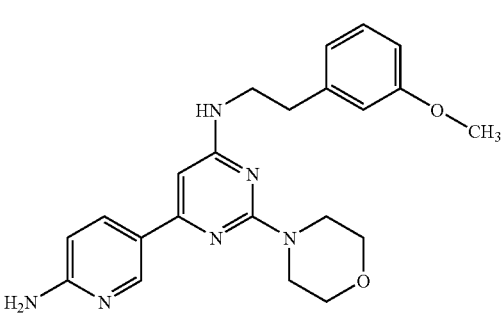 | 407.2, 2.02 | 3.77 | ++++ | N/D | +++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 304 | 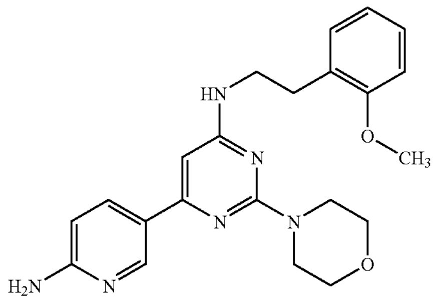 | 407.1, 2.10 | 2.25 | ++++ | N/D | ++ |
| 305 | 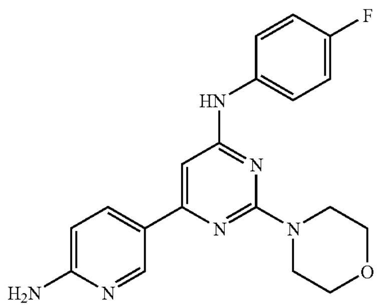 | 367.0; 2.07 | 2.28 | ++++ | N/D | +++ |
| 306 | 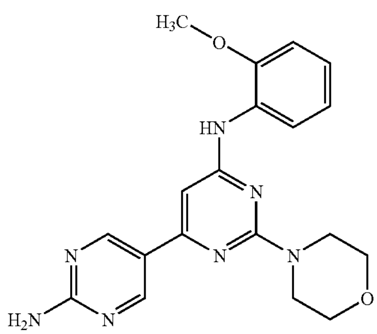 | 380.1; 2.07 | 2.29 | ++++ | N/D | +++ |
| 307 | 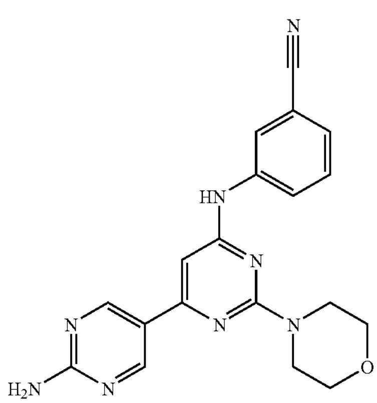 | 375.0; 2.09 | 2.39 | ++++ | N/D | +++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 308 | 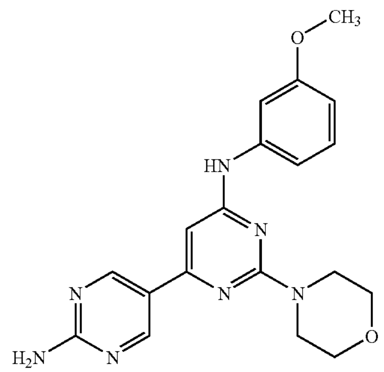 | 380.1; 2.07 | 2.32 | ++++ | N/D | +++ |
| 309 | 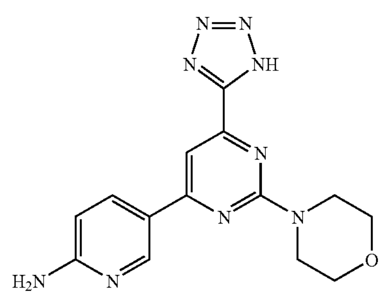 | 326.1, 1.79 | 2.99 | ++++ | N/D | N/D |
| 310 | 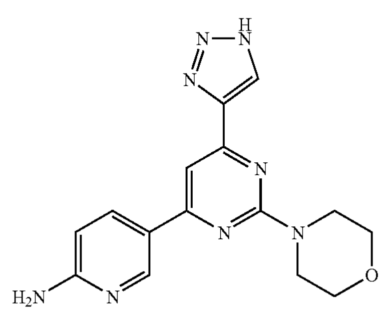 | 325.0, 1.51 | 1.88 | ++++ | N/D | N/D |
| 311 | 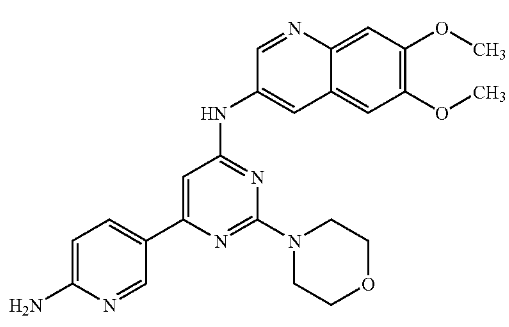 | 460.1, 1.96 | 2.09 | ++++ | N/D | ++++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 312 | 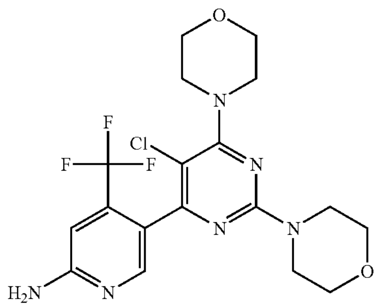 | 445.1, 2.30 | 2.7 | ++++ | N/D | N/D |
| 313 | 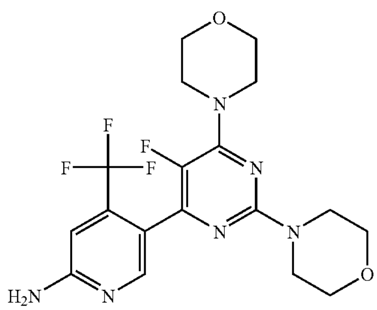 | 429.1 | 2.32 | ++++ | N/D | ++ |
| 314 | 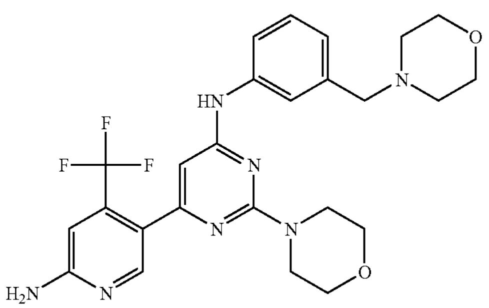 | 516.1 | 1.78 | ++++ | N/D | ++ |
| 315 | 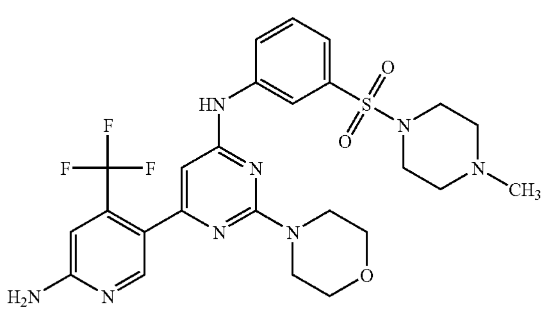 | 579.1 | 2.09 | ++++ | N/D | +++ |
| 316 | 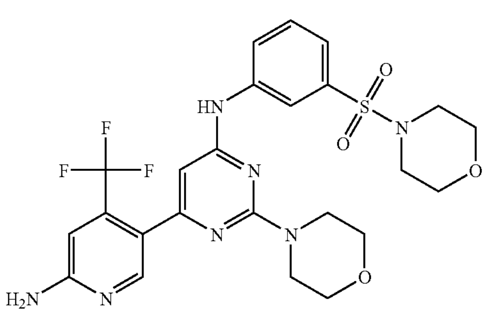 | 566 | 2.64 | ++++ | N/D | +++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
| --- | --- | --- | --- | --- | --- | --- |
| 317 | 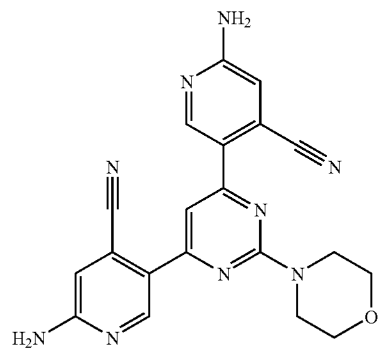 | 400.1, 2.02 | 2.27 | ++++ | N/D | +++ |
| 318 | 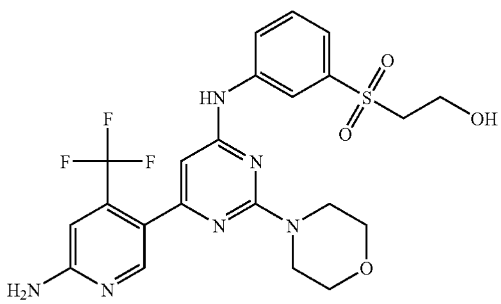 | 525.1 | 2.15 | ++++ | N/D | +++ |
| 319 | 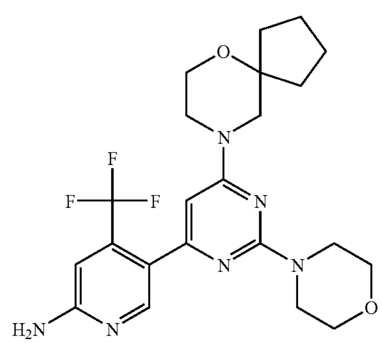 | 465.1, 2.28 | 2.5 | ++++ | N/D | N/D |
| 320 | 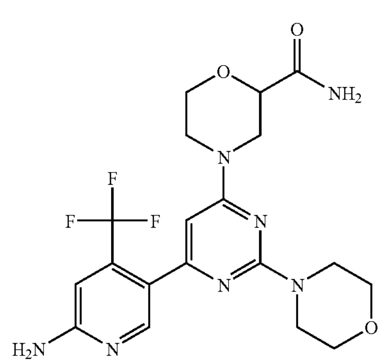 | 454.1, 1.74 | 1.74 | ++++ | N/D | +++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
| --- | --- | --- | --- | --- | --- | --- |
| 321 | 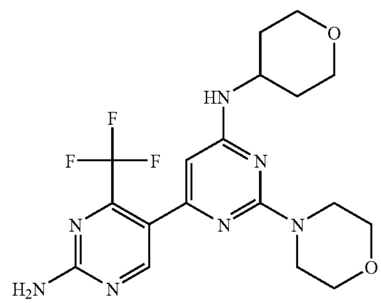 | 426.1 | 2.08 | ++++ | N/D | +++ |
| 322 | 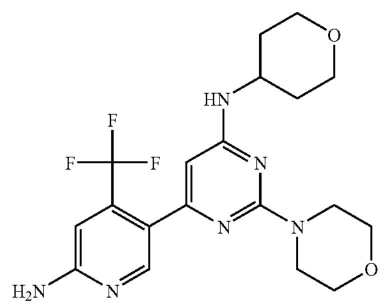 | 425.1, 1.92 | 1.97 | ++++ | N/D | ++ |
| 323 | 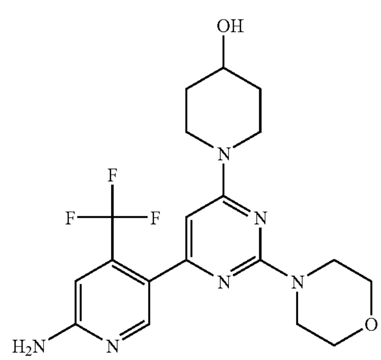 | 425.0, 1.78 | 1.83 | ++++ | N/D | ++ |
| 324 | 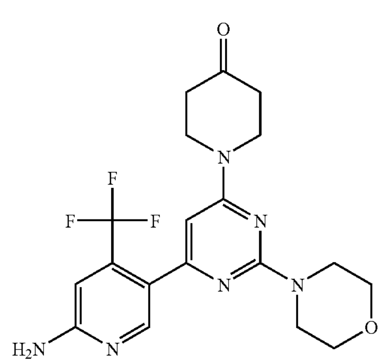 | 423.0, 1.82 | 1.79 | ++++ | N/D | +++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 325 | 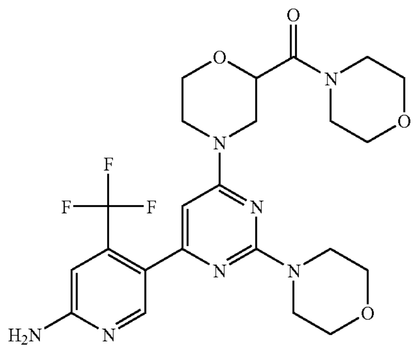 | 524.1, 1.88 | 1.96 | ++++ | N/D | ++ |
| 326 | 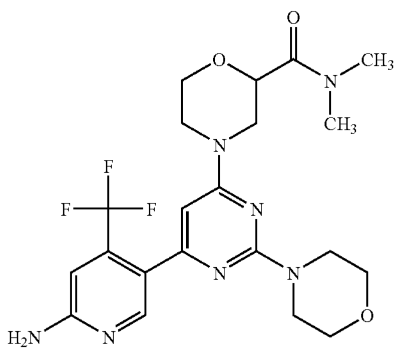 | 482.1, 1.88 | 1.93 | ++++ | N/D | ++ |
| 327 | 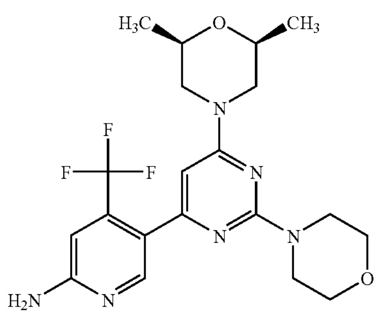 | 439.2, 2.15 | 2.38 | ++++ | N/D | +++ |
| 328 | 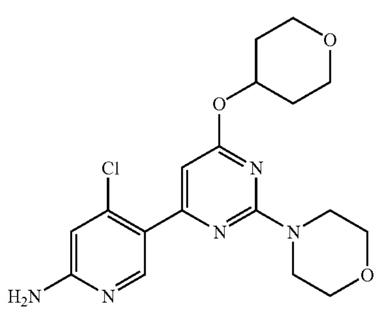 | 392.0, 2.08 | 2.26 | ++++ | N/D | ++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
| --- | --- | --- | --- | --- | --- | --- |
| 329 | 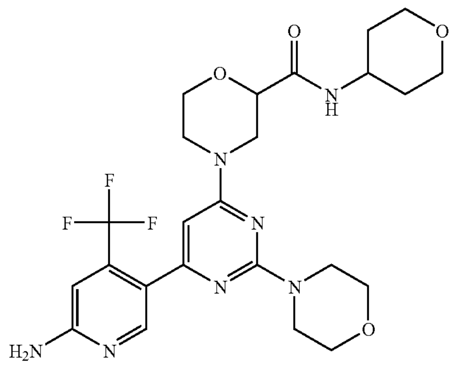 | 538.2, 1.90 | 1.98 | ++++ | N/D | ++ |
| 330 | 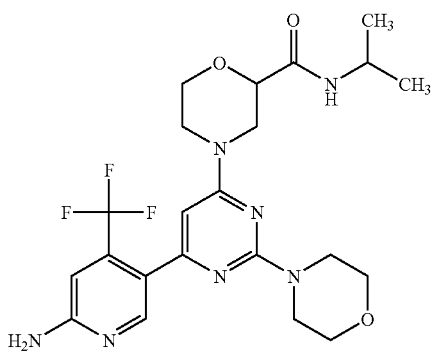 | 496.2, 2.04 | 2.2 | ++++ | N/D | ++ |
| 331 | 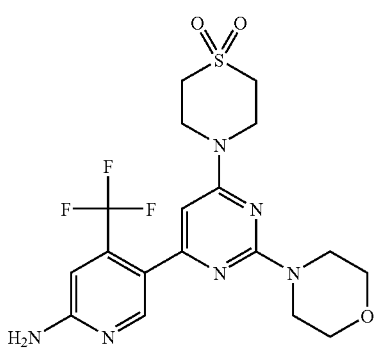 | 459.1, 1.83 | 1.89 | ++++ | N/D | ++ |
| 332 | Chiral | 413.1, 2.04 | 2.21 | ++++ | N/D | ++++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 333 | 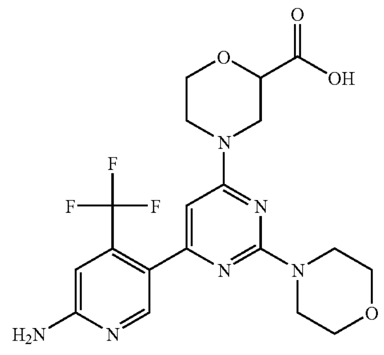 | 455.1, 1.77 | 1.79 | ++++ | N/D | ++ |
| 334 | 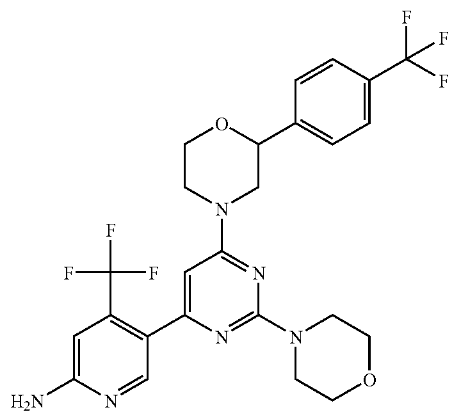 | 555.1, 2.76 | 3.36 | ++++ | N/D | +++ |
| 335 | 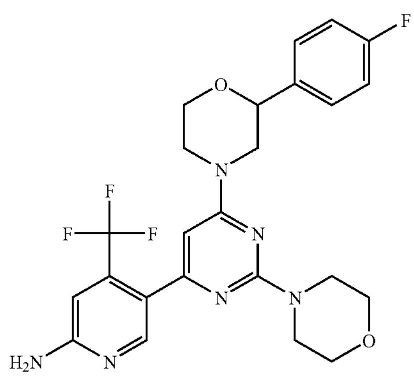 | 505.1 | 2.94 | ++++ | N/D | +++ |
| 336 | 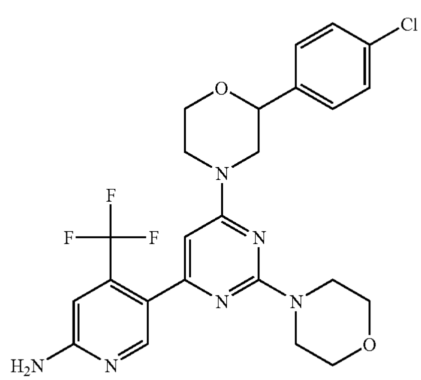 | 521.1, 2.66 | 3.18 | ++++ | N/D | +++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 337 | 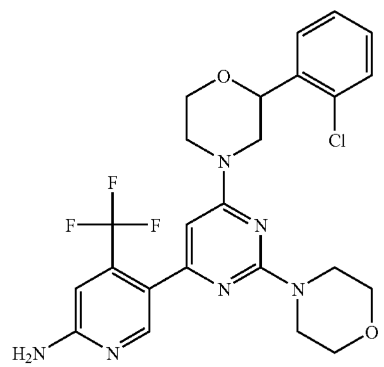 | 521.1 | 3.1 | ++++ | N/D | ++ |
| 338 | 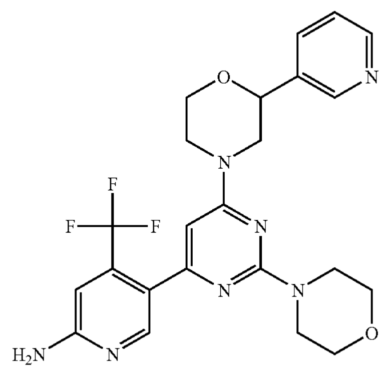 | 488.1, 1.73 | 1.67 | ++++ | N/D | +++ |
| 339 | 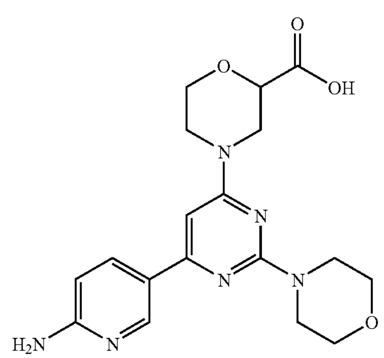 | 387.1, 1.55 | 1.44 | +++ | N/D | N/D |
| 340 | 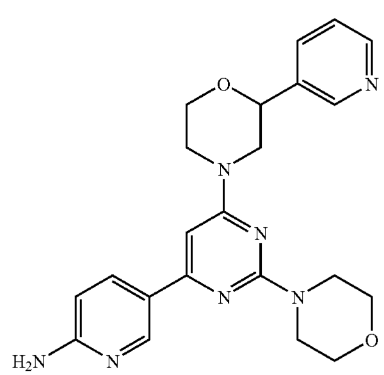 | 420.1, 1.57 | 1.44 | ++++ | N/D | N/D |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 341 | 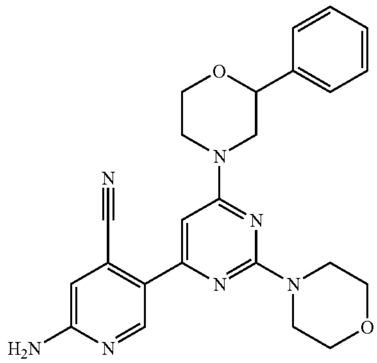 | 444.1 | 2.84 | ++++ | N/D | +++ |
| 342 | 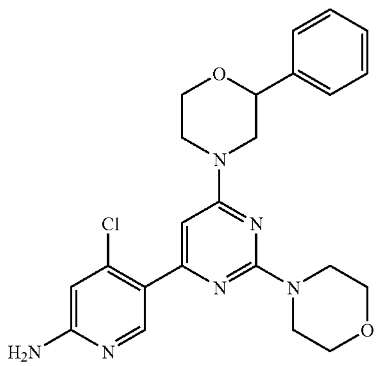 | 453.1 | 2.51 | ++++ | N/D | +++ |
| 343 | 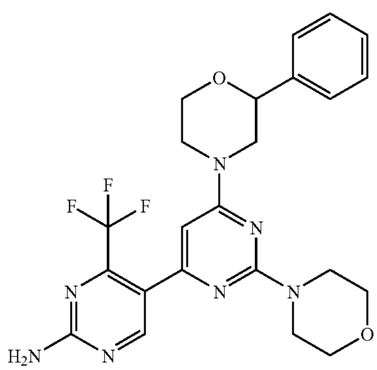 | 488.1 | 3.02 | ++++ | N/D | ++ |
| 344 | 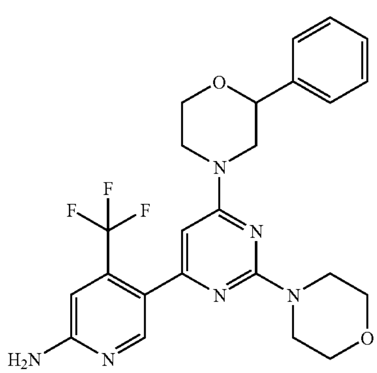 | 487.2 | 2.86 | ++++ | N/D | +++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
| --- | --- | --- | --- | --- | --- | --- |
| 345 | 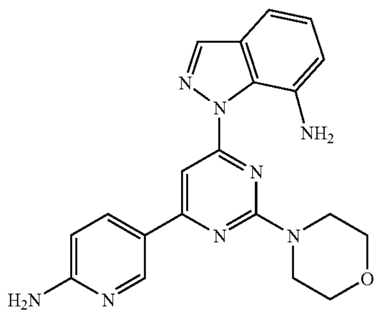 | 389.1, 2.06 | 2.28 | ++++ | N/D | +++ |
| 346 | 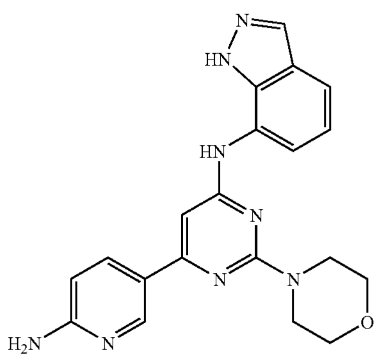 | 389.1, 1.92 | 1.94 | ++++ | N/D | N/D |
| 347 | 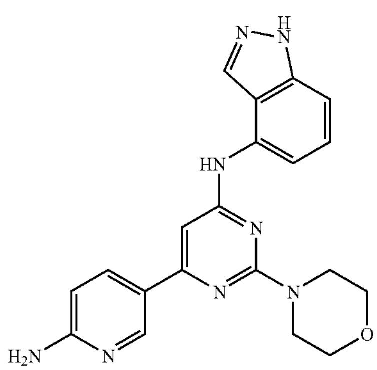 | 389.1 | 1.83 | ++++ | N/D | +++ |
| 348 | 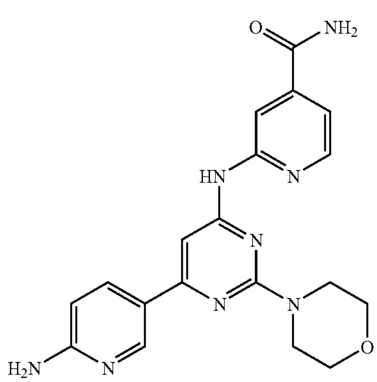 | 393.1 | 1.57 | ++++ | N/D | ++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
| --- | --- | --- | --- | --- | --- | --- |
| 349 | 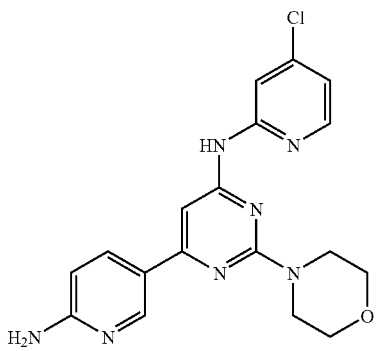 | 384.1 | 2.13 | ++++ | N/D | ++ |
| 350 | 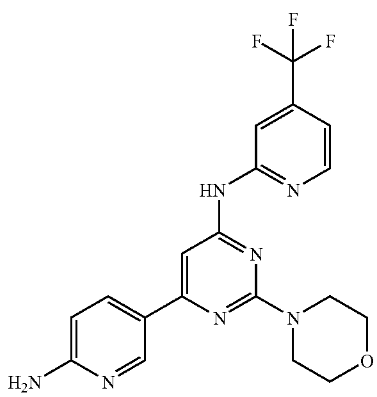 | 418.1 | 2.77 | ++++ | N/D | ++ |
| 351 | 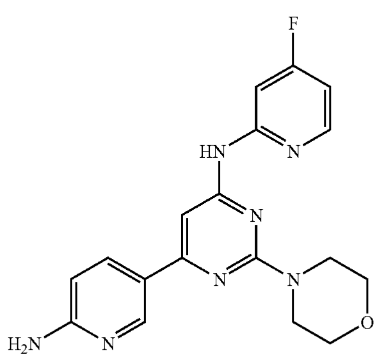 | 368.2 | 1.77 | ++++ | N/D | ++ |
| 352 | 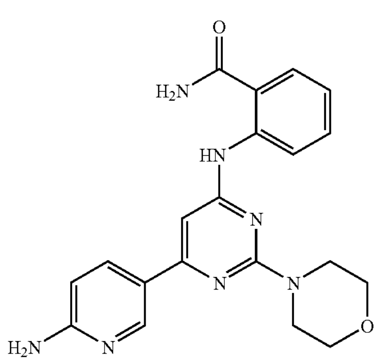 | 392.1, 1.89 | 1.94 | ++++ | N/D | +++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 353 | 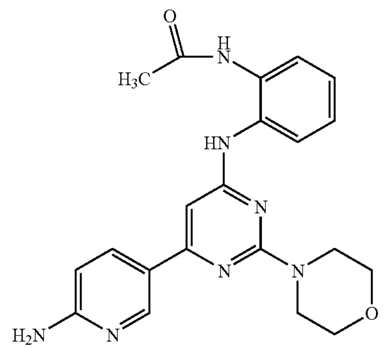 | 406.1, 1.78 | 1.77 | +++ | N/D | N/D |
| 354 | 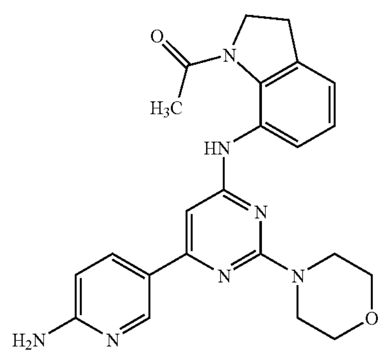 | 432.2, 2.05 | 2.25 | ++++ | N/D | N/D |
| 355 | 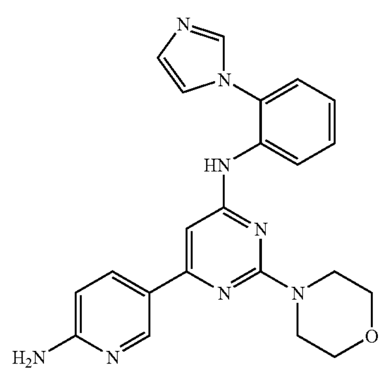 | 415.0, 1.73 | 1.61 | ++++ | N/D | N/D |
| 356 | 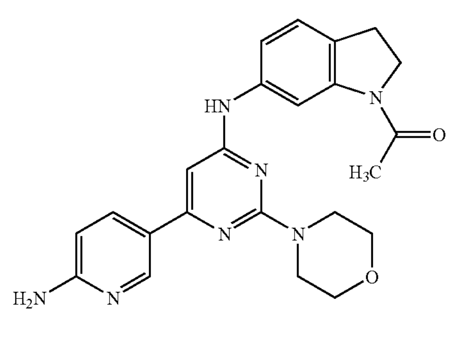 | 432.0 | 2.0 | ++++ | N/D | +++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 357 | 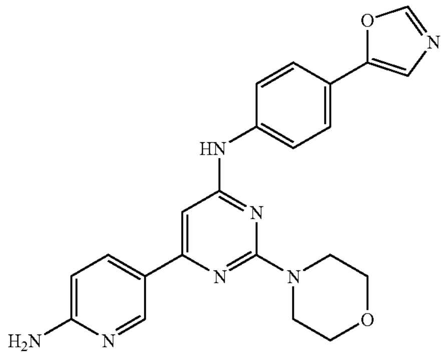 | 416.0, 2.05 | 2.21 | ++++ | N/D | ++ |
| 358 | 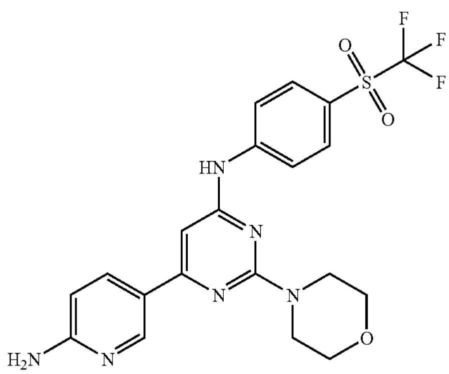 | 481.1, 2.64 | 3.27 | ++++ | N/D | +++ |
| 359 | 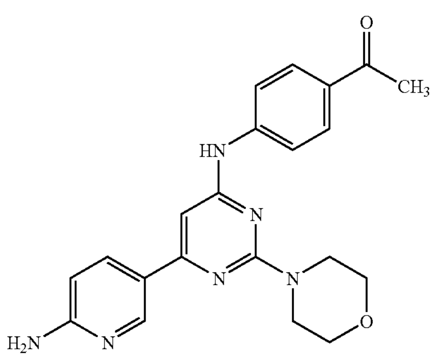 | 391.1, 2.06 | 2.28 | ++++ | N/D | ++++ |
| 360 | 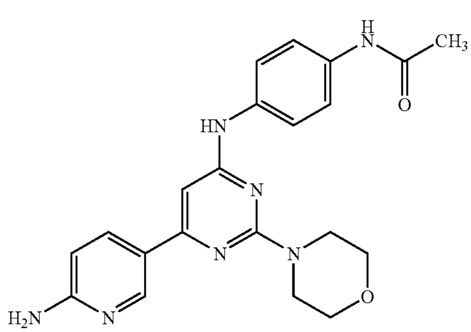 | 406.1, 1.71 | 1.71 | ++++ | N/D | +++ |

TABLE 1-continued

| Compound | Structure | LC/MS (M + H, Rt min) | hplc 10 min (L = 45 min) | PI3 Kinase Alpha, IC50 | PSer473 AKT, EC50 | Cellular Proliferation, EC50 |
|---|---|---|---|---|---|---|
| 361 | 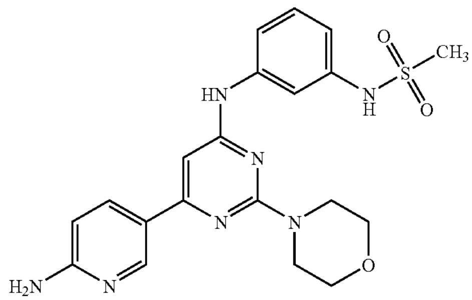 | 442.1 | 1.89 | ++++ | N/D | +++ |
| 362 | 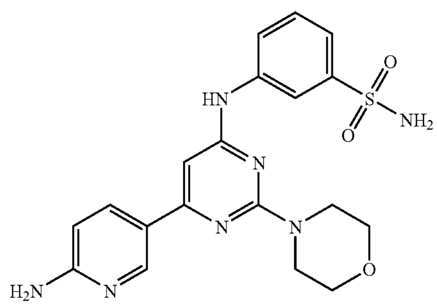 | 428.1 | 1.77 | ++++ | N/D | +++ |
| 363 | 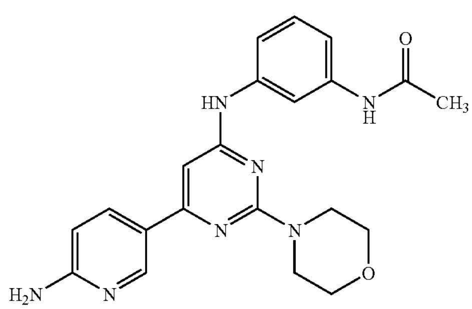 | 406.1 | 1.77 | ++++ | N/D | +++ |
| 364 | 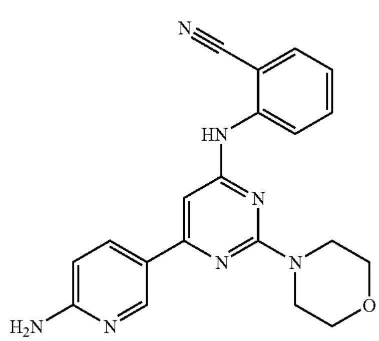 | 375.1, 1.93 | 2.04 | ++++ | N/D | ++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 365 | 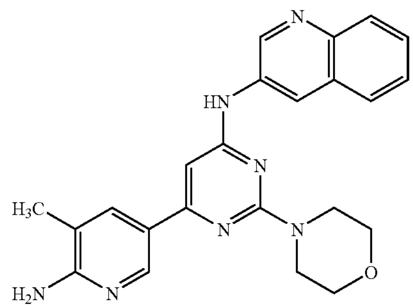 | 414.1, 1.94 | 10.78 L | +++ | N/D | N/D |
| 366 | 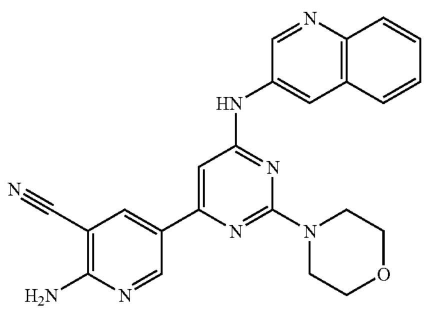 | 425.1, 2.14 | 12.06 L | +++ | N/D | N/D |
| 367 | 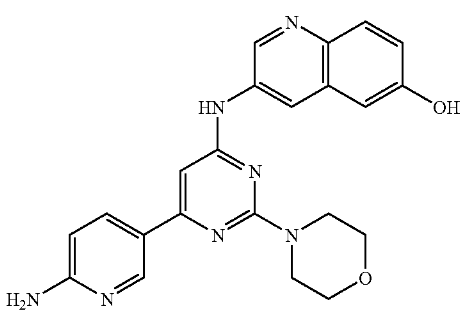 | 416.1 | 9.23 L | ++++ | N/D | +++ |
| 368 | 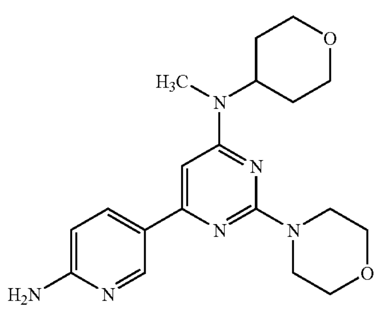 | 371.2, 1.69 | 7.86 L | ++++ | N/D | +++ |
| 369 | 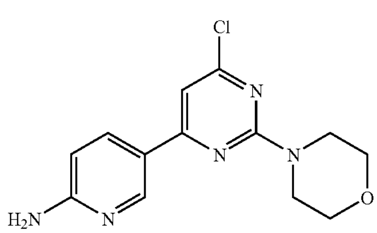 | 292.1, 2.07 | 11.31 L | ++++ | N/D | ++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 370 | 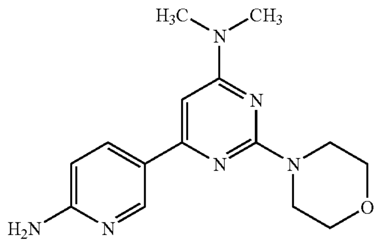 | 301.2, 1.57 | 6.77 L | +++ | N/D | N/D |
| 371 | 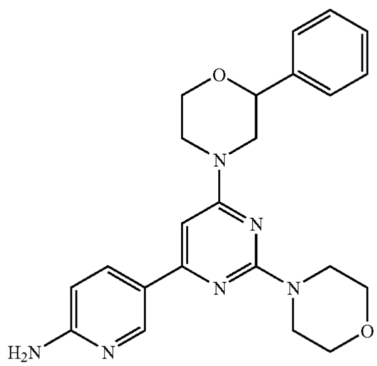 | 419.2 | 12.26 L | ++++ | N/D | +++ |
| 372 | 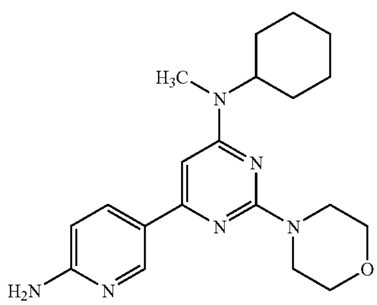 | 369.2, 2.15 | 11.91 L | +++ | N/D | N/D |
| 373 | 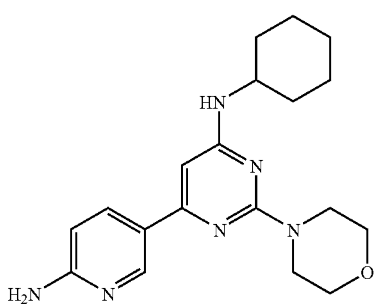 | 355.2, 2.07 | 11.27 L | +++ | N/D | N/D |
| 374 | 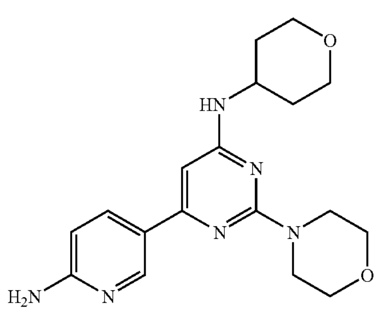 | 357.2, 1.62 | 7.19 L | +++ | N/D | N/D |

TABLE 1-continued
| Compound | Structure | LC/MS (M + H, Rt min) | hplc 10 min (L = 45 min) | PI3 Kinase Alpha, IC50 | PSer473 AKT, EC50 | Cellular Proliferation, EC50 |
|---|---|---|---|---|---|---|
| 375 | 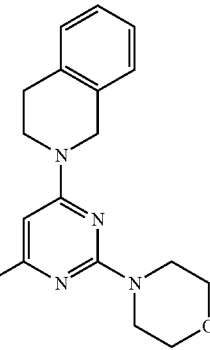 | 389.2, 2.13 | 12.07 L | ++++ | N/D | N/D |
| 376 | 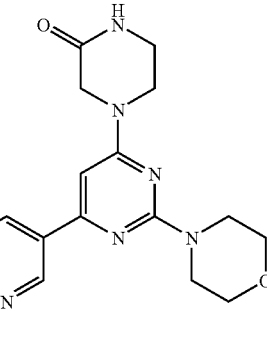 | 356.2, 1.40 | 5.75 L | +++ | N/D | N/D |
| 377 | 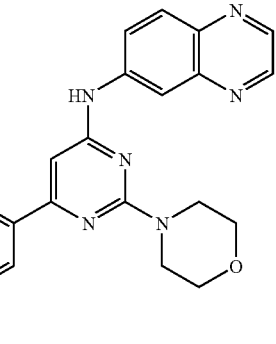 | 401.1 | 10.23 L | ++++ | N/D | +++ |
| 378 | 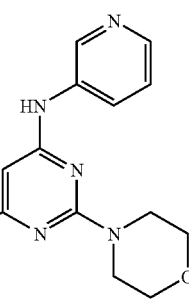 | 350.2, 1.66 | 7.63 L | ++++ | N/D | +++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 379 | 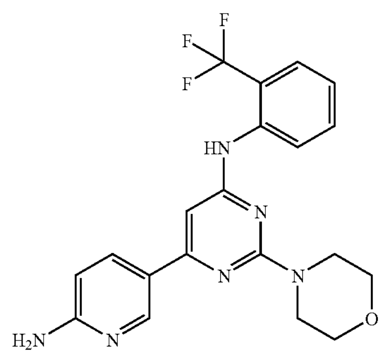 | 417.1, 2.28 | 13.32 L | ++++ | N/D | N/D |
| 380 | 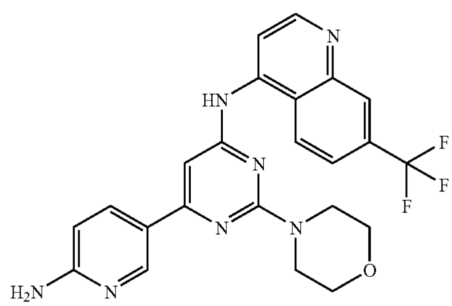 | 4.68.1, 2.16 | 11.42 L | ++++ | N/D | +++ |
| 381 | 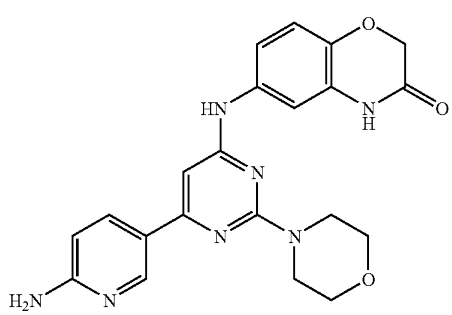 | 420.1, 1.81 | 9.41 L | ++++ | N/D | N/D |
| 382 | 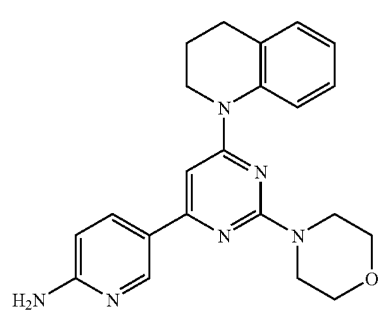 | 389.2, 2.28 | 13.47 L: | ++++ | N/D | N/D |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 383 | 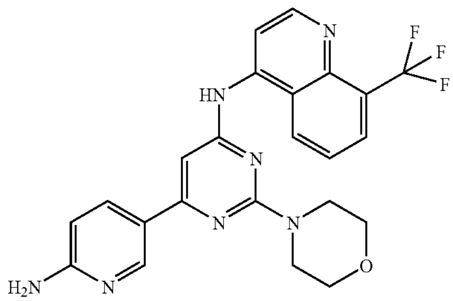 | 468.2, 2.13 | 11.64 L | ++++ | N/D | +++ |
| 384 | 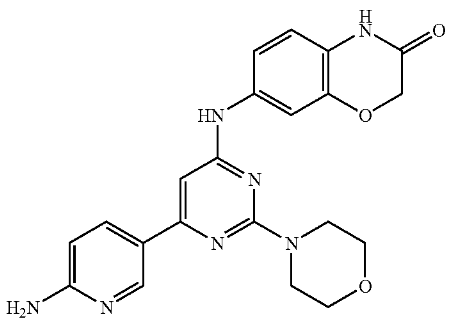 | 420.1, 1.68 | 8.71 L | ++++ | N/D | +++ |
| 385 | 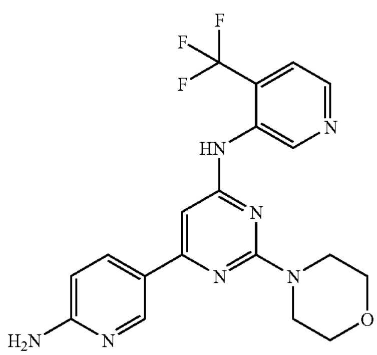 | 418.1, 1.98 | 11.04 L | ++++ | N/D | N/D |
| 386 | 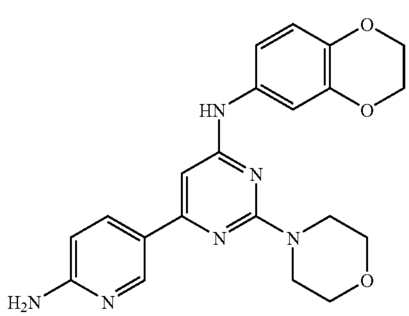 | 407.1, 1.95 | 10.57 L | ++++ | N/D | +++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 387 | 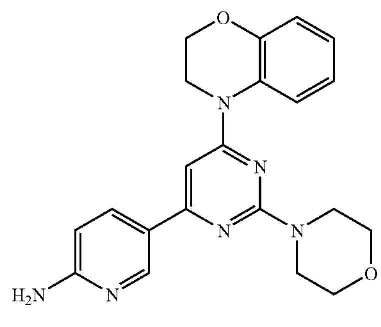 | 391.1, 2.25 | 13.62 L | ++++ | N/D | +++ |
| 388 | 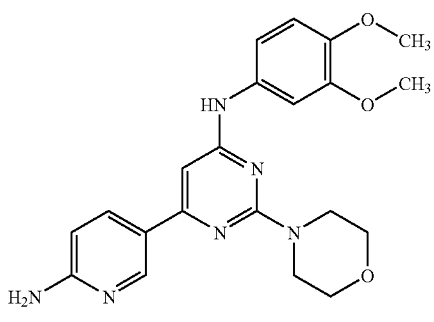 | 409.1, 1.87 | 9.91 L | ++++ | N/D | N/D |
| 389 | 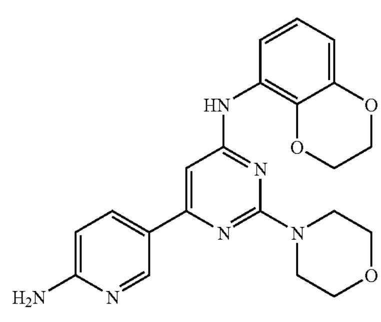 | 407.1, 2.08 | 11.36 L | ++++ | N/D | N/D |
| 390 | 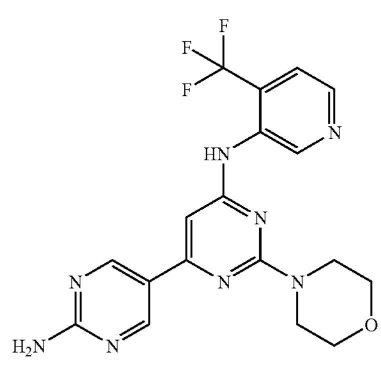 | 419.1 | 10.41 L | ++++ | N/D | +++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 391 | 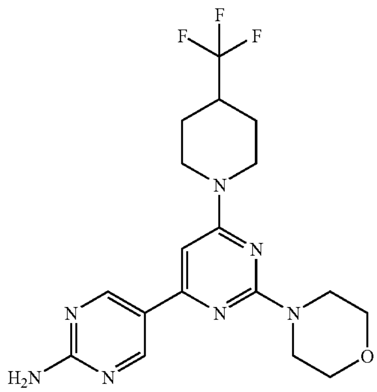 | 410.1, 2.20 | 12.63 L | ++++ | N/D | N/D |
| 392 | 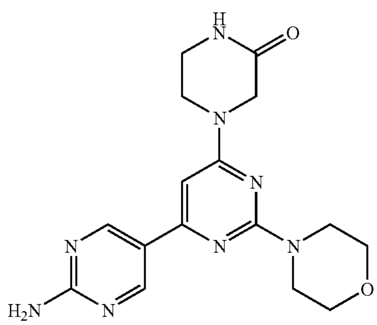 | 357.1 | 5.96 L | ++++ | N/D | +++ |
| 393 | 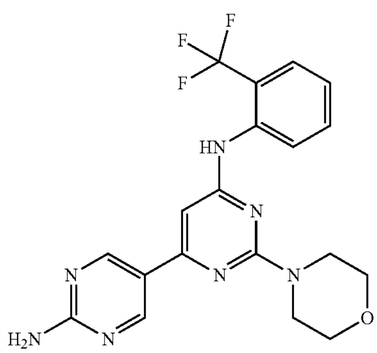 | 418.1 | 13.00 L | ++++ | N/D | +++ |
| 394 | 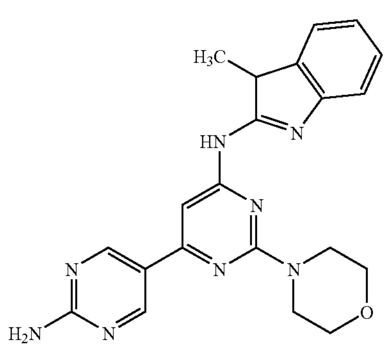 | 404.2 | 10.64 L | ++++ | N/D | +++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 395 | Chiral | 462.2, 2.38 | 14.83 L | ++++ | N/D | N/D |
| 396 | Chiral | 448.2 | 14.53 L | ++++ | N/D | +++ |
| 397 | Chiral | 462.2, 2.40 | 14.82 L | ++++ | N/D | N/D |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 398 | Chiral | 448.2, 2.38 | 14.52 L | ++++ | N/D | N/D |
| 399 | 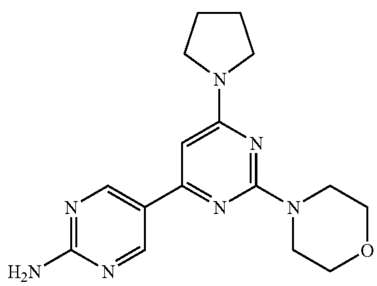 | 328.2 | 9.63 L | ++++ | N/D | +++ |
| 400 | 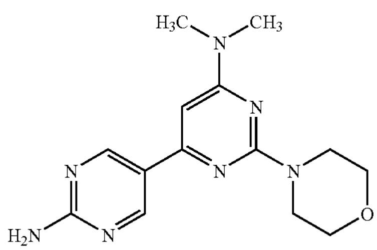 | 302.2 | 7.77 L | ++++ | N/D | +++ |
| 401 | 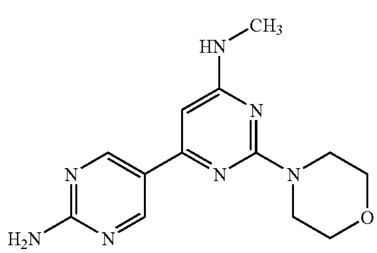 | 288.2 | 6.92 L | ++++ | N/D | ++ |
| 402 | 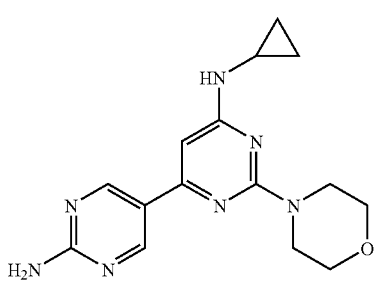 | 314.2 | 8.39 L | ++++ | N/D | +++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 403 | 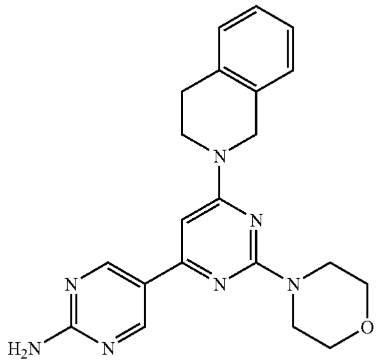 | 390.1 | 13.44 L | ++++ | N/D | +++ |
| 404 | 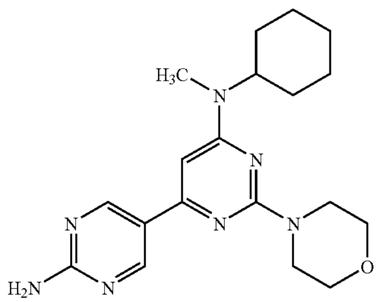 | 370.2 | 13.71 L | ++++ | N/D | +++ |
| 405 | 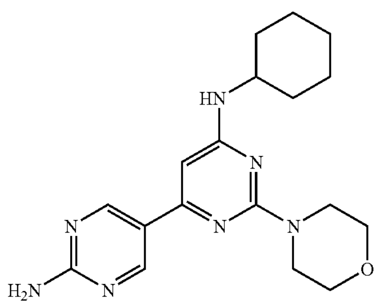 | 356.2 | 12.73 L | ++++ | N/D | +++ |
| 406 | 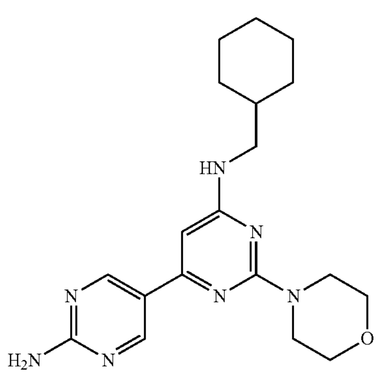 | 370.2 | 14.24 L | ++++ | N/D | ++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 407 | 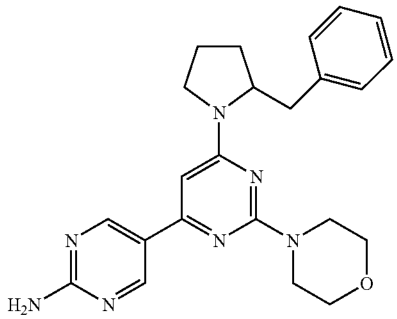 | 418.2 | 14.81 L | ++++ | N/D | +++ |
| 408 | 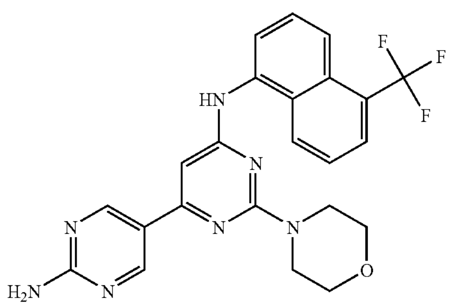 | 469.1 | 12.14 L | ++++ | N/D | +++ |
| 409 | 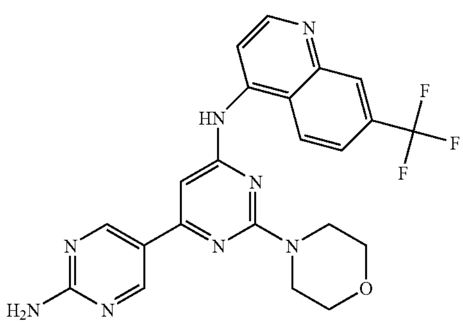 | 469.1 | 12.17 L | ++++ | N/D | ++++ |
| 410 | 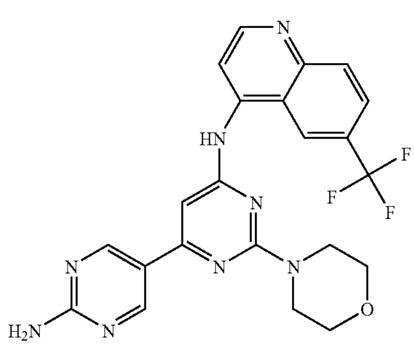 | 469.1 | 12.17 L | ++++ | N/D | +++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 411 | 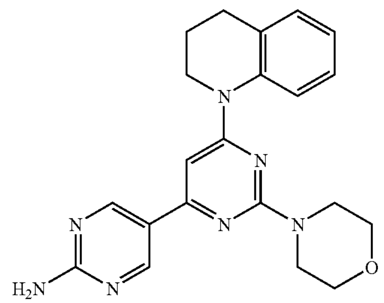 | 390.1 | 13.47 L | ++++ | N/D | +++ |
| 412 | 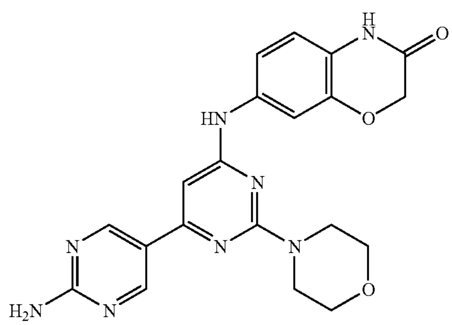 | 421.1 | 8.70 L | ++++ | N/D | ++++ |
| 413 | 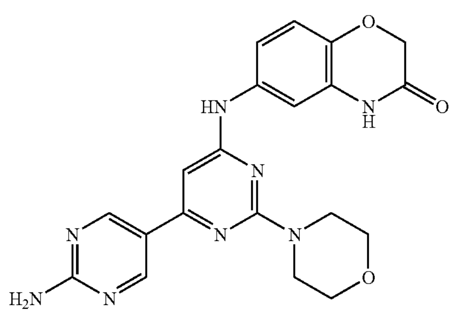 | 421.1 | 9.60 L | ++++ | N/D | +++ |
| 414 | 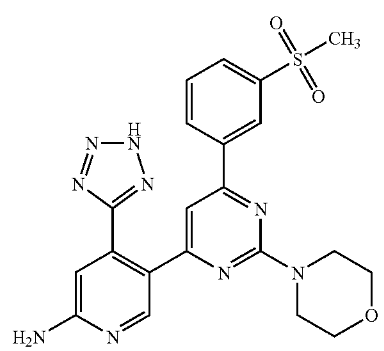 | 480.0, 1.98 | 2.19 | ++++ | N/D | N/D |
| 415 | 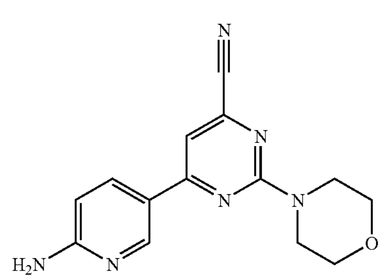 | 283.2, 1.95 | | ++++ | N/D | ++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 416 | 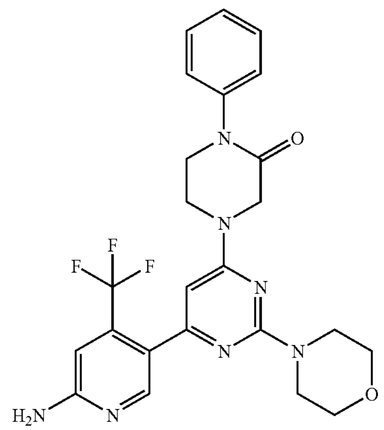 | 500.0, 1.83 | 2.36 | ++++ | N/D | N/D |
| 417 | 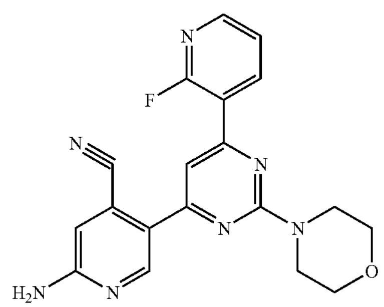 | 378.0, 3.02 | 2.79 | ++++ | N/D | ++ |
| 418 | 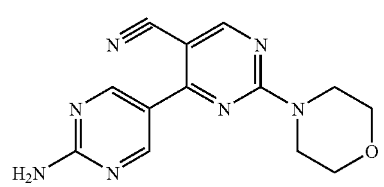 | 284.2, 1.94 | 2.2 | ++++ | N/D | ++ |
| 419 | 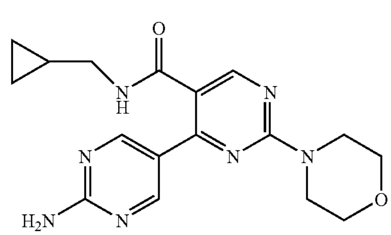 | 356.2, 1.77 | 1.86 | +++ | N/D | N/D |
| 420 | 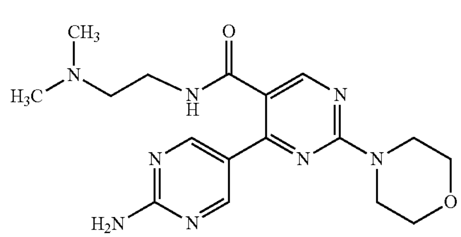 | 373.2, 1.37 | 1.23 | +++ | N/D | N/D |

TABLE 1-continued
| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 421 | 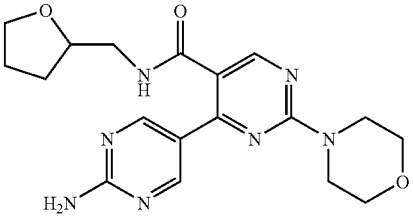 | 386.2, 1.57 | 1.73 | +++ | N/D | N/D |
| 422 | 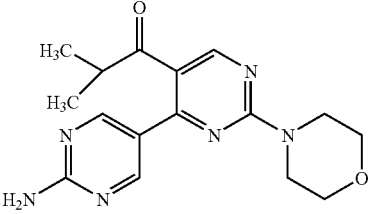 | 330.2, 1.47 | 1.58 | +++ | N/D | N/D |
| 423 | 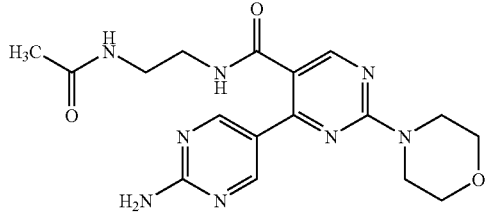 | 387.2, 1.47 | 1.32 | +++ | N/D | N/D |
| 424 | 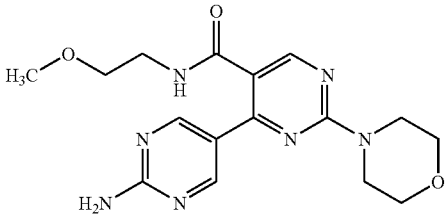 | 360.2, 1.57 | 1.47 | +++ | N/D | N/D |
| 425 | 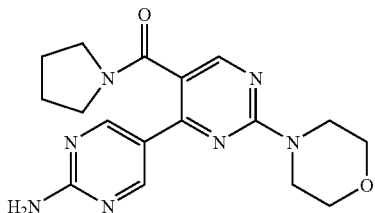 | 356.2, 1.79 | 1.83 | +++ | N/D | N/D |
| 426 | 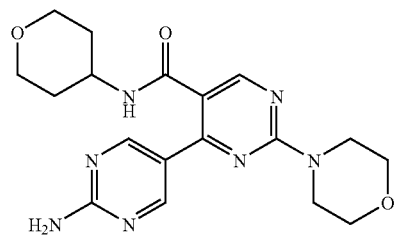 | 386.2, 1.61 | 1.56 | +++ | N/D | N/D |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 427 | 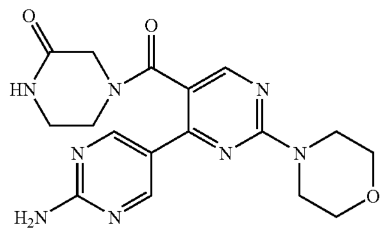 | 385.2, 1.48 | 1.4 | +++ | N/D | ++ |
| 428 | 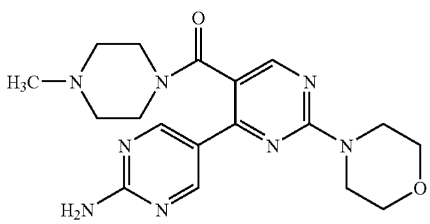 | 385.2, 0.5 | 1.34 | +++ | N/D | ++ |
| 429 | 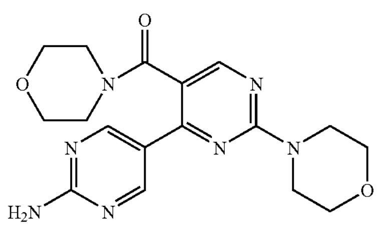 | 372.3, 1.39 | 1.69 | +++ | N/D | N/D |
| 430 | 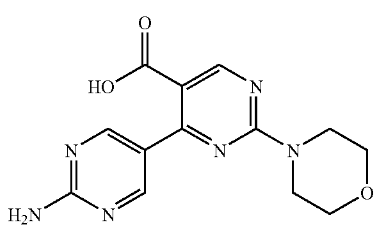 | 303.1, 1.66 | 1.66 | +++ | N/D | N/D |
| 431 | 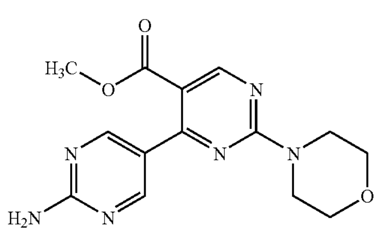 | 317.2, 1.59 | 2.02 | ++++ | N/D | ++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 432 | 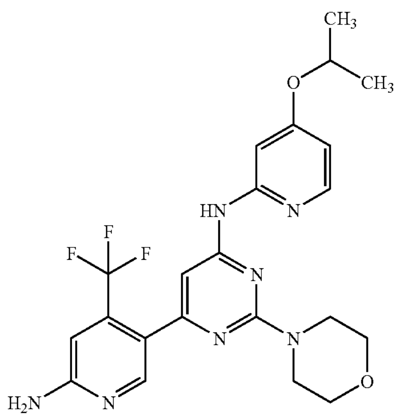 | 476.1, 2.16 | 2.46 | ++++ | N/D | +++ |
| 433 | 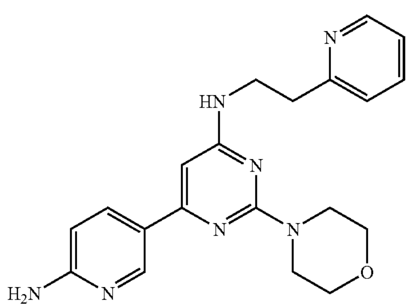 | 378.1, 1.31 | 1.13 | +++ | N/D | N/D |
| 434 | 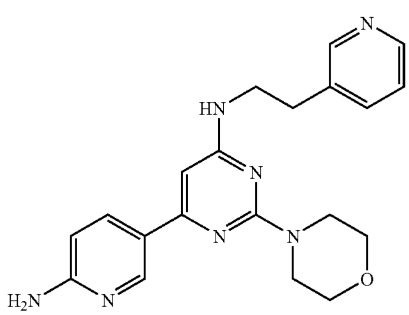 | 378.2, 1.46 | 1.14 | +++ | N/D | N/D |
| 435 | 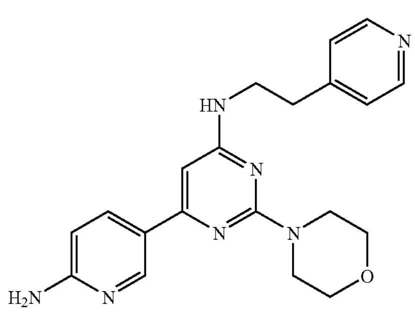 | 378.2, 1.44 | 1.13 | +++ | N/D | N/D |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 436 | 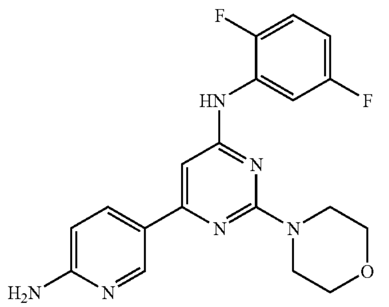 | 385.1, 2.25 | 2.58 | ++++ | N/D | +++ |
| 437 | 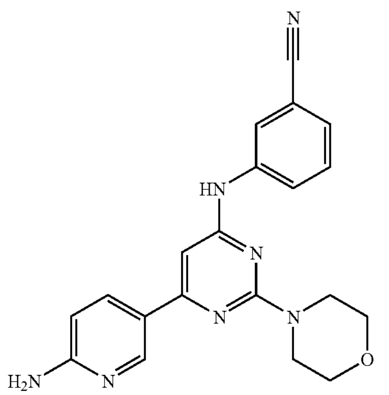 | 374.0, 2.14 | 2.42 | ++++ | N/D | +++ |
| 438 | 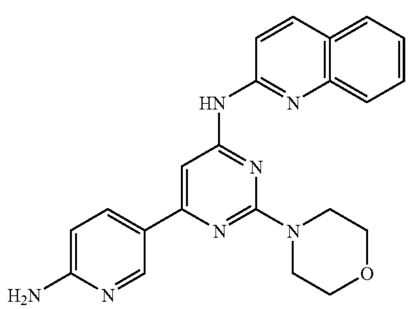 | 400.0, 1.90 | 2.04 | ++++ | N/D | +++ |
| 439 | 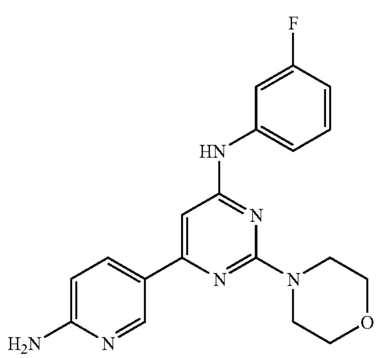 | 367.1, 2.20 | 2.47 | ++++ | N/D | +++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 440 | 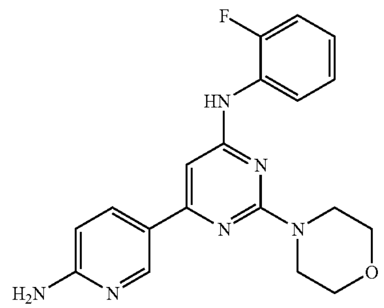 | 367.1, 2.07 | 2.29 | ++++ | N/D | +++ |
| 441 | 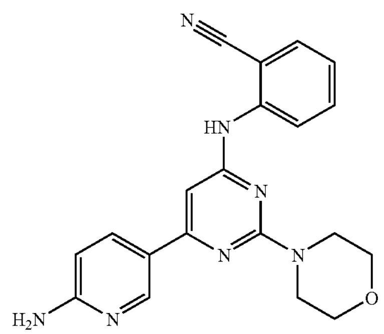 | 374.1, 2.07 | 2.26 | ++++ | N/D | +++ |
| 442 | 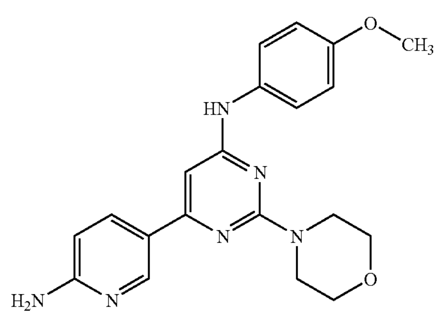 | 379.1, 1.94 | 2.19 | ++++ | N/D | +++ |
| 443 | 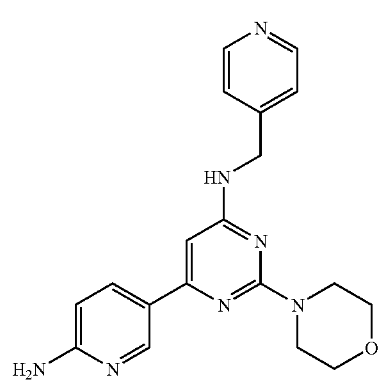 | 364.1, 1.41 | 1.10 | ++++ | N/D | N/D |

TABLE 1-continued
| Compound | Structure | LC/MS (M + H, Rt min) | hplc 10 min (L = 45 min) | PI3 Kinase Alpha, IC50 | PSer473 AKT, EC50 | Cellular Proliferation, EC50 |
|---|---|---|---|---|---|---|
| 444 | 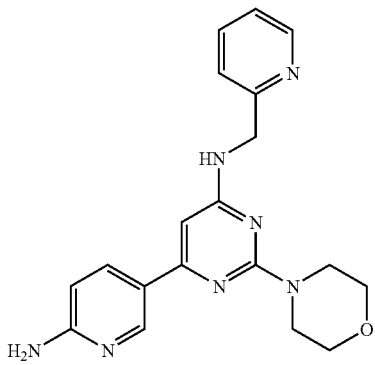 | 364.1, 1.33 | 1.16 | ++++ | N/D | N/D |
| 445 | 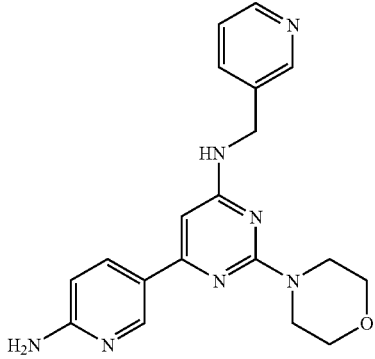 | 364.1, 1.37 | 1.10 | ++++ | N/D | N/D |
| 446 | 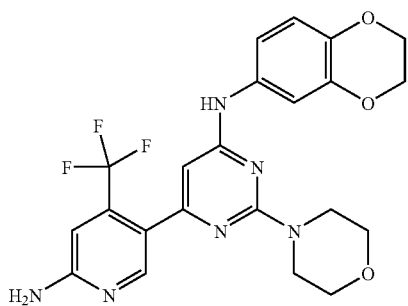 | 475.4, 1.99 | 2.52 | ++++ | N/D | ++ |
| 447 | 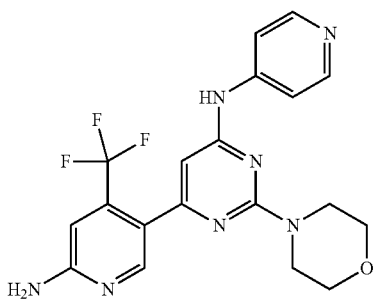 | 418.3, 1.54 | 1.93 | ++++ | N/D | ++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 448 | 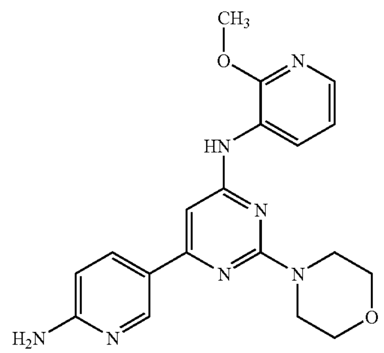 | 380.1, 1.98 | 2.06 | ++++ | N/D | +++ |
| 449 | 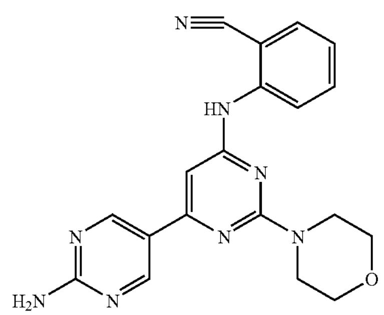 | 375.0, 2.00 | 2.21 | ++++ | N/D | +++ |
| 450 | 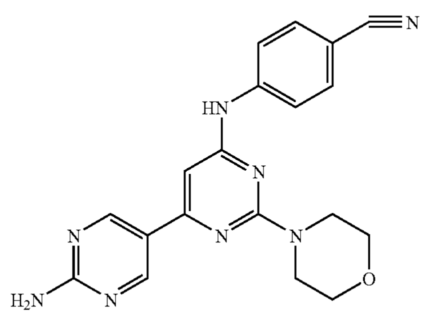 | 380.1, 2.01 | 2.19 | ++++ | N/D | ++ |
| 451 | 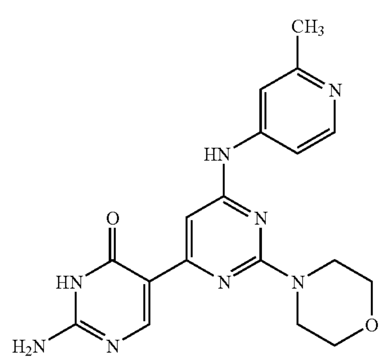 | 381.0, 1.30 | 1.48, (7.22) | ++++ | N/D | +++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 452 | Chiral | 483.0, 2.83 | | ++++ | N/D | +++ |
| 453 | Chiral | 467.0, 2.87 | | ++++ | N/D | +++ |
| 454 | Chiral | 483.0, 2.83 | | ++++ | N/D | +++ |
| 455 | Chiral | 467.0, 2.87 | | ++++ | N/D | +++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 456 | 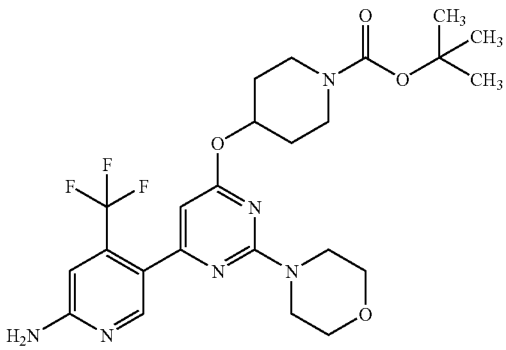 | 525.1, 2.90 | | ++++ | N/D | +++ |
| 457 | 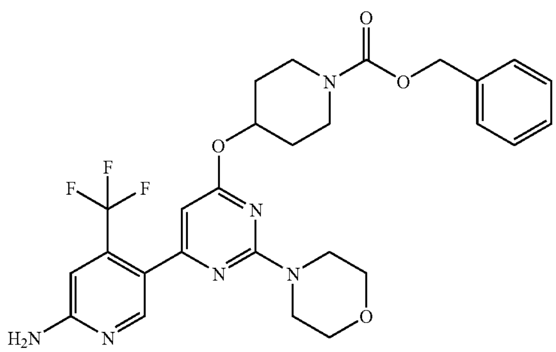 | 599.2, 3.60 | | ++++ | N/D | +++ |
| 458 | 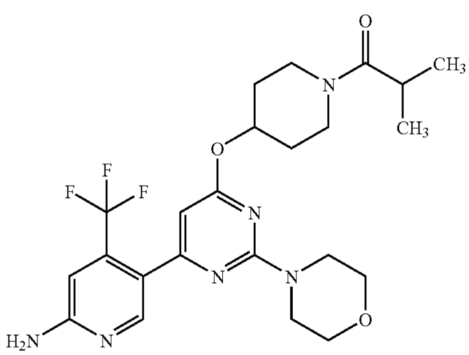 | 495.1, 2.77 | | ++++ | N/D | +++ |
| 459 | 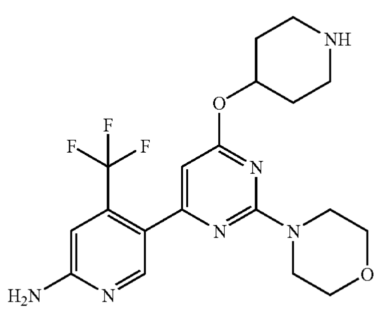 | 425.1, 1.80 | | ++++ | N/D | N/D |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 460 | 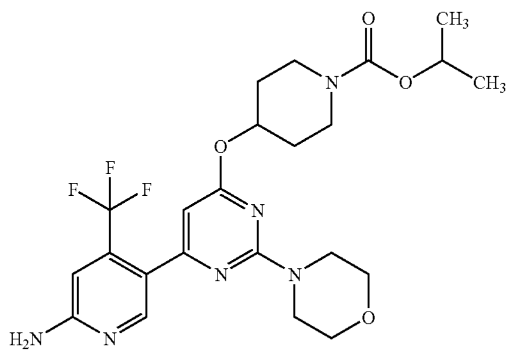 | 511.1, 3.28 | | ++++ | N/D | +++ |
| 461 | 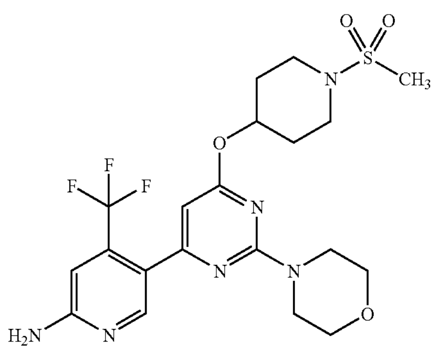 | 503.1, 2.66 | | ++++ | N/D | +++ |
| 462 | 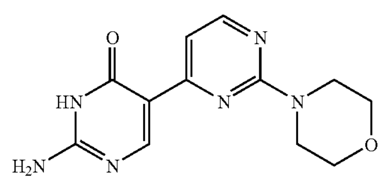 | 275.0, 1.16 | 1.23, (5.79) | ++++ | N/D | +++ |
| 463 | 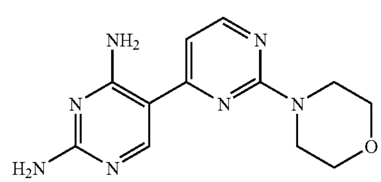 | 274.0, 1.36 | | ++++ | N/D | ++ |
| 464 | 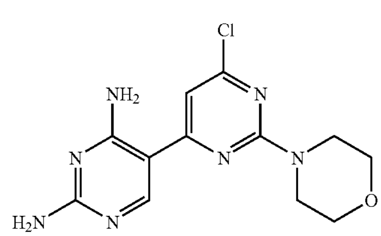 | 307.9, 2.09 | | ++++ | N/D | ++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 465 | 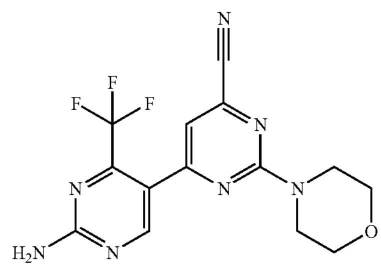 | 352.0, 2.46 | 357, (17.04) | ++++ | N/D | +++ |
| 466 | 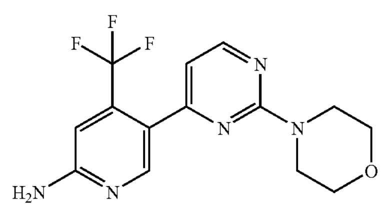 | 326.2, 1.66 | 2.04, (10.20) | ++++ | N/D | ++ |
| 467 | 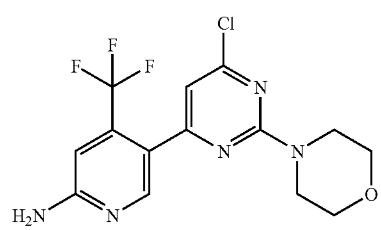 | 360.2, 2.18 | 2.92, (14.71) | ++++ | N/D | ++ |
| 468 | 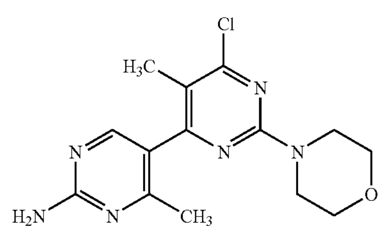 | 321.2, 1.84 | 2.35, 11.87 | ++++ | N/D | ++ |
| 469 | 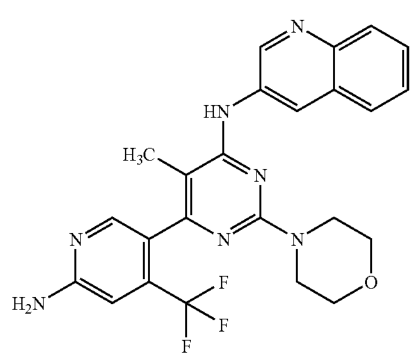 | 482.4, 1.70 | 2.08, (10.76) | ++++ | N/D | N/D |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 470 | 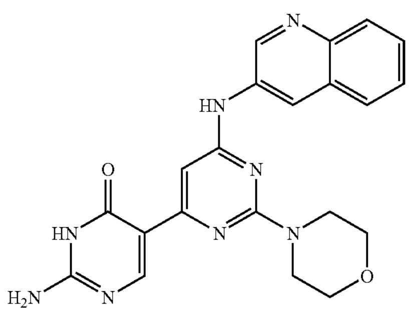 | 417.3, 1.58 | 1.83, (9.39) | ++++ | N/D | +++ |
| 471 | 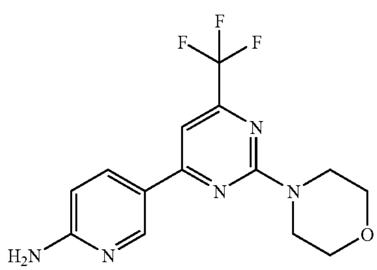 | 326.3, 1.98 | 2.53, (13.21) | ++++ | N/D | N/D |
| 472 | 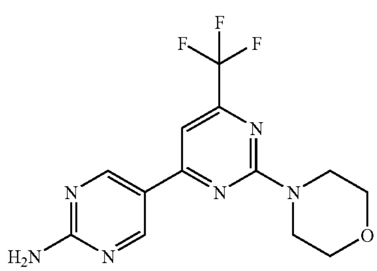 | 327.2, 2.21 | 3.13, (15.01) | ++++ | N/D | +++ |
| 473 | 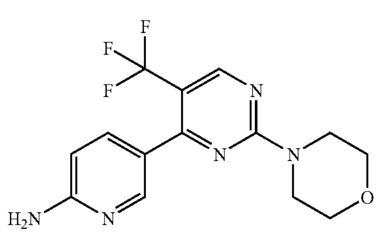 | 326.3, 1.76 | 2.24, (11.11) | +++ | N/D | N/D |
| 474 | 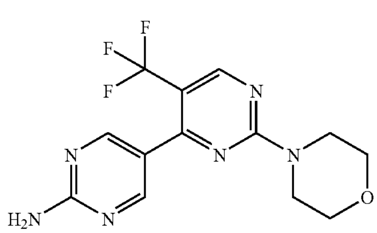 | 327.3, 1.97 | 269, (12.81) | ++++ | N/D | ++ |

TABLE 1-continued
| Compound | Structure | LC/MS (M + H, Rt min) | hplc 10 min (L = 45 min) | PI3 Kinase Alpha, IC50 | PSer473 AKT, EC50 | Cellular Proliferation, EC50 |
|---|---|---|---|---|---|---|
| 475 | 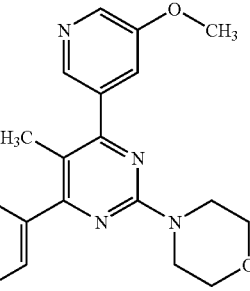 | 380.3, 1.49 | 1.76, (8.70) | ++++ | N/D | +++ |
| 476 | 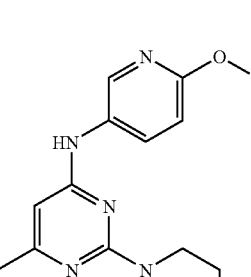 | 395.3, 1.89 | | ++++ | N/D | +++ |
| 477 | 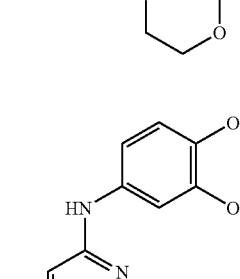 | 422.3, 2.15 | | ++++ | N/D | +++ |
| 478 | 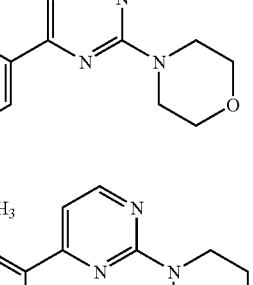 | 273.2, 1.55 | 1.44, (6.80) | ++++ | N/D | ++ |
| 479 | 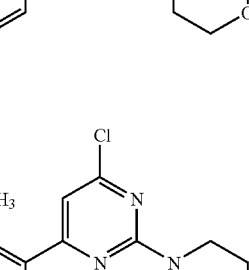 | 307.1, 2.05 | 2.33, (11.43) | ++++ | N/D | N/D |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 480 | 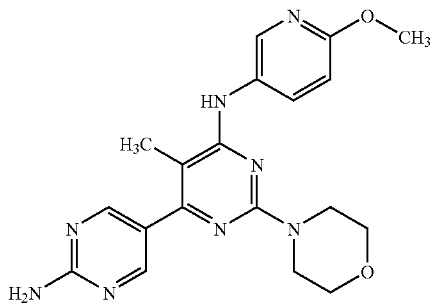 | 395.3, 1.79 | | ++++ | N/D | +++ |
| 481 | 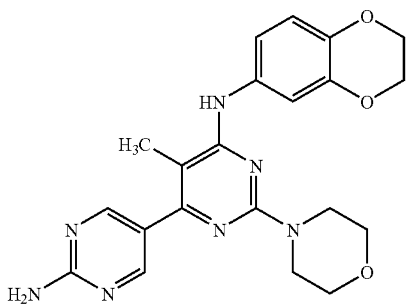 | 422.3, 2.10 | | ++++ | N/D | ++++ |
| 482 | 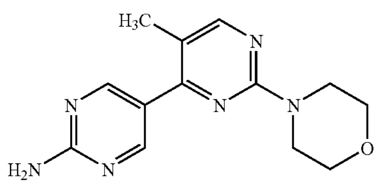 | 2.73.2, 1.29 | 1.43, (6.78) | ++++ | N/D | +++ |
| 483 | 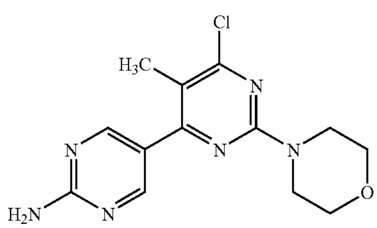 | 307.2, 1.96 | 2.58, (12.75) | ++++ | N/D | ++ |
| 484 | 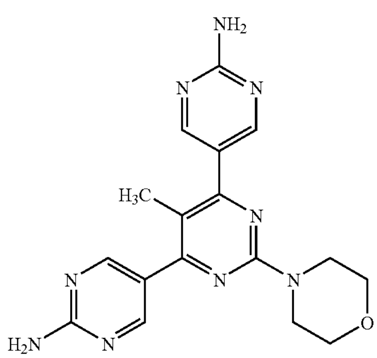 | 366.3, 1.39 | 1.63, (7.75) | ++++ | N/D | +++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 485 | 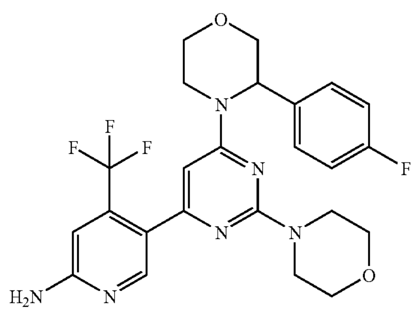 | 505.1, 2.35 | 14.35 L | ++++ | N/D | N/D |
| 486 | 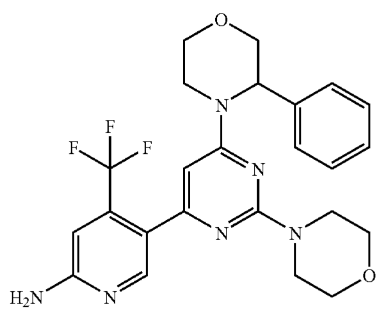 | 487.2, 2.31 | 13.84 L | ++++ | N/D | N/D |
| 487 | 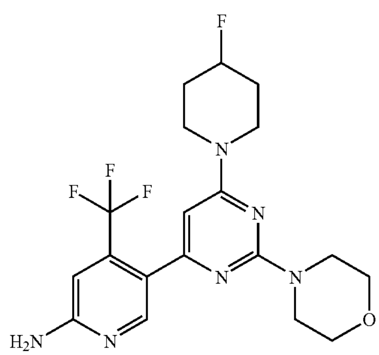 | 427.1, 2.12 | 11.84 L | ++++ | N/D | N/D |
| 488 | 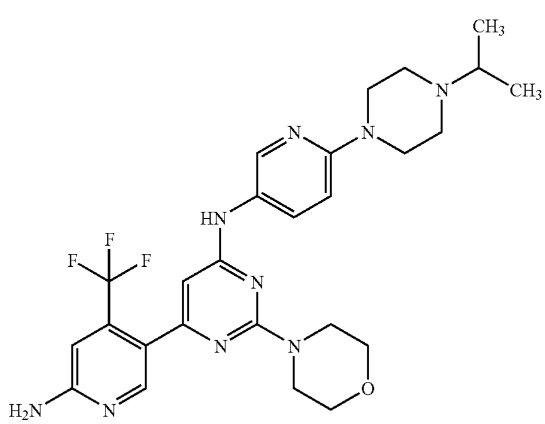 | 544.2, 1.76 | 1.67 | ++++ | N/D | +++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 489 | 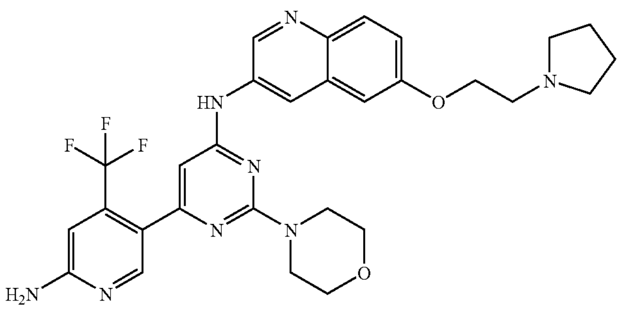 | 581.2, 1.82 | 1.90 | ++++ | N/D | +++ |
| 490 | 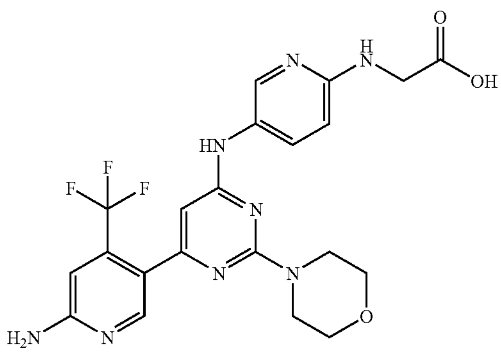 | 491.1, 1.70 | 1.59 | ++++ | N/D | N/D |
| 491 | 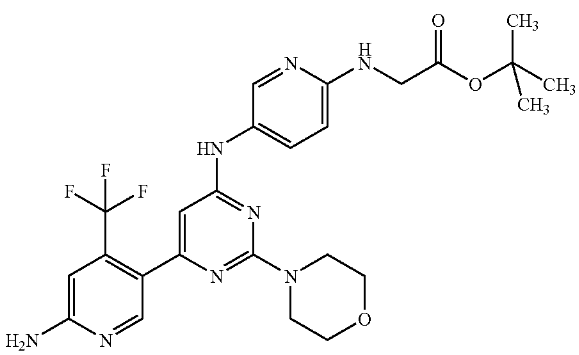 | 547.1, 2.09 | 11.59 L | ++++ | N/D | ++ |
| 492 | 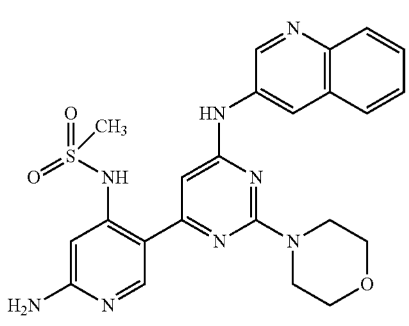 | 492.9, 1.78 | 2.24 | ++++ | N/D | N/D |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 493 | 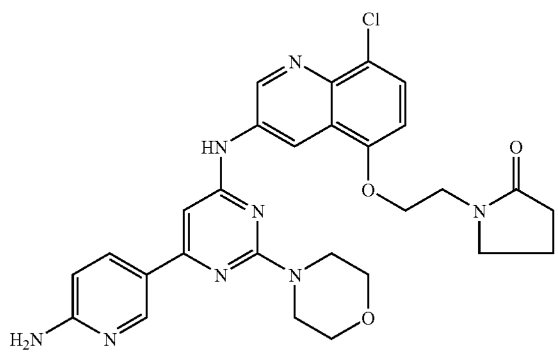 | 561.1, 2.20 | 2.46 | ++++ | N/D | N/D |
| 494 | 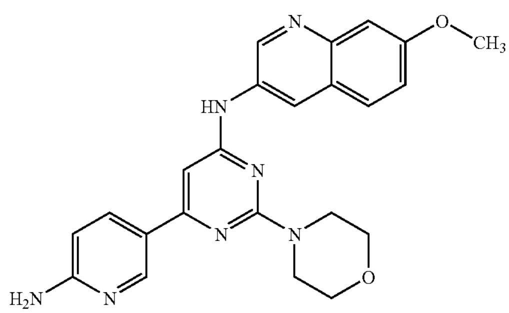 | 430.2, 1.97 | 10.65 L | ++++ | N/D | ++ |
| 495 | 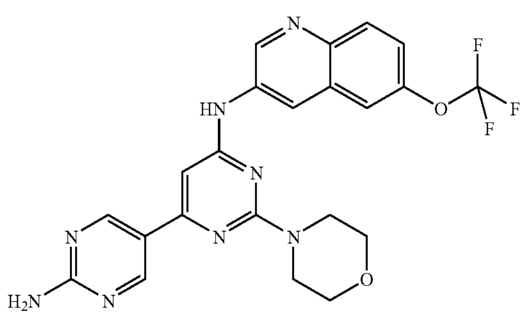 | 485.0, 2.47 | 15.16 L | ++++ | N/D | ++ |
| 496 | 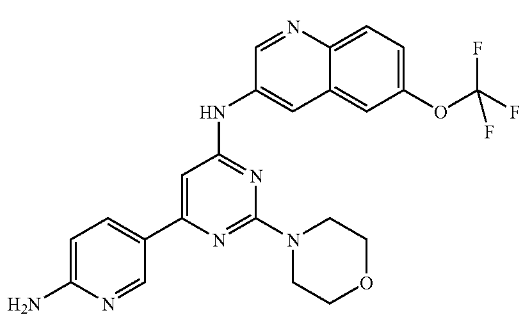 | 484.1, 2.47 | 15.14 L | ++++ | N/D | N/D |

TABLE 1-continued
| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 497 | 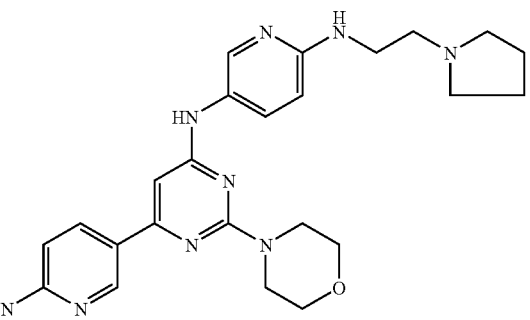 | 462.4, 1.29 | 7.09 L | ++++ | N/D | +++ |
| 498 | 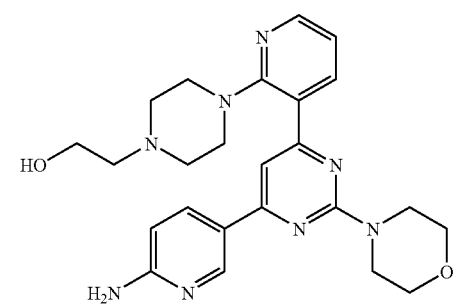 | 463.2, 1.77 | 8.92 L | +++ | N/D | N/D |
| 499 | 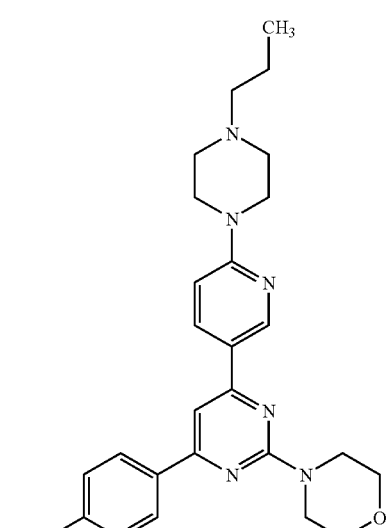 | 463.2, 1.72 | 8.24 L | ++++ | N/D | +++ |
| 500 | 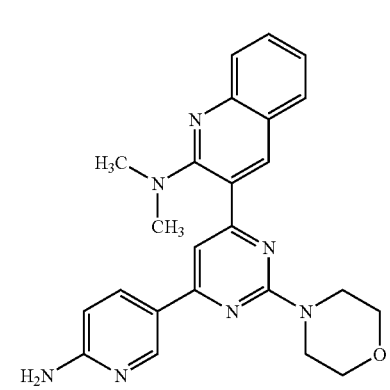 | 428.4, 1.63 | 10.17 L | ++++ | N/D | +++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 501 | 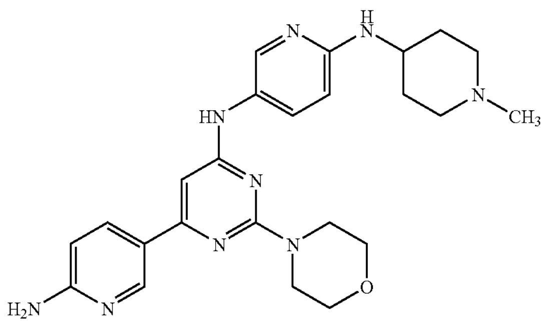 | 462.4, 1.28 | 1.51 | ++++ | N/D | +++ |
| 502 | 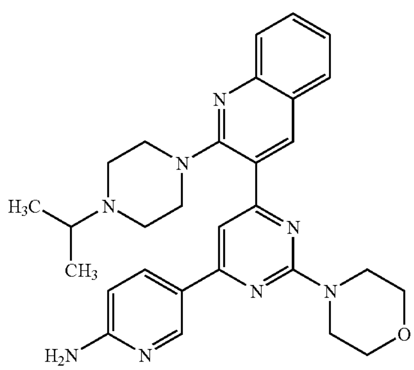 | 511.3, 2.08 | 11.82 L | +++ | N/D | N/D |
| 503 | 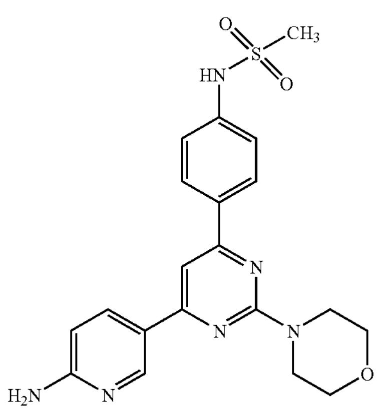 | 428.2, 1.93 | 10.1 L | ++++ | N/D | +++ |
| 504 | 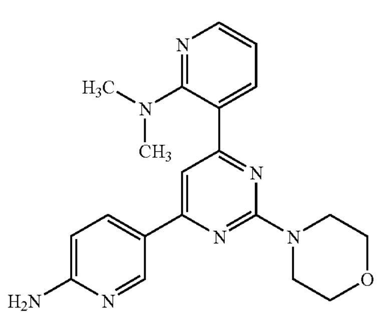 | 378.2, 1.66 | 7.72 L | +++ | N/D | N/D |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
| --- | --- | --- | --- | --- | --- | --- |
| 505 | 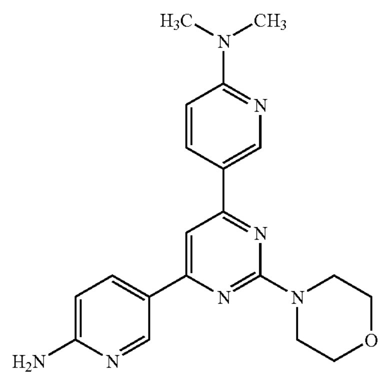 | 378.2, 1.76 | 8.73 L | ++++ | N/D | +++ |
| 506 | 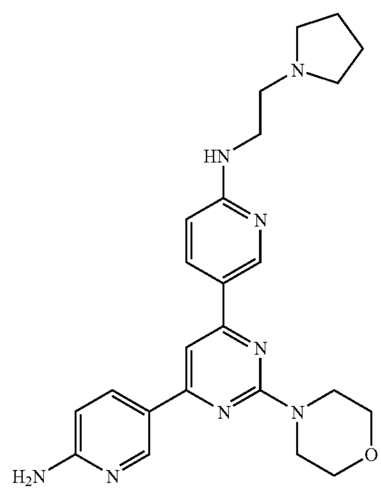 | 447.3, 1.78 | 8.02 | ++++ | N/D | N/D |
| 507 | 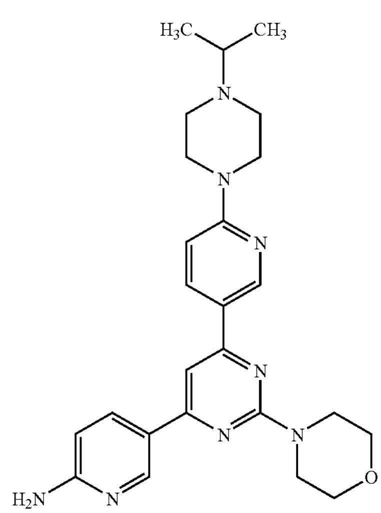 | 461.2, 1.8 | 8.93 | ++++ | N/D | N/D |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 508 | 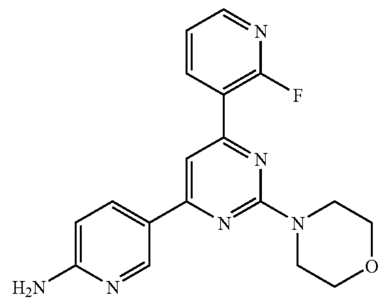 | 353.1, 2.16 | 2.34 | ++++ | N/D | +++ |
| 509 | 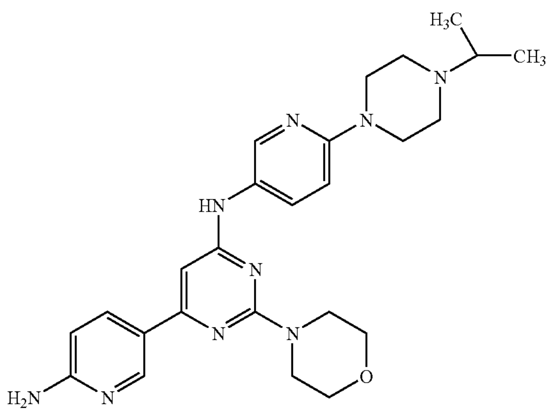 | 476.3, 1.65 | 7.27 L | ++++ | N/D | +++ |
| 510 | 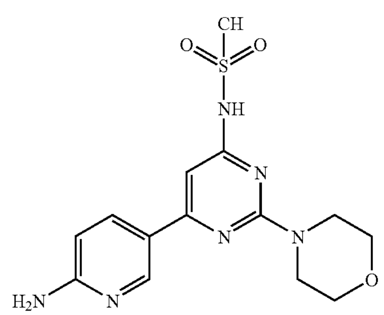 | 351.1, 1.74 | 1.70 | +++ | N/D | N/D |
| 511 | 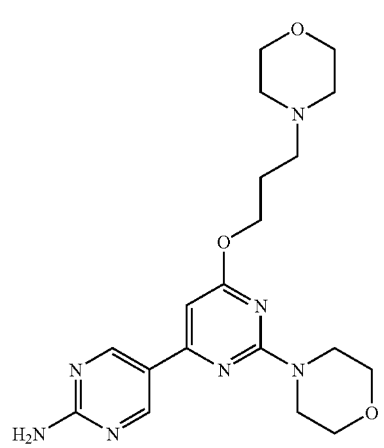 | 402.2, 1.65 | 7.51 L | ++++ | N/D | +++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 512 | 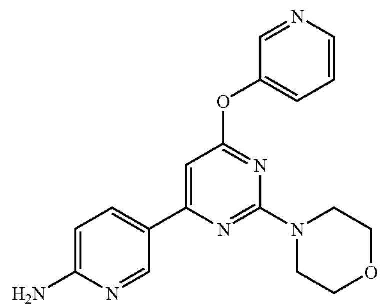 | 351.2, 1.66 | 7.85 L | ++++ | N/D | +++ |
| 513 | 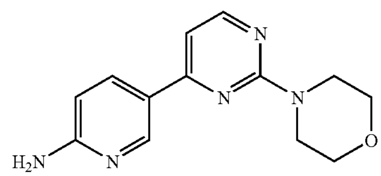 | 258.2, 1.48 | 6.33 L | ++++ | N/D | N/D |
| 514 | 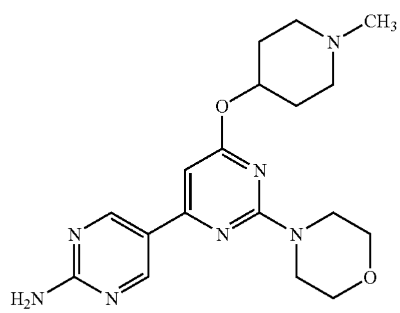 | 372.2, 1.65 | 7.49 | ++++ | N/D | +++ |
| 515 | 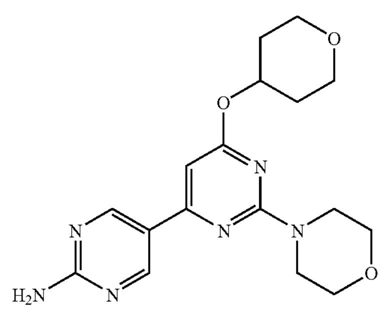 | 359.2, 2.05 | 11.16 L | ++++ | N/D | ++++ |
| 516 | 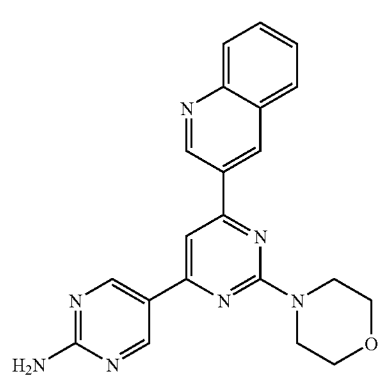 | 308.2, 1.54 | 6.71 L | ++++ | N/D | +++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 517 | 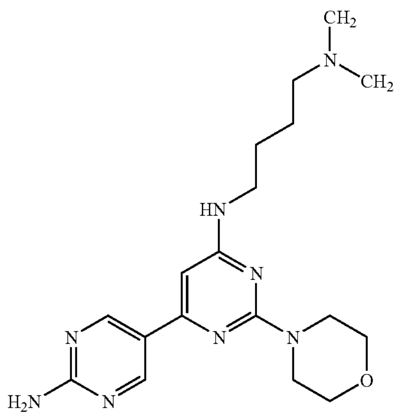 | 373.2, 0.71 | 5.93 | +++ | N/D | N/D |
| 518 | 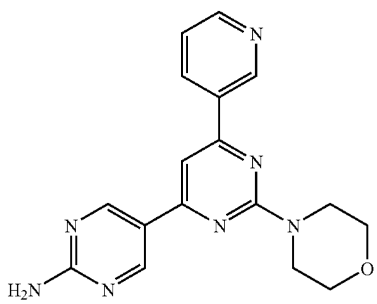 | 336.2, 1.61 | 8.11 L | ++++ | N/D | ++++ |
| 519 | Chiral | 383.2, 1.44 | 2.04 | ++++ | N/D | N/D |
| 520 | Chiral | 383.2, 1.53 | 2.09 | ++++ | N/D | +++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 521 | 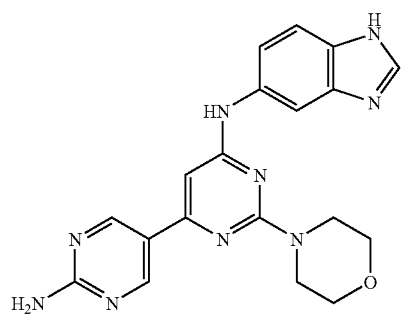 | 390.1, 1.59 | 7.15 L | ++++ | N/D | +++ |
| 522 | 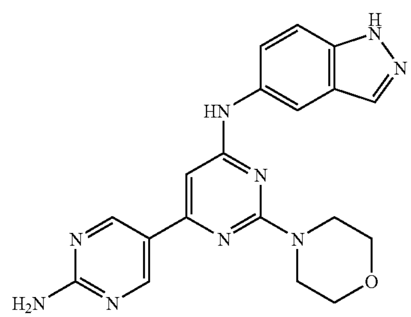 | 390.1, 1.75 | 8.62 L | ++++ | N/D | +++ |
| 523 | 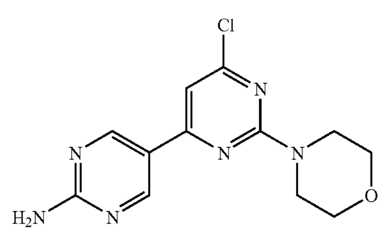 | 293.1, 1.93 | 2.20 | ++++ | N/D | +++ |
| 524 | 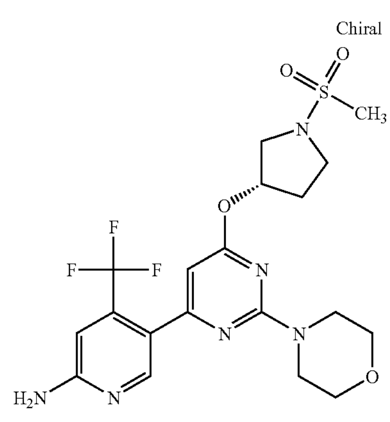 | 489.1, 2.47 | | ++++ | N/D | +++ |

TABLE 1-continued
| Compound | Structure | LC/MS (M + H, Rt min) | hplc 10 min (L = 45 min) | PI3 Kinase Alpha, IC50 | PSer473 AKT, EC50 | Cellular Proliferation, EC50 |
|---|---|---|---|---|---|---|
| 525 | 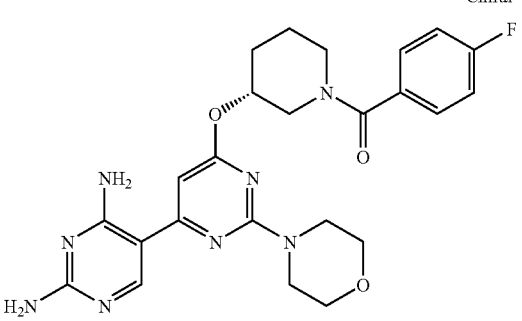 Chiral | 495.2, 2.49 | | ++++ | N/D | N/D |
| 526 | 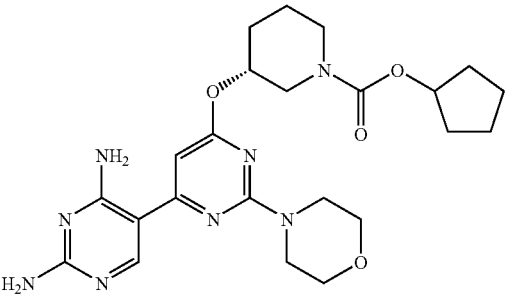 Chiral | 485.1, 2.90 | | ++++ | N/D | +++ |
| 527 | 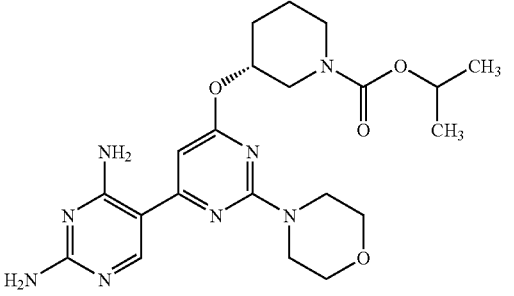 Chiral | 459.2, 2.75 | | ++++ | N/D | +++ |
| 528 | 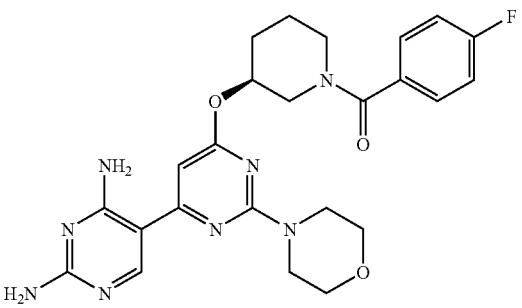 Chiral | 495.2, 2.47 | | ++++ | N/D | +++ |

TABLE 1-continued
| Compound | Structure | LC/MS (M + H, Rt min) | hplc 10 min (L = 45 min) | PI3 Kinase Alpha, IC50 | PSer473 AKT, EC50 | Cellular Proliferation, EC50 |
| --- | --- | --- | --- | --- | --- | --- |
| 529 | Chiral 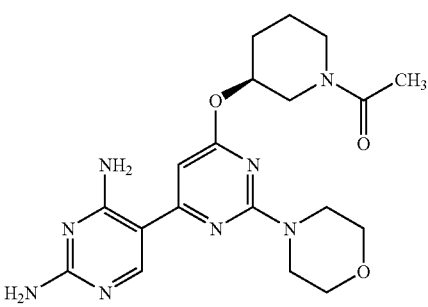 | 415.1, 2.06 | | ++++ | N/D | +++ |
| 530 | Chiral 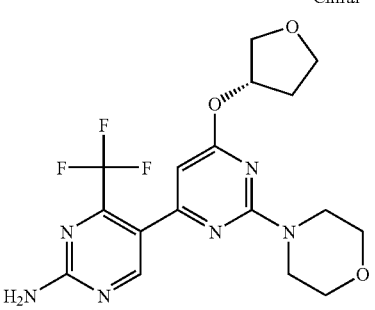 | 413.1, 3.09 | | ++++ | N/D | +++ |
| 531 | Chiral 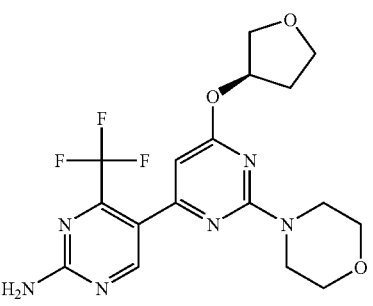 | 413.1, 3.07 | | ++++ | N/D | +++ |
| 532 | Chiral 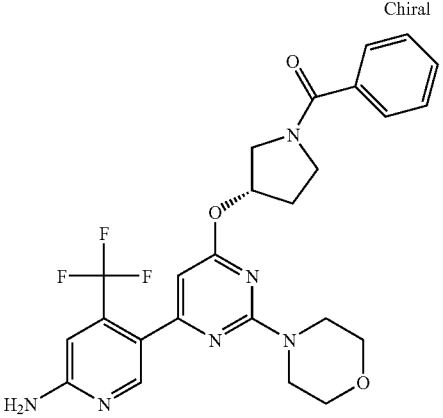 | 515.1, 2.74 | | ++++ | N/D | +++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 533 | Chiral | 481.1, 2.54 | | +++ | N/D | N/D |
| 534 | Chiral | 497.1, 3.01 | | ++++ | N/D | +++ |
| 535 | Chiral | 545.1, 3.37 | | ++++ | N/D | N/D |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 536 | 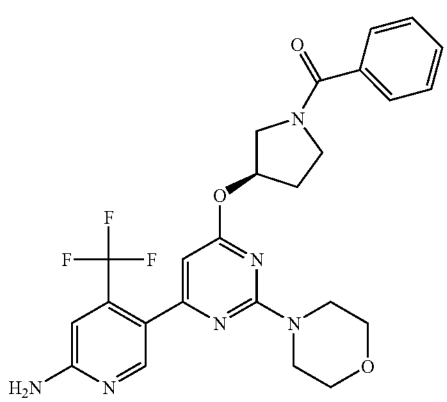 | 515.1, 2.79 | | ++++ | N/D | N/D |
| 537 | 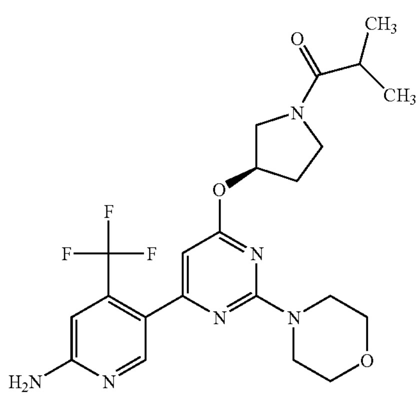 | 481.1, 2.55 | | ++++ | N/D | N/D |
| 538 | 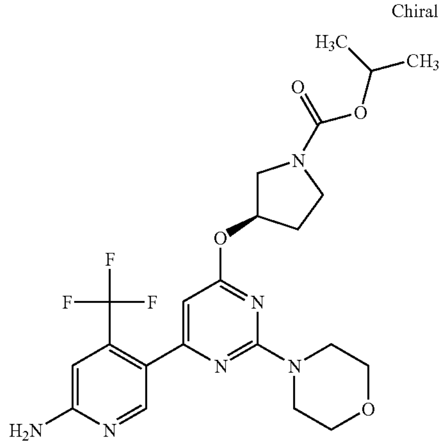 | 497.1, 2.54 | 3.00, (15.55) | ++++ | N/D | N/D |

TABLE 1-continued
| Compound | Structure | LC/MS (M + H, Rt min) | hplc 10 min (L = 45 min) | PI3 Kinase Alpha, IC50 | PSer473 AKT, EC50 | Cellular Proliferation, EC50 |
|---|---|---|---|---|---|---|
| 539 | Chiral 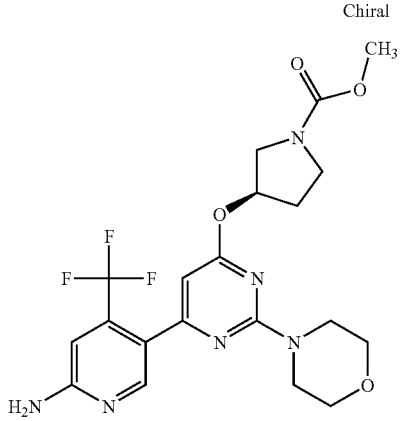 | 469.1, 2.56 | | ++++ | N/D | +++ |
| 540 | Chiral 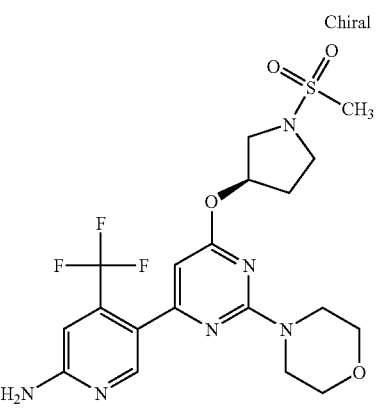 | 489.1, 2.47 | | ++++ | N/D | +++ |
| 541 | 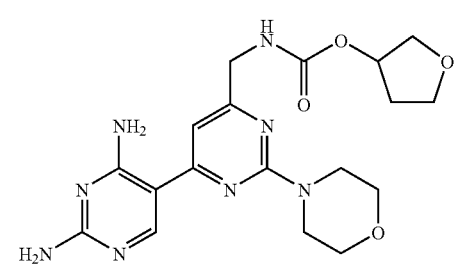 | 417.0, 1.51 | 1.84, (8.78) | ++++ | N/D | ++ |
| 542 | 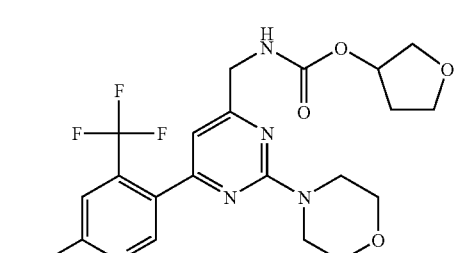 | 469.0, 1.76 | 2.27, (10.99) | ++++ | N/D | N/D |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 543 | 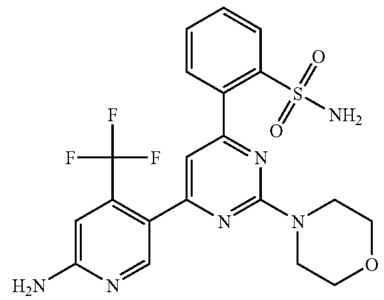 | 481.1, 1.93 | 2.57, (12.58) | ++++ | N/D | +++ |
| 544 | 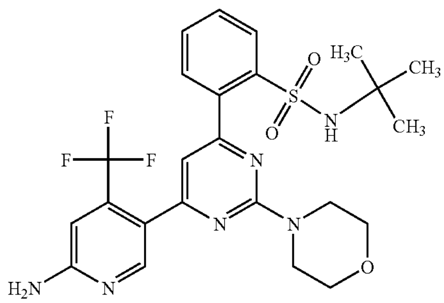 | 536.9, 2.47 | 3.38, (17.30) | ++++ | N/D | ++ |
| 545 | 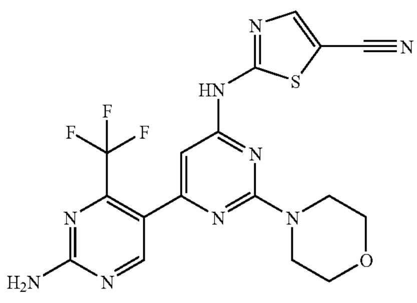 | 449.9, 3.44 | | N/D | N/D | ++ |
| 546 | 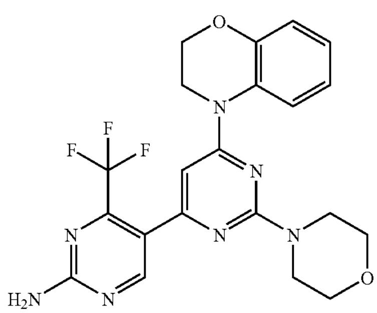 | 460.0, 3.00 | | ++++ | N/D | +++ |
| 547 | 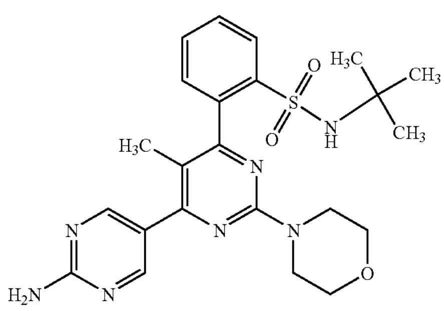 | 484.5, 2.28 | 3.12, (15.46) | +++ | N/D | N/D |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
| --- | --- | --- | --- | --- | --- | --- |
| 548 | 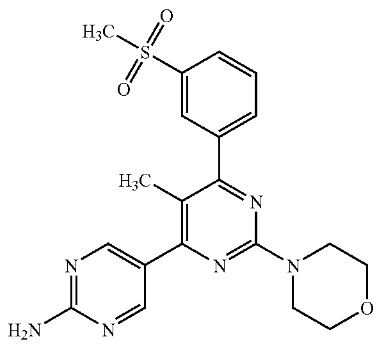 | 427.3, 1.83 | 2.49, (11.84) | ++++ | N/D | +++ |
| 549 | 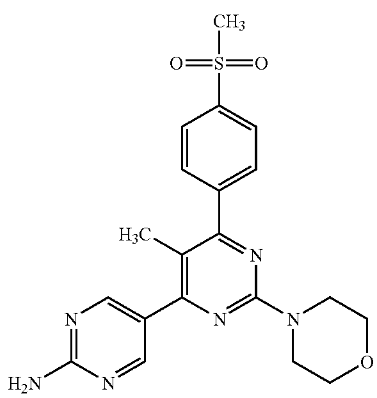 | 427.3, 1.82 | 2.51, (11.79) | ++++ | N/D | +++ |
| 550 | 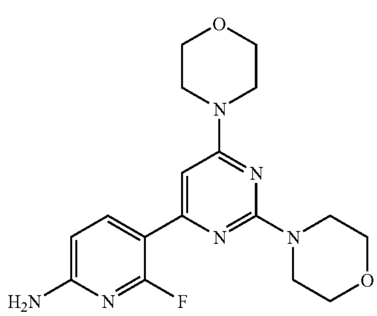 | 360.9, 1.56 | | N/D | N/D | +++ |
| 551 | 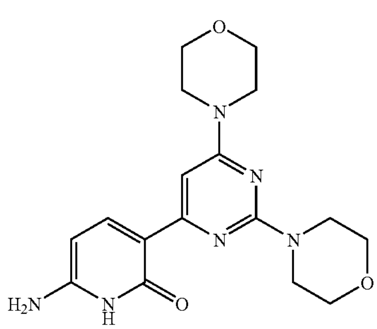 | 358.9, 1.63 | | ++++ | N/D | +++ |

TABLE 1-continued

| Compound | Structure | LC/MS (M + H, Rt min) | hplc 10 min (L = 45 min) | PI3 Kinase Alpha, IC$_{50}$ | PSer473 AKT, EC$_{50}$ | Cellular Proliferation, EC$_{50}$ |
|---|---|---|---|---|---|---|
| 552 | 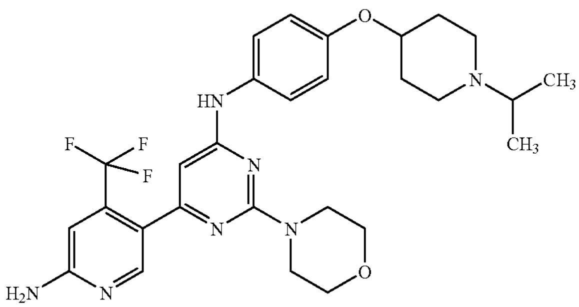 | 558.3, 1.90 | | ++++ | ++++ | +++ |
| 553 | 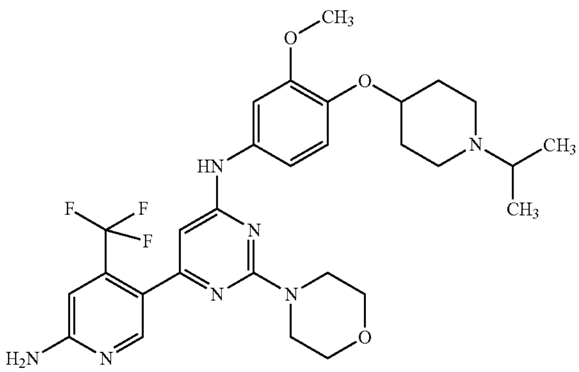 | 588.3, 1.92 | | ++++ | ++++ | ++++ |
| 554 | 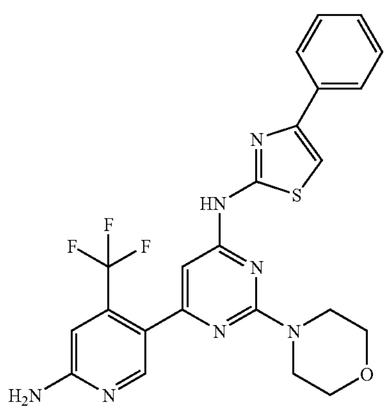 | 500.0; 2.46 | | ++++ | N/D | +++ |
| 555 | 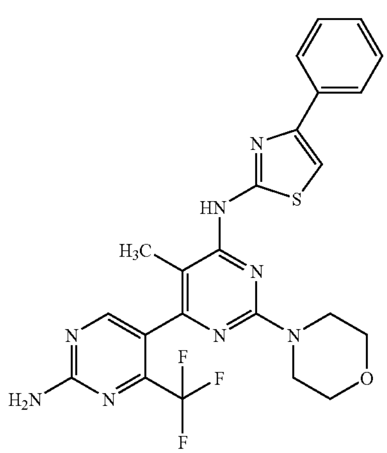 | 514.0; 2.62 | | +++ | N/D | N/D |

The compounds in Table 1 were synthesized according to Methods 1-30 and Examples 1-35 provided above. PI3K $IC_{50}$ values and pSer473 Akt $EC_{50}$ values for inhibition of Akt phosphorylation were determined according to Biological Methods 1 and 2, respectively. The cellular proliferation $EC_{50}$ values shown in Table 1 were determined according to Biological Method 3.

Table 1 shows the $IC_{50}$ and $EC_{50}$ values of the compounds as determined by the Biological Methods 1, 2, 3 and 4 as described herein. In Table 1, "+" indicates that the compound had an $IC_{50}$ or $EC_{50}$ value of >25 µM; "++" indicates that the compound had an $IC_{50}$ or $EC_{50}$ value of <25 µM; "+++" indicates that the compound had an $IC_{50}$ or $EC_{50}$ value of >10 µM; and "++++" indicates that the compound had an $IC_{50}$ or $EC_{50}$ value of >1 µM. An "N/D" in Table 1 indicates that the values were not determined.

Each of the Compounds in Table 1 exhibited $IC_{50}$ values of less than 10 µM with respect to inhibition of PI3K. Many of the Compounds of Table 1 exhibited $IC_{50}$ values of less than 1 µM and even less than 0.1 µM with respect to inhibition of PI3K. For this reason, each of the compounds is individually preferred and is preferred as a group. The PI3 kinase alpha $IC_{50}$ values shown in Table 1 were determined according to the ATP depletion assay as disclosed herein in Biological Method 1.

Furthermore, many of the compounds of Table 1 exhibited an $EC_{50}$ value with respect inhibition of pSer473 Akt phosphorylation of less than 10 µM. Many of those compounds exhibited $EC_{50}$ values of less than 1 µM and even less than 0.1 µM with respect to pAkt inhibition. Table 1 shows the $EC_{50}$ values for inhibition of phosphorylation of pSER473 AKT. The assays were performed according to the Biological Method 2 described herein.

In addition, many of the compounds of Table 1 were tested to determine their inhibitory activity in a cellular proliferation assay according to Biological Method 4. Many of those compounds exhibited $EC_{50}$ values of less than 1 µM and even less than 0.1 µM, demonstrating their potent ability to inhibit cellular proliferation. Table 1 shows the $EC_{50}$ values for inhibition of cellular proliferation of an ovarian cancer cell line, A2780/

Biological Method 1

Phosphorylation Assays

Assay 1: Homogenous Solution Phase Assay

Compounds to be tested are dissolved in DMSO and directly distributed into 384-well flashplates at 1.25 µL per well. To start the reaction, 20 µL of 6 nM PI3 kinase are added into each well followed by 20 µL of 400 nM ATP containing a trace of radiolabeled ATP and 900 nM 1-alpha-phosphatidylinositol (PI). The plates are briefly centrifuged to remove any air gap. The reaction is performed for 15 minutes and then stopped by the addition of 20 µL of 100 mM EDTA. The stopped reaction is incubated overnight at RT to allow the lipid substrate to bind by hydrophobic interaction to the surface of the flashplate. The liquid in the wells is then washed away, and the labeled substrate is detected with scintillation counting.

Assay 2: One Step Solid Phase Assay

This method is similar to Assay 1 except that the lipid substrate (1-alpha-phosphatidylinositol (PIP)) is first dissolved in a coating buffer and incubated on flashplate at room temperature overnight to allow the lipid substrate to bind by hydrophobic interaction to the surface of the flashplate. Unbound substrate is then washed away. On the day of assay, 20 µL of 6 nM PI3 kinase are added into each well followed by 20 µL of 400 nM ATP containing trace of radiolabeled ATP. Compounds are added together with enzyme and ATP to the lipid-coated plates. The plates are briefly centrifuged to remove any air gap. The reaction is performed for two to three hours. The reaction is stopped by addition of 20 µL of 100 mM EDTA or by immediate plate washing. Phosphorylated lipid substrate is detected by scintillation counting.

Assay 3: ATP Depletion Assay

Compounds to be tested are dissolved in DMSO and directly distributed into a black 384-well plate at 1.25 µL per well. To start the reaction, 25 µL of 10 nM PI3 kinase and 5 µg/mL 1-alpha-phosphatidylinositol (PI) are added into each well followed by 25 µL of 2 µM ATP. The reaction is performed until approx 50% of the ATP is depleted, and then stopped by the addition of 25 µL of KinaseGlo solution purchased from Promega. The stopped reaction is incubated for 5 minutes and the remaining ATP is then detected via luminescence.

Biological Method 2 pSer473 Akt Assays to Monitor PI3K Pathway

In this method, an assay for measuring the PI3K-mediated pSer473-Akt status after treatment with representative inhibitor compounds of the invention is described.

A2780 cells were cultured in DMEM supplemented with 10% FBS. L-glutamine, sodium pyruvate, and antibiotics. Cells were plated in the same medium at a density of 15,000 cells per well into 96 well tissue culture plates, with outside wells vacant, and allowed to adhere overnight.

Test compounds supplied in DMSO were diluted further into DMSO at 500 times the desired final concentrations before dilution into culture media to 2 times the final concentrations. Equal volumes of 2x compounds were added to the cells in 96 well plates and incubated at 37° C. for one hour. The media and compounds were then removed, the plates chilled and cells lysed in a lysis buffer (150 mM NaCl, 20 mM Tris pH 7.5, 1 mM EDTA, 1 mM EGTA, 1% Triton X-100) supplemented with phosphatase and protease inhibitors. After thorough mixing, lysates were transferred to both pSer473Akt and total Akt assay plates from Meso Scale Discovery (MSD), and incubated overnight with shaking at 4° C. The plates were washed with 1xMSD wash buffer and the captured analytes detected with secondary antibodies. After incubation with the secondary antibody at room temperature for 1-2 hours, the plates were washed again and 1.5x concentration of Read Buffer T (MSD) was added to the wells.

The assays were read on a SECTOR Imager 6000 instrument (Meso Scale Discovery). Ratios of the signal from pSer473Akt and total Akt assays were used to correct for any variability and the percent inhibition of pSer473Akt from the total signal seen in cells treated with compound versus DMSO alone was calculated and used to determine $EC_{50}$ values for each compound.

Biological Method 3

Pharmacology Target Modulation and Efficacy Study in Ovarian Cancer Xenograft Model A2780 ovarian cancer cells obtained from George Coukos (Fox Chase Cancer Center, University of Pennsylvania, Philadelphia, Pa.) were maintained in DMEM (Invitrogen, Inc.) supplemented with 10% heat-inactivated fetal bovine serum with 1% glutamine. Cells were propagated as recommended by the Dr. Coukos and colleagues. Female nu/nu mice (8-12 weeks old, 20-25 g, Charles River) were used for all in vivo pharmacology studies. The mice were housed and maintained in accordance with state and federal guidelines for the humane treatment and care of laboratory animals and received food and water ad libitum. Cancer cells were harvested from mid-log phase cultures using trypsin-EDTA (Invitrogen, Inc.). Five million cells were subcutaneously injected into the right flank of each mouse. Compound treatment was initiated when tumor size reached to 300-400 mm$^3$ for PK/PD studies and 200-300 mm$^3$ for efficacy studies. All compound treatment was administrated orally. Tumor volumes were determined by using StudyDirector software.

For in vivo target modulation PK/PD time-course studies, tumor tissues were resected from individual mice at different time points ranging from 30 min to 36 hr after a single dose of compound (60 or 100 mg/kg) or vehicle was administrated orally. For PK/PD dose-dependent studies, tumor-bearing mice were given a single oral dose of compound at different concentrations (10, 30, 60 and 100 mg/kg or vehicle) and tumors were resected at 10 hr or 24 hr after dosing. Blood samples were taken by cardiac puncture using a syringe primed with heparin sulfate. Resected tumors were snap frozen on dry ice and pulverized using a liquid nitrogen-cooled cryomortar and pestle, and lysed in cold cell extraction buffer (Biosource) containing protease inhibitor tablet (Complete; EDTA-free, Amersham). Supernatants were taken after centrifugation of tumor lysates at 300×g for 10 min at 4° C. and the protein concentration in each supernatant was determined by BCA (BioRad). An equal amount of protein from each tumor lysate was loaded onto 10% Tris-glycine gels (Invitrogen), for sodiumdoceylsulfate-polyacrylamide gel electrophoresis (SDS-PAGE) after which proteins were transferred from the gel onto PVDF membrane. Membranes were probed with antibodies that recognize phosphoAkt$^{Ser473}$ or phospho-Akt$^{Thr308}$ (Cell Signaling) followed by secondary goat anti-rabbit IgG conjugated to HRP(Amersham). Positive bands were visualized by enhanced chemiluminescence with X-ray film. Similar procedures were used to determine total AKT in the same tumor lysates to serve as normalization for total protein in each determination. The density of the positive band on the X-ray film was scanned and the target modulation for each compound was expressed as percentage inhibition by each compound compared to vehicle treatment. A rank order (<50%, 50-75%, >75%, as compared to vehicle treatment) of target inhibition is used to present compound target modulation activity.

For efficacy studies, A2780 cancer cells (5×10$^6$ in 100 µl of DMEM culture medium) were injected subcutaneously into the right flank of each nu/nu mouse. When average tumor sizes reached about 200 mm$^3$, mice were dosed orally daily (q.d.) or twice a day (b.i.d.) at three different compound concentrations (typically at 10, 30 and 100 mg/kg) in 100 µl incipient. Tumor growth and animal body weight was measured twice weekly with daily clinical observation to monitor potential toxicities related to the treatment. Typically, studies were terminated when tumors in vehicle-treated group reached 2500 mm$^3$ or adverse clinical effects were observed. Activation of the PI3K signaling pathway results in the phosphorylation of the downstream signaling molecule Akt at Ser$^{473}$ and/or Thr$^{308}$. Compound modulation of Akt$^{Ser473}$ phosphorylation was examined in A2780 xenograft tumors at time points ranging from 30 min to 36 hr after a single compound dose at 60 or 100 mg/kg. Table 2 summarizes modulation of AKT$^{Ser473}$ phosphorylation by representative compounds at 8 hr or 10 hr time points. Percentage inhibition was ranked as <50%, 50-75%, and >75%, as compared to vehicle treatment.

TABLE 2

Modulation of Akt$^{Ser473}$ phosphorylation by representative pyrimidine compounds of the invention.

| Compound | 60 mg/kg | 100 mg/kg |
| --- | --- | --- |
| 91 at 8 hr | | >50% |
| 183 at 8 hr | | 50-75% |
| 103 at 8 hr | | <50% |
| 10 at 10 hr | >75% | >75% |
| 84 at 10 hr | 50-75% | |
| 76 at 10 hr | >75% | >75% |
| 66 at 10 hr | <50% | |

Efficacy of Compound 91 was tested in the A2780 tumor xenograft model. Mice bearing A2780 tumors received oral administration of Compound 91 twice daily at 10 and 60 mg/kg. Tumor growth inhibition (50%) was observed at 60 mg/kg treatment, while at 10 mg/kg no inhibitory activity was observed (FIG. 1).

Figure 2:
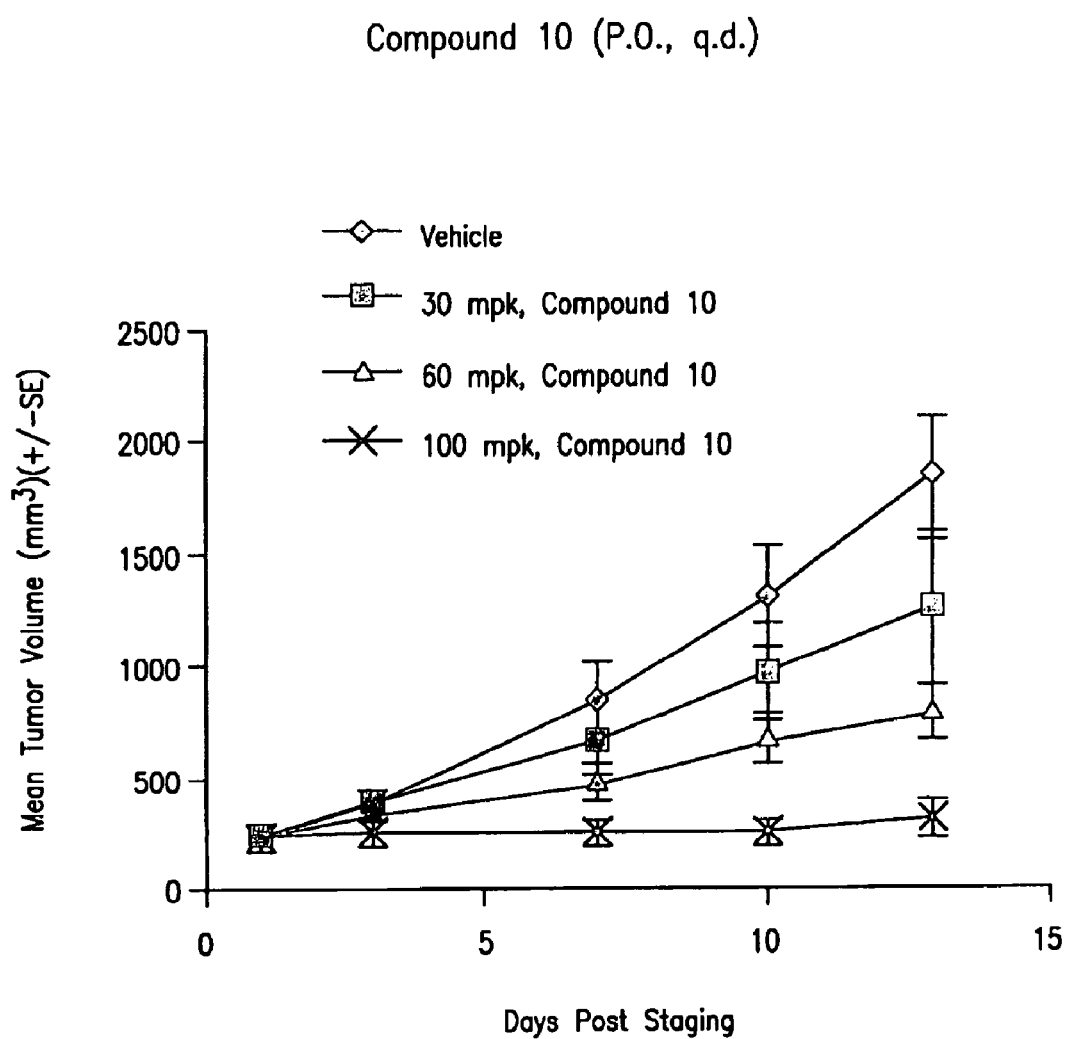
FIG. 2 is a graph illustrating tumor growth inhibition for a representative compound of the invention at three dosages compared to a control vehicle.
Figure 3:
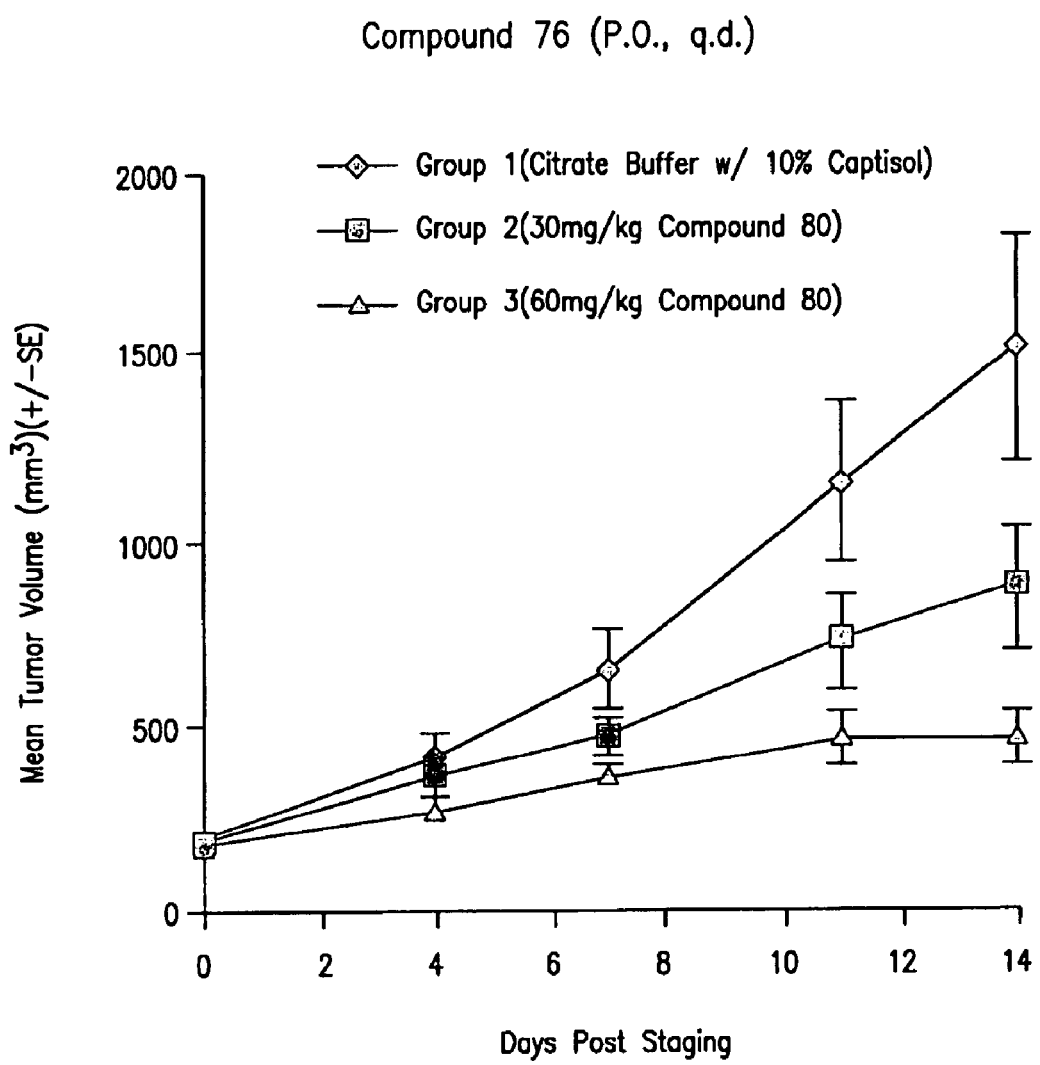
FIG. 3 is a graph illustrating tumor growth inhibition for a representative compound of the invention at two dosages compared to a control vehicle.
Figure 4:
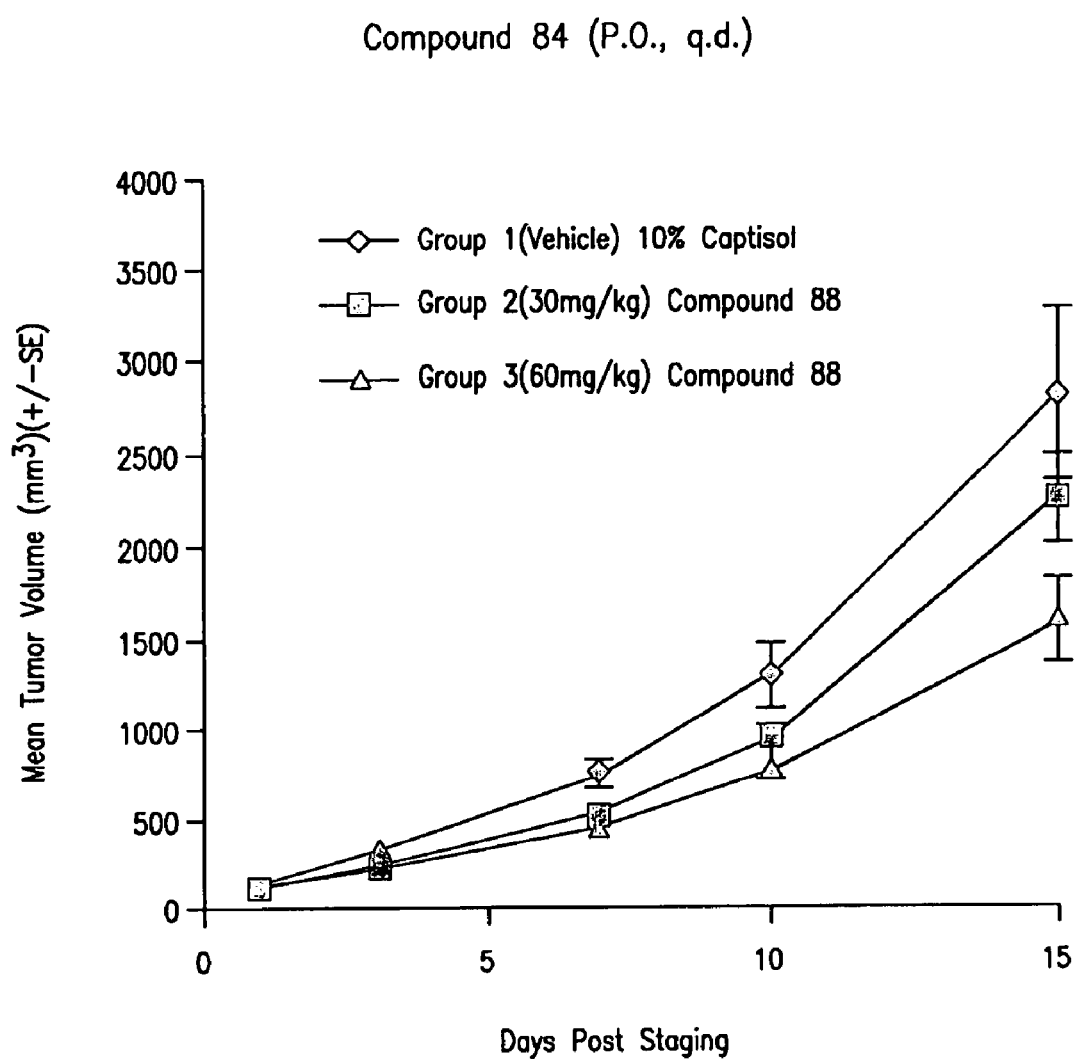
FIG. 4 is a graph illustrating tumor growth inhibition for a representative compound of the invention at two dosages compared to a control vehicle.

The modest tumor growth inhibition by Compound 91 at 60 mg/kg q.d. was due to its short-lived target modulation (50% inhibition lasted for 8 hr). Therefore, antitumor efficacy of three other compounds (Compound 10, Compound 76, and Compound 66), that demonstrated longer inhibition of Akt$^{Ser473}$ (>50% inhibition>10 hr) in A2780 tumors were evaluated in A2780 model. Compounds were orally administrated daily when tumor sizes reached to about 200 mm$^3$. Compound 10 demonstrated a dose-dependent tumor growth inhibition: 40% at 30 mg/kg, 70% at 60 mg/kg and tumor growth stasis at 100 mg/kg (FIG. 2). A similar dose-dependent tumor growth inhibition was observed with Compound 76 treatment at 30 and 60 mg/kg in the A2780 tumor model (FIG. 3) while Compound 84 was found to possess weaker antitumor activity (<50% TGI at 60 mg/kg) (FIG. 4).

Figure 5:
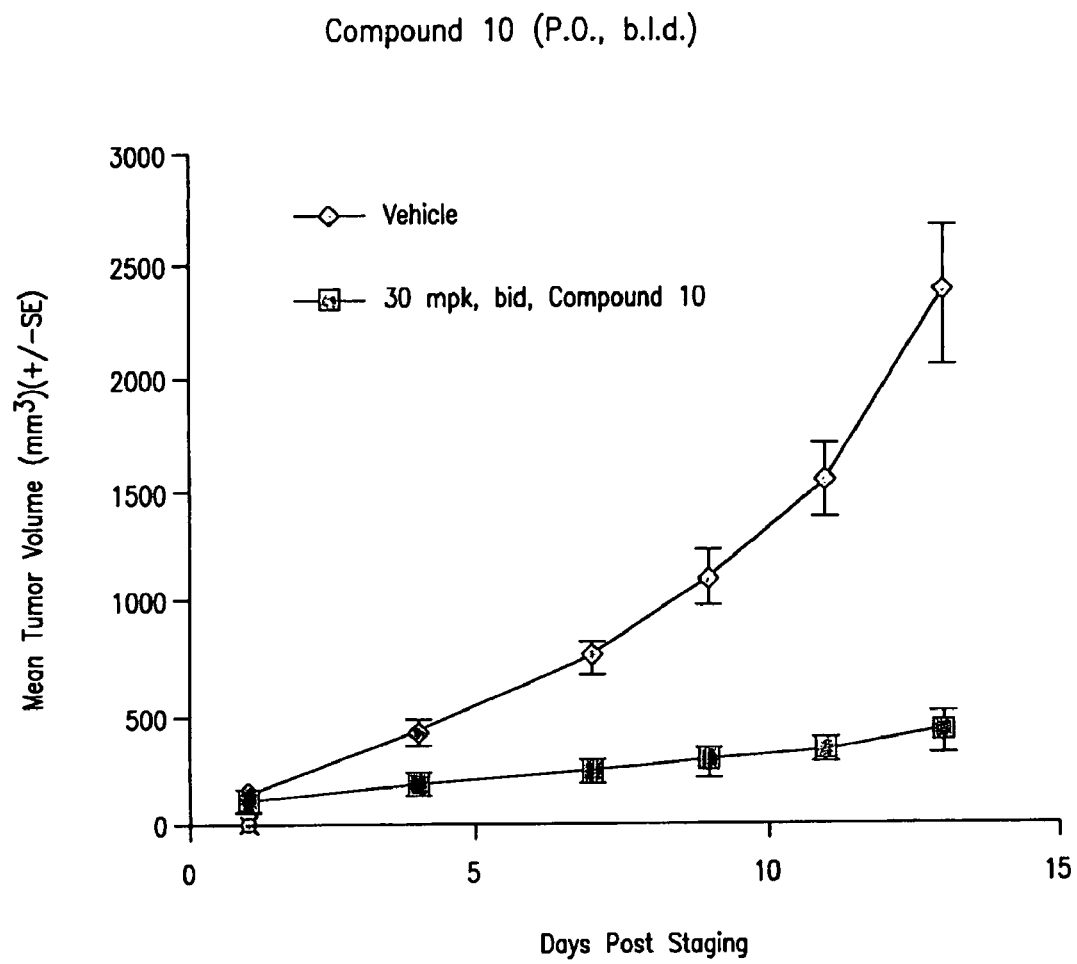
FIG. 5 is a graph illustrating tumor growth inhibition for a representative compound of the invention compared to a control vehicle.

Antitumor activity of Compound 10 was also evaluated at more frequent dosing regimen (b.i.d). As shown in FIG. 5, Compound 10 demonstrated a significant antitumor activity at 30 mg/kg when orally dosed b.i.d. Notably, tumor growth inhibition at 30 mg/kg b.i.d. was more potent than when dosed on a schedule at an equivalent daily dose (60 mg/kg, FIG. 2). The compounds were well tolerated in this study. This result indicated that a sustained but less profound target inhibition (covering the whole dosing period, but with <75% target inhibition) in A2780 tumors by Compound 10 was able to induce significant antitumor efficacy.

While the preferred embodiment of the invention has been illustrated and described, it will be appreciated that various changes can be made therein without departing from the spirit and scope of the invention.

Biological Method 4

Cellular Proliferation Studies in A2780 Cell

The ability of the compounds of the invention to inhibit cellular proliferation were determined by using Cell Titer Glo, a commercially available assay from Promega Corporation. A2780 ovarian cancer cells were seeded in TC treated 96-well plates at a density of 1,000 per well in DMEM, 10% FBS, 1% Sodium Pyruvate, and 1% Penicillin Streptomycin for a minimum of 2 hrs prior to addition of compound. For each concentration of test compound, 2 µl (500×) aliquots of compound or 100% DMSO diluted in 500 µl of culture medium for 2× concentration then diluted 1× on the Cells. Cells were incubated for 72 hrs at 37° C., 5% $CO_2$. After the 72 hour incubation, Cell Titer Glo reagent is added to determine number of viable cells remaining after exposure to the compound, and the $EC_{50}$ value was calculated. The assay was performed according to the manufacturer's instruction (Promega Corporation, Madison, Wis. USA). Each experimental condition was performed in duplicate. The results are provided in Table 1

What is claimed is:

1. The compound 4-(trifluoromethyl)-5-(2,6-dimorpholinopyrimidin-4-yl)pyridin-2-amine, of structure:

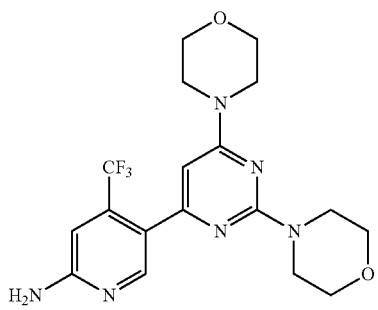

or a pharmaceutically acceptable salt thereof.

2. A composition, comprising a pharmaceutically acceptable carrier and an amount of a compound of claim 1 effective to inhibit PI3-K activity in a human or animal subject when administered thereto.

3. The composition of claim 2 further comprising at least one agent for the treatment of cancer.

4. The composition of claim 3, wherein the at least one agent for the treatment of cancer is vatalanib, imatinib, erlotinib, lapatinib, pertuzumab, trastuzumab, capecitabine, gemcitabine, irinotecan, paclitaxel, cisplatin, carboplatin, fulvestrant, dexamethasone, bevacizumab, docetaxel or gefitinib.

5. A method for treating ovarian cancer in a human or animal subject having ovarian cancer, comprising administering to the human or animal subject a composition comprising an amount of a compound of claim 1 effective to inhibit PI3-K activity in the human or animal subject.

6. The method of claim 5 further comprising administering to the human or animal subject at least one agent for the treatment of cancer.

7. The method of claim 6, wherein the at least one agent for the treatment of cancer is vatalanib, imatinib, erlotinib, lapatinib, pertuzumab, trastuzumab, capecitabine, gemcitabine, irinotecan, paclitaxel, cisplatin, carboplatin, fulvestrant, dexamethasone, bevacizumab, docetaxel or gefitinib.

* * * * *